US008889354B2

(12) United States Patent  (10) Patent No.: US 8,889,354 B2
Bryant et al.  (45) Date of Patent: *Nov. 18, 2014

(54) METHODS FOR THE IDENTIFICATION, ASSESSMENT, AND TREATMENT OF PATIENTS WITH CANCER THERAPY

(75) Inventors: Barbara M. Bryant, Cambridge, MA (US); Andrew I. Damokosh, West Hartford, CT (US); George J. Mulligan, Lexington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/600,260

(22) Filed: Aug. 31, 2012

(65) Prior Publication Data

US 2013/0013334 A1  Jan. 10, 2013

Related U.S. Application Data

(63) Continuation of application No. 11/449,195, filed on Jun. 8, 2006, now Pat. No. 8,278,038.

(60) Provisional application No. 60/688,634, filed on Jun. 8, 2005.

(51) Int. Cl.
| | | |
|---|---|---|
| *C12Q 1/68* | (2006.01) | |
| *G01N 33/574* | (2006.01) | |
| *G06F 19/20* | (2011.01) | |
| *G06Q 50/22* | (2012.01) | |
| *G06F 19/24* | (2011.01) | |

(52) U.S. Cl.
CPC .............. *G06F 19/20* (2013.01); *C12Q 1/6886* (2013.01); *G01N 33/57423* (2013.01); *G01N 2800/44* (2013.01); *G06F 19/24* (2013.01); *G01N 33/57407* (2013.01); *G01N 33/57419* (2013.01); *G01N 33/57434* (2013.01); *G01N 33/57449* (2013.01); *G01N 33/57438* (2013.01); *C12Q 2600/106* (2013.01); *C12Q 2600/136* (2013.01); *G06Q 50/22* (2013.01); *G01N 33/57415* (2013.01)
USPC ........................................................ 435/6.1

(58) Field of Classification Search
CPC .................................................... C12Q 1/6886
See application file for complete search history.

(56) References Cited

U.S. PATENT DOCUMENTS

2004/0156854 A1  8/2004  Mulligan et al.

FOREIGN PATENT DOCUMENTS

WO  WO 2004/053066 A2  6/2004

OTHER PUBLICATIONS

Tockman et al (Cancer Res., 1992, 52:2711s-2718s).*
Ferrandina et al (BMC Cancer, 2006, 6(182): 1-5).*
Chauhan et al (Oncogene, 2002, 21: 1346-1358).*
Hideshima et al (Cancer Research, 2001, 61: 3071-3076).*
Adams, Julian, et al., "Proteasome Inhibitors: A Novel Class of Potent and Effective Antitumor Agents," *Cancer Research*, vol. 59 (Jun. 1, 1999) pp. 2615-2622.
Adams, Julian, "Development of the Proteasome Inhibitor PS-341," *The Oncologist*, vol. 7 (2002) pp. 9-16.
Lightcap, Eric S., et al., "Proteasome Inhibition Measurements: Clinical Application," *Clinical Chemsitry*, vol. 46, No. 5 (2000) pp. 673-683.
Hochwald, Steven N., et al., "Antineoplastic Therapy in Colorectal Cancer through Proteasome Inhibition," *The American Surgeon*, vol. 69 (Jan. 2003) pp. 15-23.
Richardson, Paul G., et al., "A Phase 2 Study of Bortezomib in Relapsed, Refractory Myeloma," *The New England Journal of Medicine*, vol. 348, No. 26 (Jun. 26, 2003) pp. 2609-2617.
van de Vijver, Marc J., et al., "A Gene-Expression Signature as a Predictor of Survival in Breast Cancer," *The New England Journal of Medicine*, vol. 347, No. 25 (Dec. 19, 2002) pp. 1999-2009.
Barden, Catherine B., et al., "Classification of Follicular Thyroid Tumors by Molecular Signature: Results of Gene Profiling," *Clinical Cancer Research*, vol. 9 (May 2003) pp. 1792-1800.
Mulligan, George, et al., "Gene expression profiling and correlation with outcome in clinical trials of the proteasome inhibitor bortezomib," *Blood*, vol. 109, No. 8 (Apr. 15, 2007) pp. 3177-3188.
Toczyski, David P., et al., "The Epstein-Barr virus (EBV) small RNA EBER1 binds and relocalizes ribosomal protein L22 in EBV-infected human B lymphocytes," *Proceedings of the National Academy of Science USA*, vol. 91 (Apr. 1994) pp. 3463-3467.
Maglott, Donna, et al., "Entrez Gene: gene-centered information at NCBI," *Nucleic Acids Research*, vol. 33, Database issue (2005) pp. D54-D58.
Affymetrix, Inc., "Annotation Methodology," Affymetrix—Annotation Methodology Technical Note [online] Affymetrix, Santa Clara, CA, downloaded Jul. 23, 2008 (3 pages).
Affymetrix, Inc., "GeneChip Human Genome U133 Set," [online] 701092 Rev. 3 (Nov. 2004) downloaded Jul. 23, 2008 ( 2 pages).
Affymetrix, Inc., "Human Genome U133 Set—Support Materials," Affymetrix—Technical Support Documentation for Human Genome U133 Set [online] downloaded Jul. 24, 2008 (3 pages).
International Prelminary Examination Report (IPER) and Written Opinion of the International Searching Authority dated Dec. 11, 2007 in corresponding PCT Application PCT/US06/022515.
Office Action dated Jun. 23, 2008 in co-pending U.S. Appl. No. 10/728,055.

(Continued)

*Primary Examiner* — Sean Aeder
(74) *Attorney, Agent, or Firm* — Millennium Pharmaceuticals, Inc.

(57) ABSTRACT

The present invention is directed to the identification of predictive markers that can be used to determine whether patients with cancer are clinically responsive or non-responsive to a therapeutic regimen prior to treatment. In particular, the present invention is directed to the use of certain individual and/or combinations of predictive markers, wherein the expression of the predictive markers correlates with responsiveness or non-responsiveness to a therapeutic regimen. Thus, by examining the expression levels of individual predictive markers and/or predictive markers comprising a marker set, it is possible to determine whether a therapeutic agent, or combination of agents, will be most likely to reduce the growth rate of tumors in a clinical setting.

11 Claims, No Drawings

(56) References Cited

OTHER PUBLICATIONS

Supplementary Partial European Search Report dated Jun. 24, 2009 in European Patent Application No. 06784710.3 which corresponds to U.S. Appl. No. 11/449,195.

Glatt, Christine M., et al., "Molecular characterization of thyroid toxicity: anchoring gene expression profiles to biochemical and pathologic end points," *Environmental Health Perspectives*, vol. 113, No. 10 (Oct. 2005) pp. 1354-1361.

Wessels, Lodewyk F. A., et al., "A protocol for building and evaluating predictors of disease state based on microarray data," *Bioinformatics*, vol. 21, No. 19 (Apr. 7, 2005) pp. 3755-3762.

Tockman, Melvyn S., et al., "Considerations in bringing a cancer biomarker to clinical application," *Cancer Research (Supplement)*, vol. 52 (May 1, 1992) pp. 2711s-27182.

Ferrandina, Gabriella, et al., "Cyclooxygenase-2 (Cox-2) expression and resistance to platinum versus platinum/paclitaxel containing chemotherapy in advanced ovarian cancer," *BMC Cancer*, vol. 6 No. 182 (Jul. 11, 2006) pp. 1-5.

Chauhan, Dharminder, et al., "Identification of genes regulated by Dexamethasone in multiple myeloma cells using oligonucleotide arrays," *Oncogene*, vol. 21 (2002) pp. 1346-1358.

Hideshima, Teru, et al., "The proteasome inhibitor PS-341 inhibits growth, induces apoptosis, and overcomes drug resistance in human multiple myeloma cells," *Cancer Research*, vol. 61 (Apr. 1, 2001) pp. 3071-3076.

Alberts, Bruce, et al., Molecular Biology of The Cell, Third Edition, published by Garland Publishing, Inc., New York, New York (1994) p. 465.

Greenbaum, Dov, et al., "Comparing protein abundance and mRNA expression levels on a genomic scale," *Genome Biology*, vol. 4, No. 9 (2003) pp. 117.1-117.8.

Lichtinghagen, Ralf, et al., "Different mRNA and protein expression of matrix metalloproteinases 2 and 9 and tissue inhibitor of metalloproteinases 1 in benign and malignant prostate tissue," *European Urology*, vol. 42 (2002) pp. 398-406.

\* cited by examiner

METHODS FOR THE IDENTIFICATION, ASSESSMENT, AND TREATMENT OF PATIENTS WITH CANCER THERAPY

CROSS REFERENCE TO RELATED APPLICATIONS

This application is a Continuation of U.S. patent application Ser. No. 11/449,195, filed Jun. 8, 2006, now U.S. Pat. No. 8,278,038, which claims the benefit of U.S. Provisional Application No. 60/688,634, filed Jun. 8, 2005. The entire contents of each of these applications are incorporated herein by reference.

The contents of the Sequence Listing were submitted on compact disc in the parent U.S. patent application Ser. No. 11/449,195 and are being transferred to this application. The compact disc has a copy of the Sequence Listing file, created on Sep. 26, 2008 and named "sequence listing.txt," the contents of which are incorporated herein by this reference. This file is 5.91 MB (6,203,392 bytes) and was copied onto compact disc on Sep. 30, 2008.

BACKGROUND OF THE INVENTION

One of the continued problems with therapy in cancer patients is individual differences in response to therapies. With the narrow therapeutic index and the toxic potential of many available cancer therapies, such differential responses potentially contribute to patients undergoing unnecessary ineffective and even potentially harmful therapy regimens. If a designed therapy could be optimized to treat individual patients, such situations could be reduced or even eliminated. Furthermore, targeted designed therapy may provide more focused, successful patient therapy overall. Accordingly, there is a need to identify particular cancer patients which are particularly responsive to particular cancer therapies, either alone or in combination with other chemotherapies. It would therefore be beneficial to provide for the diagnosis, staging, prognosis, and monitoring of cancer patients, including, e.g., hematological cancer patients (e.g., multiple myeloma, leukemias, lymphoma, etc) as well as solid tumor cancer patients (e.g., lung, breast, prostate, ovary, colon, kidney, liver), who would benefit from particular cancer inhibition therapies; or to indicate a predisposition of such patients to non-responsiveness to therapy, thus resulting in appropriate preventative measures.

Proteasome inhibition represents an important strategy in cancer treatment. The proteasome is a multi-enzyme complex present in all cells which play a role in degradation of proteins involved in regulation of the cell cycle. For example, King et al., demonstrated that the ubiquitin-proteasome pathway plays an essential role in regulating cell cycle, neoplastic growth and metastasis. A number of key regulatory proteins, including p53, cyclins, and the cyclin-dependent kinases p21 and p27$^{KIP1}$, are temporally degraded during the cell cycle by the ubiquitin-proteasome pathway. The ordered degradation of these proteins is required for the cell to progress through the cell cycle and to undergo mitosis. See, e.g., *Science* 274: 1652-1659 (1996). Furthermore, the ubiquitin-proteasome pathway is required for transcriptional regulation. Palombella et al., teach that the activation of the transcription factor NF-kB is regulated by proteasome-mediated degradation of the inhibitor protein IkB. See International Patent Application Publication No. WO 95/25533. In turn, NF-kB plays a central role in the regulation of genes involved in the immune and inflammatory responses. For example, Read et al. demonstrated that the ubiquitin-proteasome pathway is required for expression of cell adhesion molecules, such as E-selectin, ICAM-1, and VCAM-1. See *Immunity* 2:493-506 (1995). Additional findings further support the role for proteasome inhibition in cancer therapy, as Zetter found that cell adhesion molecules are involved in tumor metastasis and angiogenesis in vivo, by directing the adhesion and extravastation of tumor cells to and from the vasculature to distant tissue sites within the body. See, e.g., *Seminars in Cancer Biology* 4:219-229 (1993). Moreover, Beg and Baltimore, found that NF-kB is an anti-apoptotic factor, and inhibition of NF-kB activation makes cells more sensitive to environmental stress and cytotoxic agents. See *Science* 274:782 (1996).

The first proteasome inhibitor described as having antitumor activity, bortezomib (N-pyrazinecarbonyl-L-phenylalanine-L-leucineboronic acid, PS-341) (VELCADE® for injection, Millennium Pharmaceuticals, Inc., Cambridge, Mass.; Johnson & Johnson Pharmaceutical Research and Development L.L.C.) has been approved for treatment of relapsed multiple myeloma. Presently clinical trials are underway in additional indications, including additional hematological cancers as well as solid tumors. This and other peptide boronic ester and acid proteasome inhibitors have been described by Adams et al. See, e.g., U.S. Pat. No. 5,780, 454 (1998), U.S. Pat. No. 6,066,730 (2000), and U.S. Pat. No. 6,083,903 (2000). They describe the use of the disclosed boronic ester and boronic acid compounds to reduce the rate of muscle protein degradation, to reduce the activity of NF-kB in a cell, to reduce the rate of degradation of p53 protein in a cell, to inhibit cyclin degradation in a cell, to inhibit the growth of a cancer cell, and to inhibit NF-kB dependent cell adhesion.

Bortezomib specifically and selectively inhibits the proteasome by binding tightly (Ki=0.6 nM) to one of the enzyme's active sites. Bortezomib is selectively cytotoxic, and has a novel pattern of cytotoxicity in National Cancer Institute (NCI) in vitro and in vivo assays. Adams J, et al. *Cancer Res* 59:2615-22. (1999). In addition, bortezomib has cytotoxic activity in a variety of xenograft tumor models. Teicher B A, et al. *Clin Cancer Res.* 5:2638-45 (1999). Bortezomib inhibits nuclear factor-κB (NF-κB) activation, attenuates interleukin-6 (IL-6) mediated cell growth, and has a direct apoptotic effect, and possibly an anti-angiogenic effect. Additionally, bortezomib is directly cytotoxic to myeloma cells in culture, independent of their p53 status. See, e.g., Hideshima T, et al. *Cancer Res.* 61:3071-6 (2001). In addition to a direct cytotoxic effect of bortezomib on myeloma cells, bortezomib inhibits tumor necrosis factor alpha (TNFα stimulated intercellular adhesion molecule-1 (ICAM-1) expression by myeloma cells and ICAM-1 and vascular cell adhesion molecule-1 (VCAM-1) expression on bone marrow stromal cells (BMSCs), resulting in decreased adherence of myeloma cells and, consequently, in decreased cytokine secretion. Hideshima T, et al. *Oncogene.* 20:4519-27 (2001). By inhibiting interactions of myeloma cells with the surrounding bone marrow, bortezomib can inhibit tumor growth and survival, as well as angiogenesis and tumor cell migration. The antineoplastic effect of bortezomib may involve several distinct mechanisms, including inhibition of cell growth signaling pathways, dysregulation of the cell cycle, induction of apoptosis, and inhibition of cellular adhesion molecule expression. Notably, bortezomib induces apoptosis in cells that over express B-cell lymphoma 2 (Bcl-2), a genetic trait that confers unregulated growth and resistance to conventional chemotherapeutics. McConkey D J, et al. *The proteasome as a new drug target in metastatic prostate cancer.* 7th Annual Genitourinary Oncology Conference, Houston, Tex. Abstract (1999).

Glucocorticoidal steroids are capable of causing apoptotic death of many varieties of cells, and a selection of glucocorticoidal steroids have consequently be used in the treatment of various malignancies, including lymphoid malignancies, and combination therapies in solid tumors. For example, the optimal therapy for relapsed myeloma is not established, but high-dose dexamethasone is commonly used. See, e.g., Kumar A, et al. *Lancet Oncol;* 4:293-304 (2003); Alexanian R, et al. *Ann Intern Med.* 105:8-11 (1986); Friedenberg W R, et al. *Am J Hematol.* 36:171-75. (1991). Response rates with this treatment are similar to those with vincristine, doxorubicin, and dexamethasone (VAD), and the dexamethasone component is estimated to account for 85 percent of the effect of VAD. See, e.g., Alexanian R, et al. *Blood.* 80:887-90 (1992); Sonneveld P, et al. *Br J Haematol.* 115:895-902. (2001). High-dose chemotherapy followed by autologous stem cell transplantation improves patient survival, but in most cases the disease relapses. Attal M et al. *N Engl J Med.* 335:91-97 (1996); Child J A, et al. *N Engl J Med.* 348:1875-83 (2003).

In addition to use of dexamethasone, additional corticosteroids have demonstrated use in cancer treatments, including hydrocortisone in combination therapy for prostate cancer, predisolone in leukemia, prednisolone in lymphoma treatment, and triamcinolone has recently demonstrated some anti-cancer activity. See, e.g., Scholz M., et al., *J. Urol.* 173: 1947-52 (2005); Sano J., et al., *Res Vet Sci.* (May 10, 005); Zinzani P L. et al., *Semin Oncol.* 32(1 Suppl 1):S4-10. (2005); and Abrams, M T et al., *J Cancer Res Clin Oncol.* 131:347-54 (2005). It is believed gene transcription resulting from treatment with glucocorticoids results in apoptotic death and therapeutic effect. Analysis of sensitive and resistant cell lines have demonstrated differential gene expression patterns, suggesting expression differences account for varied response rates to glucocorticoid therapy. See, e.g., Thompson, E. B., et al., *Lipids.* 39:821-5 (2004), and references cited therein.

While advances in development of successful cancer therapies progress, individual patient responses continue to demonstrate subsets of patient response to any particular therapy. We have conducted gene expression analysis studies to assess patient populations undergoing glucocorticoid therapy or proteasome inhibition therapy. Analyses were carried out to identify predictive markers associated with particular patients who respond well to treatment (responders) with a glucocorticoid and/or proteasome inhibitor versus those patients who do not respond to treatment (non-responders) with a glucocorticoid and/or proteasome inhibitor.

DESCRIPTION OF THE INVENTION

The present invention is based, in part, on the identification of individual markers and marker sets that can be used to determine whether a tumor may be effectively treated by treatment with a proteasome inhibition therapy and/or a glucocorticoid therapy. For example, the compositions and methods provided herein can be used to determine whether a patient will be responsive or non-responsive to a proteasome inhibition therapeutic agent. Furthermore the compositions and methods provided herein can be used to determine whether a patient will be responsive or non-responsive to a glucocorticoid therapeutic agent. Based on these identifications, the present invention provides, without limitation: 1) methods and compositions for determining whether a proteasome inhibition therapy and/or a glucocorticoid therapy will or will not be effective in stopping or slowing tumor growth and patient treatment; 2) methods and compositions for monitoring the effectiveness of a proteasome inhibition therapy (a proteasome inhibitor agent or a combination of agents) and/or a glucocorticoid therapy used for the treatment of tumors; 3) methods and compositions for treatments of tumors comprising proteasome inhibition therapy and/or glucocorticoid therapy; and 4) methods and compositions for identifying specific therapeutic agents and combinations of therapeutic agents that are effective for the treatment of tumors in specific patients.

The markers of the present invention, whose expression correlates with the response to an agent, are identified in Table 1A, Table 1B, Table 2A, Table 2B, and Table 3. By examining the expression of one or more of the identified markers or marker sets in a tumor, it is possible to determine which therapeutic agent or combination of agents will be most likely to reduce the growth rate of the cancer cells. By examining the expression of one or more of the identified markers or marker sets in a cancer, it is also possible to determine which therapeutic agent or combination of agents will be the least likely to reduce the growth rate of cancer cells. By examining the expression of one or more of the identified markers or marker sets, it is therefore possible to eliminate ineffective or inappropriate therapeutic agents Importantly, these determinations can be made on a patient by patient basis or on an agent by agent basis. Thus, one can determine whether or not a particular therapeutic regimen is likely to benefit a particular patient or type of patient, and/or whether a particular regimen should be continued.

The present invention is directed to methods of identifying and/or selecting a cancer patient who is responsive to a therapeutic regimen. In particular, the methods are directed to identifying or selecting a cancer patient who is responsive to a therapeutic regimen comprising proteasome inhibition therapy and/or glucocorticoid therapy. Additionally provided are methods of identifying a patient who is non-responsive to such a therapeutic regimen. These methods typically include the determining the level of expression of one or more predictive markers in a patient's tumor (e.g., a patient's cancer cells), comparing the level of expression to a reference expression level, and identifying whether expression in the sample includes a pattern or profile of expression of a selected predictive marker or marker set which corresponds to response or non-response to proteasome inhibition therapy and/or glucocorticoid therapy.

Additionally provided methods include therapeutic methods which further include the step of beginning, continuing, or commencing, or stopping, discontinuing or halting a therapy accordingly where a patient's predictive marker profile indicates that the patient would respond or not respond to the proteasome inhibition and/or glucocorticoid therapeutic regimen. In another aspect, methods are provided for analysis of a patient not yet being treated with a proteasome inhibition therapy or glucocorticoid therapy and identification and prediction that the patient would not be a responder to the therapeutic agent and such patient should not be treated with the proteasome inhibition therapy and/or glucocorticoid therapy when the patient's marker profile indicates that the patient is a non-responder. Thus, the provided methods of the invention can eliminate ineffective or inappropriate use of proteasome inhibition therapy and/or glucocorticoid therapy regimens.

Additionally provided are classifiers which can be used to develop a diagnostic test or a readable array useful for identifying patients who will be responsive or non-responsive to proteasome inhibition therapy and/or glucocorticoid therapy. Probes or peptides identified in a classifier of the invention can be included in a diagnostic or prognostic test to select a therapy, e.g., proteasome inhibition therapy and/or glucocorticoid therapy or a test which is used to determine continuation of therapy, e.g., proteasome inhibition therapy and/or glucocorticoid therapy.

Additional methods include methods to determine the activity of an agent, the efficacy of an agent, or identify new therapeutic agents or combinations. Such methods include methods to identify an agent useful as a proteasome inhibitor and/or a glucocorticoid inhibitor, for treating a cancer, e.g. a hematological cancer (e.g., multiple myeloma, leukemias, lymphoma, etc) or cancer from a solid tumor (e.g., in lung, breast, prostate, ovary, colon, kidney or liver), based on its ability to affect the expression of markers in a marker set of the invention. For example, an inhibitor which decreases or increases the level of expression of a marker or markers provided as upregulated or down-regulated, respectively, in a set predictive for responsiveness to proteasome inhibition of the cancer would be a candidate inhibitor for the cancer. In another example, an inhibitor which decreases or increases the level of expression of a marker or markers provided as upregulated or downregulated, respectively, in a set predictive for responsiveness to glucocorticoid inhibition of the cancer would be a candidate inhibitor for the cancer.

The present invention is also directed to methods of treating a cancer patient, with a therapeutic regimen, in particular a proteasome inhibitor therapy (e.g., a proteasome inhibitor agent, alone, or in combination with an additional agent such as a chemotherapeutic agent) and/or glucocorticoid therapy regimen (a glucocorticoid agent, alone or in combination with an additional agent), which includes the step of selecting a patient whose predictive marker profile indicates that the patient will respond to the therapeutic regimen, and treating the patient with the proteasome inhibition therapy and/or glucocorticoid therapy.

Additional methods include selecting patients that are unlikely to experience response or increased time to progression upon treatment with a cancer therapy (e.g., proteasome inhibition therapy, glucocorticoid therapy). Furthermore provided are methods for selection of a patient having aggressive disease and more rapid time to progression.

Additional methods include a method to evaluate whether to treat or pay for the treatment of cancer, e.g. hematological cancer (e.g., multiple myeloma, leukemias, lymphoma, etc) or cancer from a solid tumor (e.g., in lung, breast, prostate, ovary, colon, kidney or liver), by reviewing a patient's predictive marker profile for responsiveness or non-responsiveness to proteasome inhibition and/or glucococorticoid therapy.

DEFINITIONS

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, preferred methods and materials are described herein. The content of all database accession records (e.g., representative public identifier ID from Affymetrix HG133 annotation files, Entrez, GenBank, RefSeq) cited throughout this application (including the Tables) are also hereby incorporated by reference. The contents of files disclosing the Affymetrix HG-133A Probe Sequences and HG-133B Probe Sequences, both FASTA files dated Jun. 9, 2003 (Affymetrix, Inc., Santa Clara, Calif.), also hereby are incorporated by reference. In the case of conflict, the present specification, including definitions, will control.

The articles "a" and "an" are used herein to refer to one or to more than one (i.e. at least one) of the grammatical object of the article. By way of example, "an element" means at least one element and can include more than one element.

A "marker" is a naturally-occurring polymer corresponding to at least one of the nucleic acids or proteins associated with Affymetrix probe set identifiers listed in any one of Table 1A, Table 1B, Table 2A, Table 2B, and Table 3. For example, markers include, without limitation, sequences recognized by the Affymetric probes and probeset identifiers, sense and anti-sense strands of genomic DNA (i.e. including any introns occurring therein), RNA generated by transcription of genomic DNA (i.e. prior to splicing), RNA generated by splicing of RNA transcribed from genomic DNA, and proteins generated by translation of spliced RNA (i.e. including proteins both before and after cleavage of normally cleaved regions such as transmembrane signal sequences). As used herein, a "marker" may also include a cDNA made by reverse transcription of an RNA generated by transcription of genomic DNA (including spliced RNA). A "marker set" is a group of markers, comprising two or more predictive markers of the invention. Markers of the present invention include the predictive markers identified in Table 1A, Table 1B, Table 2A, Table 2B, and Table 3; as identified by the particular probeset identifier, representative public identifier, title, gene symbol, and/or Entrez gene identifier, and include the representative nucleotide and/or protein sequence or fragment thereof which corresponds to the identifier.

A "predictive marker" as used herein, includes a marker which has been identified as having differential expression in tumor cells of a patient and furthermore that expression is characteristic of a patient who is responsive in either a positive or negative manner to treatment with a proteasome inhibitor regimen and/or glucocorticoid regimen. For example, a predictive marker includes a marker which is demonstrates higher expression in a non-responsive patient; alternatively a predictive marker includes a marker which demonstrates higher expression in a responsive patient. Similarly, a predictive marker is intended to include those markers which demonstrate lower expression in a non-responsive patient as well as those markers which demonstrate lower expression in a responsive patient. Thus, as used herein, predictive marker is intended to include each and every one of these possibilities, and further can include each single marker individually as a predictive marker; or alternatively can include one or more, or all of the characteristics collectively when reference is made to "predictive markers" or "predictive marker sets." A predictive marker set also can be known as a "classifier."

As used herein, a "naturally-occurring" refers to a molecule (e.g., RNA, DNA, protein, etc.) that occurs in nature (e.g. encodes a natural protein, a naturally produced protein, etc).

The term "probe" refers to any molecule which is capable of selectively binding to a specifically intended target molecule, for example a marker of the invention. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic monomers.

The "normal" level of expression of a marker is the level of expression of the marker in cells in a similar environment or response situation, in a patient not afflicted with cancer. A normal level of expression of a marker may also refer to the level of expression of a "reference sample", (e.g., sample from a healthy subjects not having the marker associated disease). A reference sample expression may be comprised of an expression level of one or more markers from a reference database. Alternatively, a "normal" level of expression of a marker is the level of expression of the marker in non-tumor cells in a similar environment or response situation from the same patient that the tumor is derived from.

"Differential expression" of a marker refers to expression of a marker that varies in level across patients. Furthermore, in this invention we refer to a marker as "differentially expressed" when its expression level is correlated with, or otherwise indicative of, response or non-response to treatment.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, "informative" expression is intended to refer to the expression level of a differentially expressed predictive marker which corresponds to responsiveness or non-responsiveness. The expression level of a marker in a patient is "informative" if it is greater than a reference level by an amount greater than the standard error of the assay employed to assess expression. Alternatively, a marker that is differentially expressed will have typical ranges of expression level that are predictive of responsiveness or non-responsiveness. An informative expression level is a level that falls within the responsive or non-responsive range of expressions. Still further, a set of markers may together be "informative" if the combination of their expression levels either meets or is above or below a pre-determined score for a predictive marker set as determined by methods provided herein.

A given marker may be indicative of both responsive and non-responsive patients; for example, expression of a predictive marker provided herein above a given threshold (e.g., an informative expression level) may be indicative of a responsive patient, as described herein. Expression of that marker below a given threshold (e.g., below an informative level) may be indicative of a non-responsive patient A cancer or tumor is treated or diagnosed according to the present methods. "Cancer" or "tumor" is intended to include any neoplastic growth in a patient, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkins lymphoma). Solid tumors can originate in organs, and include cancers such as lung, breast, prostate, ovary, colon, kidney, and liver. As used herein, cancer cells, including tumor cells, refer to cells that divide at an abnormal (increased) rate. Cancer cells include, but are not limited to, carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), and lymphomas (e.g., follicular lymphoma, mantle cell lymphoma, diffuse large Bcell lymphoma, malignant lymphoma, plasmocytoma, reticulum cell sarcoma, or Hodgkins disease); and tumors of the nervous system including glioma, meningoma, medulloblastoma, schwannoma or epidymoma.

A cancer is "responsive" to a therapeutic agent if its rate of growth is inhibited as a result of contact with the therapeutic agent, compared to its growth in the absence of contact with the therapeutic agent. Growth of a cancer can be measured in a variety of ways, for instance, the size of a tumor or the expression of tumor markers appropriate for that tumor type may be measured. For example, the response definitions used to identify markers associated with myeloma and its response to proteasome inhibition therapy and/or glucocorticoid therapy, the Southwestern Oncology Group (SWOG) criteria as described in Blade et al., Br J Haematol. 1998 September; 102(5): 1115-23 were used (also see e.g., Table C). These criteria define the type of response measured in myeloma and also the characterization of time to disease progression which is another important measure of a tumor's sensitivity to a therapeutic agent. The quality of being responsive to a proteasome inhibition therapy and/or glucocorticoid therapy is a variable one, with different cancers exhibiting different levels of "responsiveness" to a given therapeutic agent, under different conditions. Still further, measures of responsiveness can be assessed using additional criteria beyond growth size of a tumor, including patient quality of life, degree of metastases, etc. In addition, clinical prognostic markers and variables can be assessed (e.g., M protein in myeloma, PSA levels in prostate cancer) in applicable situations.

A cancer is "non-responsive" to a therapeutic agent if its rate of growth is not inhibited, or inhibited to a very low degree, as a result of contact with the therapeutic agent when compared to its growth in the absence of contact with the therapeutic agent. As stated above, growth of a cancer can be measured in a variety of ways, for instance, the size of a tumor or the expression of tumor markers appropriate for that tumor type may be measured. For example, the response definitions used to identify markers associated with non-response of multiple myeloma to therapeutic agents, the Southwestern Oncology Group (SWOG) criteria as described in Blade et. al. were used in the experiments described herein. The quality of being non-responsive to a therapeutic agent is a highly variable one, with different cancers exhibiting different levels of "non-responsiveness" to a given therapeutic agent, under different conditions. Still further, measures of non-responsiveness can be assessed using additional criteria beyond growth size of a tumor, including patient quality of life, degree of metastases, etc. In addition, clinical prognostic markers and variables can be assessed (e.g., M protein in myeloma, PSA levels in prostate cancer) in applicable situations.

"Treatment" shall mean preventing or inhibiting further tumor growth, as well as causing shrinkage of a tumor. Treatment is also intended to include prevention of metastasis of tumor. A tumor is "inhibited" or "treated" if at least one symptom (as determined by responsiveness/non-responsiveness, time to progression, or indicators known in the art and described herein) of the cancer or tumor is alleviated, terminated, slowed, minimized, or prevented. Any amelioration of any symptom, physical or otherwise, of a tumor pursuant to treatment using a therapeutic regimen (e.g., proteasome inhibition regimen, glucocorticoid regimen) as further described herein, is within the scope of the invention.

As used herein, the term "agent" is defined broadly as anything that cancer cells, including tumor cells, may be exposed to in a therapeutic protocol. In the context of the present invention, such agents include, but are not limited to, proteasome inhibition agents, glucocorticoidal steroid agents, as well as chemotherapeutic agents as known in the art and described in further detail herein.

A "kit" is any article of manufacture (e.g. a package or container) comprising at least one reagent, e.g. a probe, for specifically detecting a marker or marker set of the invention. The article of manufacture may be promoted, distributed, or sold as a unit for performing the methods of the present invention. The reagents included in such a kit comprise probes/primers and/or antibodies for use in detecting responsive and non-predictive marker expression. In addition, the kits of the present invention may preferably contain instructions which describe a suitable detection assay. Such kits can be conveniently used, e.g., in clinical settings, to diagnose and evaluate patients exhibiting symptoms of cancer, in particular patients exhibiting the possible presence of an a cancer capable of treatment with proteasome inhibition therapy and/or glucocorticoid therapy, including, e.g., hematological cancers e.g., myelomas (e.g., multiple myeloma), lymphomas (e.g., non-hodgkins lymphoma), leukemias, and solid tumors (e.g., lung, breast, ovarian, etc.).

The present methods and compositions are designed for use in diagnostics and therapeutics for a patient suffering from cancer. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkins lymphoma). Solid tumors can originate in organs, and include cancers such as lung, breast, prostate, ovary, colon, kidney, and liver.

The invention provides methods for determining or assessing an appropriate cancer therapy regimen for treating a tumor in a patient. The cancer therapy regimens appropriate for use in or in conjunction with the provided methods comprise proteasome inhibition therapy and/or glucocorticoid therapy. For example, proteasome inhibitor therapy comprises treatment of a patient with a proteasome inhibitor (e.g., bortezomib, or any other proteasome inhibitor described in further detail herein), alone or in combination with one or more additional agents. In another example, glucocorticoid therapy comprises treatment of a patient with a glucocorticoid (e.g., dexamethasone, or any other glucocorticoid described in further detail herein), alone or in combination with one or more additional agents.

The provided methods comprise measuring the level of expression of at least one predictive marker in the patient's tumor and determining a cancer therapy regimen for treating the tumor based on the expression level of the predictive marker or markers, as relevant. An informative expression level of a predictive marker or markers in the patient sample is an indication that the patient is a responsive patient and would benefit from proteasome inhibition therapy and/or glucocorticoid therapy when the predictive marker or marker set provided herein indicate such responsiveness. Additionally, an informative expression level of a predictive marker or markers in a patient is an indication that the patient is a non-responsive patient and would not benefit from proteasome inhibition therapy and/or glucocorticoid therapy when the marker or markers provided herein indicate such non-responsiveness.

The invention further provides methods for determining whether a patient will be responsive to a cancer therapy regimen for treating a tumor. Such methods comprise measuring the level of expression of at least one predictive marker in the patient's tumor and determining a proteasome inhibition based regimen and/or glucocorticoid based regimen for treating the tumor based on the expression level of the predictive marker or marker set. An informative expression level of a predictive marker in the patient sample is an indication that the patient is a responsive patient and would benefit from proteasome inhibition and/or glucocorticoid therapy. An informative expression level of a predictive marker set in the patient is an indication that the patient is a responsive patient and would benefit from proteasome inhibition therapy and/or glucocorticoid therapy when the marker or markers provided herein indicate such responsiveness. Selected predictive markers for use in the methods comprise predictive markers which demonstrate increased expression in responsive patients and/or longer time to disease progression.

The invention provides methods for determining whether a patient has aggressive disease and will progress in disease faster than a patient not demonstrating aggressive disease. A patient indicative of having aggressive disease also may be non-responsive to a cancer therapy regimen for treating a tumor. Such methods comprise measuring the level of expression of at least one predictive marker in the patient's tumor and identifying the patient as having aggressive disease based on the expression level of the predictive marker or marker set. An informative expression level of a predictive marker in the patient sample is an indication that the patient has aggressive disease patient and is likely to progress and may not benefit from proteasome inhibition based regimen and/or glucocorticoid based regimen therapy. An informative expression level of a predictive marker set in the patient is an indication that the patient is a patient having aggressive disease and would not benefit from proteasome inhibition based regimen and/or glucocorticoid based regimen when the selected marker or marker set provided herein indicate such disease aggressiveness. Selected predictive markers for use in the methods comprise predictive markers which demonstrate increased expression in non-responsive patients and/or shorter time to disease progression in patients and are not specific to treatment with proteasome inhibition therapy or glucocorticoid therapy.

Still further, the invention provides methods for determining whether a patient will be non-responsive to a cancer therapy regimen for treating a tumor. Such methods comprise measuring the level of expression of at least one predictive marker in the patient's tumor and determining a proteasome inhibition based regimen and/or glucocorticoid based regimen for treating the tumor based on the expression level of the predictive marker or marker set. An informative expression level of a predictive marker in the patient sample is an indication that the patient is a non-responsive patient and would not benefit from proteasome inhibition based regimen and/or glucocorticoid based regimen therapy. An informative expression level of a predictive marker set in the patient is an indication that the patient is a non-responsive patient and would not benefit from proteasome inhibition based regimen and/or glucocorticoid based regimen when the selected marker or marker set provided herein indicate such non-responsiveness. Selected predictive markers for use in the methods comprise predictive markers which demonstrate increased expression in non-responsive patients and/or shorter time to disease progression.

The invention further provides methods for treating a tumor in a patient with a proteasome inhibition based regimen and/or glucocorticoid based regimen therapy. Such therapeutic methods comprise measuring the level of expression of at least one predictive marker in a patient's tumor; determining whether a proteasome inhibition based regimen and/or glucocorticoid based regimen for treating the tumor is appropriate based on the expression level of the predictive marker or markers, and treating a patient with a proteasome inhibition based therapy and/or glucocorticoid based therapy when the patient's expression level indicates a responsive patient. An informative expression level of predictive marker in the patient sample is an indication that the patient is a responsive patient and would benefit from proteasome inhibition based regimen and/or glucocorticoid based regimen therapy when the predictive marker or marker set provided herein indicate the patient is a responsive patient.

Methods of the invention use at least one of the predictive markers set forth in any one of Table 1A, Table 1B, Table 2A, Table 2B, and Table 3. Additionally, the methods provided can use two, three, four, five, six, or more markers to form a predictive marker set. For example, marker sets selected from the markers in Table 1A, Table 1B, Table 2A, Table 2B, and/or Table 3 can be generated using the methods provided herein and can comprise between two, and all of the markers set forth in Table 1A, Table 1B, Table 2A, Table 2B, or Table 3 and each and every combination in between (e.g., four selected markers, 16 selected markers, 74 selected markers, etc.). In some embodiments, the predictive marker set comprises at least 5, 10, 20, 40, 60, 100, 150, 200, or 300 or more markers. In other embodiments, the predictive marker set comprises no more than 5, 10, 20, 40, 60, 100, 150, 200, 300, 400, 500, 600 or 700 markers. In some embodiments, the predictive marker set includes a plurality of genes associated with cancer, e.g. a hematological cancer (e.g., multiple myeloma, leukemias, lymphoma, etc) or cancer from a solid tumor (e.g., in lung, breast, prostate, ovary, colon, kidney or liver). In some embodiments, the predictive marker set includes a plurality of markers listed in Table 1A, Table 1B, Table 2A, Table 2B, or Table 3. In some embodiments the predictive marker set includes at least about 1%, about 5%, about 10%, about 20%, about 30%, about 40%, about 50%, about 60%, about 70%, about 80%, about 90%, about 95%, about 96%, about 97%, about 98%, or about 99% of the markers listed in Table 1B, Table 2A, Table 2B, or Table 3. Selected predictive marker sets can be assembled from the predictive markers provided using methods provided herein and analogous methods known in the art. An exemplary predictive marker sets is provided in Table 4. In certain aspects, the markers comprise those set forth in Table 4.

Methods of the invention further provide the ability to construct marker sets from the individual predictive markers set forth in Table 1A, Table 1B, Table 2A, Table 2B, and Table 3 using the methods described in further detail herein. In a further aspect, more than one marker set can be used in combination for the diagnostic, prognostic and treatment methods provided.

The methods of the invention can be performed such that determination of the level of expression of a predictive marker is measured prior to tumor therapy in order to identify whether the patient will be responsive to a proteasome inhibition therapy and/or glucocorticoid therapy.

In addition, the methods of the invention can be performed concurrently with ongoing tumor therapy to determine if the patient is either responding to present proteasome inhibition therapy and/or glucocorticoid therapy or will respond to additional therapy comprising proteasome inhibition therapy and/or glucocorticoid therapy.

Still further, the methods of the invention can be performed after tumor therapy has been carried out in order to assess whether the patient will be responsive to future course of proteasome inhibition therapy and/or glucocorticoid therapy.

Whether the methods are performed during ongoing tumor therapy or after a course of tumor therapy, the tumor therapy can comprise proteasome inhibition therapy and/or glucocorticoid therapy, alone or alternative forms of cancer therapy. The methods provided are designed to determine if the patient will benefit from additional or future proteasome inhibition and/or glucocorticoid therapy, and can include such proteasome inhibition and/or glucocorticoid therapy alone or in combination with additional therapeutic agents.

In certain aspects, the level of expression of predictive marker in the patient's tumor is measured by isolating a sample of the tumor and performing analysis on the isolated sample, or a portion thereof. In another aspect, the level of expression of predictive marker in the patient's tumor is measured using in vivo imaging techniques.

In certain aspects, determining the level of expression of a predictive marker comprises detection of mRNA. Such detection can be carried out by any relevant method, including e.g., PCR, northern, nucleotide array detection, in vivo imaging using probes capable of detection of the appropriate nucleic acid. In other aspects, determining the level of expression of the predictive marker comprises detection of protein. Such detection can be carried out using any relevant method for protein detection, including e.g., ELISA, western blot, immunoassay, protein array detection, in vivo imaging using probes capable of detection of the appropriate peptide.

Determining the level of expression of a predictive marker is compared to a reference expression level. For example, a reference expression level can be a predetermined standard reference level of expression in order to evaluate if expression of a marker or marker set is informative and make an assessment for determining whether the patient is responsive or non-responsive. Additionally, determining the level of expression of a predictive marker can be compared to an internal reference marker level of expression which is measured at the same time as the predictive marker in order to make an assessment for determining whether the patient is responsive or non-responsive. For example, expression of a distinct marker or markers which is/are not predictive markers of the invention, but which is known to demonstrate a constant expression level can be assessed as an internal reference marker level, and the level of the predictive marker expression is determined as compared to the reference. In an alternative example, expression of the selected predictive marker or markers in a tissue sample which is a non-tumor sample can be assessed as an internal reference marker level. The level of expression of a marker or markers may be determined as having increased expression in certain aspects. The level of expression of a marker or markers may be determined as having decreased expression in other aspects. The level of expression may be determined as no informative change in expression as compared to a reference level. In still other aspects, the level of expression is determined against a predetermined standard expression level as determined by the methods provided herein.

The invention also relates to various reagents and kits for diagnosing, staging, prognosing, monitoring and treating a cancer patient (e.g., a patient with a liquid tumor or a solid tumor), with proteasome inhibition therapy and/or glucocorticoid therapy. Provided are reagents for detection of markers and marker sets and for use in the methods of the invention comprising at least two isolated predictive markers set forth in Table 1A, Table 1B, Table 2A, Table 2B, and Table 3. Such reagents include nucleic acid probes, primers, antibodies, antibody derivatives, antibody fragments, and peptide probes for detection of the relevant predictive markers set forth in Table 1A, Table 1B, Table 2A, Table 2B, and Table 3.

Further provided are kits for use in the provided methods. The kits of the invention include reagents for assessing predictive markers (e.g., at least one predictive marker) and predictive marker sets (e.g., at least two, three, four or more markers selected from Table 1A, Table 1B, Table 2A, Table 2B, and Table 3), as well as instructions for use in accordance with the methods provided herein. In certain aspects, the kits provided contain nucleic acid probes for assessment of predictive markers. In still other aspects, the kits provided contain antibody, antibody derivative antibody fragment, or peptide reagents for assessment of predictive markers.

Identification of Responsive and Non-Responsive Markers

The present invention provides markers that are expressed in a tumor that is responsive to proteasome inhibition therapy and/or glucocorticoid therapy and whose expression correlates with responsiveness to that therapeutic agent. The present invention also provides markers that are expressed in a tumor that is non-responsive to proteasome inhibition therapy and/or glucocorticoid therapy and whose expression correlates with non-responsiveness to such therapy. Accordingly, one or more of the markers can be used to identify cancers that can be successfully treated by proteasome inhibition therapy and/or glucocorticoid therapy. One or more of the markers of the present invention can be used to identify patients that can be successfully treated using proteasome inhibition therapy and/or glucocorticoid therapy. In addition, the markers of the present invention can be used to identify a patient that has become or is at risk of becoming refractory to treatment with proteasome inhibition therapy and/or glucocorticoid therapy. The invention also features combinations of markers, referred to herein as "marker sets," that can predict whether a patient is likely to respond or not to respond to a proteasome inhibition therapy and/or glucocorticoid therapy regimen.

Table 1 sets forth predictive markers identified using statistical analysis applied to samples from 224 patients, which are specific identifiers of response or non-response to proteasome inhibition therapy (e.g., bortezomib). The markers in Table 1 are differentially expressed in samples from patients that are either responsive or non-responsive to treatment with the proteasome inhibitor bortezomib. Thus, one would appreciate that the markers identified can function in a predictive model to prospectively identify patients' response to proteasome inhibition therapy, including response to bortezomib or other proteasome inhibition therapies known in the art as well as those described in further detail herein. In particular, the markers in Table 1 are correlated with a positive response to therapy (referred to herein as "responsive, (R)"); or a long time until disease progression (TTP) as determined by a Cox proportional hazard analysis, as described in further detail herein. A patient with a positive response (either complete, partial or minimal; see Table C) to therapy is hereinafter referred to as a "responder". Predictors of long time to progression are useful as additional indicators of patients who are likely to progress in disease at a slower rate and may be more likely to be responsive to therapy than other patients. Additionally, the predictive markers in Table 1 are correlated with a negative or poor response to an agent (referred to herein as "non-responsive, (NR)"), or a short time to disease progression (TTP). A patient with a poor response (called a progressive or refractory disease; see Table C) to treatment is hereinafter referred to as a "non-responder". These identified predictive markers are useful as additional indicators of patients who are likely to progress in disease at a faster rate, and less likely to be responsive to therapy than other patients. A patient with no response to treatment is hereinafter referred to as "stable".

Table 1A provides predictive markers which are upregulated indicators of non-response and/or correlate with shorter time to progression. Marker nos. 1-547 in Table 1A are newly identified predictive markers, and predictive markers no. 548-657 have been previously identified as associated markers predictive of non-response and/or correlation with shorter time to progression. See, International Patent Publication No. WO04053066, published Jun. 24, 2004. Table 1B provides predictive markers which are upregulated indicators of response and/or correlate with longer time to progression. Marker nos. 658-876 in Table 1B are newly associated predictive markers, and predictive markers no. 877-911 have been previously identified as associated markers predictive of response and/or correlation with longer time to progression. See, International Patent Publication No. WO04053066, published Jun. 24, 2004.

Table 2 sets forth predictive markers identified using statistical analysis applied to samples from 224 patients, which are specific identifiers of response or non-response to glucocorticoid therapy (e.g., dexamethasone). The markers in Table 2 are differentially expressed in samples from patients that are either responsive or non-responsive to treatment with the glucocorticoidal steroid agent dexamethasone. Thus, one would appreciate that the markers identified can function in a predictive model to prospectively identify patients' response to glucocorticoid therapy, including response to dexamethasone or other glucocorticoid therapies known in the art as well as those described in further detail herein. As in Table 1, Table 2 sets forth predictive markers identified which are specific identifiers of response or long time to progression; or non-response or short time to progression upon therapy with glucocorticoid treatment (e.g., dexamethasone).

Table 2A provides predictive markers which are upregulated indicators of non-response and/or correlate with shorter time to progression. Table 2B provides predictive markers which are upregulated indicators of response and/or correlate with longer time to progression.

Table 3 sets forth predictive markers identified which do not distinguish between response to proteasome inhibition therapy and response to glucocorticoid therapy, rather are indicator predictive markers of response/longer time to progression or non-response/shorter time to progression with regard to either therapy, and are indicators of general disease aggressiveness. Marker nos. 1203-1423 in Table 3 are newly associated predictive markers, and predictive markers no.

1424-1474 have been previously identified as associated markers predictive of non-response/correlation with shorter time to progression and/or response/correlation with longer time to progression related to advanced stage patient's response to bortezomib treatment. See, International Patent Publication No. WO04053066, published Jun. 24, 2004.

In the methods of the present invention, the level of expression of one or more predictive markers selected from the group consisting of the markers identified in Table 1A, Table 1B, Table 2A, Table 2B, and Table 3, is determined. As used herein, the level or amount of expression refers to the absolute level of expression of an mRNA encoded by the marker or the absolute level of expression of the protein encoded by the marker (i.e., whether or not expression is or is not occurring in the cancer cells).

Generally, it is preferable to determine the expression of two or more of the identified responsive or non-predictive markers, or three or more of the identified responsive or non-predictive markers, or still further a larger set of the identified responsive and/or non-predictive markers, selected from the predictive markers identified in Table 1A, Table 1B, Table 2A, Table 2B, and Table 3. For example, Table 4 sets forth marker sets identified using the methods described herein and can be used in the methods of the present invention. Still further, additional and/or alternative marker sets comprising the predictive markers identified herein can be generated using the methods and predictive markers provided. Thus, it is possible to assess the expression of a panel of responsive and non-predictive markers using the methods and compositions provided herein.

As an alternative to making determinations based on the absolute expression level of selected markers, determinations may be based on normalized expression levels. Expression levels are normalized by correcting the absolute expression level of a predictive marker by comparing its expression to the expression of a reference marker that is not a predictive marker, e.g., a housekeeping gene that is constitutively expressed. Suitable markers for normalization include housekeeping genes, such as the actin gene. Constitutively expressed genes are known in the art and can be identified and selected according to the relevant tissue and/or situation of the patient and the analysis methods. Such normalization allows one to compare the expression level in one sample, e.g., a tumor sample, to another sample, e.g., a non-tumor sample, or between samples from different sources.

Further, the expression level can be provided as a relative expression level. To determine a relative expression level of a marker or marker set, the level of expression of the predictive marker or marker set is determined for 10 or more individual samples, preferably 50 or more individual samples in order to establish a baseline, prior to the determination of the expression level for the sample in question. To establish a baseline measurement, mean expression level of each of the predictive markers or marker sets assayed in the larger number of samples is determined and this is used as a baseline expression level for the predictive markers or marker sets in question. The expression level of the marker or marker set determined for the test sample (absolute level of expression) is then divided by the mean expression value obtained for that marker or marker set. This provides a relative expression level and aids in identifying extreme cases of responsive or non-responsive-ness.

Determining Responsiveness or Non-Responsiveness to an Agent

The expression level (including protein level) of the identified predictive markers of responsive/non-responsive patients and may be used to: 1) determine if a patient can be treated by an agent or combination of agents; 2) determine if a patient is responding to treatment with an agent or combination of agents; 3) select an appropriate agent or combination of agents for treating a patient; 4) monitor the effectiveness of an ongoing treatment; 5) identify new cancer therapy treatments (either single agent proteasome inhibitor and/or glucocorticoid agents or complementary agents which can be used alternatively or in combination with proteasome inhibition and/or glucocorticoid agents); 6) identify aggressiveness of a cancer; and 7) select an appropriate agent or combination of agents in treating early and late recurrence of a cancer. In particular, the identified predictive markers may be utilized to determine appropriate therapy, to monitor clinical therapy and human trials of a drug being tested for efficacy, and to develop new agents and therapeutic combinations.

A cancer may be predisposed to respond to an agent if one or more of the corresponding predictive markers identified in Table 1B, Table 2B, and Table 3 (as indicated by (+) in Table 3) demonstrate increased expression. In certain aspects of the invention, the predisposition of a cancer to be responsive to an agent is determined by the methods of the present invention, wherein informative expression of the individual predictive markers of the marker sets identified in Table 4 is evaluated. Likewise, the predisposition of a patient to be responsive to an agent is determined by the methods of the present invention, wherein a marker set generated using to the methods described herein wherein the markers comprising the marker set include predictive markers set forth in Table 1B, Table 2B, and Table 3, and the expression of the marker set is evaluated.

A cancer may be predisposed to non-responsiveness to an agent if one or more of the corresponding non-predictive markers demonstrates informative expression levels. A cancer may be predisposed to non-responsiveness to an agent if one or more of the corresponding predictive markers identified in Table 1A, Table 2A, and Table 3 (as indicated by (−) in Table 3) demonstrate informative increased expression. In certain aspects of the invention, the predisposition of a cancer to be non-responsive to an agent is determined by the methods of the present invention, wherein informative expression of the individual predictive markers of the marker sets identified in Table 4 is evaluated. Likewise, the predisposition of a patient to be non-responsive to an agent is determined by the methods of the present invention, wherein a marker set is generated using the methods described herein wherein the markers comprising the marker set include predictive markers set forth in Table 1A, Table 2A, and/or Table 3, and the expression of the marker set is evaluated.

In one aspect, the predictive marker set for evaluation of a cancer predisposed to respond or predisposed to not respond to a therapy comprises markers selected from those set forth in any of Table 1A Table 1B, Table 2A Table 2B and Table 3. Still a further aspect contemplates markers set forth in either Table 1A and Table 1B alone or in combination with markers set for the in Table 2A and Table 2B and/or Table 3, or alternatively, those markers set forth in Table 2A and Table 2B alone or in combination with Table 1A and Table 1B and/or Table 3. In still another aspect the predictive marker or markers evaluated are selected from those set forth in Table 3. In certain aspects, the marker set is selected from those set forth in Table 4. According to the methods, proteasome inhibition therapy and/or glucocorticoid therapy would be continued where the expression profile indicates continued responsiveness, or decreased non-responsiveness using the evaluation methods described herein.

The present invention provides methods for determining whether a cancer therapy e.g., a proteasome inhibitor and/or glucocorticoid agent, can be used to reduce the growth rate of a tumor comprising evaluating expression of at least one predictive marker or a predictive marker set in a tumor sample; and identifying that proteasome inhibition therapy and/or glucocorticoid therapy is or is not appropriate to reduce the growth rate of the tumor based on the evaluation.

The invention provides a method for determining whether a proteasome inhibition therapeutic regimen (e.g., a proteasome inhibitor agent (e.g., bortezomib) alone or in combination with another chemotherapeutic agent) can be used to reduce the growth rate of a tumor comprising determining the expression profile of a predictive marker or predictive marker set; and identifying that a proteasome inhibition therapeutic agent is or is not appropriate to reduce the growth rate of the myeloma cells based on the expression profile.

Additionally provided are methods for determining whether a proteasome inhibitor therapy can be used to reduce the growth of a tumor, comprising obtaining a sample of tumor cells, evaluating the expression of one or more individual markers or a marker set, both in tumor cells exposed to the agent and in tumor cells that have not been exposed to the proteasome inhibition therapy; and identifying that an agent is or is not appropriate to treat the tumor based on the evaluation.

The invention provides a method for determining whether a glucocorticoid regimen (e.g., glucocorticoidal steroid agent (e.g., dexamethasone) alone or in combination with another chemotherapeutic agent) can be used to reduce the growth rate of a tumor comprising determining the expression profile of a predictive marker or predictive marker set; and identifying that a glucocorticoid therapeutic agent is or is not appropriate to reduce the growth rate of the tumor based on the expression profile.

Additionally provided are methods for determining whether a glucocorticoid therapy can be used to reduce the growth of a tumor, comprising obtaining a sample of tumor cells, evaluating the expression of one or more individual markers or a marker set, both in tumor cells exposed to the agent and in tumor cells that have not been exposed to the glucocorticoid therapy; and identifying that an agent is or is not appropriate to treat the tumor based on the evaluation.

In such methods, a proteasome inhibition therapy and/or glucocorticoid therapy regimen is determined appropriate to treat the tumor when the expression profile of the predictive marker or predictive marker set demonstrates increased responsiveness or decreased non-responsiveness according to the expression profile of the predictive markers in the presence of the agent.

The invention also provides a method for determining whether treatment with an proteasome inhibitor therapy should be initiated in in a patient selected from a multiple myeloma patient, a lymphoma patient, a leukemia patient, a lung cancer patient, a breast cancer patient, and an ovarian cancer patient, a prostate cancer patient, a colon cancer patient, a kidney cancer patient, and a liver cancer patient; comprising obtaining one or more samples, followed by determining the level of expression of one or more markers which correspond to markers identified in any of Table 1A, Table 1B, Table 2A, Table 2B, and Table 3 in the sample; and initiating proteasome inhibitor therapy when the expression profile of the predictive markers identified in any one of Table 1A, Table 1B, Table 2A, Table 2B, and Table 3 is indicative of a responsive patient to such treatment. Alternatively, the treatment is not initiated when the expression profile of the predictive markers identified in any one of Table 1A, Table 1B, Table 2A, Table 2B, and Table 3 is indicative of a non-responsive patient to treatment.

The invention also provides a method for determining whether treatment with proteasome inhibition therapy should be initiated in in a patient selected from a multiple myeloma patient, a lymphoma patient, a leukemia patient, a lung cancer patient, a breast cancer patient, and an ovarian cancer patient, a prostate cancer patient, a colon cancer patient, a kidney cancer patient, and a liver cancer patient; comprising obtaining one or more samples of tumor cells from a patient, followed by determining the expression profile in the sample of a predictive marker set comprising markers identified in Table 1A, Table 1B, Table 2A, Table 2B, and Table 3; and initiating the proteasome inhibitor treatment when the expression profile of the predictive markers identified in Table 1A, Table 1B, Table 2A, Table 2B, and Table 3 is indicative of a responsive patient. Alternatively, the treatment is not initiated when the expression profile of the predictive markers identified in Table 1A, Table 1B, Table 2A, Table 2B, and/or Table 3 is indicative of a non-responsive patient.

The invention also provides a method for determining whether treatment with an glucocorticoid therapy should be initiated in in a patient selected from a multiple myeloma patient, a lymphoma patient, a leukemia patient, a lung cancer patient, a breast cancer patient, and an ovarian cancer patient, a prostate cancer patient, a colon cancer patient, a kidney cancer patient, and a liver cancer patient; comprising obtaining one or more samples, followed by determining the level of expression of one or more markers which correspond to markers identified in any of Table 1A, Table 1B, Table 2A, Table 2B, and Table 3 in the sample; and initiating glucocorticoid therapy when the expression profile of the predictive markers identified in any one of Table 1A, Table 1B, Table 2A, Table 2B, and Table 3 is indicative of a responsive patient to such treatment. Alternatively, the treatment is not initiated when the expression profile of the predictive markers identified in any one of Table 1A, Table 1B, Table 2A, Table 2B, and Table 3 is indicative of a non-responsive patient to treatment.

The invention also provides a method for determining whether treatment with glucocorticoid therapy should be initiated in a patient selected from a multiple myeloma patient, a lymphoma patient, a leukemia patient, a lung cancer patient, a breast cancer patient, and an ovarian cancer patient, a prostate cancer patient, a colon cancer patient, a kidney cancer patient, and a liver cancer patient; comprising obtaining one or more samples of tumor cells from a patient, followed by determining the expression profile in the sample of a predictive marker set comprising markers identified in Table 1A, Table 1B, Table 2A, Table 2B, and Table 3; and initiating the glucocorticoid treatment when the expression profile of the predictive markers identified in Table 1A, Table 1B, Table 2A, Table 2B, and Table 3 is indicative of a responsive patient. Alternatively, the treatment is not initiated when the expression profile of the predictive markers identified in Table 1A, Table 1B, Table 2A, Table 2B, and/or Table 3 is indicative of a non-responsive patient.

Monitoring the Effectiveness of an Anti-Cancer Agent

As discussed above, the identified responsive and non-predictive markers can be used as pharmacodynamic markers to assess whether the tumor has become refractory to an ongoing treatment (e.g., a proteasome inhibition therapy and/or glucocorticoid therapy). When the cancer is not responding to a treatment the expression profile of the tumor cells will change: the level or relative expression of one or more of the predictive markers (e.g., those predictive markers identified in Table 1A, Table 1B, Table 2A, Table 2B, Table 3) such that the expression profile represents a non-responsive patient.

In one such use, the invention provides methods for determining whether a cancer therapy comprising proteasome inhibition therapy and/or glucocorticoid therapy should be continued in a cancer patient, comprising determining the expression of at least one predictive marker or a marker set, wherein the markers are selected from those set forth in any of Table 1A, Table 1B, Table 2A, Table 2B, or Table 3, in a tumor sample of a patient exposed to a proteasome inhibition therapy and/or glucocorticoid therapy; and continuing treatment when the expression profile of the marker or marker set demonstrates responsiveness to the agent being used.

In another such use, the invention provides methods for determining whether a proteasome inhibition therapy and/or glucocorticoid therapy should be discontinued in a cancer patient, comprising determining the expression of at least one predictive marker or a predictive marker set, wherein the markers are selected from those set forth in any of Table 1A, Table 1B, Table 2A, Table 2B, or Table 3 in a tumor sample of a patient exposed to a proteasome inhibition therapy and/or glucocorticoid therapy; and discontinuing or altering treatment when the expression profile of the markers identified in any one of Table 1A, Table 1B, Table 2A, Table 2B, or Table 3 demonstrates non-responsiveness to the agent being used.

As used herein, a patient refers to any subject undergoing proteasome inhibition therapy and/or glucocorticoid therapy for cancer treatment. The subject may be a human patient undergoing proteasome inhibition (e.g., bortezomib or other related agent) and/or glucocorticoid (e.g., dexamethasone) therapy using a sole therapeutic agent. The subject may be a human patient undergoing proteasome inhibition (e.g., bortezomib or other related agent) and/or glucocorticoid (e.g., dexamethasone) therapy using a therapeutic agent in conjunction with another agent (e.g., a chemotherapy treatment). The present invention also includes comparing two or more samples obtained from a patient undergoing anti-cancer treatment including proteasome inhibition therapy and/or glucocorticoid therapy. In general, it is conceivable to obtain a first sample from the patient prior to beginning therapy and one or more samples during treatment. In such a use, a baseline of expression prior to therapy is determined, then changes in the baseline state of expression is monitored during the course of therapy. Alternatively, two or more successive samples obtained during treatment can be used without the need of a pre-treatment baseline sample. In such a use, the first sample obtained from the subject is used as a baseline for determining whether the expression of a particular marker or marker set is increasing or decreasing.

In general, when monitoring the effectiveness of a therapeutic treatment, two or more samples from a patient are examined. In another aspect, three or more successively obtained samples are used, including at least one pretreatment sample.

The invention provides methods for determining whether treatment with a proteasome inhibitor therapy regimen should be continued in a patient selected from a multiple myeloma patient, a lymphoma patient, a leukemia patient, a lung cancer patient, a breast cancer patient, and an ovarian cancer patient, a prostate cancer patient, a colon cancer patient, a kidney cancer patient, and a liver cancer patient; comprising obtaining two or more samples of tumor cells from a patient at different times during the course of a proteasome inhibition therapy regimen, followed by evaluating the expression of one or more markers which correspond to markers identified in any of Table 1A, Table 1B, Table 2A, Table 2B, and Table 3 in the two or more samples; and continuing the treatment when the expression profile of the predictive markers identified in any one of Table 1A, Table 1B, Table 2A, Table 2B, and Table 3 is indicative of a responsive patient during the course of the treatment. In such methods, a proteasome inhibition therapy and regimen is determined appropriate to treat the patient when the expression profile of the predictive marker or predictive marker set demonstrates increased responsiveness or decreased non-responsiveness according to the expression profile of the predictive markers in the presence of the agent.

Additionally provided are methods for determining whether treatment with a proteasome inhibitor therapy regimen should be continued in in a patient selected from a multiple myeloma patient, a lymphoma patient, a leukemia patient, a lung cancer patient, a breast cancer patient, and an ovarian cancer patient, a prostate cancer patient, a colon cancer patient, a kidney cancer patient, and a liver cancer patient; comprising obtaining two or more samples of tumor cells from a patient at different times during the course of anticancer therapy treatment, followed by evaluating the expression of a predictive marker set comprising markers identified in any of Table 1A, Table 1B, Table 2A, Table 2B, and Table 3 in the two or more samples; and continuing the treatment when the expression profile of the predictive marker set indicates increased responsiveness or decreased non-responsiveness according to the expression during the course of treatment. Alternatively, the treatment is discontinued when the expression profile of the marker set demonstrates decreased responsiveness and/or increased non-responsiveness during the course of treatment.

The invention provides methods for determining whether treatment with a glucocorticoid therapy regimen should be continued in a patient selected from a multiple myeloma patient, a lymphoma patient, a leukemia patient, a lung cancer patient, a breast cancer patient, and an ovarian cancer patient, a prostate cancer patient, a colon cancer patient, a kidney cancer patient, and a liver cancer patient; comprising obtaining two or more samples of tumor cells from a patient at different times during the course of a glucocorticoid therapy regimen, followed by evaluating the expression of one or more markers which correspond to markers identified in any of Table 1A, Table 1B, Table 2A, Table 2B, and Table 3 in the two or more samples; and continuing the treatment when the expression profile of the predictive markers identified in any one of Table 1A, Table 1B, Table 2A, Table 2B, and Table 3 is indicative of a responsive patient during the course of treatment. In such methods, a glucocorticoid therapy regimen is determined appropriate to treat the patient when the expression profile of the predictive marker or predictive marker set demonstrates increased responsiveness or decreased non-responsiveness according to the expression profile of the predictive markers in the presence of the agent.

Additionally provided are methods for determining whether treatment with a glucocorticoid therapy regimen should be continued in in a patient selected from a multiple myeloma patient, a lymphoma patient, a leukemia patient, a lung cancer patient, a breast cancer patient, and an ovarian cancer patient, a prostate cancer patient, a colon cancer patient, a kidney cancer patient, and a liver cancer patient; comprising obtaining two or more samples of tumor cells from a patient at different times during the course of a glucocorticoid therapy regimen, followed by evaluating the expression of a predictive marker set comprising markers identified in any of Table 1A, Table 1B, Table 2A, Table 2B, and Table 3 in the two or more samples; and continuing the treatment when the expression profile of the predictive marker set indicates increased responsiveness or decreased non-responsiveness according to the expression during the course of treatment. Alternatively, the treatment is discontinued when the expression profile of the marker set demonstrates decreased responsiveness and/or increased non-responsiveness during the course of treatment.

The invention certain aspects of the invention relate to methods of treatment and/or diagnosis of a patient with cancer utilizing samples. The source of the cancer cells used in the present methods will be based on how the method of the present invention is being used. For example, if the method is being used to determine whether a patient's cancer can be treated with an agent, or a combination of agents, then the preferred source of sample will be cancer cells obtained from a tumor from the patient, e.g., a tumor biopsy (including a solid or a liquid tumor), a blood sample, a plasma sample, a urine sample, a saliva sample, a lymph sample or other sample can be used. A sample obtained from a tumor can be enriched for tumor cells to increase the specificity of the analysis. A variety of methods known in the art can be used to enrich for tumor cells, including differential centrifugation, fluorescence cell sorting analysis (FACS), isolating cells based on growth independent of substrate attachment, binding to a selection agent, e.g. to an antibody to a tumor marker and furthermore attaching the antibody and thus the bound tumor cell to a solid support, etc. Alternatively, a cancer cell line similar to the type of cancer being treated can be assayed. For example, if multiple myeloma is being treated, then a myeloma cell line can be used. If the method is being used to predict or monitor the effectiveness of a therapeutic protocol, then a tissue or blood sample from a patient being treated is a preferred source. If the method is being used to determine the activity of an agent, the efficacy of an agent, or identify new therapeutic agents or combinations, any cancer cells, e.g., cells of a cancer cell line, cells isolated from a tumor of an animal model, can be used.

A skilled artisan can readily select and obtain the appropriate cancer cells that are used in the present method. For cancer cell lines, sources such as The National Cancer Institute, for the NCI-60 cells, are preferred. For cancer cells obtained from a patient, standard biopsy methods, such as a needle biopsy, can be employed.

Myeloma samples were used to identify the markers of the present invention. Further, the expression level of markers can be evaluated in other tissue types including disorders of related hematological cell types, including, e.g., Waldenstroms macrogobulinemia, Myelodysplastic syndrome and other hematological cancers including lymphomas, leukemias, as well as tumors of various solid tissues. It will thus be appreciated that cells from other hematologic malignancies including, e.g., B-cell Lymphomas, Non-Hodgkins Lymphoma, Waldenstrom's syndrome, or other leukemias will be useful in the methods of the present invention. Still further, the predictive markers predicting disease aggressiveness as well as responsiveness and non-responsiveness to proteasome inhibition therapeutic agents in solid tumors (e.g., lung, breast, prostate, ovary, colon, kidney, and liver), can also be useful in the methods of the present invention.

Preferably, the samples used will be from similar tumors or from non-cancerous cells of the same tissue origin as the tumor in question. The choice of the cell source is dependent on the use of the relative expression level data. For example, using tumors of similar types for obtaining a mean expression score allows for the identification of extreme cases of responsive or non-responsive-ness. Using expression found in normal tissues as a mean expression score aids in validating whether the responsive/non-predictive marker or marker set assayed is tumor specific (versus normal cells). Such a later use is particularly important in identifying whether a responsive or non-predictive marker or marker set can serve as a target marker or marker set. In addition, as more data is accumulated, the mean expression value can be revised, providing improved relative expression values based on accumulated data.

Detection Assays

Various methods are available to examine the expression of the markers, including gene array/chip technology, RT-PCR, in-situ hybridization, immunohistochemistry, immunoblotting, FISH (fluorescence in-situ hybridization), FACS analyses, northern blot, southern blot or cytogenetic analyses. A skilled artisan can select from these or other appropriate and available methods based on the nature of the marker(s), tissue sample and disease in question. Different methods or combinations of methods could be appropriate in different cases or, for instance in different solid or hematological tumor types.

In certain aspects of the invention, the expression of predictive marker or markers identified in Table 1A, Table 1B, Table 2A, Table 2B, and Table 3 is detected by measuring mRNA which corresponds to the predictive marker or marker set. In yet another aspects of the invention, the expression of markers which correspond to markers or marker sets identified in Table 1A, Table 1B, Table 2A, Table 2B, and Table 3, is detected by measuring protein which corresponds to the marker or marker set.

An exemplary method for detecting the presence or absence of a nucleic acid or polypeptide corresponding to a marker of the invention in a biological sample involves obtaining a biological sample (e.g. a tumor sample) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations. in situ hybridizations, and TaqMan assays (Applied Biosystems) under GLP approved laboratory conditions. In vitro techniques for detection of a polypeptide corresponding to a marker of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide corresponding to a marker of the invention include introducing into a subject a labeled antibody directed against the polypeptide. For example, the antibody can be labeled with a radioactive marker whose presence and location in a subject can be detected by standard imaging techniques.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one example of such a method, a sample from a subject, which is to be assayed for presence and/or concentration of marker, can be anchored onto a carrier or solid phase support. In another example, the reverse situation is possible, in which the probe can be anchored to a solid phase and a sample from a subject can be allowed to react as an unanchored component of the assay. One example of such an example includes use of an array or chip which contains a predictive marker or marker set anchored for expression analysis of the sample.

There are many established methods for anchoring assay components to a solid phase. These include, without limitation, marker or probe molecules which are immobilized through conjugation of biotin and streptavidin. Such biotinylated assay components can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain aspects, the surfaces with immobilized assay components can be prepared in advance and stored. Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein. In one example, when the probe is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another example, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C., 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another example, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci.* 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, *J. Mol. Recognit.* Winter 11(1-6):141-8; Hage, D. S., and Tweed, S. A. *J Chromatogr B Biomed Sci Appl* 1997 Oct. 10; 699(1-2):499-525). Gel electrophoresis may also be employed to separate complexed assay components from unbound components (see, e.g., Ausubel et al., ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

The level of mRNA corresponding to the marker can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from tumor cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

One diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA corresponding to a marker of the present invention in a sample involves the process of nucleic acid amplification, e.g., by rtPCR (the experimental description set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cancer cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a reference gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-cancer sample, or between samples from different sources.

Alternatively, the expression level can be provided as a relative expression level. To determine a relative expression level of a marker, the level of expression of the marker is determined for 10 or more samples of normal versus cancer cell isolates, preferably 50 or more samples, prior to the determination of the expression level for the sample in question. The mean expression level of each of the markers and marker sets assayed in the larger number of samples is determined and this is used as a baseline expression level for the marker. The expression level of the marker determined for the test sample (absolute level of expression) is then divided by the mean expression value obtained for that marker. This provides a relative expression level.

In another aspect of the present invention, a polypeptide corresponding to a marker is detected. A preferred agent for detecting a polypeptide of the invention is an antibody capable of binding to a polypeptide corresponding to a marker of the invention, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether a sample comprising cancer cells express a marker of the present invention.

In one format, antibodies, or antibody fragments, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from tumor cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

Another method for determining the level of a polypeptide corresponding to a marker is mass spectrometry. For example, intact proteins or peptides, e.g., tryptic peptides can be analyzed from a sample, e.g., a tumor sample, blood, plasma, urine, etc, containing one or more polypeptide markers. The method can further include treating the sample to lower the amounts of abundant proteins, e.g. serum albumin, to increase the sensitivity of the method. For example, liquid chromatography can be used to fractionate the sample so portions of the sample can be analyzed separately by mass spectrometry. The steps can be performed in separate systems or in a combined liquid chromatography/mass spectrometry system (LC/MS, see for example, Liao, et al. *Arthritis Rheum.* 50:3792-3803 (2004)). The mass spectrometry system also can be in tandem (MS/MS) mode. The charge state distribution of the protein or peptide mixture can be acquired over one or multiple scans and analyzed by statistical methods, e.g. using the retention time and mass-to-charge ratio (m/z) in the LC/MS system, to identify proteins expressed at statistically significant levels differentially in samples from patients responsive or non-responsive to proteasome inhibition and/or glucocorticoid therapy. Examples of mass spectrometers which can be used are an ion trap system (ThermoFinnigan, San Jose, Calif.) or a quadrupole time-of-flight mass spectrometer (Applied Biosystems, Foster City, Calif.). The method can further include the step of peptide mass fingerprinting, e.g. in a matrix-assisted laser desorption ionization with time-of-flight (MALDI-TOF) mass spectrometry method. The method can further include the step of sequencing one or more of the tryptic peptides. Results of this method can be used to identify proteins from primary sequence databases, e.g. maintained by the National Center for Biotechnology Information, Bethesda, Md., or the Swiss Institute for Bioinformatics, Geneva, Switzerland, and based on mass spectrometry tryptic peptide m/z base peaks.

Electronic Apparatus Readable Arrays

Electronic apparatus, including readable arrays comprising at least one predictive marker of the present invention is also contemplated for use in conjunction with the methods of the invention. As used herein, "electronic apparatus readable media" refers to any suitable medium for storing, holding or containing data or information that can be read and accessed directly by an electronic apparatus. As used herein, the term "electronic apparatus" is intended to include any suitable computing or processing apparatus or other device configured or adapted for storing data or information. Examples of electronic apparatus suitable for use with the present invention and monitoring of the recorded information include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems. As used herein, "recorded" refers to a process for storing or encoding information on the electronic apparatus readable medium. Those skilled in the art can readily adopt any of the presently known methods for recording information on known media to generate manufactures comprising the markers of the present invention.

For example, microarray systems are well known and used in the art for assessment of samples, whether by assessment gene expression (e.g., RNA detection, protein detection), or metabolite production, for example. Microarrays for use according to the invention include one or more probes of predictive marker(s) of the invention characteristic of response and/or non-response to a therapeutic regimen as described herein. In one embodiment, the microarray comprises one or more probes corresponding to one or more of markers selected from the group consisting of markers which demonstrate increased expression in responsive patients, and genes which demonstrate non-response in patients. A number of different microarray configurations and methods for their production are known to those of skill in the art and are disclosed, for example, in U.S. Pat. Nos. 5,242,974; 5,384,261; 5,405,783; 5,412,087; 5,424,186; 5,429,807; 5,436,327; 5,445,934; 5,556,752; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,624,711; 5,700,637; 5,744,305; 5,770,456; 5,770,722; 5,837,832; 5,856,101; 5,874,219; 5,885,837; 5,919,523; 5,981,185; 6,022,963; 6,077,674; 6,156,501; 6,261,776; 6,346,413; 6,440,677; 6,451,536; 6,576,424; 6,610,482; 5,143,854; 5,288,644; 5,324,633; 5,432,049; 5,470,710; 5,492,806; 5,503,980; 5,510,270; 5,525,464; 5,547,839; 5,580,732; 5,661,028; 5,848,659; and 5,874,219; Shena, et al., Tibtech 16:301, 1998; Duggan, et al., Nat. Genet. 21:10, 1999; Bowtell, et al., Nat. Genet. 21:25, 1999; Lipshutz, et al., 21 Nature Genet. 20-24, 1999; Blanchard, et al., 11 Biosensors and Bioelectronics, 687-90, 1996; Maskos, et al., 21 Nucleic Acids Res. 4663-69, 1993; Hughes, et al., Nat. Biotechol. 19:342, 2001; each of which are herein incorporated by reference. A tissue microarray can be used for protein identification (see Hans et al *Blood* 103:275-282 (2004)). A phage-epitope microarray can be used to identify one or more proteins in a sample based on whether the protein or proteins induce auto-antibodies in the patient (Bradford et al. *Urol. Oncol.* 24:237-242 (2006)).

A microarray thus comprises one or more probes corresponding to one or more predictive markers identified in Table 1A, Table 1B, Table 2A, Table 2B, and Table 3. The microarray may comprise probes corresponding to, for example, at least 10, at least 20, at least 50, at least 100, or at least 1000 predictive markers of the invention characteristic of patient response to proteasome inhibition therapy and/or glucocorticoid therapy. The microarray may comprise probes corresponding to one or more predictive markers as set forth herein. Still further, the microarray may comprise complete marker sets as set forth herein and which may be selected and compiled according to the methods set forth herein. The microarray can be used to assay expression of one or more predictive markers or predictive marker sets in the array. In one example, the array can be used to assay more than one predictive marker or marker set expression in a sample to ascertain an expression profile of markers in the array. In this manner, up to about 44,000 markers can be simultaneously assayed for expression. This allows a profile to be developed showing a battery of markers specifically expressed in one or more samples. Still further, this allows a profile to be developed to assess responsiveness to one or more therapies (e.g., glucocorticoid therapy or proteasome inhibition therapy).

The array is also useful for ascertaining differential expression patterns of one or more markers in normal and abnormal (e.g., sample, e.g., tumor) cells. This provides a battery of predictive markers that could serve as a tool for ease of identification of responsive and non-responsive patients. Further, the array is useful for ascertaining expression of reference markers for reference expression levels. In another example, the array can be used to monitor the time course of expression of one or more predictive markers in the array.

In addition to such qualitative determination, the invention allows the quantitation of marker expression. Thus, predictive markers can be grouped on the basis of marker sets or responsive and non-responsive indications by the level of expression in the sample. This is useful, for example, in ascertaining the responsive or non-responsive indication of the sample by virtue of scoring the expression levels according to the methods provided herein.

The array is also useful for ascertaining the effect of the expression of a marker on the expression of other predictive markers in the same cell or in different cells. This provides, for example, a selection of alternate molecular targets for therapeutic intervention if the proteasome inhibition regimen and/or glucocorticoid therapy regimen is non-responsive.

Reagents and Kits

The invention also encompasses kits for detecting the presence of a polypeptide or nucleic acid corresponding to a marker of the invention in a sample (e.g. a tumor sample). Such kits can be used to determine if a subject is predisposed to response or non-response to an anti-cancer therapy regimen. In another aspect, the invention provides a test kit for monitoring the efficacy of a compound or therapeutic in a sample. For example, the kit may comprise a labeled probe capable of detecting a polypeptide or an mRNA encoding a polypeptide corresponding to a marker of the invention in a biological sample and means for determining the amount of the polypeptide or mRNA in the sample (e.g., an antibody which binds the polypeptide or an oligonucleotide probe which binds to DNA or mRNA encoding the polypeptide). Kits may further include instructions for use of the provided kits and interpreting the results obtained using the kit; additional reagents for preparation of probes for use in the methods provided; and detectable label, alone or conjugated to the provided probe(s).

For antibody-based kits, the kit can comprise, for example: (1) a first antibody (e.g., attached to a solid support) which binds to a polypeptide corresponding to a marker of the invention; and, optionally, (2) a second, different antibody which binds to either the polypeptide or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a polypeptide corresponding to a marker of the invention; (2) a pair of primers useful for amplifying a nucleic acid molecule corresponding to a marker of the invention; or (3) a marker set comprising oligonucleotides which hybridize to at least two nucleic acid sequences encoding polypeptide predictive markers of the invention. The kit can also comprise, e.g., a buffering agent, a preservative, or a protein stabilizing agent. The kit can further comprise components necessary for detecting the detectable label (e.g., an enzyme or a substrate). For marker sets, the kit can comprise a marker set array or chip for use in detecting the predictive markers. The kit can also contain a reference sample or a series of reference samples which can be assayed and compared to the test sample. Each component of the kit can be enclosed within an individual container and all of the various containers can be within a single package, along with instructions for interpreting the results of the assays performed using the kit.

Therapeutic Agents

The markers and marker sets of the present invention are predictive of patients who are responsive or non-responsive (sensitive or resistant) proteasome inhibition therapy and/or glucocorticoid therapy regimens, generally.

Therapeutic agents for use in the methods of the invention include a class of therapeutic agents known as proteosome inhibitors. "Proteasome inhibitor" shall mean any substance which directly or indirectly inhibits the 20S or 26S proteasome or the activity thereof. Preferably, such inhibition is specific, i.e., the proteasome inhibitor inhibits proteasome activity at a concentration that is lower than the concentration of the inhibitor concentration required to produce another, unrelated biological effect. Preferably, the concentration of the proteasome inhibitor required for proteasome inhibition is at least 2-fold lower, more preferably at least 5-fold lower, even more preferably at least 10-fold lower, and most preferably at least 20-fold lower than the concentration required to produce an unrelated biological effect. Proteasome inhibitor compounds of this invention are those compounds which are useful for inhibiting tumor growth, (e.g., multiple myeloma tumor growth, other hematological or solid tumors as described in further detail herein) in patients. Proteasome inhibitor also is intended to include pharmaceutically acceptable salts of the compounds.

Proteasome inhibition therapy, generally comprises at least an agent which inhibits proteasome activity in a cell, and can comprise additional therapeutic agents. In certain applications of the invention, the agent used in methods of the invention is a proteasome inhibitor. One example of a proteosome inhibitor has been approved for treatment of multiple myeloma patients who have received at least two prior therapies and have demonstrated disease progression on the last therapy and is presently being tested in clinical trials for additional indications is bortezomib. Proteasome inhibition therapy regimens can also include additional therapeutic agents such as chemotherapeutic agents. Some examples of traditional chemotherapeutic agents are set forth in Table A. Alternatively or in combination with these chemotherapeutic agents, newer classes of chemotherapeutic agents can also be used in proteasome inhibition therapy.

The examples described herein entail use of the proteasome inhibitor N-pyrazinecarbonyl-L-phenylalanine-L-leucineboronic acid, bortezomib ((VELCADE™); formerly known as MLN341 or PS-341). The language "proteasome inhibitor" is intended to include bortezomib, compounds which are structurally similar to bortezomib and/or analogs of bortezomib. "Proteasome inhibitor" can also include "mimics". "Mimics" is intended to include compounds which may not be structurally similar to bortezomib but mimic the therapeutic activity of bortezomib or structurally similar compounds in vivo.

Proteasome inhibitors for use in the practice of the invention include additional peptide boronic acids such as those disclosed in Adams et al., U.S. Pat. No. 5,780,454 (1998), U.S. Pat. No. 6,066,730 (2000), U.S. Pat. No. 6,083,903 (2000), U.S. Pat. No. 6,548,668 (2003), and Siman et al. WO 91/13904, each of which is hereby incorporated by reference in its entirety, including all compounds and formulae disclosed therein. Preferably, a boronic acid compound for use in the present invention is selected from the group consisting of: N-(4-morpholine)carbonyl-.beta.-(1-naphthyl)-L-alanine-L-leucine boronic acid; N-(8-quinoline)sulfonyl-.beta.-(1-naphthyl)-L-alanine-L-alanine-L-leucine boronic acid; N-(2-pyrazine)carbonyl-L-phenylalanine-L-leucine boronic acid, and N-(4-morpholine)carbonyl-[O-(2-pyridylmethyl)]-L-tyrosine-L-leucine boronic acid.

Additionally, proteasome inhibitors include peptide aldehyde proteasome inhibitors such as those disclosed in Stein et al. U.S. Pat. No. 5,693,617 (1997), and International patent publications WO 95/24914 published Sep. 21, 1995 and Siman et al. WO 91/13904 published Sep. 19, 1991; Iqbal et al. J. Med. Chem. 38:2276-2277 (1995), as well as Bouget et al. Bioorg Med Chem 17:4881-4889 (2003) each of which is hereby incorporated by reference in its entirety, including all compounds and formulae disclosed therein.

Further, proteasome inhibitors include lactacystin and lactacycstin analogs which have been disclosed in Fentany et al, U.S. Pat. No. 5,756,764 (1998), and U.S. Pat. No. 6,147,223 (2000), Schreiber et al U.S. Pat. No. 6,645,999 (2003), and Fenteany et al. Proc. Natl. Acad. Sci. USA (1994) 91:3358, each of which is hereby incorporated by reference in its entirety, including all compounds and formulae disclosed therein.

Additionally, synthetic peptide vinyl sulfone proteasome inhibitors and epoxyketone proteasome inhibitors have been disclosed and are useful in the methods of the invention. See, e.g., Bogyo et al., Proc. Natl. Acad. Sci. 94:6629 (1997); Spaltenstein et al. Tetrahedron Lett. 37:1343 (1996); Meng L, Proc. Natl. Acad Sci 96: 10403 (1999); and Meng L H, Cancer Res 59: 2798 (1999), each of which is hereby incorporated by reference in its entirety.

Still further, naturally occurring compounds have been recently shown to have proteasome inhibition activity can be used in the present methods. For example, TMC-95A, a cyclic peptide, or Gliotoxin, both fungal metabolites or polyphenols compounds found in green tea have been identified as proteasome inhibitors. See, e.g., Koguchi Y, Antibiot (Tokyo) 53:105. (2000); Kroll M, Chem Biol 6:689 (1999); and Nam S, J. Biol Chem 276: 13322 (2001), each of which is hereby incorporated by reference in its entirety.

Additional therapeutic agents for use in the methods of the invention comprise a known class of therapeutic agents comprising glucocorticoid steroids. Glucocorticoid therapy, generally comprises at least one glucocorticoid agent (e.g., dexamethasone). In certain applications of the invention, the agent used in methods of the invention is a glucocorticoid agent. One example of a glucocorticoid utilized in the treatment of multiple myeloma patients as well as other cancer therapies is dexamethasone. Additional glucocorticoids utilized in treatment of hematological and combination therapy in solid tumors include hydrocortisone, predisolone, prednisone, and triamcinolone. Glucocorticoid therapy regimens can be used alone, or can be used in conjunction with additional chemotherapeutic agents. Chemotherapeutic agents are known in the art and described in further detail herein. Examples of chemotherapeutic agents are set forth in Table A. As with proteasome inhibition therapy, new classes of cancer therapies may be combined with glucocorticoid therapy regimens as they are developed. Finally, the methods of the invention include combination of proteasome inhibition therapy with glucocorticoid therapy, either alone, or in conjunction with further agents.

In one aspect, one or more of the markers listed in any one of Table 1A, Table 1B, Table 2A, Table 2B, and/or Table 3, can be used to identify candidate agents for use in a treatment regimen which will produce a response in a patient. For example, the method can identify an agent or a combination of agents useful as a proteasome inhibitor. In another example, the method can identify an agent or combination of glucocorticoids. In another example, the method can identify a set of patients likely to be non-responsive to current therapies, and therefore good candidates for inclusion in a clinical trial of a drug aimed at meeting the unmet need of non-responsive patients. For example, a marker or marker set associated with non-response to bortezomib can identify a patient or a test system comprising the capacity to express the marker or marker set. The method can identify a candidate agent which achieves a response in such a patient or test system. In the method, an assay composition comprising a cell, e.g. a tumor cell, capable of expressing a marker or a plurality of markers listed in any one of Table 1A, Table 1B, Table 2A, Table 2B, and/or Table 3 is contacted with the test agent, e.g. for an amount of time for the test agent to affect the level of marker, detecting the level of the marker and comparing the level to the level in a reference cell, e.g., a cell contacted with a known proteasome inhibitor (e.g., bortezomib) or glucocorticoid (e.g., dexamethasone) or a normal cell, and identifying the agent as a candidate proteasome inhibitor or glucocorticoid if the test agent produces an informative expression level of the marker or markers typical of a responsive patient. Conversely, the test agent may not be identified as a candidate agent if it is used in the method and produces an informative expression level typical of a non-responsive patient. The assay composition can comprise a tumor cell isolated from a patient with cancer, e.g. a hematological cancer (e.g., multiple myeloma, leukemias, lymphoma, etc) or cancer from a solid tumor (e.g., in lung, breast, prostate, ovary, colon, kidney or liver). Alternatively, the assay composition can comprise a tumor cell line. The composition comprising the cell can be an in vivo tumor model, e.g. an immunocompromised mouse or a rat with an ectopic, e.g. subcutaneous or ascites, tumor, e.g. a human tumor. The assay composition can be a human subject.

Further to the above, the language, proteasome inhibition therapy regimen and/or glucocorticoid therapy regimen can include additional agents in addition to proteasome inhibition agents, including chemotherapeutic agents. A "chemotherapeutic agent" is intended to include chemical reagents which inhibit the growth of proliferating cells or tissues wherein the growth of such cells or tissues is undesirable. Chemotherapeutic agents such as anti-metabolic agents, e.g., Ara AC, 5-FU and methotrexate, antimitotic agents, e.g., taxane, vinblastine and vincristine, alkylating agents, e.g., melphanlan, BCNU and nitrogen mustard, Topoisomerase II inhibitors, e.g., VW-26, topotecan and Bleomycin, strand-breaking agents, e.g., doxorubicin and DHAD, cross-linking agents, e.g., cisplatin and CBDCA, radiation and ultraviolet light. In a preferred embodiment, the agent is a proteasome inhibitor (e.g., bortezomib or other related compounds) are well known in the art (see e.g., Gilman A. G., et al., *The Pharmacological Basis of Therapeutics,* 8th Ed., Sec 12:1202-1263 (1990)), and are typically used to treat neoplastic diseases. The chemotherapeutic agents generally employed in chemotherapy treatments are listed below in Table A.

The agents tested in the present methods can be a single agent or a combination of agents. For example, the present methods can be used to determine whether a single chemotherapeutic agent, such as methotrexate, can be used to treat a cancer or whether a combination of two or more agents can be used in combination with a proteasome inhibitor (e.g., bortezomib) and/or a glucocorticoid agent (e.g., dexamethasone). Preferred combinations will include agents that have different mechanisms of action, e.g., the use of an anti-mitotic agent in combination with an alkylating agent and a proteasome inhibitor.

The agents disclosed herein may be administered by any route, including intradermally, subcutaneously, orally, intraarterially or intravenously. Preferably, administration will be by the intravenous route. Preferably parenteral administration may be provided in a bolus or by infusion.

The concentration of a disclosed compound in a pharmaceutically acceptable mixture will vary depending on several factors, including the dosage of the compound to be administered, the pharmacokinetic characteristics of the compound(s) employed, and the route of administration. The agent may be administered in a single dose or in repeat doses. Treatments may be administered daily or more frequently depending upon a number of factors, including the overall health of a patient, and the formulation and route of administration of the selected compound(s).

TABLE A

| | | Chemotherapeutic Agents |
|---|---|---|
| CLASS | TYPE OF AGENT | NONPROPRIETARY NAMES (OTHER NAMES) |
| Alkylating | Nitrogen Mustards | Mechlorethamine ($HN_2$) Cyclophosphamide Ifosfamide Melphalan (L-sarcolysin) Chlorambucil |

TABLE A-continued

Chemotherapeutic Agents

| CLASS | TYPE OF AGENT | NONPROPRIETARY NAMES (OTHER NAMES) |
|---|---|---|
| | Ethylenimines And Methylmelamines | Hexamethylmelamine Thiotepa |
| | Alkyl Sulfonates | Busulfan |
| Alkylating | Nitrosoureas | Carmustine (BCNU) Lomustine (CCNU) Semustine (methyl-CCNU) Streptozocin (streptozotocin) |
| Alkylating | Triazenes | Decarbazine (DTIC; dimethyltriazenoimi-dazolecarboxamide) |
| | Alkylator | cis-diamminedichloroplatinum II (CDDP) |
| Antimetab-olites | Folic Acid Analogs | Methotrexate (amethopterin) |
| | Pyrimidine Analogs | Fluorouracil ('5-fluorouracil; 5-FU) Floxuridine (fluorode-oxyuridine; FUdR) Cytarabine (cytosine arabinoside) |
| | Purine Analogs and Related Inhibitors | Mercaptopuine (6-mercaptopurine; 6-MP) Thioguanine (6-thioguanine; TG) Pentostatin (2'-deoxycoformycin) |
| | *Vinca* Alkaloids | Vinblastin (VLB) Vincristine |
| | Topoisomerase Inhibitors | Etoposide Teniposide Camptothecin Topotecan 9-amino-campotothecin CPT-11 |
| Natural Products | Antibiotics | Dactinomycin (actinomycin D) Adriamycin Daunorubicin (daunomycin; rubindomycin) Doxorubicin Bleomycin Plicamycin (mithramycin) Mitomycin (mitomycin C) TAXOL Taxotere |
| | Enzymes | L-Asparaginase |
| Natural Products | Biological Response Modifiers | Interfon alfa Interleukin 2 |
| | Platinum Coordination Complexes | cis-diamminedichloroplatinum II (CDDP) Carboplatin |
| | Anthracendione | Mitoxantrone |
| | Substituted Urea | Hydroxyurea |
| Miscellaneous Agents | Methyl Hydraxzine Derivative | Procarbazine (N-methylhydrazine, (MIH) |
| | Adrenocortical Suppressant | Mitotane (o,p'-DDD) Aminoglutethimide |
| Hormones and Antagonists | Progestins | Hydroxyprogesterone caproate Medroxyprogesterone acetate Megestrol acetate |
| | Estrogens | Diethylstilbestrol Ethinyl estradiol |
| | Antiestrogen | Tamoxifen |
| | Androgens | Testosterone propionate Fluoxymesterone |
| | Antiandrogen | Flutamide |
| | Gonadotropin-releasing Hormone analog | Leuprolide |

Isolated Nucleic Acid Molecules, Vectors and Host Cells

One aspect of the invention pertains to isolated nucleic acid molecules that correspond to a predictive marker of the invention, including nucleic acids which encode a polypeptide corresponding to a predictive marker of the invention or a portion of such a polypeptide. Isolated nucleic acids of the invention also include nucleic acid molecules sufficient for use as hybridization probes to identify nucleic acid molecules that correspond to a predictive marker of the invention, including nucleic acids which encode a polypeptide corresponding to a predictive marker of the invention, and fragments of such nucleic acid molecules, e.g., those suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule of the present invention, e.g., a nucleic acid encoding a protein corresponding to a marker listed in any one of Table 1A, Table 1B, Table 2A, Table 2B, and/or Table 3, can be isolated and manipulated (e.g., amplified, cloned, synthesized, etc.) using standard molecular biology techniques and the sequence information in the database records described herein. (e.g., described in Sambrook et al., ed., *Molecular Cloning: A Laboratory Manual*, 2nd ed., Cold Spring Harbor Laboratory Press, Cold Spring Harbor, N.Y., 1989).

Moreover, a nucleic acid molecule of the invention can comprise only a portion of a nucleic acid sequence, wherein the full length nucleic acid sequence comprises a predictive marker of the invention or which encodes a polypeptide corresponding to a marker of the invention. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a nucleic acid of the invention.

Probes based on the sequence of a nucleic acid molecule of the invention can be used to detect transcripts or genomic sequences corresponding to one or more predictive markers of the invention. The probe comprises a label group attached thereto, e.g., a radioisotope, a fluorescent compound, an enzyme, or an enzyme co-factor. Such probes can be used as part of a diagnostic test kit for identifying cells or tissues which express the protein, such as by measuring levels of a nucleic acid molecule encoding the protein in a sample of cells from a subject, e.g., detecting mRNA levels or determining whether a gene encoding the protein has been mutated or deleted.

In addition to the nucleotide sequences described in the database records described herein, it will be appreciated by those skilled in the art that DNA sequence polymorphisms that lead to changes in the amino acid sequence can exist within a population (e.g., the human population). Such genetic polymorphisms can exist among individuals within a population due to naturally occurring allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the terms "gene" and "recombinant gene" refer to nucleic acid molecules comprising an open reading frame encoding a polypeptide corresponding to a marker of the invention, including, e.g., sequences which differ, due to degeneracy of the genetic code, from the nucleotide sequence of nucleic acids encoding a protein which corresponds to a marker of the invention, and thus encode the same protein.

As used herein, the phrase "allelic variant" refers to a nucleotide sequence which occurs at a given locus or to a polypeptide encoded by the nucleotide sequence. Such naturally occurring allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of naturally occurring allelic variation and that do not alter the functional activity are intended to be within the scope of the invention.

The present invention encompasses antisense nucleic acid molecules, i.e., molecules which are complementary to a sense nucleic acid of the invention, e.g., complementary to the coding strand of a double-stranded cDNA molecule corresponding to a marker of the invention or complementary to an mRNA sequence corresponding to a marker of the invention. Accordingly, an antisense nucleic acid of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another aspect, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

The oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

The invention also includes molecular beacon nucleic acids having at least one region which is complementary to a marker of the invention, such that the molecular beacon is useful for quantitating the presence of the predictive marker of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

Vectors, including expression vectors, containing a nucleic acid encoding a polypeptide corresponding to a predictive marker of the invention can be used for production of nucleic acid and proteins corresponding to predictive markers of the invention; as well as for production of compositions relating to the predictive markers. Useful vectors further comprise promoter and/or regulatory sequences for effective expression of the nucleic acid and/or protein corresponding to the predictive marker of interest. In certain instances, promoters can include constitutive promoter/regulatory sequences, inducible promoter/regulatory sequences, tissue specific promoter/regulatory sequences, or the naturally occurring endogenous promoter/regulatory sequences corresponding to the predictive marker of interest, as required. Various expression vectors are well known in the art and can be adapted to suit the particular system for expression. For example, recombinant expression vectors of the invention can be designed for expression of a polypeptide corresponding to a marker of the invention in prokaryotic (e.g., *E. coli*) or eukaryotic cells (e.g., insect cells {using baculovirus expression vectors}, yeast cells or mammalian cells). Suitable host cells are known in the art and include those discussed in Goeddel, supra. Alternatively, the recombinant expression vector can be transcribed and translated in vitro, for example using T7 promoter regulatory sequences and T7 polymerase. Vectors and host cells can be produced using routine methodology known in the art. Furthermore, use of vectors and host cells can be utilized for production of nucleic acids, polypeptides and fragments thereof corresponding to markers of the invention.

Isolated Proteins and Antibodies

One aspect of the invention pertains to isolated proteins which correspond to predictive markers of the invention, and biologically active portions thereof, as well as polypeptide fragments suitable for use as immunogens to raise antibodies directed against a polypeptide corresponding to a predictive marker of the invention. Polypeptides for use in the invention can be isolated, purified, or produced using the gene identification information provided herein in combination with routine molecular biology, protein purification and recombinant DNA techniques well known in the art.

Preferred polypeptides have the amino acid sequence listed in the one of the GenBank and Entrez database records described herein. Other useful proteins are substantially identical (e.g., at least about 70%, preferably 80%, 90%, 95%, or 99%) to one of these sequences and retain the functional activity of the protein of the corresponding naturally-occurring protein yet differ in amino acid sequence due to natural allelic variation or mutagenesis.

The determination of percent identity between two sequences can be accomplished using a mathematical algorithm determining the number of identical positions shared between two sequences. Determination can be carried out using any known method in the art for comparison of identity and similarity. Examples of methods used can include for example, a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used (accessible at the website maintained by National Center for Biotechnology Information, Bethesda, Md., USA. Another example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2. The percent identity between two sequences can be determined using techniques similar to those described above, with or without allowing gaps. In calculating percent identity, only exact matches are counted.

The invention also provides chimeric or fusion proteins corresponding to a marker of the invention. As used herein, a "chimeric protein" or "fusion protein" comprises all or part (preferably a biologically active part) of a polypeptide corresponding to a marker of the invention operably linked to a heterologous polypeptide (i.e., a polypeptide other than the polypeptide corresponding to the marker). Within the fusion protein, the term "operably linked" is intended to indicate that the polypeptide of the invention and the heterologous polypeptide are fused in-frame to each other. The heterologous polypeptide can be fused to the amino-terminus or the carboxyl-terminus of the polypeptide of the invention. Useful fusion proteins can include GST, c-myc, FLAG, HA, and any other well known heterologous tag for use in fusion protein production. Such fusion proteins can facilitate the purification of a recombinant polypeptide of the invention.

In addition, fusion proteins can include a signal sequence from another protein such as gp67, melittin, human placental alkaline phosphatase, and phoA. In yet another aspect, the fusion protein is an immunoglobulin fusion protein in which all or part of a polypeptide corresponding to a predictive marker of the invention is fused to sequences derived from a member of the immunoglobulin protein family. The immunoglobulin fusion proteins of the invention can be used as immunogens to produce antibodies directed against a polypeptide of the invention in a subject, to purify ligands and in screening assays to identify molecules which inhibit the interaction of receptors with ligands.

An isolated polypeptide corresponding to a predictive marker of the invention, or a fragment thereof, can be used as an immunogen to generate antibodies using standard techniques for polyclonal and monoclonal antibody preparation. For example, an immunogen typically is used to prepare antibodies by immunizing a suitable (i.e. immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Accordingly, another aspect of the invention pertains to antibodies directed against a polypeptide of the invention. The terms "antibody" and "antibody substance" as used interchangeably herein refer to immunoglobulin molecules and immunologically active portions of immunoglobulin molecules, i.e., molecules that contain an antigen binding site which specifically binds an antigen, such as a polypeptide of the invention, e.g., an epitope of a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. Synthetic and genetically engineered variants (See U.S. Pat. No. 6,331,415) of any of the foregoing are also contemplated by the present invention. Polyclonal and monoclonal antibodies can be produced by a variety of techniques, including conventional murine monoclonal antibody methodology e.g., the standard somatic cell hybridization technique of Kohler and Milstein, *Nature* 256: 495 (1975) the human B cell hybridoma technique (see Kozbor et al., 1983, *Immunol. Today* 4:72), the EBV-hybridoma technique (see Cole et al., pp. 77-96 *In Monoclonal Antibodies and Cancer Therapy*, Alan R. Liss, Inc., 1985) or trioma techniques. See generally, Harlow, E. and Lane, D. (1988) *Antibodies: A Laboratory Manual*, Cold Spring Harbor Laboratory Press, Cold Spring Harbor, N.Y.; and *Current Protocols in Immunology*, Coligan et al. ed., John Wiley & Sons, New York, 1994. Preferably, for diagnostic applications, the antibodies are monoclonal antibodies. Additionally, for use in in vivo applications the antibodies of the present invention are preferably human or humanized antibodies. Hybridoma cells producing a monoclonal antibody of the invention are detected by screening the hybridoma culture supernatants for antibodies that bind the polypeptide of interest, e.g., using a standard ELISA assay.

If desired, the antibody molecules can be harvested or isolated from the subject (e.g., from the blood or serum of the subject) and further purified by well-known techniques, such as protein A chromatography to obtain the IgG fraction. Alternatively, antibodies specific for a protein or polypeptide of the invention can be selected or (e.g., partially purified) or purified by, e.g., affinity chromatography to obtain substantially purified and purified antibody. By a substantially purified antibody composition is meant, in this context, that the antibody sample contains at most only 30% (by dry weight) of contaminating antibodies directed against epitopes other than those of the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Cancer Res. 47:999-1005; Wood et al. (1985) Nature 314:446-449; and Shaw et al. (1988) J. Natl. Cancer Inst. 80:1553-1559); Morrison (1985) Science 229:1202-1207; Oi et al. (1986) Bio/Techniques 4:214; U.S. Pat. No. 5,225,539; Jones et al. (1986) Nature 321:552-525; Verhoeyan et al. (1988) Science 239:1534; and Beidler et al. (1988) J. Immunol. 141:4053-4060.

Methods for making human antibodies are known in the art. One method for making human antibodies employs the use of transgenic animals, such as a transgenic mouse. These transgenic animals contain a substantial portion of the human antibody producing genome inserted into their own genome and the animal's own endogenous antibody production is rendered deficient in the production of antibodies. Methods for making such transgenic animals are known in the art. Such transgenic animals can be made using XENOMOUSE™ technology or by using a "minilocus" approach. Methods for making XENOMICE™ are described in U.S. Pat. Nos. 6,162,963, 6,150,584, 6,114,598 and 6,075,181, which are incorporated herein by reference. Methods for making transgenic animals using the "minilocus" approach are described in U.S. Pat. Nos. 5,545,807, 5,545,806 and 5,625,825; also see International Publication No. WO93/12227, which are each incorporated herein by reference.

Antibody fragments may be derived from any of the antibodies described above. For example, antigen-binding fragments, as well as full-length monomeric, dimeric or trimeric polypeptides derived from the above-described antibodies are themselves useful. Useful antibody homologs of this type include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature 341:544-546 (1989)), which consists of a VH domain; (vii) a single domain functional heavy chain antibody, which consists of a VHH domain (known as a nanobody) see e.g., Cortez-Retamozo, et al., Cancer Res. 64: 2853-2857 (2004), and references cited therein; and (vii) an isolated complementarity determining region (CDR), e.g., one or more isolated CDRs together with sufficient framework to provide an antigen binding fragment. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. Science 242:423-426 (1988); and Huston et al. Proc. Natl. Acad. Sci. USA 85:5879-5883 (1988). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Antibody fragments, such as Fv, F(ab')$_2$ and Fab may be prepared by cleavage of the intact protein, e.g. by protease or chemical cleavage.

An antibody directed against a polypeptide corresponding to a predictive marker of the invention (e.g., a monoclonal antibody) can be used to detect the predictive marker (e.g., in a cellular sample) in order to evaluate the level and pattern of expression of the predictive marker. The antibodies can also be used diagnostically to monitor protein levels in tissues or body fluids (e.g. in an tumor sample) as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Accordingly, in one aspect, the invention provides substantially purified antibodies or fragments thereof, and non-human antibodies or fragments thereof, which antibodies or fragments specifically bind to a polypeptide comprising an amino acid sequence encoded by a predictive marker identified herein. The substantially purified antibodies of the invention, or fragments thereof, can be human, non-human, chimeric and/or humanized antibodies.

In another aspect, the invention provides non-human antibodies or fragments thereof, which antibodies or fragments specifically bind to a polypeptide comprising an amino acid sequence which is encoded by a nucleic acid molecule of a predictive marker of the invention. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies.

In still a further aspect, the invention provides monoclonal antibodies or fragments thereof, which antibodies or fragments specifically bind to a polypeptide comprising an amino acid sequence selected from the group consisting of the amino acid sequences of the present invention, an amino acid sequence encoded by the cDNA of the present invention, a fragment of at least 15 amino acid residues of an amino acid sequence of the present invention, an amino acid sequence which is at least 95% identical to an amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C. The monoclonal antibodies can be human, humanized, chimeric and/or non-human antibodies.

The substantially purified antibodies or fragments thereof may specifically bind to a signal peptide, a secreted sequence, an extracellular domain, a transmembrane or a cytoplasmic domain or cytoplasmic membrane of a polypeptide of the invention. The substantially purified antibodies or fragments thereof, the non-human antibodies or fragments thereof, and/or the monoclonal antibodies or fragments thereof, of the invention specifically bind to a secreted sequence or an extracellular domain of the amino acid sequences of the present invention.

The invention also provides a kit containing an antibody of the invention conjugated to a detectable substance, and instructions for use. Still another aspect of the invention is a diagnostic composition comprising an antibody of the invention and a pharmaceutically acceptable carrier. In certain aspects, the diagnostic composition contains an antibody of the invention, a detectable moiety, and a pharmaceutically acceptable carrier.

Sensitivity Assays

A sample of cancerous cells is obtained from a patient. An expression level is measured in the sample for a marker corresponding to at least one of the predictive markers set forth in Table 1A, Table 1B, Table 2A, Table 2B, and/or Table 3. Preferably a marker set is utilized comprising markers identified in Table 1A, Table 1B, Table 2A, Table 2B, and/or Table 3, and put together in a marker set using the methods described herein. For example, marker sets can comprise the marker sets identified in Table 4, or any marker set prepared by similar methods. Such analysis is used to obtain an expression profile of the tumor in the patient. Evaluation of the expression profile is then used to determine whether the patient is a responsive patient and would benefit from proteasome inhibition therapy (e.g., treatment with a proteasome inhibitor (e.g., bortezomib) alone, or in combination with additional agents) and/or glucocorticoid therapy (e.g., treatment with a glucocorticoid (e.g., dexamethasone) alone, or in combination with additional agents). Evaluation can include use of one marker set prepared using any of the methods provided or other similar scoring methods known in the art (e.g., weighted voting, CTF). Still further, evaluation can comprise use of more than one prepared marker set. A proteasome inhibition therapy and/or glucocorticoid therapy will be identified as appropriate to treat the cancer when the outcome of the evaluation demonstrates decreased non-responsiveness or increased responsiveness in the presence of the agent.

In one aspect, the invention features a method of evaluating a patient, e.g., a patient with cancer, e.g. a hematological cancer (e.g., multiple myeloma, leukemias, lymphoma, etc) or cancer from a solid tumor (e.g., in lung, breast, prostate, ovary, colon, kidney, or liver) for responsiveness or non-responsiveness to treatment with a proteasome inhibition and/or a glucocorticoid therapy regimen. The method includes providing an evaluation of the expression of the markers in a predictive marker set of markers in the patient, wherein the predictive marker set has the following properties: it includes a plurality of genes, each of which is differentially expressed as between patients responsive or non-responsive to treatment with a proteasome inhibition and/or a glucocorticoid therapy regimen and non-afflicted subjects and it contains a sufficient number of differentially expressed markers such that differential expression (e.g., as compared to a level in a non-afflicted reference sample) of each of the markers in the predictive marker set in a subject is predictive of responsiveness or nonresponsiveness with no more than about 15%, about 10%, about 5%, about 2.5%, or about 1% false positives (wherein false positive means predicting that a patient as responsive or non-responsive when the subject is not); and providing a comparison of the expression of each of the markers in the set from the patient with a reference value, thereby evaluating the patient.

Examining the expression of one or more of the identified markers or marker sets in a tumor sample taken from a patient during the course of proteasome inhibition therapy and/or glucocorticoid treatment, it is also possible to determine whether the therapeutic agent is continuing to work or whether the cancer has become non-responsive (refractory) to the treatment protocol. For example, a patient receiving a treatment of bortezomib would have tumor cells removed and monitored for the expression of a marker or marker set. If the expression profile of one or more marker sets identified in Table 1A, Table 1B, Table 2A, Table 2B, and/or Table 3 demonstrates increased responsiveness in the presence of the agent, the treatment with proteasome inhibitor would continue. However, if the expression profile of one or more marker sets identified in Table 1A, Table 1B, Table 2A, Table 2B, and/or Table 3 demonstrates increased non-responsiveness in the presence of the agent, then the cancer may have become resistant to proteasome inhibition therapy and/or glucocorticoid therapy, and another treatment protocol should be initiated to treat the patient.

Importantly, these determinations can be made on a patient by patient basis or on an agent by agent (or combinations of agents). Thus, one can determine whether or not a particular proteasome inhibition therapy and/or glucocorticoid therapy is likely to benefit a particular patient or group/class of patients, or whether a particular treatment should be continued.

Use of Information

In one method, information, e.g., about the patient's marker expression levels (e.g., the result of evaluating a predictive marker or predictive marker set described herein), or about whether a patient will be responsive or non-responsive to a proteasome inhibition therapy and/or glucocorticoid therapy, is provided (e.g., communicated, e.g., electronically communicated) to a third party, e.g., a hospital, clinic, a government entity, reimbursing party or insurance company (e.g., a life insurance company). For example, choice of medical procedure, payment for a medical procedure, payment by a reimbursing party, or cost for a service or insurance can be function of the information. E.g., the third party receives the information, makes a determination based at least in part on the information, and optionally communicates the information or makes a choice of procedure, payment, level of payment, coverage, etc. based on the information. In the method, informative expression level of a predictive marker or a predictive marker set selected from or derived from Table 1A, Table 1B, Table 2A, Table 2B, and Table 3 is determined.

In one embodiment, a premium for insurance (e.g., life or medical) is evaluated as a function of information about one or more marker expression levels, e.g., a predictive marker or predictive marker set, e.g., a level of expression associated with responsiveness or non-responsiveness to a proteasome inhibition therapy and/or glucocorticoid therapy (e.g., the informative expression level). For example, premiums can be increased (e.g., by a certain percentage) if the markers of a patient or a patient's predictive marker set described herein are differentially expressed between an insured candidate (or a candidate seeking insurance coverage) and a reference value (e.g., a non-afflicted person). As another example, premiums can be decreased if levels of a predictive marker or predictive marker set are sustained (as described herein) after treatment with a proteasome inhibitor or a glucocorticoid. Premiums can also be scaled depending on marker expression levels, e.g., the result of evaluating a predictive marker or predictive marker set described herein. For example, premiums can be assessed to distribute risk, e.g., as a function of marker expression levels, e.g., the result of evaluating a predictive marker or predictive marker set described herein. In another example, premiums are assessed as a function of actuarial data that is obtained from patients that are enhanced or non-enhanced responders.

Information about marker expression levels, e.g., the result of evaluating a predictive marker or predictive marker set described herein (e.g., the informative expression level), can be used, e.g., in an underwriting process for life insurance. The information can be incorporated into a profile about a subject. Other information in the profile can include, for example, date of birth, gender, marital status, banking information, credit information, children, and so forth. An insurance policy can be recommended as a function of the information on marker expression levels, e.g., the result of evaluating a predictive marker or predictive marker set described herein, along with one or more other items of information in the profile. An insurance premium or risk assessment can also be evaluated as function of the predictive marker or predictive marker set information. In one implementation, points are assigned on the basis of being responsive or non-responsive to a proteasome inhibition therapy and/or glucocorticoid therapy.

In one embodiment, information about marker expression levels, e.g., the result of evaluating a predictive marker or predictive marker set described herein, is analyzed by a function that determines whether to authorize the transfer of funds to pay for a service or treatment provided to a subject (or make another decision referred to herein). For example, the results of analyzing a expression of a predictive marker or predictive marker set described herein may indicate that a subject is responsive or non-responsive to a proteasome inhibition therapy and/or glucocorticoid therapy, suggesting that a treatment course is needed, thereby triggering an outcome that indicates or causes authorization to pay for a service or treatment provided to a subject. In one example, informative expression level of a predictive marker or a predictive marker set selected from or derived from Table 1A, Table 1B, Table 2A, Table 2B, and Table 3 is determined and payment is authorized if the informative expression level identifies a responsive patient. For example, an entity, e.g., a hospital, care giver, government entity, or an insurance company or other entity which pays for, or reimburses medical expenses, can use the outcome of a method described herein to determine whether a party, e.g., a party other than the subject patient, will pay for services (e.g., a particular therapy) or treatment provided to the patient. For example, a first entity, e.g., an insurance company, can use the outcome of a method described herein to determine whether to provide financial payment to, or on behalf of, a patient, e.g., whether to reimburse a third party, e.g., a vendor of goods or services, a hospital, physician, or other care-giver, for a service or treatment provided to a patient. For example, a first entity, e.g., an insurance company, can use the outcome of a method described herein to determine whether to continue, discontinue, enroll an individual in an insurance plan or program, e.g., a health insurance or life insurance plan or program.

In one aspect, the disclosure features a method of providing data. The method includes providing data described herein, e.g., generated by a method described herein, to provide a record, e.g., a record described herein, for determining if a payment will be provided. In some embodiments, the data is provided by computer, compact disc, telephone, facsimile, email, or letter. In some embodiments, the data is provided by a first party to a second party. In some embodiments, the first party is selected from the subject, a healthcare provider, a treating physician, a health maintenance organization (HMO), a hospital, a governmental entity, or an entity which sells or supplies the drug. In some embodiments, the second party is a third party payor, an insurance company, employer, employer sponsored health plan, HMO, or governmental entity. In some embodiments, the first party is selected from the subject, a healthcare provider, a treating physician, an HMO, a hospital, an insurance company, or an entity which sells or supplies the drug and the second party is a governmental entity. In some embodiments, the first party is selected from the subject, a healthcare provider, a treating physician, an HMO, a hospital, an insurance company, or an entity which sells or supplies the drug and the second party is an insurance company.

In another aspect, the disclosure features a record (e.g., computer readable record) which includes a list and value of expression for the predictive marker or predictive marker set for a patient. In some embodiments, the record includes more than one value for each marker.

EXEMPLIFICATION

Based on positive findings in multiple myeloma in Phase 1 clinical trials (Orlowski, J Clin Oncol. 2002 Nov. 15; 20(22): 4420-7., Aghajanian, Clin Cancer Res. 2002 August; 8(8): 2505-11,) Phase 2 myeloma studies were conducted in order to better to allow a more precise estimate of anti-tumor activity of bortezomib in a more homogeneous population of patients. The safety and efficacy of bortezomib in subjects with multiple myeloma was investigated in two phase 2 clinical studies, M34100-024 (subjects with first relapse) and M34100-025 (subjects with second or greater relapse and refractory to their last prior therapy). In Study M34100-025, the CR+PR rate to bortezomib alone was 27% (53 of 193 patients), and the overall response rate (CR+PR+MR) to bortezomib alone was 35% (67 of 193 patients). See Richardson P G, et al. *N Engl J Med.,* 348:2609-17 (2003). In Study M34100-024 CR+PR rates of were 30% and 38% were seen among patients with relapsed multiple myeloma treated with bortezomib 1.0 mg/m$^2$ and 1.3 mg/m$^2$, respectively. See Jagannath, *Br J Haematol.* 127:165-72 (2004). Patient samples and response criteria from patients participating in these studies, as well as the following additional studies described below were sought for use in pharmacogenomic analyses to identify markers associated with patient response to treatments.

An Open-Label Study Comparison of Bortezomib Versus High Dose Dexamethasone in Patients with Relapsed and Refractory Myeloma A multicenter, open-label, randomized study was conducted, comprising 627 enrolled patients with relapsed or refractory multiple myeloma (Protocol M34101-039). See Richardson et. al., *N. Engl. J. Med.,* 352:2487-2498 (2005). Patients were treated with either bortezomib (315 patients) or high-dose dexamethasone (312 patients).

Treatment Dosage and Administration

Drug Supply and Storage

Bortezomib for injection (VELCADE™ Millennium Pharmaceuticals, Inc., Cambridge, Mass.), a sterile lyophilized powder for reconstitution, was supplied in vials containing 2.5 mg bortezomib and 25 mg mannitol USP. Each vial was reconstituted with 2.5 mL of normal (0.9%) saline, Sodium Chloride Injection USP, such that the reconstituted solution contained bortezomib at a concentration of 1 mg/mL. The reconstituted solution was clear and colorless with a final pH between 5 and 6.

Dexamethasome tablets (DECADRON® Merck & Co., Inc.).

TABLE B

| Drug Information | | |
|---|---|---|
| Chemical Name | N-Pyrazinecarbonyl-L-phenylalanine-L-leucineboronic acid | |
| Research Name | MLN341 or PS-341 | |
| Generic Name | bortezomib | dexamethasone |
| Proprietary Name | VELCADE ™ | Decadron ® |
| CAS Registry No. | 179324-69-7 | 312-93-6 |
| U.S. Patent No. | 5,780,454 | |
| Classification | Proteasome Inhibitor | Steroid |
| Molecular Formula | $C_{19}H_{25}BN_4O_4$ | $C_{22}H_{29}FO_5$ |
| Molecular Weight | 384.25 | 392.47 |
| Structure | Boronic acid derivative of a leucine phenylalanine dipeptide | Synthetic adrenocorticosteroid |

Patients were assigned to receive bortezomib or high-dose dexamethasone by random allocation at a 1:1 ratio. Randomization was to be stratified, based on the number of lines of prior therapy (one prior line versus more than one prior line of therapy), time of progression relative to treatment (progression while on their most recent therapy or within 6 months of stopping their most recent therapy, or relapse >6 months after receiving their most recent therapy), and screening $\beta_2$-microglobulin levels (>2.5 mg/L versus ≤2.5 mg/L).

Patients assigned to the bortezomib group received treatment for a maximum of 273 days. Patients in this treatment group received up to eight 3-week treatment cycles followed by up to three 5-week treatment cycles of bortezomib. Within each 3-week treatment cycle, the patient received bortezomib 1.3 mg/m²/dose alone as a bolus intravenous (IV) injection twice weekly for two weeks (on Days 1, 4, 8, and 11) of a 21-day cycle. Within each 5-week treatment cycle, the patient received bortezomib 1.3 mg/m²/dose alone as a bolus IV injection once weekly (on Days 1, 8, 15, and 22) of a 35-day cycle.

Patients assigned to the high-dose dexamethasone group received treatment for a maximum of 280 days. Patients in this treatment group received up to four 5-week treatment cycles, followed by up to five 4-week treatment cycles. Within each 5-week treatment cycle, the patient received dexamethasone 40 mg/day PO, once daily on Days 1 to 4, 9 to 12, and 17 to 20 of a 35-day cycle. Within each 4-week treatment cycle, the patient received dexamethasone 40 mg/day PO once daily on Days 1 to 4 of a 28 day cycle. The protocol provided for patients in the dexamethasone group who experienced confirmed progressive disease (PD) to receive bortezomib on a companion study (An International, Non-Comparative, Open-Label Study of PS-341 Administered to Patients with Multiple Myeloma Who Received High-dose Dexamethasone or Experienced Progressive Disease after Receiving at Least Four Previous Therapies, (Protocol M34101-040). An additional 240 patients who did not participate in this study, enrolled in the companion study and according to the protocol would have received at least four prior therapies. Pharmacogenomic samples were also sought for these 240 patients.

During the study, disease response was assessed according to the European Group for Blood and Marrow Transplant (EBMT) criteria as presented in Table C.

TABLE C

| Disease Response Criteria | |
|---|---|
| Table C Disease Response Criteria[1] | |
| Response | Criteria for response |
| Complete response (CR)[2] | Requires all of the following: Disappearance of the original monoclonal protein from the blood and urine on at least two determinations for a minimum of six weeks by immunofixation studies. <5% plasma cells in the bone marrow[3]. No increase in the size or number of lytic bone lesions (development of a compression fracture does not exclude response). Disappearance of soft tissue plasmacytomas for at least six weeks. |
| Partial response (PR) | PR includes patients in whom some, but not all, criteria for CR are fulfilled providing the remaining criteria satisfy the requirements for PR. Requires all of the following: ≥50% reduction in the level of serum monoclonal protein for at least two determinations six weeks apart. If present, reduction in 24-hour urinary light chain excretion by either ≥90% or to <200 mg for at least two determinations six weeks apart. ≥50% reduction in the size of soft tissue plasmacytomas (by clinical or radiographic examination) for at least six weeks. No increase in size or number of lytic bone lesions (development of compression fracture does not exclude response). |
| Minimal response (MR) | MR includes patients in whom some, but not all, criteria for PR are fulfilled providing the remaining criteria satisfy the requirements for MR. Requires all of the following: ≥25% to ≤50% reduction in the level of serum monoclonal protein for at least two determinations six weeks apart. If present, a 50 to 89% reduction in 24-hour light chain excretion, which still exceeds 200 mg/24 h, for at least two determinations six weeks apart. 25-49% reduction in the size of plasmacytomas (by clinical or radiographic examination (e.g., 2D MRI, CT scan). No increase in size or number of lytic bone lesions (development of compression fracture does not exclude response). |

TABLE C-continued

Disease Response Criteria
Table C Disease Response Criteria[1]

| Response | Criteria for response |
|---|---|
| No change (NC) | Not meeting the criteria for MR or PD. |
| Progressive disease (PD) (for patients not in CR) | Requires one or more of the following: >25% increase in the level of serum monoclonal paraprotein, which must also be an absolute increase of at least 5 g/L and confirmed on a repeat investigation one to three weeks later[4,5]. >25% increase in 24-hour urinary light chain excretion, which must also be an absolute increase of at least 200 mg/24 h and confirmed on a repeat investigation one to three weeks later[4,5]. >25% increase in plasma cells in a bone marrow aspirate or on trephine biopsy, which must also be an absolute increase of at least 10%. Definite increase in the size of existing lytic bone lesions or soft tissue plasmacytomas. Development of new bone lesions or soft tissue plasmacytomas (not including compression fracture). Development of hypercalcemia (corrected serum calcium >11.5 mg/dL or 2.8 mmol/L not attributable to any other cause)[4]. |
| Relapse from CR | Requires at least one of the following: Reappearance of serum or urine monoclonal paraprotein on immunofixation or routine electrophoresis to an absolute value of >5 g/L for serum and >200 mg/24 hours for urine, and excluding oligoclonal immune reconstitution. Reappearance of monoclonal paraprotein must be confirmed by at least one follow-up. ≥5% plasma cells in the bone marrow aspirate or biopsy. Development of new lytic bone lesions or soft tissue plasmacytomas or definite increase in the size of residual bone lesions (not including compression fracture). Development of hypercalcemia (corrected serum calcium >11.5 mg/dL or 2.8 mmol/L not attributable to any other cause). |

[1]Based on the EBMT criteria. See, Blade J, et al. *Br J Haematol*; 102(5): 1115-23 (1998).
[2]For proper evaluation of CR, bone marrow should be ≥20% cellular and serum calcium should be within normal limits.
[3]A bone marrow collection and evaluation is required to document CR. Repeat collection and evaluation of bone marrow is not required to confirm CR for patients with secretory myeloma who have a sustained absence of monoclonal protein on immunofixation for a minimum of 6 weeks; however, repeat collection and evaluation of bone marrow is required at the Response Confirmation visit for patients with non-secretory myeloma.
[4]The need for urgent therapy may require repeating these tests earlier or eliminating a repeat examination.
[5]For determination of PD, increase in paraprotein is relative to the nadir.

Patients were evaluable for response if they had received at least one dose of study drug and had measurable disease at baseline (627 total patients: 315 in the bortezomib group and 312 in the dexamethasone group). The evaluation of confirmed response to treatment with bortezomib or dexamethasone according to the European Group for Blood and Marrow Transplant (EBMT) criteria is provided in Table D. Response and date of disease progression was determined by computer algorithm that integrated data from a central laboratory and case report forms from each clinical site, according to the Blade criteria (Table C). The response rate (complete plus partial response (CR+PR)) in the bortezomib group was 38 percent; and in the dexamethasone group was 18 percent (P<0.0001). Complete response was achieved in 20 patients (6 percent) who received bortezomib, and in 2 patients (<1 percent) who received dexamethasone (P<0.001), with complete response plus near-complete response in 13 and 2 percent (P<0.0001) in patients receiving bortezomib and dexamethasone, respectively. These data have been submitted for publication. See Richardson P G, et al. [submitted NEJM].

TABLE D

Summary of Best Confirmed Response to Treatment[1,2] (Population, N = 627)

| Best Confirmed Response | bortezomib n (%) (n = 315) | dexamethasone n (%) (n = 312) | Difference (95% CI)[a] | p-value[b] |
|---|---|---|---|---|
| Overall Response Rate (CR + PR) | 121 (38) | 56 (18) | 0.20 (0.14, 0.27) | <0.0001 |
| Complete Response | 20 (6) | 2 (<1) | 0.06 (0.03, 0.09) | 0.0001 |
| Partial Response | 101 (32) | 54 (17) | 0.15 (0.08, 0.21) | <0.0001 |
| Near CR: IF+ | 21 (7) | 3 (<1) | 0.06 (0.03, 0.09) | |
| SWOG Remission | 46 (15) | 17 (5) | 0.09 (0.05, 0.14) | |
| Minor Response | 25 (8) | 52 (17) | −0.09 (−0.14, −0.04) | |
| CR + PR + MR | 146 (46) | 108 (35) | 0.12 (0.04, 0.19) | |

TABLE D-continued

Summary of Best Confirmed Response to Treatment[1,2] (Population, N = 627)

| Best Confirmed Response | bortezomib n (%) (n = 315) | dexamethasone n (%) (n = 312) | Difference (95% CI)[a] | p-value[b] |
|---|---|---|---|---|
| No Change | 137 (43) | 149 (48) | −0.04 (−0.12, 0.04) | |
| Progressive Disease | 22 (7) | 41 (13) | −0.06 (−0.11, −0.01) | |
| Not Evaluable | 10 (3) | 14 (4) | −0.01 (−0.04, 0.02) | |

[1]Response based on computer algorithm using the protocol-specified EBMT criteria.
[2]Percents calculated for the statistical output in section 14 are 'rounded' to the nearest integer including percents ≥0.5% but <1% rounding to 1%; these are reported in the in-text tables as <1%.
[a]Asymptotic confidence interval for the difference in response rates.
[b]P-value from the Cochran-Mantel-Haenszel chi-square test adjusted for the actual randomization stratification factors.

Disease progression was determined by Bladé criteria as described in Table C and above. The median time to disease progression in the bortezomib group was 6.2 month (189 days); and the in the dexamethasone group was 3.5 months (106 days) (hazard ratio 0.55, P<0.0001). The date of progression was determined by computer algorithm. P-value from log-rank test adjusted by actual randomization factors. See, Richardson et al., New Engl J. Med., submitted.

Median time to response was 43 days for patients in both groups. Median duration of response was 8 months in the bortezomib group and 5.6 months in the dexamethasone group.

Patients given bortezomib had a superior overall survival. One-year survival was 80% on bortezomib and 66% on dexamethasone (P<0.0030). This represents a 41% decrease in risk of death in the bortezomib group during the first year after enrollment. The hazard ratio for overall survival was 0.57 (P<0.0013), favoring bortezomib. The analysis of overall survival includes data from 147 patients (44 percent) in the dexamethasone group who had disease progression and subsequently crossed over to receive bortezomib in a companion study.

Quality of Life assessment can be analyzed to determine if response to therapy was accompanied by measurable improvement in quality of life. Analysis is performed on summary scores as well as individual items, with specific analytical methods outlined in a formal statistical analysis plan developed prior to database lock.

Pharmacogenomic Samples Collected

Pharmacogenomic tumor samples (bone marrow aspirate) were collected from patients for evaluation of the expression of global mRNA levels.

Statistical Procedures

Summary tabulations were presented that displayed the number of observations, mean, standard deviation, median, minimum, and maximum for continuous variables, and the number and percent per category for categorical data. The categories for summarization were the two assigned treatment groups.

A formal statistical analysis plan was developed and finalized prior to database lock. The primary efficacy analyses were performed on the intent-to-treat (ITT) population. The primary efficacy analysis was performed on the rates of responders, where a responder was defined as a CR, PR, or MR using the criteria prospectively established in Table C. Two-sided 90% confidence limits on proportions of responders in each dose group were established, corresponding to a 95% one-sided lower limit.

For those patients who participated in the pharmacogenomic portion of the study, correlation between RNA expression levels and response to therapy were evaluated descriptively. In addition, duration of response, time to disease progression, quality of life, and overall patient survival may be analyzed using RNA expression as a factor.

TABLE E

Summary of Pharmacogenomic Patient Response

| Study | CR | PR | MR | NC | PD | IE | TOTAL with evaluable response |
|---|---|---|---|---|---|---|---|
| all | 10 | 69 | 25 | 59 | 61 | 22 | 224 |
| 024 | 1 | 1 | 0 | 1 | 4 | 0 | 7 |
| 025 | 2 | 10 | 3 | 10 | 14 | 5 | 39 |
| 040 | 1 | 20 | 6 | 13 | 8 | 2 | 48 |
| 039 341 | 5 | 25 | 5 | 19 | 13 | 9 | 67 |
| 039 Dex | 1 | 13 | 11 | 16 | 22 | 6 | 62 |

A total of 224 patient samples were assessed for pharmacogenomic analyses. These patient samples were collected from the clinical trials of bortezomib for the treatment of multiple myeloma See Table E. The overall response rate to bortezomib in this set of patients was 46.4% (CR+PR rate of 35%). The overall response rate to dexamethasone was 39.7% (CR+PR rate of 22.2%). All pharmacogenomic analyses relied on the European Group for Blood and Marrow Transplant (EBMT) criteria of response category.

Identification of Responsive and Non-Predictive Markers

Biopsies from 224 multiple myeloma patients resulted in generation of high quality gene expression data which was used to identify predictive markers. Candidate markers that are correlated with the outcome of multiple myeloma patients to proteasome inhibition (e.g., bortezomib) therapy or glucocorticoid (e.g., dexamethasone) therapy were selected by using a combination of marker ranking algorithms. Supervised learning and feature selection algorithms were then used to identify the markers of the present invention.

A data set comprising 224 discovery samples, time to progression data and short-term response categorization was used to identify genes associated with patient outcome to one of two treatments (bortezomib or dexamethasone). The data set consisted of discovery samples matched with the patient's outcome as measured by best response and time to disease progression. For best response, each patient was classified as responder ($N_R$), stable disease ($N_S$), or progression ($N_P$). For marker identification, the three response classes were further grouped into responders vs. non-responders (stable and progression) ($N_{P+S}$), responders vs. progression, or progression vs. others (stable and responders) ($N_{R+S}$). The analyses further separated the patients based on the treatment they received. For bortezomib analyses $N_R$=79, $N_S$=43, and $N_P$=41. Thus, the responder vs. non-responder analysis utilizes 79 vs. 84 samples. The responder vs. progression analysis utilizes 79 vs. 41 and the progression vs. other analysis utilizes 41 vs. 122 samples. For the dexamethasone analysis $N_R=25$, $N_S=16$, and $N_P=21$. Accordingly, the responder vs. non-responder analysis utilizes 25 vs. 37 samples. The responder vs. progression analysis utilizes 25 vs. 21 and the progression vs. other analysis utilizes 21 vs. 41 samples.

44,928 gene transcripts (Affymetrix probe sets) were profiled for each sample on the two Affymetrix U133 microarrays (A and B) according to manufacturer's directions. Total RNA was isolated from homogenized patient tumor tissue by Triazol™ (Life Technologies, Inc.) and stored at 80° C., following the manufacturer's recommendations. Detailed methods for labeling the samples and subsequent hybridization to the arrays are available from Affymetrix (Santa Clara, Calif.). Briefly, 1.5 of total RNA was converted to double-stranded cDNA (Superscript; Life Technologies, Inc.) priming the first-strand synthesis with a T7-(dT)24 primer containing a T7 polymerase promoter (Affymetrix Inc.). All of the double-stranded cDNA was subsequently used as a template to generate biotinylated cRNA using the incorporated T7 promoter sequence in an in vitro transcription system (Megascript kit; Ambion and Bio-11-CTP and Bio-16-UTP; Enzo). Reference oligonucleotides and spikes were added to 6-10 µg of cRNA, which was then hybridized to U133 A and B oligonucleotide arrays for 16 h at 45° C. with constant rotation. The arrays were then washed and stained on an Affymetrix fluidics station using the EUKGE-WS 1 protocol and scanned on an Affymetrix GeneArray scanner.

Normalization and Logarithmic Transformation.

Expression values for all markers on each microarray were normalized to a trimmed mean of 150. Expression values were determined using MASS gene expression analysis data processing software (Affymetrix, Santa Clara, Calif.). These values will be referred to as the "normalized expression" in the remainder of this section. In a further processing step, the number 1 was added to each normalized expression value. The logarithm base 2 was taken of the resulting number, and this value will be referred to as the "log expression" in the remainder of this section.

Variance Components Analysis.

There were up to six replicate hybridizations for each patient: three replicate hybridizations for each of two T7 RNA labelings. To summarize replicates into a single estimate of intensity for each patient, a mixed effects linear model was used. For each probe set, a model was fit which included terms the patient sample specific random effect representing the deviation from the overall mean intensity, and the replicate hybridization random effect. These random effects are referred to as the variance components of the model. Model fitting includes assessing the variance due to these two random effects, resulting in estimates of patient sample variance and replicate variance.

Summarizing Expression Across Replicates.

The final summary expression value, for each sample on each probe set, was obtained by estimating the best linear unbiased predictor (BLUP). The BLUP can be viewed as a weighted average of each subject's replicates with weights inversely proportional to the linear combination of the variance components. The weights influence how much each subject's estimate of intensity deviates away from the overall mean. Details on mixed effects models and calculating BLUP estimates can be found in most texts which discuss linear mixed effects models and variance components. See, for example, "Variance Components" by Searle, Casella, and McCulloch. Wiley Series in Probability and Mathematical Statistics, 1992 John Wiley & Sons.

Removal of Genes with Low Inter-Patient Variance.

The probe sets were reduced in number to include only those having more than 75% of their variance due to patient sample variance. Of 44,928 probe sets, 7,017 passed this filter and were carried on to further analysis.

Optional Reverse Log Transformation.

The BLUP expression value was used for differential expression analysis with the t-test. For computing the digital differential expression scores, the final summary value, x, was transformed back to the original scale by exponentiating, thus reversing the log transformation:

$$y=2^x-1$$

Single Marker Selection.

Single gene transcripts that appear associated with patient response categories or with patient time to progression can be identified using the feature ranking and filtering methodology described below. Single marker identification of predictive markers using the methodology described herein are set forth in Table 1 (Table 1A and Table 1B), Table 2 (Table 2A and Table 2B), and Table 3.

Model Selection.

A set of one or more gene transcripts that together classify samples into sensitive and resistant groups (or responsive and non-responsive) or predict TTP, in the context if a particular classifier algorithm, is referred to as a "model." The gene transcripts are referred to as "features." Determining which combination of gene transcript(s) best classifies samples into sensitive and resistant groups is referred to as "model selection." The following section describes the process of how the models of the present invention were identified. An exemplary model is set forth in Table 4. The methods provided herein along with the single marker identification or predictive markers can be used to identify additional models comprising markers of the invention.

Feature Ranking and Filtering

The first step in predictive model selection is to filter the 7,017 features down to a smaller number which show a correspondence with the sample classifications. Filtering involves first ranking the features by a scoring method, and then taking only the highest ranking features for further analysis. The filtering algorithms used in the present invention were: (1) t-test, and (2) Pooled Fold Change ("PFC). In certain aspects, the t-test was used to identify genes showing a small but consistent change in levels, and PFC was used to identify genes that were "off" in one class, but "on" in a fraction of the other class. For time to progression data, Cox proportional hazards modeling was used to determine a p-value for the association of a feature with time to progression.

The t-test is a standard statistical method to test for significant difference of means between two sets of points presumed to have normal distribution. It is closely related to the more ad hoc measure of differential expression SNR (signal to noise ratio), which is the difference of the class means divided by the sum of the class standard deviations, and has been used to analyze expression data before; for example, see the definition of $P(g,c)$, a measure of correlation between expression of gene g and class vector c, in Golub et al., "Molecular Classification of Cancer: Class discovery and class prediction by marker expression monitoring," Science, 286:531-537 (1999), the contents of which are incorporated herein by reference.

The Pooled Fold Change ("PFC") method is a measure of differential expression between two groups of samples, arbitrarily designated "control" and "tester." PFC finds genes with higher expression in the tester than in the control samples. For the two-class comparisons described in this invention, each class was used in turn as the tester. To qualify as having higher expression, tester samples must be above the $k^{th}$ percentile of the control sample. The fold-change values of tester samples are subjected to a nonlinear transformation that rises to a user-specified asymptote, in order to distinguish moderate levels of fold-change, but not make distinctions between very large fold-changes. The squashed fold-change values of the over-expressed tester samples are averaged to get the POOF score. In particular, PFC for a given tester sample, s, and gene, g, is computed as the average across tester samples of the compressed tester:control ratio R(s,g): $R(s,g)=C(x_{gs}/(k+x_g^Q))$, where $C(x)$ is the compression function $C(z)=A(1-e^{-z/A})$ for $z \geq T$, and $C(z)=0$ for $z<T$, where T is a threshold value no less than 1.0. A is an upper asymptote on the fold-change value, k is a constant reflecting the additive noise in the data, i.e., the fixed component of the variance in repeated measurements. $x_{gs}$ is the expression value of gene g in sample s, $x_g^Q$ is the Qth percentile of the control samples' expression value.

A minimum fraction f of the tester samples must have R(s,g) greater than 0; if this does not hold true, then the value of R(s,g) is set to 0.

We used the following parameters in our application of this algorithm:

| Parameter | Q | f | T | A | k |
|---|---|---|---|---|---|
| Value in run 1 | 0.9 | 0.3 | 1.2 | 5 | 0.25 |

Markers using the 7,017 probe sets were analyzed for differential expression across the 224 patient samples using the t-test and PFC methods described above. Probe sets found to be significant by t-test with a p-value less than 0.01, or having a PFC score other than 0, are reported in Table 1A, Table 1B, Table 2A, Table 2B and Table 3. These probe sets can be used in building marker sets as exemplified below.

A Cox proportional hazard analysis was performed to determine predictors of time until disease progression (TTP) in patients with relapsed and refractory multiple myeloma after treatment. This methodology is designed to analyze time to event data where some of the data may be censored (see E. T. Lee, Statistical Methods for Survival Data Analysis, $2^{nd}$ ed. 1992, John Wiley & Sons, Inc.). The median time to disease progression in the bortezomib group was 6.2 month (189 days); and the in the dexamethasone group was 3.5 months (106 days) (hazard ratio 0.55, P<0.0001). The date of progression was determined by computer algorithm. The statistical package SAS was used to perform the analysis; what parameters used to assess, etc.

We estimated Cox proportional hazard models for each of the 7017 transcripts passing the variance filter. That is, 7,017 models were estimated where each model contained 1 transcript. From each model, we obtained estimates of relative risk, 95% confidence intervals and p-values for the association of each transcript to TTP. From the 7017 models, we found 294 transcripts which had p-values of less than 0.01 in analyzing the 162 patients treated with bortezomib. We found 187 transcripts which had p-values of less than 0.01 in analyzing the 63 patients treated with dexamethasone. That is, these transcripts were significantly associated with TTP. These probe sets are listed in Table 1A, Table 1B, Table 2A, Table 2B and Table 3.

The rank reported in Tables 1A, 1B, 2A, 2B and 3 is determined by independently ranking the different scores of the markers. Ranks are generated for TTP, for PD vs R, for PD vs NC+R, for NR vs R. For the response comparisons, both T-test and digital scores are ranked. Thus there can be up to 7 different #1 ranks for proteasome inhibitor-specific predictive markers of treatment outcome.

Summary of the Data Provided in the Tables

The following terms are used throughout the Tables:

"No." or "Number" corresponds to an identification number for the predictive markers.

"Probeset ID" corresponds to the Affymetrix (Santa Clara, Calif.) identifier from the Human Genome U133A, B set oligonucleotide arrays which were used;

"Rep Public ID" refers to a Representative Public identifier for the gene corresponding to the probe set, and was taken from HG-U133A and HG-U133B annotation files, dated Apr. 12, 2005 which was available and downloaded from the GeneChip support area of the Affymetrix web site (accessible in the Human Genome U133 Set-Support Materials in the Support section of the website maintained by Affymetrix, Inc., Santa Clara, Calif.);

"SEQ ID NO" is the identification number in the sequence listing of the sequence corresponding to the sequence in the GenBank record identified by the Representative Public Identifier.

"Title" corresponds to a common description, where available, and was also taken from the Affymetrix annotation files;

"Gene symbol" corresponds to a symbol the gene is commonly known by, and was also taken from the Affymetrix annotation files;

"Entrez Gene ID" corresponds to the NCBI Unigene unique gene identifier;

"TTP Marker" represents indication of predictive marker which is significantly upregulated in samples with a correlation to longer time to progression (+), or are significantly upregulated in samples with a correlation to shorter time to progression (−);

"Response Marker" represents indication of predictive marker which is significantly upregulated in samples which are responsive to therapy (+), or are significantly upregulated in samples which are non-responsive to therapy (−);

"Type of Specificity" indicates the significance of TTP and/or response indicator as significant indicator of the predictive marker;

"Rank" corresponds to the process of determining which individual markers may be used in combination to group or classify a sample, for example, as responsive or non-responsive. Rank is indicated as the lowest rank score identified among all the methods for each of the predictive markers. In Table 3 where predictive markers are indicative of responsive or non-responsive for proteasome inhibition or glucocorticoid therapy, the rank indicates the lowest rank across various methods for bortezomib or dexamethasone treated samples. Three different feature selection methods were utilized for determining the best classifier, and rank determination: (1) t-test, (2) Pooled Fold Change ("PFC"), and (3) the Wilcoxon Rank-Sum Test.

Predictive markers of the invention are provided in Tables 1A, 1B, 2A, 2B, and 3. Table 1 sets forth predictive markers identified which are specific identifiers of response or non-response to proteasome inhibition therapy (e.g., bortezomib). Table 1A provides predictive markers which are upregulated indicators of non-response and/or correlate with shorter time to progression. Marker nos. 1-547 in Table 1A are newly associated predictive markers, and predictive markers no. 548-657 have been previously identified as associated markers predictive of non-response and/or correlation with shorter time to progression. See, International Patent Publication No. WO04053066, published Jun. 24, 2004. Table 1B provides predictive markers which are upregulated indicators of response and/or correlate with longer time to progression. Marker nos. 658-876 in Table 1B are newly associated predictive markers, and predictive markers no. 877-911 have been previously identified as associated markers predictive of response and/or correlation with longer time to progression. See, International Patent Publication No. WO04053066, published Jun. 24, 2004. Table 2 sets forth predictive markers identified which are specific identifiers of response or non-response to glucocorticoid therapy (e.g., dexamethasone). Table 2A provides predictive markers which are upregulated indicators of non-response and/or correlate with shorter time to progression. Marker nos. 912-1062 in Table 2A are newly associated predictive markers, and predictive markers no. 1063-1070 have been previously identified as associated markers predictive of non-response and/or correlation with shorter time to progression related to advanced stage patient's non-response to bortezomib treatment. See, International Patent Publication No. WO04053066, published Jun. 24, 2004. Table 2B provides predictive markers which are upregulated indicators of response and/or correlate with longer time to progression. Marker nos. 1071-1185 in Table 2B are newly associated predictive markers, and predictive markers no. 1186-1202 have been previously identified as associated markers predictive of response and/or correlation with longer time to progression related to advanced stage patient's response to bortezomib treatment. See, International Patent Publication No. WO04053066, published Jun. 24, 2004. Table 3 sets forth predictive markers identified which are not specific to proteasome inhibition therapy or glucocorticoid therapy, rather are indicator predictive markers of response/longer time to progression (+) or non-response/shorter time to progression (−) with regard to either therapy, and are indicators of general disease aggressiveness. Marker nos. 1203-1423 in Table 3 are newly associated predictive markers, and predictive markers no. 1424-1474 have been previously identified as associated markers predictive of non-response/correlation with shorter time to progression and/or response/correlation with longer time to progression related to advanced stage patient's response to bortezomib treatment. See, International Patent Publication No. WO04053066, published Jun. 24, 2004.

TABLE 1

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 1 | 220960_x_at | HG-U133A | NM_000983 | 1 | ribosomal protein L22 | RPL22 | 6146 | — | — | resp | 1 |
| 2 | 213941_x_at | HG-U133A | AI970731 | 2 | ribosomal protein S7 | RPS7 | 6201 | — | — | resp | 3 |
| 3 | 208752_x_at | HG-U133A | AI888672 | 3 | nucleosome assembly protein 1-like 1 | NAP1L1 | 4673 | — | — | resp | 7 |
| 4 | 200017_at | HG-U133A | NM_002954 | 4 | ribosomal protein S27a | RPS27A | 6233 | — | — | resp | 8 |
| 5 | 218589_at | HG-U133A | NM_005767 | 5 | purinergic receptor P2Y, G-protein coupled, 5 | P2RY5 | 10161 | — | — | resp | 8 |
| 6 | 200971_s_at | HG-U133A | NM_014445 | 6 | stress-associated endoplasmic reticulum protein 1 | SERP1 | 27230 | — | — | resp | 9 |
| 7 | 201094_at | HG-U133A | NM_001032 | 7 | ribosomal protein S29 | RPS29 | 6235 | — | — | resp | 10 |
| 8 | 201256_at | HG-U133A | NM_004718 | 8 | cytochrome c oxidase subunit VIIa polypeptide 2 like | COX7A2L | 9167 | — | — | resp | 11 |
| 9 | 233252_s_at | HG-U133B | AK024960 | 9 | spermatid perinuclear RNA binding protein | STRBP | 55342 | — | — | resp | 13 |
| 10 | 208517_x_at | HG-U133A | NM_001207 | 10 | basic transcription factor 3 | BTF3 | 689 | — | — | resp | 15 |
| 11 | 211939_x_at | HG-U133A | X74070 | 11 | basic transcription factor 3 | BTF3 | 689 | — | — | resp | 16 |
| 12 | 201592_at | HG-U133A | NM_003756 | 12 | eukaryotic translation initiation factor 3, subunit 3 gamma, 40 kDa | EIF3S3 | 8667 | — | — | resp | 19 |
| 13 | 200018_at | HG-U133A | NM_001017 | 13 | ribosomal protein S13 | RPS13 | 6207 | — | — | resp | 20 |
| 14 | 224468_s_at | HG-U133B | BC006151 | 14 | multidrug resistance-related protein | MGC13170 | 84798 | — | — | resp | 21 |
| 15 | 200074_s_at | HG-U133B | U16738 | 15 | ribosomal protein L14 | RPL14 | 9045 | — | — | resp | 22 |
| 16 | 201516_at | HG-U133A | NM_003132 | 16 | spermidine synthase | SRM | 6723 | — | — | resp | 22 |
| 17 | 213687_s_at | HG-U133B | BE968801 | 17 | ribosomal protein L35a | RPL35A | 6165 | — | — | resp | 22 |
| 18 | 200781_s_at | HG-U133A | NM_001019 | 18 | ribosomal protein S15a /// ADP-ribosylation factor-like 6 interacting protein | RPS15A /// ARL6IP | 23204 /// 6210 | — | — | resp | 23 |
| 19 | 225794_s_at | HG-U133B | AV751709 | 19 | hypothetical gene supported by AL449243 | LOC91689 | 91689 | — | — | resp | 24 |
| 20 | 200036_s_at | HG-U133A | NM_007104 | 20 | ribosomal protein L10A | RPL10A | 4736 | — | — | resp | 25 |
| 21 | 217491_x_at | HG-U133A | AF042165 | 21 | cytochrome c oxidase subunit VIIc | COX7C | 1350 | — | — | resp | 25 |
| 22 | 204118_at | HG-U133A | NM_001778 | 22 | CD48 antigen (B-cell membrane protein) | CD48 | 962 | — | — | resp | 26 |
| 23 | 221775_x_at | HG-U133A | BG152979 | 23 | ribosomal protein L22 | RPL22 | 6146 | — | — | resp | 26 |
| 24 | 200091_s_at | HG-U133A | AA888388 | 24 | ribosomal protein S25 | RPS25 | 6230 | — | — | resp | 27 |
| 25 | 200088_x_at | HG-U133A | AK026491 | 25 | ribosomal protein L12 | RPL12 | 6136 | — | — | resp | 28 |
| 26 | 208768_x_at | HG-U133A | D17652 | 26 | ribosomal protein L22 | RPL22 | 6146 | — | — | resp | 28 |
| 27 | 200010_at | HG-U133A | NM_000975 | 27 | ribosomal protein L11 | RPL11 | 6135 | — | — | resp | 29 |
| 28 | 213846_at | HG-U133A | AA382702 | 28 | cytochrome c oxidase subunit VIIc | COX7C | 1350 | — | — | resp | 30 |
| 29 | 225795_at | HG-U133B | AV751709 | 19 | hypothetical gene supported by AL449243 | LOC91689 | 91689 | — | — | resp | 30 |
| 30 | 200036_s_at | HG-U133A | NM_007104 | 20 | ribosomal protein L10a | RPL10A | 4736 | — | — | resp | 31 |
| 31 | 200034_s_at | HG-U133A | NM_000970 | 29 | ribosomal protein L6 | RPL6 | 6128 | — | — | resp | 32 |
| 32 | 211938_at | HG-U133B | BF247371 | 30 | eukaryotic translation initiation factor 4B | EIF4B | 1975 | — | — | resp | 32 |
| 33 | 227141_at | HG-U133B | AW205739 | 31 | hypothetical protein BC009514 | LOC127253 | 127253 | — | — | resp | 34 |
| 34 | 225230_at | HG-U133B | AI735261 | 32 | hypothetical protein MGC54289 | MGC54289 | 128338 | — | — | resp | 35 |
| 35 | 208697_s_at | HG-U133A | BC000734 | 33 | eukaryotic translation initiation factor 3, subunit 6 48 kDa | EIF3S6 | 3646 | — | — | resp | 36 |
| 36 | 200005_at | HG-U133A | NM_003753 | 34 | eukaryotic translation initiation factor 3, subunit 7 zeta, 66/67 kDa | EIF3S7 | 8664 | — | — | resp | 44 |
| 37 | 209058_at | HG-U133A | AB002282 | 35 | endothelial differentiation-related factor 1 | EDF1 | 8721 | — | — | resp | 47 |
| 38 | 201134_x_at | HG-U133A | NM_001867 | 36 | cytochrome c oxidase subunit VIIc | COX7C | 1350 | — | — | resp | 48 |
| 39 | 225951_s_at | HG-U133B | AV756026 | 37 | LOC440309 | | 440309 | — | — | resp | 49 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 40 | 216342_x_at | HG-U133A | AL121916 | 38 | ribosomal protein L15 | RPL15 | 6138 | — | — | resp | 50 |
| 41 | 221475_s_at | HG-U133A | NM_002948 | 39 | ribosomal protein L19 | RPL19 | 6143 | — | — | resp | 50 |
| 42 | 200029_at | HG-U133B | NM_000981 | 40 | ribosomal protein L19 | RPL19 | 6143 | — | — | resp | 55 |
| 43 | 201773_at | HG-U133A | NM_015339 | 40 | activity-dependent neuroprotector | ADNP | 23394 | — | — | resp | 56 |
| 44 | 200858_s_at | HG-U133B | NM_001012 | 41 | ribosomal protein S8 | RPS8 | 6202 | — | — | resp | 57 |
| 45 | 200005_at | HG-U133B | NM_003753 | 34 | eukaryotic translation initiation factor 3, subunit 7 zeta, 66/67 kDa | EIF3S7 | 8664 | — | — | resp | 58 |
| 46 | 200981_x_at | HG-U133A | NM_016592 | 43 | GNAS complex locus | GNAS | 2778 | — | — | resp | 59 |
| 47 | 203484_at | HG-U133A | NM_014302 | 44 | Sec61 gamma subunit | SEC61G | 23480 | — | — | resp | 60 |
| 48 | 200074_s_at | HG-U133A | U16738 | 15 | ribosomal protein L14 | RPL14 | 9045 | — | — | resp | 61 |
| 49 | 224196_x_at | HG-U133B | AF161492 | 45 | CGI-30 protein | CGI-30 | 51611 | — | — | resp | 61 |
| 50 | 228622_s_at | HG-U133B | AW071239 | 46 | DnaJ (Hsp40) homolog, subfamily C, member 4 | DNAJC4 | 3338 | — | — | resp | 61 |
| 51 | 208635_x_at | HG-U133A | BF976260 | 47 | nascent-polypeptide-associated complex alpha polypeptide | NACA | 4666 | — | — | resp | 62 |
| 52 | 200705_s_at | HG-U133A | NM_001959 | 48 | eukaryotic translation elongation factor 1 beta 2 | EEF1B2 | 1933 | — | — | resp | 66 |
| 53 | 200010_at | HG-U133A | NM_000975 | 27 | ribosomal protein L11 | RPL11 | 6135 | — | — | resp | 67 |
| 54 | 200013_at | HG-U133A | NM_000986 | 49 | ribosomal protein L24 | RPL24 | 6152 | — | — | resp | 69 |
| 55 | 200099_s_at | HG-U133B | AL356115 | 50 | ribosomal protein S3A | RPS3A | 6189 | — | — | resp | 71 |
| 56 | 200025_s_at | HG-U133B | NM_000988 | 51 | ribosomal protein L27 | RPL27 | 6155 | — | — | resp | 74 |
| 57 | 200091_s_at | HG-U133B | AA888388 | 24 | ribosomal protein S25 | RPS25 | 6230 | — | — | resp | 75 |
| 58 | 202231_at | HG-U133A | NM_006360 | 52 | dendritic cell protein | GA17 | 10480 | — | — | resp | 76 |
| 59 | 217408_at | HG-U133A | AL050361 | 53 | mitochondrial ribosomal protein S18B | MRPS18B | 28973 | — | — | resp | 76 |
| 60 | 200626_s_at | HG-U133A | NM_018834 | 54 | matrin 3 | MATR3 | 9782 | — | — | resp | 78 |
| 61 | 213762_x_at | HG-U133B | AI452524 | 55 | RNA binding motif protein, X-linked | RBMX | 27316 | — | — | resp | 80 |
| 62 | 200081_s_at | HG-U133A | BE741754 | 56 | ribosomal protein S6 | RPS6 | 6194 | — | — | resp | 81 |
| 63 | 213890_x_at | HG-U133A | AI200589 | 57 | ribosomal protein S16 | RPS16 | 6217 | — | — | resp | 81 |
| 64 | 200099_s_at | HG-U133B | AL356115 | 50 | ribosomal protein S3A | RPS3A | 6189 | — | — | resp | 83 |
| 65 | 200002_at | HG-U133B | NM_007209 | 58 | ribosomal protein L35 | RPL35 | 11224 | — | — | resp | 87 |
| 66 | 200062_s_at | HG-U133A | L05095 | 59 | ribosomal protein L30 | RPL30 | 6156 | — | — | resp | 87 |
| 67 | 200013_at | HG-U133B | NM_000986 | 49 | ribosomal protein L24 | RPL24 | 6152 | — | — | resp | 88 |
| 68 | 200018_at | HG-U133B | NM_001017 | 13 | ribosomal protein S13 | RPS13 | 6207 | — | — | resp | 91 |
| 69 | 201622_at | HG-U133A | NM_014390 | 60 | staphylococcal nuclease domain containing 1 | SND1 | 27044 | — | — | resp | 92 |
| 70 | 200029_at | HG-U133A | NM_000981 | 40 | ribosomal protein L19 | RPL19 | 6143 | — | — | resp | 93 |
| 71 | 223015_at | HG-U133B | AF212241 | 61 | eukaryotic translation initiation factor (eIF) 2A | eIF2A | 83939 | — | — | resp | 94 |
| 72 | 200624_s_at | HG-U133A | AA577695 | 62 | matrin 3 | MATR3 | 9782 | — | — | resp | 96 |
| 73 | 212600_at | HG-U133B | AV727381 | 63 | ubiquinol-cytochrome c reductase core protein II | UQCRC2 | 7385 | — | — | resp | 97 |
| 74 | 200034_s_at | HG-U133A | NM_000970 | 29 | ribosomal protein L6 | RPL6 | 6129 | — | — | resp | 99 |
| 75 | 212042_x_at | HG-U133A | BG389744 | 64 | ribosomal protein L7 | RPL7 | 6129 | — | — | resp | 99 |
| 76 | 208319_s_at | HG-U133B | NM_006743 | 65 | RNA binding motif (RNP1, RRM) protein 3 | RBM3 | 5935 | — | — | resp | 100 |
| 77 | 226296_s_at | HG-U133B | AK021626 | 66 | mitochondrial ribosomal protein S15 | MRPS15 | 64960 | — | — | resp | 101 |
| 78 | 223245_at | HG-U133B | AK024285 | 67 | spermatid perinuclear RNA binding protein | STRBP | 55342 | — | — | resp | 102 |
| 79 | 200755_x_at | HG-U133A | NM_005594 | 68 | nascent-polypeptide-associated complex alpha polypeptide | NACA | 4666 | — | — | resp | 103 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 80 | 201600_at | HG-U133A | NM_007273 | 69 | repressor of estrogen receptor activity | REA | 11331 | — | — | resp | 109 |
| 81 | 203857_s_at | HG-U133A | NM_006810 | 70 | for protein disulfide isomerase-related | PDIR | 10954 | — | — | resp | 109 |
| 82 | 212826_s_at | HG-U133A | AI961224 | 71 | solute carrier family 25 (mitochondrial carrier; adenine nucleotide translocator), member 6 | SLC25A6 | 293 | — | — | resp | 111 |
| 83 | 203621_at | HG-U133A | NM_002492 | 72 | NADH dehydrogenase (ubiquinone) 1 beta subcomplex, 5, 16 kDa | NDUFB5 | 4711 | — | — | resp | 112 |
| 84 | 200963_x_at | HG-U133A | NM_000993 | 73 | ribosomal protein L31 | RPL31 | 6160 | — | — | resp | 113 |
| 85 | 200909_s_at | HG-U133A | NM_001004 | 74 | ribosomal protein, large P2 | RPLP2 | 6181 | — | — | resp | 114 |
| 86 | 217768_at | HG-U133A | NM_016039 | 75 | chromosome 14 open reading frame 166 | C14orf166 | 51637 | — | — | resp | 115 |
| 87 | 200936_at | HG-U133A | NM_000973 | 76 | ribosomal protein L8 | RPL8 | 6132 | — | — | resp | 117 |
| 88 | 214800_x_at | HG-U133A | R83000 | 77 | basic transcription factor 3 | BTF3 | 689 | — | — | resp | 119 |
| 89 | 224935_at | HG-U133A | BG165815 | 78 | Eukaryotic translation initiation factor 2, subunit 3 gamma, 52 kDa | EIF2S3 | 1968 | — | — | resp | 123 |
| 90 | 200823_x_at | HG-U133A | NM_000992 | 79 | ribosomal protein L29 | RPL29 | 6159 | — | — | resp | 125 |
| 91 | 216520_s_at | HG-U133A | AF072098 | 80 | tumor protein, translationally-controlled 1 | TPT1 | 7178 | — | — | resp | 126 |
| 92 | 207040_s_at | HG-U133A | NM_003932 | 81 | suppression of tumorigenicity 13 (colon carcinoma) (Hsp70 interacting protein) | ST13 | 6767 | — | — | resp | 127 |
| 93 | 222993_at | HG-U133B | AF325707 | 82 | mitochondrial ribosomal protein L37 | MRPL37 | 51253 | — | — | resp | 127 |
| 94 | 200016_x_at | HG-U133A | NM_002136 | 83 | heterogeneous nuclear ribonucleoprotein A1 | HNRPA1 | 3178 | — | — | resp | 128 |
| 95 | 202233_s_at | HG-U133A | NM_006004 | 84 | ubiquinol-cytochrome c reductase hinge protein | UQCRH | 7388 | — | — | resp | 128 |
| 96 | 217673_x_at | HG-U133A | AA650558 | 85 | GNAS complex locus | GNAS | 2778 | — | — | resp | 130 |
| 97 | 202515_at | HG-U133B | BG251175 | 86 | discs, large homolog 1 (Drosophila) | DLG1 | 1739 | — | — | resp | 131 |
| 98 | 212967_x_at | HG-U133A | AW148801 | 87 | nucleosome assembly protein 1-like 1 | NAP1L1 | 4673 | — | — | resp | 131 |
| 99 | 218213_s_at | HG-U133A | NM_014206 | 88 | chromosome 11 open reading frame 10 | C11orf10 | 746 | — | — | resp | 133 |
| 100 | 228095_at | HG-U133B | AA608749 | 89 | | | | — | — | resp | 133 |
| 101 | 200062_s_at | HG-U133B | L05095 | 59 | ribosomal protein L30 | RPL30 | 6156 | — | — | resp | 134 |
| 102 | 212273_x_at | HG-U133A | AI591100 | 90 | GNAS complex locus | GNAS | 2778 | — | — | resp | 135 |
| 103 | 200055_at | HG-U133A | NM_006284 | 91 | TAF10 RNA polymerase II, TATA box binding protein (TBP)-associated factor, 30 kDa | TAF10 | 6881 | — | — | resp | 136 |
| 104 | 222832_s_at | HG-U133B | AA746206 | 92 | chromosome 2 open reading frame 33 | C2orf33 | 56947 | — | — | resp | 136 |
| 105 | 218147_s_at | HG-U133A | NM_018446 | 93 | glycosyltransferase 8 domain containing 1 | GLT8D1 | 55830 | — | — | resp | 137 |
| 106 | 217927_at | HG-U133A | NM_014041 | 94 | signal peptidase complex subunit 1 homolog (S. cerevisiae) | SPCS1 | 28972 | — | — | resp | 139 |
| 107 | 200651_at | HG-U133A | NM_006098 | 95 | guanine nucleotide binding protein (G protein), beta polypeptide 2-like 1 | GNB2L1 | 10399 | — | — | resp | 140 |
| 108 | 201894_s_at | HG-U133A | NM_001920 | 96 | signal sequence receptor, alpha (translocon-associated protein alpha) | SSR1 | 6745 | — | — | resp | 140 |
| 109 | 201812_s_at | HG-U133A | NM_019059 | 97 | translocase of outer mitochondrial membrane 7 homolog (yeast) /// hypothetical protein LOC201725 | TOMM7 /// LOC201725 | 201725 /// 54543 | — | — | resp | 141 |
| 110 | 208717_at | HG-U133A | BC001669 | 98 | oxidase (cytochrome c) assembly 1-like | OXA1L | 5018 | — | — | resp | 144 |
| 111 | 212995_x_at | HG-U133A | BG255188 | 99 | hypothetical protein FLJ14346 | FLJ14346 | 80097 | — | — | resp | 145 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 112 | 203113_s_at | HG-U133A | NM_001960 | 100 | eukaryotic translation elongation factor 1 delta (guanine nucleotide exchange protein) | EEF1D | 1936 | — | — | resp | 147 |
| 113 | 213041_s_at | HG-U133A | BE798517 | 101 | ATP synthase, H+ transporting, mitochondrial F1 complex, delta subunit | ATP5D | 513 | — | — | resp | 147 |
| 114 | 204944_at | HG-U133A | NM_002841 | 102 | protein tyrosine phosphatase, receptor type, G | PTPRG | 5793 | — | — | resp | 149 |
| 115 | 224615_x_at | HG-U133B | AL110115 | 103 | histocompatibility (minor) 13 | HM13 | 81502 | — | — | resp | 149 |
| 116 | 225547_at | HG-U133B | BG169443 | 104 | U87HG mRNA, complete sequence | | | — | — | resp | 150 |
| 117 | 223671_x_at | HG-U133B | AF248965 | 105 | CGI-30 protein | CGI-30 | 51611 | — | — | resp | 151 |
| 118 | 214042_s_at | HG-U133A | AW071997 | 106 | ribosomal protein L22 | RPL22 | 6146 | — | — | resp | 152 |
| 119 | 200094_s_at | HG-U133A | AI004246 | 107 | eukaryotic translation elongation factor 2 | EEF2 | 1938 | — | — | resp | 153 |
| 120 | 200017_at | HG-U133A | NM_002954 | 4 | ribosomal protein S27a | RPS27A | 6233 | — | — | resp | 154 |
| 121 | 200012_x_at | HG-U133A | NM_000982 | 108 | ribosomal protein L21 | RPL21 | 6144 | — | — | resp | 156 |
| 122 | 200016_x_at | HG-U133A | NM_002136 | 83 | heterogeneous nuclear ribonucleoprotein A1 | HNRPA1 | 3178 | — | — | resp | 157 |
| 123 | 224523_at | HG-U133B | BC006475 | 109 | hypothetical protein MGC4308 | MGC4308 | 84319 | — | — | resp | 157 |
| 124 | 204102_s_at | HG-U133A | NM_001961 | 110 | eukaryotic translation elongation factor 2 | EEF2 | 1938 | — | — | resp | 161 |
| 125 | 200025_s_at | HG-U133A | NM_000988 | 51 | ribosomal protein L27 | RPL27 | 6155 | — | — | resp | 162 |
| 126 | 221263_s_at | HG-U133A | NM_031287 | 111 | splicing factor 3b, subunit 5, 10 kDa | SF3B5 | 83443 | — | — | resp | 163 |
| 127 | 210027_s_at | HG-U133A | M80261 | 112 | APEX nuclease (multifunctional DNA repair enzyme) 1 | APEX1 | 328 | — | — | resp | 164 |
| 128 | 220994_s_at | HG-U133A | NM_014178 | 113 | syntaxin binding protein 6 (amisyn) | STXBP6 | 29091 | — | — | resp | 166 |
| 129 | 209397_at | HG-U133A | BC000147 | 114 | malic enzyme 2, NAD(+)-dependent, mitochondrial | ME2 | 4200 | — | — | resp | 167 |
| 130 | 223847_at | HG-U133B | AF267855 | 115 | endoplasmic reticulum-golgi intermediate compartment 32 kDa protein | KIAA1181 | 57222 | — | — | resp | 168 |
| 131 | 223246_s_at | HG-U133B | BC002693 | 116 | spermatid perinuclear RNA binding protein | STRBP | 55342 | — | — | resp | 169 |
| 132 | 224439_x_at | HG-U133B | BC005966 | 117 | ring finger protein 7 | RNF7 | 9616 | — | — | resp | 169 |
| 133 | 211666_x_at | HG-U133A | L22453 | 118 | ribosomal protein L3 | RPL3 | 6122 | — | — | resp | 171 |
| 134 | 218101_s_at | HG-U133A | NM_004549 | 119 | NADH dehydrogenase (ubiquinone) 1, subcomplex unknown, 2, 14.5 kDa | NDUFC2 | 4718 | — | — | resp | 172 |
| 135 | 207628_s_at | HG-U133A | NM_017528 | 120 | Williams Beuren syndrome chromosome region 22 | WBSCR22 | 114049 | — | — | resp | 173 |
| 136 | 200093_s_at | HG-U133A | N32864 | 121 | histidine triad nucleotide binding protein 1 | HINT1 | 3094 | — | — | resp | 174 |
| 137 | 201106_at | HG-U133A | NM_002085 | 122 | glutathione peroxidase 4 (phospholipid hydroperoxidase) | GPX4 | 2879 | — | — | resp | 174 |
| 138 | 201593_s_at | HG-U133A | AV716798 | 123 | likely ortholog of mouse immediate early response, erythropoietin 4 | LEREPO4 | 55854 | — | — | resp | 175 |
| 139 | 211971_s_at | HG-U133A | AI653608 | 124 | leucine-rich PPR-motif containing | LRPPRC | 10128 | — | — | resp | 178 |
| 140 | 214173_x_at | HG-U133A | AW514900 | 125 | chromosome 19 open reading frame 2 | C19orf2 | 8725 | — | — | resp | 178 |
| 141 | 208887_at | HG-U133A | BC000733 | 126 | eukaryotic translation initiation factor 3, subunit 4 delta, 44 kDa | EIF3S4 | 8666 | — | — | resp | 180 |
| 142 | 216570_x_at | HG-U133A | AL096829 | 127 | | | | — | — | resp | 181 |
| 143 | 212085_at | HG-U133A | AA916851 | 128 | solute carrier family 25 (mitochondrial carrier; adenine nucleotide translocator), member 6 | SLC25A6 | 293 | — | — | resp | 182 |
| 144 | 218927_s_at | HG-U133A | NM_018641 | 129 | carbohydrate (chondroitin 4) sulfotransferase 12 | CHST12 | 55501 | — | — | resp | 183 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 145 | 235721_at | HG-U133B | N62126 | 130 | deltex 3 homolog (Drosophila) | DTX3 | 196403 | — | — | resp | 184 |
| 146 | 218146_at | HG-U133A | NM_018446 | 93 | glycosyltransferase 8 domain containing 1 | GLT8D1 | 55830 | — | — | resp | 185 |
| 147 | 200094_s_at | HG-U133A | AI004246 | 107 | eukaryotic translation elongation factor 2 | EEF2 | 1938 | — | — | resp | 186 |
| 148 | 211662_s_at | HG-U133A | L08666 | 131 | voltage-dependent anion channel 2 | VDAC2 | 7417 | — | — | resp | 186 |
| 149 | 218774_at | HG-U133A | NM_014026 | 132 | decapping enzyme, scavenger | DCPS | 28960 | — | — | resp | 188 |
| 150 | 227558_at | HG-U133B | AI570531 | 133 | chromobox homolog 4 (Pc class homolog, Drosophila) | CBX4 | 8535 | — | — | resp | 190 |
| 151 | 209059_s_at | HG-U133A | AB002282 | 35 | endothelial differentiation-related factor 1 | EDF1 | 8721 | — | — | resp | 191 |
| 152 | 201784_s_at | HG-U133A | NM_014267 | 134 | small acidic protein | SMAP | 10944 | — | — | resp | 192 |
| 153 | 218495_at | HG-U133A | NM_004182 | 135 | ubiquitously-expressed transcript | UXT | 8409 | — | — | resp | 193 |
| 154 | 218684_at | HG-U133A | NM_018103 | 136 | leucine rich repeat containing 5 | LRRC5 | 55144 | — | — | resp | 194 |
| 155 | 200967_at | HG-U133A | NM_000942 | 137 | peptidylprolyl isomerase B (cyclophilin B) | PPIB | 5479 | — | — | resp | 196 |
| 156 | 219293_s_at | HG-U133A | NM_013341 | 138 | GTP-binding protein PTD004 | PTD004 | 29789 | — | — | resp | 200 |
| 157 | 213864_s_at | HG-U133A | AI985751 | 139 | nucleosome assembly protein 1-like 1 | NAP1L1 | 4673 | — | — | resp | 202 |
| 158 | 217926_at | HG-U133A | NM_014047 | 140 | HSPC023 protein | HSPC023 | 28974 | — | — | resp | 205 |
| 159 | 208746_x_at | HG-U133A | AF070655 | 141 | ATP synthase, H+ transporting, mitochondrial F0 complex, subunit g | ATP5L | 10632 | — | — | resp | 207 |
| 160 | 229742_at | HG-U133B | AA420989 | 142 | hypothetical LOC145853 | LOC145853 | 145853 | — | — | resp | 207 |
| 161 | 207585_s_at | HG-U133A | NM_001001 | 143 | ribosomal protein L36a-like | RPL36AL | 6166 | — | — | resp | 208 |
| 162 | 214271_x_at | HG-U133A | AA281332 | 144 | ribosomal protein L12 | RPL12 | 6136 | — | — | resp | 210 |
| 163 | 213080_x_at | HG-U133A | BF214492 | 145 | ribosomal protein L5 | RPL5 | 6125 | — | — | resp | 213 |
| 164 | 222229_x_at | HG-U133A | AL121871 | 146 | ribosomal protein L26 /// similar to 60S ribosomal protein L26 | RPL26 /// LOC400055 /// LOC441073 | 400055 /// 441073 /// 6154 | — | — | resp | 213 |
| 165 | 224932_at | HG-U133B | AI814909 | 147 | chromosome 22 open reading frame 16 | C22orf16 | 400916 | — | — | | 214 |
| 166 | 200055_at | HG-U133A | NM_006284 | 91 | TAF10 RNA polymerase II, TATA box binding protein (TBP)-associated factor, 30 kDa | TAF10 | 6881 | — | — | | 215 |
| 167 | 225220_at | HG-U133B | BF340290 | 148 | CDNA clone IMAGE: 4184613, partial cds | | | — | — | resp | 218 |
| 168 | 221476_s_at | HG-U133A | AF279903 | 149 | ribosomal protein L15 | RPL15 | 6138 | — | — | resp | 219 |
| 169 | 223165_s_at | HG-U133B | BC004469 | 150 | inositol hexaphosphate kinase 2 | IHPK2 | 51447 | — | — | resp | 221 |
| 170 | 229803_s_at | HG-U133B | AI347000 | 151 | Nudix (nucleoside diphosphate linked moiety X)-type motif 3 | NUDT3 | 11165 | — | — | resp | 223 |
| 171 | 200048_s_at | HG-U133A | NM_006694 | 152 | jumping translocation breakpoint | JTB | 10899 | — | — | resp | 228 |
| 172 | 209330_s_at | HG-U133A | D55674 | 153 | heterogeneous nuclear ribonucleoprotein D (AU-rich element RNA binding protein 1, 37 kDa) | HNRPD | 3184 | — | — | resp | 230 |
| 173 | 213860_x_at | HG-U133B | AW268585 | 154 | casein kinase 1, alpha 1 | CSNK1A1 | 1452 | — | — | resp | 231 |
| 174 | 200006_at | HG-U133A | NM_007262 | 155 | Parkinson disease (autosomal recessive, early onset) 7 | PARK7 | 11315 | — | — | resp | 232 |
| 175 | 213086_s_at | HG-U133A | BF341845 | 156 | casein kinase 1, alpha 1 | CSNK1A1 | 1452 | — | — | resp | 232 |
| 176 | 226131_s_at | HG-U133B | AA583817 | 157 | ribosomal protein S16 | RPS16 | 6217 | — | — | resp | 235 |
| 177 | 200038_s_at | HG-U133A | NM_000985 | 158 | ribosomal protein L17 | RPL17 | 6139 | — | — | resp | 237 |
| 178 | 208620_at | HG-U133A | U24223 | 159 | poly(rC) binding protein 1 | PCBP1 | 5093 | — | — | resp | 238 |
| 179 | 200811_at | HG-U133A | NM_001280 | 160 | cold inducible RNA binding protein | CIRBP | 1153 | — | — | resp | 239 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 180 | 208669_s_at | HG-U133A | AF109873 | 161 | CREBBP/EP300 inhibitor 1 | CRI1 | 23741 | — | — | resp | 240 |
| 181 | 215227_x_at | HG-U133A | BG035989 | 162 | acid phosphatase 1, soluble | ACP1 | 52 | — | — | resp | 244 |
| 182 | 202961_s_at | HG-U133A | NM_004889 | 163 | ATP synthase, H+ transporting, mitochondrial F0 complex, subunit f, isoform 2 | ATP5J2 | 9551 | — | — | resp | 247 |
| 183 | 200048_s_at | HG-U133A | NM_006694 | 152 | jumping translocation breakpoint | JTB | 10899 | — | — | resp | 248 |
| 184 | 200093_s_at | HG-U133A | N32864 | 121 | histidine triad nucleotide binding protein 1 | HINT1 | 3094 | — | — | resp | 250 |
| 185 | 209009_at | HG-U133A | BC001169 | 164 | esterase D/formylglutathione hydrolase | ESD | 2098 | — | — | resp | 252 |
| 186 | 202649_x_at | HG-U133A | NM_001022 | 165 | ribosomal protein S19 | RPS19 | 6223 | — | — | resp | 254 |
| 187 | 213801_x_at | HG-U133A | AW304232 | 166 | ribosomal protein SA /// similar to Laminin receptor 1 | RPSA /// LOC388524 | 388524 /// 3921 | — | — | resp | 254 |
| 188 | 222580_at | HG-U133B | AK023596 | 167 | zinc finger protein 644 | ZNF644 | 84146 | — | — | resp | 256 |
| 189 | 200669_s_at | HG-U133A | NM_003340 | 168 | ubiquitin-conjugating enzyme E2D 3 (UBC4/5 homolog, yeast) | UBE2D3 | 7323 | — | — | resp | 257 |
| 190 | 200038_s_at | HG-U133B | NM_000985 | 158 | ribosomal protein L17 | RPL17 | 6139 | — | — | resp | 258 |
| 191 | 222412_s_at | HG-U133B | AW150923 | 169 | signal sequence receptor, gamma (translocon-associated protein gamma) | SSR3 | 6747 | — | — | resp | 259 |
| 192 | 201001_s_at | HG-U133A | BG164064 | 170 | ubiquitin-conjugating enzyme E2 variant 1 | UBE2V1 /// Kua-UEV | 387522 /// 7335 | — | — | resp | 260 |
| 193 | 209150_s_at | HG-U133A | U94831 | 171 | transmembrane 9 superfamily member 1 | TM9SF1 | 10548 | — | — | resp | 263 |
| 194 | 216559_x_at | HG-U133A | AL050348 | 172 | heterogeneous nuclear ribonucleoprotein A1 | HNRPA1 | 3178 | — | — | resp | 265 |
| 195 | 225063_at | HG-U133B | BF568780 | 173 | bone marrow stromal cell-derived ubiquitin-like | BMSC-UbP | 84993 | — | — | resp | 269 |
| 196 | 217790_s_at | HG-U133A | NM_007107 | 174 | signal sequence receptor, gamma (translocon-associated protein gamma) | SSR3 | 6747 | — | — | resp | 271 |
| 197 | 211942_x_at | HG-U133A | BF979419 | 175 | ribosomal protein L13a | RPL13A | 23521 | — | — | resp | 275 |
| 198 | 212716_s_at | HG-U133A | AW083133 | 176 | eukaryotic translation initiation factor 3, subunit 12 | EIF3S12 | 27335 | — | — | resp | 275 |
| 199 | 200990_at | HG-U133A | NM_005762 | 177 | tripartite motif-containing 28 | TRIM28 | 10155 | — | — | resp | 276 |
| 200 | 239082_at | HG-U133B | BF437161 | 178 | | | | — | — | resp | 276 |
| 201 | 224577_at | HG-U133B | AB033007 | 179 | endoplasmic reticulum-golgi intermediate compartment 32 kDa protein | KIAA1181 | 57222 | — | — | resp | 278 |
| 202 | 202785_at | HG-U133A | NM_005001 | 180 | NADH dehydrogenase (ubiquinone) 1 alpha subcomplex, 7, 14.5 kDa | NDUFA7 | 4701 | — | — | resp | 279 |
| 203 | 213356_x_at | HG-U133A | AL568186 | 181 | heterogeneous nuclear ribonucleoprotein A1 /// similar to Heterogeneous nuclear ribonucleoprotein A1 (Helix-destabilizing protein) (Single-strand binding protein) (hnRNP core protein A1) (HDP) | HNRPA1 /// LOC441507 | 3178 /// 441507 | — | — | resp | 279 |
| 204 | 200726_at | HG-U133A | NM_002710 | 182 | protein phosphatase 1, catalytic subunit, gamma isoform | PPP1CC | 5501 | — | — | resp | 280 |
| 205 | 201781_s_at | HG-U133A | AL558532 | 183 | aryl hydrocarbon receptor interacting protein | AIP | 9049 | — | — | resp | 282 |
| 206 | 227711_at | HG-U133B | BG150433 | 184 | hypothetical protein FLJ32942 | FLJ32942 | 121355 | — | — | resp | 283 |
| 207 | 201002_s_at | HG-U133A | U39361 | 185 | ubiquitin-conjugating enzyme E2 variant 1 | UBE2V1 /// Kua-UEV | 387522 /// 7335 | — | — | resp | 284 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 208 | 200032_s_at | HG-U133B | NM_000661 | 186 | ribosomal protein L9 | RPL9 | 6133 | — | — | resp | 285 |
| 209 | 227134_at | HG-U133B | AI341537 | 187 | synaptotagmin-like 1 | SYTL1 | 84958 | — | — | resp | 288 |
| 210 | 213129_s_at | HG-U133A | AI970157 | 188 | glycine cleavage system protein H (aminomethyl carrier) | GCSH | 2653 | — | — | resp | 292 |
| 211 | 225706_at | HG-U133B | AI761989 | 189 | glucocorticoid induced transcript 1 | GLCCI1 | 113263 | — | — | resp | 293 |
| 212 | 200002_at | HG-U133A | NM_007209 | 58 | ribosomal protein L35 | RPL35 | 11224 | — | — | resp | 294 |
| 213 | 223193_x_at | HG-U133B | AF201944 | 190 | growth and transformation-dependent protein | E2IG5 | 26355 | — | — | resp | 297 |
| 214 | 200022_at | HG-U133A | NM_000979 | 191 | ribosomal protein L18 | RPL18 | 6141 | — | — | resp | 298 |
| 215 | 200088_x_at | HG-U133A | AK026491 | 25 | ribosomal protein L12 | RPL12 | 6136 | — | — | resp | 299 |
| 216 | 225700_at | HG-U133B | AC006042 | 192 | glucocorticoid induced transcript 1 | GLCCI1 | 113263 | — | — | resp | 300 |
| 217 | 209787_s_at | HG-U133A | BC001282 | 193 | high mobility group nucleosomal binding domain 4 | HMGN4 | 10473 | — | — | resp | 301 |
| 218 | 200081_s_at | HG-U133A | BE741754 | 56 | ribosomal protein S6 | RPS6 | 6194 | — | — | resp | 303 |
| 219 | 224345_x_at | HG-U133B | AF107495 | 194 | growth and transformation-dependent protein | E2IG5 | 26355 | — | — | resp | 304 |
| 220 | 209329_x_at | HG-U133A | BC000587 | 195 | hypothetical protein MGC2198 | MGC2198 | 192286 | — | — | resp | 307 |
| 221 | 217773_s_at | HG-U133A | NM_002489 | 196 | NADH dehydrogenase (ubiquinone) 1 alpha subcomplex, 4, 9 kDa | NDUFA4 | 4697 | — | — | resp | 308 |
| 222 | 201665_x_at | HG-U133A | NM_001021 | 197 | ribosomal protein S17 | RPS17 | 6218 | — | — | resp | 309 |
| 223 | 200674_s_at | HG-U133A | NM_000994 | 198 | ribosomal protein L32 | RPL32 | 6161 | — | — | resp | 311 |
| 224 | 202209_at | HG-U133A | NM_014463 | 199 | LSM3 homolog, U6 small nuclear RNA associated (S. cerevisiae) | LSM3 | 27258 | — | — | resp | 311 |
| 225 | 229563_s_at | HG-U133B | BG231561 | 200 | ribosomal protein L10a | RPL10A | 4736 | — | — | resp | 312 |
| 226 | 200057_s_at | HG-U133B | NM_007363 | 201 | non-POU domain containing, octamer-binding | NONO | 4841 | — | — | resp | 313 |
| 227 | 212352_s_at | HG-U133A | BE780075 | 202 | transmembrane trafficking protein | TMP21 | 10972 | — | — | resp | 313 |
| 228 | 221972_s_at | HG-U133B | AL571362 | 203 | calcium binding protein Cab45 precursor | Cab45 | 51150 | — | — | resp | 314 |
| 229 | 226386_at | HG-U133B | BG397444 | 204 | chromosome 7 open reading frame 30 | C7orf30 | 115416 | — | — | resp | 315 |
| 230 | 200741_s_at | HG-U133A | NM_001030 | 205 | ribosomal protein S27 (metallopanstimulin 1) | RPS27 | 6232 | — | — | resp | 317 |
| 231 | 226073_at | HG-U133B | BE857362 | 206 | hypothetical protein LOC219854 | LOC219854 | 219854 | — | — | resp | 318 |
| 232 | 238026_at | HG-U133B | AI458020 | 207 | | | | — | — | resp | 318 |
| 233 | 207871_s_at | HG-U133A | NM_018412 | 208 | suppression of tumorigenicity 7 | ST7 | 7982 | — | — | resp | 323 |
| 234 | 213376_at | HG-U133B | AI656706 | 209 | zinc finger and BTB domain containing 1 | ZBTB1 | 22890 | — | — | resp | 323 |
| 235 | 200891_s_at | HG-U133A | NM_003144 | 210 | signal sequence receptor, alpha (translocon-associated protein alpha) | SSR1 | 6745 | — | — | resp | 324 |
| 236 | 223157_at | HG-U133B | BC004894 | 211 | chromosome 4 open reading frame 14 | C4orf14 | 84273 | — | — | resp | 324 |
| 237 | 225606_at | HG-U133B | AI949179 | 212 | BCL2-like 11 (apoptosis facilitator) | BCL2L11 | 10018 | — | — | resp | 327 |
| 238 | 200968_s_at | HG-U133A | NM_000942 | 137 | peptidylprolyl isomerase B (cyclophilin B) | PPIB | 5479 | — | — | resp | 328 |
| 239 | 213414_s_at | HG-U133A | BE259729 | 213 | ribosomal protein S19 | RPS19 | 6223 | — | — | resp | 330 |
| 240 | 226845_at | HG-U133B | AL036350 | 214 | helicase/primase complex protein | LOC150678 | 150678 | — | — | resp | 331 |
| 241 | 212460_at | HG-U133A | BE738425 | 215 | chromosome 14 open reading frame 147 | C14orf147 | 171546 | — | — | resp | 332 |
| 242 | 231530_s_at | HG-U133B | BG150085 | 216 | chromosome 11 open reading frame 1 | C11orf1 | 64776 | — | — | resp | 332 |
| 243 | 219762_s_at | HG-U133B | NM_015414 | 217 | ribosomal protein L36 | RPL36 | 25873 | — | — | resp | 333 |
| 244 | 213897_s_at | HG-U133A | AI832239 | 218 | mitochondrial ribosomal protein L23 | MRPL23 | 6150 | — | — | resp | 335 |
| 245 | 200682_s_at | HG-U133A | BG531983 | 219 | ubiquitin-conjugating enzyme E2L 3 | UBE2L3 | 7332 | — | — | resp | 342 |
| 246 | 203338_at | HG-U133A | NM_006246 | 220 | protein phosphatase 2, regulatory subunit B (B56), epsilon isoform | PPP2R5E | 5529 | — | — | resp | 343 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 247 | 224936_at | HG-U133B | BE252813 | 221 | eukaryotic translation initiation factor 2, subunit 3 gamma, 52 kDa | EIF2S3 | 1968 | — | — | resp | 343 |
| 248 | 228690_s_at | HG-U133B | AI743115 | 222 | NADH dehydrogenase (ubiquinone) 1 alpha subcomplex, 11, 14.7 kDa | NDUFA11 | 126328 | — | — | resp | 344 |
| 249 | 208645_s_at | HG-U133A | AF116710 | 223 | ribosomal protein S14 | RPS14 | 6208 | — | — | resp | 345 |
| 250 | 202737_s_at | HG-U133A | NM_012321 | 224 | LSM4 homolog, U6 small nuclear RNA associated (S. cerevisiae) | LSM4 | 25804 | — | — | resp | 346 |
| 251 | 212790_x_at | HG-U133A | BF942308 | 225 | ribosomal protein L13a | RPL13A | 23521 | — | — | resp | 346 |
| 252 | 227126_at | HG-U133B | AI857788 | 226 | Transcribed locus | | | — | — | resp | 347 |
| 253 | 200707_at | HG-U133A | NM_002743 | 227 | protein kinase C substrate 80K-H | PRKCSH | 5589 | — | — | resp | 349 |
| 254 | 226453_at | HG-U133B | BF982002 | 228 | AYP1 protein | AYP1 | 84153 | — | — | resp | 350 |
| 255 | 223191_at | HG-U133B | AF151037 | 229 | chromosome 14 open reading frame 112 | C14orf112 | 51241 | — | — | resp | 352 |
| 256 | 204246_s_at | HG-U133A | NM_007234 | 230 | dynactin 3 (p22) | DCTN3 | 11258 | — | — | resp | 353 |
| 257 | 208907_s_at | HG-U133A | BC005373 | 231 | mitochondrial ribosomal protein S18B | MRPS18B | 28973 | — | — | resp | 353 |
| 258 | 203095_at | HG-U133A | NM_002453 | 232 | mitochondrial translational initiation factor 2 | MTIF2 | 4528 | — | — | resp | 356 |
| 259 | 221700_at | HG-U133A | AF348700 | 233 | ubiquitin A-52 residue ribosomal protein fusion product 1 | UBA52 | 7311 | — | — | resp | 356 |
| 260 | 200095_x_at | HG-U133A | AA320764 | 234 | ribosomal protein S10 | RPS10 | 6204 | — | — | resp | 358 |
| 261 | 208826_x_at | HG-U133A | U27143 | 235 | histidine triad nucleotide binding protein 1 | HINT1 | 3094 | — | — | resp | 358 |
| 262 | 226236_at | HG-U133B | BF675218 | 236 | hypothetical gene supported by AF147354 | LOC388789 | 388789 | — | — | resp | 358 |
| 263 | 217774_s_at | HG-U133A | NM_016404 | 237 | hypothetical protein HSPC152 | HSPC152 | 51504 | — | — | resp | 359 |
| 264 | 200089_s_at | HG-U133A | AI953886 | 238 | ribosomal protein L4 | RPL4 | 6124 | — | — | resp | 361 |
| 265 | 202300_at | HG-U133A | NM_006402 | 239 | hepatitis B virus x interacting protein | HBXIP | 10542 | — | — | resp | 365 |
| 266 | 210470_x_at | HG-U133A | BC003129 | 240 | non-POU domain containing, octamer-binding | NONO | 4841 | — | — | resp | 367 |
| 267 | 200092_s_at | HG-U133A | BF216701 | 241 | ribosomal protein L37 | RPL37 | 6167 | — | — | resp | 368 |
| 268 | 200716_x_at | HG-U133A | NM_012423 | 242 | ribosomal protein L13a | RPL13A | 23521 | — | — | resp | 369 |
| 269 | 210434_x_at | HG-U133A | AF151056 | 243 | jumping translocation breakpoint | JTB | 10899 | — | — | resp | 372 |
| 270 | 200819_s_at | HG-U133A | NM_001018 | 244 | ribosomal protein S15 | RPS15 | 6209 | — | — | resp | 373 |
| 271 | 201049_s_at | HG-U133A | NM_022551 | 245 | ribosomal protein S18 | RPS18 | 6222 | — | — | resp | 373 |
| 272 | 201922_at | HG-U133A | NM_014886 | 246 | TGF beta-inducible nuclear protein 1 | TINP1 | 10412 | — | — | resp | 374 |
| 273 | 201113_at | HG-U133A | NM_003321 | 247 | Tu translation elongation factor, mitochondrial | TUFM | 7284 | — | — | resp | 375 |
| 274 | 206174_s_at | HG-U133A | NM_002721 | 248 | protein phosphatase 6, catalytic subunit | PPP6C | 5537 | — | — | resp | 380 |
| 275 | 203720_s_at | HG-U133A | NM_001983 | 249 | excision repair cross-complementing rodent repair deficiency, complementation group 1 (includes overlapping antisense sequence) | ERCC1 | 2067 | — | — | resp | 381 |
| 276 | 223034_s_at | HG-U133B | BC000152 | 250 | chromosome 1 open reading frame 43 | C1orf43 | 25912 | — | — | resp | 385 |
| 277 | 200092_s_at | HG-U133A | BF216701 | 241 | ribosomal protein L37 | RPL37 | 6167 | — | — | resp | 387 |
| 278 | 217729_s_at | HG-U133A | NM_001130 | 251 | amino-terminal enhancer of split | AES | 166 | — | — | resp | 392 |
| 279 | 202467_s_at | HG-U133A | NM_004236 | 252 | COP9 constitutive photomorphogenic homolog subunit 2 (Arabidopsis) | COPS2 | 9318 | — | — | resp | 393 |
| 280 | 208066_s_at | HG-U133A | NM_001514 | 253 | general transcription factor IIB | GTF2B | 2959 | — | — | resp | 395 |
| 281 | 207721_x_at | HG-U133A | NM_005340 | 254 | histidine triad nucleotide binding protein 1 | HINT1 | 3094 | — | — | resp | 397 |
| 282 | 214687_x_at | HG-U133A | AK026577 | 255 | aldolase A, fructose-bisphosphate | ALDOA | 226 | — | — | resp | 398 |
| 283 | 213969_x_at | HG-U133A | BF683426 | 256 | ribosomal protein L29 | RPL29 | 6159 | — | — | resp | 400 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 284 | 221524_s_at | HG-U133A | AF272036 | 257 | Ras-related GTP binding D | RRAGD | 58528 | — | — | resp | 402 |
| 285 | 223376_s_at | HG-U133B | AB055977 | 258 | brain protein I3 | BRI3 | 25798 | — | — | resp | 404 |
| 286 | 203107_x_at | HG-U133A | NM_002952 | 259 | ribosomal protein S2 | RPS2 | 6187 | — | — | resp | 405 |
| 287 | 202514_at | HG-U133A | AW139131 | 260 | discs, large homolog 1 (*Drosophila*) | DLG1 | 1739 | — | — | resp | 406 |
| 288 | 208756_at | HG-U133A | U36764 | 261 | eukaryotic translation initiation factor 3, subunit 2 beta, 36 kDa | EIF3S2 | 8668 | — | — | resp | 407 |
| 289 | 227525_at | HG-U133B | AA058770 | 262 | glucocorticoid induced transcript 1 | GLCCI1 | 113263 | — | — | resp | 411 |
| 290 | 220261_s_at | HG-U133A | NM_018106 | 263 | zinc finger, DHHC domain containing 4 | ZDHHC4 | 55146 | — | — | resp | 412 |
| 291 | 217990_at | HG-U133A | NM_016576 | 264 | guanosine monophosphate reductase 2 | GMPR2 | 51292 | — | — | resp | 413 |
| 292 | 212391_x_at | HG-U133A | AI925635 | 265 | ribosomal protein S3A | RPS3A | 6189 | — | — | resp | 414 |
| 293 | 219033_at | HG-U133A | NM_024615 | 266 | poly (ADP-ribose) polymerase family, member 8 | PARP8 | 79668 | — | — | resp | 416 |
| 294 | 203034_s_at | HG-U133A | NM_000990 | 267 | ribosomal protein L27a | RPL27A | 6157 | — | — | resp | 418 |
| 295 | 208856_x_at | HG-U133A | BC003655 | 268 | ribosomal protein, large, P0 | RPLP0 | 6175 | — | — | resp | 421 |
| 296 | 224767_at | HG-U133B | AL044126 | 269 | Ribosomal protein L37 | RPL37 | 6167 | — | — | resp | 422 |
| 297 | 202758_s_at | HG-U133A | NM_003721 | 270 | regulatory factor X-associated ankyrin-containing protein | RFXANK | 8625 | — | — | resp | 424 |
| 298 | 223436_s_at | HG-U133B | BC005133 | 271 | tRNA splicing 2' phosphotransferase 1 | MGC11134 | 83707 | — | — | resp | 427 |
| 299 | 203190_at | HG-U133A | NM_002496 | 272 | NADH dehydrogenase (ubiquinone) Fe—S protein 8, 23 kDa (NADH-coenzyme Q reductase) | NDUFS8 | 4728 | — | — | resp | 428 |
| 300 | 200818_at | HG-U133A | NM_001697 | 273 | ATP synthase, H+ transporting, mitochondrial F1 complex, O subunit (oligomycin sensitivity conferring protein) | ATP5O | 539 | — | — | resp | 430 |
| 301 | 227228_s_at | HG-U133B | AB040942 | 274 | KIAA1509 | KIAA1509 | 440193 | — | — | resp | 430 |
| 302 | 234000_s_at | HG-U133B | AJ271091 | 275 | butyrate-induced transcript 1 | HSPC121 | 51495 | — | — | resp | 432 |
| 303 | 205849_s_at | HG-U133A | NM_006294 | 276 | ubiquinol-cytochrome c reductase binding protein | UQCRB | 7381 | — | — | resp | 436 |
| 304 | 226165_at | HG-U133B | BF674436 | 277 | hypothetical gene supported by BC055092 | LOC401466 | 401466 | — | — | resp | 438 |
| 305 | 220942_x_at | HG-U133B | NM_014367 | 278 | growth and transformation-dependent protein | E2IG5 | 26355 | — | — | resp | 440 |
| 306 | 231870_s_at | HG-U133B | BG291007 | 279 | CGI-07 protein | CGI-07 | 51068 | — | — | resp | 440 |
| 307 | 212270_x_at | HG-U133A | BG168283 | 280 | ribosomal protein L17 | RPL17 | 6139 | — | — | resp | 443 |
| 308 | 212773_s_at | HG-U133A | BG165094 | 281 | translocase of outer mitochondrial membrane 20 homolog (yeast) | TOMM20 | 9804 | — | — | resp | 443 |
| 309 | 222785_x_at | HG-U133B | AJ250229 | 282 | chromosome 11 open reading frame 1 | C11orf1 | 64776 | — | — | resp | 443 |
| 310 | 222497_x_at | HG-U133B | AL520719 | 283 | NMD3 homolog (*S. cerevisiae*) | NMD3 | 51068 | — | — | resp | 444 |
| 311 | 200933_x_at | HG-U133A | NM_001007 | 284 | ribosomal protein S4, X-linked | RPS4X | 6191 | — | — | resp | 448 |
| 312 | 226650_at | HG-U133B | AI984061 | 285 | hypothetical protein LOC90637 | LOC90637 | 90637 | — | — | resp | 453 |
| 313 | 200031_s_at | HG-U133A | NM_001015 | 286 | ribosomal protein S11 | RPS11 | 6205 | — | — | resp | 454 |
| 314 | 217747_s_at | HG-U133A | NM_001013 | 287 | ribosomal protein S9 | RPS9 | 6203 | — | — | resp | 454 |
| 315 | 211720_x_at | HG-U133A | BC005863 | 288 | ribosomal protein, large, P0 | RPLP0 | 6175 | — | — | resp | 455 |
| 316 | 203403_s_at | HG-U133A | NM_005977 | 289 | ring finger protein (C3H2C3 type) 6 | RNF6 | 6049 | — | — | resp | 457 |
| 317 | 215963_x_at | HG-U133A | Z98200 | 290 | | | | — | — | resp | 459 |
| 318 | 218034_at | HG-U133A | NM_016068 | 291 | tetratricopeptide repeat domain 11 | TTC11 | 51024 | — | — | resp | 460 |
| 319 | 218258_at | HG-U133A | NM_015972 | 292 | polymerase (RNA) I polypeptide D, 16 kDa | POLR1D | 51082 | — | — | resp | 462 |
| 320 | 201154_x_at | HG-U133A | NM_000968 | 293 | ribosomal protein L4 | RPL4 | 6124 | — | — | resp | 463 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 321 | 200846_s_at | HG-U133A | NM_002708 | 294 | protein phosphatase 1, catalytic subunit, alpha isoform | PPP1CA | 5499 | — | — | resp | 464 |
| 322 | 217313_at | HG-U133A | AC004692 | 295 | mannosyl (alpha-1,6-)-glycoprotein beta-1,2-N-acetylglucosaminyltransferase | MGAT2 | 4247 | — | — | resp | 465 |
| 323 | 211061_s_at | HG-U133A | BC006390 | 296 |  |  |  | — | — | resp | 467 |
| 324 | 216383_at | HG-U133A | U52111 | 297 | ribosomal protein L18a | RPL18A | 6142 | — | — | resp | 470 |
| 325 | 222467_s_at | HG-U133B | AK023950 | 298 | chromosome 11 open reading frame 23 | C11orf23 | 55291 | — | — | resp | 471 |
| 326 | 202276_at | HG-U133A | NM_006304 | 299 | split hand/foot malformation (ectrodactyly) type 1 | SHFM1 | 7979 | — | — | resp | 480 |
| 327 | 65588_at | HG-U133A | AA827892 | 300 | hypothetical LOC388796 | LOC388796 | 388796 | — | — | resp | 481 |
| 328 | 234339_s_at | HG-U133B | AF296124 | 301 | glioma tumor suppressor candidate region gene 2 | GLTSCR2 | 29997 | — | — | resp | 484 |
| 329 | 211487_x_at | HG-U133A | BC004886 | 302 | ribosomal protein S17 | RPS17 | 6218 | — | — | resp | 492 |
| 330 | 201406_at | HG-U133A | NM_021029 | 303 | ribosomal protein L36a | RPL36A | 6173 | — | — | resp | 494 |
| 331 | 212537_x_at | HG-U133A | BE733979 | 304 | ribosomal protein L17 | RPL17 | 6139 | — | — | resp | 495 |
| 332 | 220647_s_at | HG-U133A | NM_016565 | 305 | E2IG2 protein | E2IG2 | 51287 | — | — | resp | 502 |
| 333 | 200717_x_at | HG-U133A | NM_000971 | 306 | ribosomal protein L7 | RPL7 | 6129 | — | — | resp | 504 |
| 334 | 223461_at | HG-U133B | AF151073 | 307 | TBC1 domain family, member 7 | TBC1D7 | 51256 | — | — | resp | 506 |
| 335 | 207831_x_at | HG-U133A | NM_013407 | 308 | deoxyhypusine synthase | DHPS | 1725 | — | — | resp | 508 |
| 336 | 201119_s_at | HG-U133A | NM_004074 | 309 | cytochrome c oxidase subunit 8A (ubiquitous) | COX8A | 1351 | — | — | resp | 509 |
| 337 | 206782_s_at | HG-U133A | NM_005528 | 310 | DnaJ (Hsp40) homolog, subfamily C, member 4 | DNAJC4 | 3338 | — | — | resp | 509 |
| 338 | 218836_at | HG-U133A | NM_024839 | 311 | ribonuclease P 21 kDa subunit | RPP21 | 79897 | — | — | resp | 510 |
| 339 | 200084_at | HG-U133B | BE748698 | 312 | small acidic protein | SMAP | 10944 | — | — | resp | 513 |
| 340 | 201033_x_at | HG-U133A | NM_001002 | 313 | ribosomal protein, large, P0 | RPLP0 | 6175 | — | — | resp | 514 |
| 341 | 222212_s_at | HG-U133B | AK001105 | 314 | LAG1 longevity assurance homolog 2 (S. cerevisiae) | LASS2 | 29956 | — | — | resp | 515 |
| 342 | 202029_x_at | HG-U133A | NM_000999 | 315 | ribosomal protein L38 | RPL38 | 6169 | — | — | resp | 518 |
| 343 | 208910_s_at | HG-U133A | L04636 | 316 | complement component 1, q subcomponent binding protein | C1QBP | 708 | — | — | resp | 520 |
| 344 | 217816_s_at | HG-U133A | NM_020357 | 317 | PEST-containing nuclear protein | PCNP | 57092 | — | — | resp | 521 |
| 345 | 210646_x_at | HG-U133A | BC001675 | 318 | ribosomal protein L13a | RPL13A | 23521 | — | — | resp | 527 |
| 346 | 223423_at | HG-U133B | BC000181 | 319 | G protein-coupled receptor 160 | GPR160 | 26996 | — | — | resp | 532 |
| 347 | 209091_s_at | HG-U133A | AF263293 | 320 | SH3-domain GRB2-like endophilin B1 | SH3GLB1 | 51100 | — | — | resp | 533 |
| 348 | 200809_x_at | HG-U133A | NM_000976 | 321 | ribosomal protein L12 | RPL12 | 6136 | — | — | resp | 541 |
| 349 | 224068_x_at | HG-U133B | U39402 | 322 | RNA binding motif protein 22 | RBM22 | 55696 | — | — | resp | 541 |
| 350 | 200032_s_at | HG-U133A | NM_000661 | 186 | ribosomal protein L9 | RPL9 | 6133 | — | — | resp | 548 |
| 351 | 227990_at | HG-U133A | AA843238 | 323 | Step II splicing factor SLU7 | SLU7 | 10569 | — | — | resp | 548 |
| 352 | 223038_s_at | HG-U133B | BG479856 | 324 | chromosome 12 open reading frame 14 | C12orf14 | 58516 | — | — | resp | 558 |
| 353 | 224930_x_at | HG-U133B | BE559788 | 325 | ribosomal protein L7a | RPL7A | 6130 | — | — | resp | 558 |
| 354 | 218401_s_at | HG-U133A | NM_012482 | 326 | zinc finger protein 281 | ZNF281 | 23528 | — | — | resp | 561 |
| 355 | 213588_x_at | HG-U133A | AA838274 | 327 | ribosomal protein L14 | RPL14 | 9045 | — | — | resp | 566 |
| 356 | 226816_s_at | HG-U133B | AI745170 | 328 | KIAA1143 protein | KIAA1143 | 57456 | — | — | resp | 566 |
| 357 | 212397_at | HG-U133A | AL137751 | 329 | radixin | RDX | 5962 | — | — | resp | 568 |
| 358 | 200084_at | HG-U133A | BE748698 | 312 | small acidic protein | SMAP | 10944 | — | — | resp | 570 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 359 | 202983_at | HG-U133A | AI760760 | 330 | SWI/SNF related, matrix associated, actin dependent regulator of chromatin, subfamily a, member 3 | SMARCA3 | 6596 | — | — | resp | 571 |
| 360 | 201338_x_at | HG-U133A | NM_002097 | 331 | general transcription factor IIIA | GTF3A | 2971 | — | — | resp | 573 |
| 361 | 214182_at | HG-U133A | AA243143 | 332 | | | | — | — | resp | 573 |
| 362 | 200689_x_at | HG-U133A | NM_001404 | 333 | eukaryotic translation elongation factor 1 gamma | EEF1G | 1937 | — | — | resp | 577 |
| 363 | 225002_s_at | HG-U133B | BE349022 | 334 | sulfatase modifying factor 2 | SUMF2 | 25870 | — | — | resp | 582 |
| 364 | 210024_s_at | HG-U133A | AB017644 | 335 | ubiquitin-conjugating enzyme E2E 3 (UBC4/5 homolog, yeast) | UBE2E3 | 10477 | — | — | resp | 588 |
| 365 | 200089_s_at | HG-U133A | AI953886 | 238 | ribosomal protein L4 | RPL4 | 6124 | — | — | resp | 594 |
| 366 | 217256_x_at | HG-U133A | Z98950 | 336 | | | | — | — | resp | 594 |
| 367 | 200926_at | HG-U133A | NM_001025 | 337 | ribosomal protein S23 | RPS23 | 6228 | — | — | resp | 596 |
| 368 | 225237_s_at | HG-U133B | BF435123 | 338 | musashi homolog 2 (Drosophila) | MSI2 | 124540 | — | — | resp | 598 |
| 369 | 203517_at | HG-U133A | NM_006554 | 339 | metaxin 2 | MTX2 | 10651 | — | — | resp | 602 |
| 370 | 200929_at | HG-U133A | NM_006827 | 340 | transmembrane trafficking protein | TMP21 | 10972 | — | — | resp | 614 |
| 371 | 203897_at | HG-U133A | BE963444 | 341 | hypothetical protein A-211C6.1 | LOC57149 | 57149 | — | — | resp | 621 |
| 372 | 224479_s_at | HG-U133B | BC006235 | 342 | mitochondrial ribosomal protein L45 | MRPL45 | 84311 | — | — | resp | 623 |
| 373 | 223244_s_at | HG-U133B | AF217092 | 343 | 13 kDa differentiation-associated protein | DAP13 | 55967 | — | — | resp | 625 |
| 374 | 208699_x_at | HG-U133A | BF696840 | 344 | transketolase (Wernicke-Korsakoff syndrome) | TKT | 7086 | — | — | resp | 626 |
| 375 | 200892_s_at | HG-U133A | BC000451 | 345 | splicing factor, arginine/serine-rich 10 (transformer 2 homolog, Drosophila) | SFRS10 | 6434 | — | — | resp | 636 |
| 376 | 228089_x_at | HG-U133B | H72927 | 346 | similar to RIKEN cDNA 1810059G22 | LOC374395 | 374395 | — | — | resp | 637 |
| 377 | 202736_at | HG-U133A | AA112507 | 347 | LSM4 homolog, U6 small nuclear RNA associated (S. cerevisiae) | LSM4 | 25804 | — | — | resp | 641 |
| 378 | 217906_at | HG-U133A | NM_014315 | 348 | kelch domain containing 2 | KLHDC2 | 23588 | — | — | resp | 644 |
| 379 | 224703_at | HG-U133B | AI814644 | 349 | | | | — | — | resp | 646 |
| 380 | 218930_s_at | HG-U133B | NM_018374 | 350 | hypothetical protein FLJ11273 | FLJ11273 | 54664 | — | — | resp | 651 |
| 381 | 200810_s_at | HG-U133A | NM_001280 | 160 | cold inducible RNA binding protein | CIRBP | 1153 | — | — | resp | 652 |
| 382 | 225312_at | HG-U133B | AV704551 | 351 | COMM domain containing 6 | COMMD6 | 170622 | — | — | resp | 654 |
| 383 | 210101_x_at | HG-U133A | AF257318 | 352 | SH3-domain GRB2-like endophilin B1 | SH3GLB1 | 51100 | — | — | resp | 656 |
| 384 | 222452_at | HG-U133B | AA741071 | 353 | hypothetical protein SP192 | SP192 | 60313 | — | — | resp | 658 |
| 385 | 202169_s_at | HG-U133A | AF302110 | 354 | aminoadipate-semialdehyde dehydrogenase-phosphopantetheinyl transferase | AASDHPPT | 60496 | — | — | resp | 662 |
| 386 | 211710_x_at | HG-U133A | BC005817 | 355 | ribosomal protein L4 | RPL4 | 6124 | — | — | resp | 663 |
| 387 | 202343_x_at | HG-U133A | NM_001862 | 356 | cytochrome c oxidase subunit Vb | COX5B | 1329 | — | — | resp | 667 |
| 388 | 208097_s_at | HG-U133A | NM_030755 | 357 | thioredoxin domain containing | TXNDC | 81542 | — | — | resp | 680 |
| 389 | 217339_x_at | HG-U133B | AJ275978 | 358 | cancer/testis antigen 1B | CTAG1B | 1485 | — | — | resp | 4 |
| 390 | 202469_s_at | HG-U133A | AU149367 | 359 | cleavage and polyadenylation specific factor 6, 68 kDa | CPSF6 | 11052 | — | — | resp | 38 |
| 391 | 214548_x_at | HG-U133A | AF064092 | 360 | GNAS complex locus | GNAS | 2778 | — | — | resp | 138 |
| 392 | 200780_x_at | HG-U133A | NM_000516 | 361 | GNAS complex locus | GNAS | 2778 | — | — | resp | 190 |
| 393 | 224972_at | HG-U133B | BF381837 | 362 | Chromosome 20 open reading frame 52 | C20orf52 | 140823 | — | — | resp | 198 |
| 394 | 208833_s_at | HG-U133A | AF119662 | 363 | ataxin 10 | ATXN10 | 25814 | — | — | resp | 280 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 395 | 202107_s_at | HG-U133A | NM_004526 | 364 | MCM2 minichromosome maintenance deficient 2, mitotin (S. cerevisiae) | MCM2 | 4171 | — | | TTP | 8 |
| 396 | 210766_s_at | HG-U133A | AF053640 | 365 | CSE1 chromosome segregation 1-like (yeast) | CSE1L | 1434 | — | | TTP | 9 |
| 397 | 221601_s_at | HG-U133A | AI084226 | 366 | regulator of Fas-induced apoptosis | TOSO | 9214 | — | | TTP | 15 |
| 398 | 209568_s_at | HG-U133A | AF186779 | 367 | ral guanine nucleotide dissociation stimulator-like 1 | RGL1 | 23179 | — | | TTP | 17 |
| 399 | 201555_at | HG-U133A | NM_002388 | 368 | MCM3 minichromosome maintenance deficient 3 (S. cerevisiae) | MCM3 | 4172 | — | | TTP | 21 |
| 400 | 212563_at | HG-U133A | BG491842 | 369 | block of proliferation 1 | BOP1 | 23246 | — | | TTP | 23 |
| 401 | 221602_s_at | HG-U133A | AF057557 | 370 | regulator of Fas-induced apoptosis | TOSO | 9214 | — | | TTP | 25 |
| 402 | 200608_s_at | HG-U133A | NM_006265 | 371 | RAD21 homolog (S. pombe) | RAD21 | 5885 | — | | TTP | 26 |
| 403 | 202589_at | HG-U133A | NM_001071 | 372 | thymidylate synthetase | TYMS | 7298 | — | | TTP | 33 |
| 404 | 201930_at | HG-U133A | NM_005915 | 373 | MCM6 minichromosome maintenance deficient 6 (MIS5 homolog, S. pombe) (S. cerevisiae) | MCM6 | 4175 | — | | TTP | 34 |
| 405 | 201726_at | HG-U133A | BC003376 | 374 | ELAV (embryonic lethal, abnormal vision, Drosophila)-like 1 (Hu antigen R) | ELAVL1 | 1994 | — | | TTP | 36 |
| 406 | 217821_s_at | HG-U133A | AF118023 | 375 | WW domain binding protein 11 | WBP11 | 51729 | — | | TTP | 44 |
| 407 | 216237_s_at | HG-U133A | AA807529 | 376 | MCM5 minichromosome maintenance deficient 5, cell division cycle 46 (S. cerevisiae) | MCM5 | 4174 | — | | TTP | 45 |
| 408 | 201589_at | HG-U133A | D80000 | 377 | SMC1 structural maintenance of chromosomes 1-like 1 (yeast) | SMC1L1 | 8243 | — | | TTP | 46 |
| 409 | 213911_s_at | HG-U133A | BF718636 | 378 | H2A histone family, member Z | H2AFZ | 3015 | — | | TTP | 47 |
| 410 | 208766_s_at | HG-U133A | BC001449 | 379 | heterogeneous nuclear ribonucleoprotein R | HNRPR | 10236 | — | | TTP | 54 |
| 411 | 226547_at | HG-U133B | AI817830 | 380 | MYST histone acetyltransferase (monocytic leukemia) 3 | MYST3 | 7994 | — | | TTP | 56 |
| 412 | 221952_x_at | HG-U133A | AB037814 | 381 | KIAA1393 | KIAA1393 | 57570 | — | | TTP | 60 |
| 413 | 202642_s_at | HG-U133A | NM_003496 | 382 | transformation/transcription domain-associated protein | TRRAP | 8295 | — | | TTP | 64 |
| 414 | 218350_s_at | HG-U133A | NM_015895 | 383 | geminin, DNA replication inhibitor | GMNN | 51053 | — | | TTP | 69 |
| 415 | 225827_at | HG-U133B | AI832074 | 384 | eukaryotic translation initiation factor 2C, 2 | EIF2C2 | 27161 | — | | TTP | 70 |
| 416 | 223024_at | HG-U133B | AL562950 | 385 | adaptor-related protein complex 1, mu 1 subunit | AP1M1 | 8907 | — | | TTP | 72 |
| 417 | 210983_s_at | HG-U133A | AF279900 | 386 | MCM7 minichromosome maintenance deficient 7 (S. cerevisiae) | MCM7 | 4176 | — | | TTP | 75 |
| 418 | 200045_at | HG-U133A | NM_001090 | 387 | ATP-binding cassette, sub-family F (GCN20), member 1 | ABCF1 | 23 | — | | TTP | 77 |
| 419 | 212316_at | HG-U133A | AA502912 | 388 | nucleoporin 210 kDa | NUP210 | 23225 | — | | TTP | 79 |
| 420 | 200882_s_at | HG-U133A | NM_002810 | 389 | proteasome (prosome, macropain) 26S subunit, non-ATPase, 4 | PSMD4 | 5710 | — | | TTP | 80 |
| 421 | 201639_s_at | HG-U133A | NM_013291 | 390 | cleavage and polyadenylation specific factor 1, 160 kDa | CPSF1 | 29894 | — | | TTP | 83 |
| 422 | 213893_x_at | HG-U133A | AA161026 | 391 | postmeiotic segregation increased 2-like 5 | PMS2L5 | 5383 | — | | TTP | 84 |
| 423 | 226936_at | HG-U133B | BG492359 | 392 | CDNA clone IMAGE: 4452583, partial cds | C6orf173 | 408186 | — | | TTP | 88 |
| 424 | 228245_s_at | HG-U133B | AW594320 | 393 | ovostatin /// similar to ovostatin-2 | OVOS /// LOC440080 | /// 440080 | — | | TTP | 89 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 425 | 225655_at | HG-U133B | AK025578 | 394 | ubiquitin-like, containing PHD and RING finger domains, 1 | UHRF1 | 29128 | — | | TTP | 91 |
| 426 | 223516_s_at | HG-U133B | AF216754 | 395 | chromosome 6 open reading frame 49 | C6orf49 | 29964 | — | | TTP | 97 |
| 427 | 201128_s_at | HG-U133A | NM_001096 | 396 | ATP citrate lyase | ACLY | 47 | — | | TTP | 100 |
| 428 | 208821_at | HG-U133A | J04564 | 397 | small nuclear ribonucleoprotein polypeptides B and B1 | SNRPB | 6628 | — | | TTP | 102 |
| 429 | 200090_at | HG-U133B | BG168896 | 398 | farnesyltransferase, CAAX box, alpha | FNTA | 2339 | — | | TTP | 105 |
| 430 | 218437_s_at | HG-U133A | NM_020347 | 399 | leucine zipper transcription factor-like 1 | LZTFL1 | 54585 | — | | TTP | 106 |
| 431 | 225549_at | HG-U133B | BF129093 | 400 | DEAD (Asp-Glu-Ala-Asp) box polypeptide 6 | DDX6 | 1656 | — | | TTP | 107 |
| 432 | 201180_s_at | HG-U133A | J03198 | 401 | guanine nucleotide binding protein (G protein), alpha inhibiting activity polypeptide 3 | GNAI3 | 2773 | — | | TTP | 108 |
| 433 | 235242_at | HG-U133B | BE739287 | 402 | CDNA FLJ41375 fis, clone BRCAN2007700 | | | — | | TTP | 110 |
| 434 | 225834_at | HG-U133B | AL135396 | 403 | Similar to RIKEN cDNA 2700049P18 gene | MGC57827 | 389835 | — | | TTP | 112 |
| 435 | 200098_s_at | HG-U133B | T33068 | 404 | anaphase promoting complex subunit 5 | ANAPC5 | 51433 | — | | TTP | 121 |
| 436 | 210543_s_at | HG-U133A | U34994 | 405 | protein kinase, DNA-activated, catalytic polypeptide | PRKDC | 5591 | — | | TTP | 126 |
| 437 | 213378_s_at | HG-U133A | AI983033 | 406 | DEAD/H (Asp-Glu-Ala-Asp/His) box polypeptide 11 (CHL1-like helicase homolog, S. cerevisiae) | DDX11 | 1663 | — | | TTP | 131 |
| 438 | 220448_at | HG-U133A | NM_022055 | 407 | potassium channel, subfamily K, member 12 | KCNK12 | 56660 | — | | TTP | 136 |
| 439 | 228273_at | HG-U133B | BG165011 | 408 | Hypothetical protein FLJ11029 | FLJ11029 | 55771 | — | | TTP | 140 |
| 440 | 222988_s_at | HG-U133B | AF151020 | 409 | transmembrane protein 9 | TMEM9 | 252839 | — | | TTP | 146 |
| 441 | 209773_s_at | HG-U133A | BC001886 | 410 | ribonucleotide reductase M2 polypeptide | RRM2 | 6241 | — | | TTP | 148 |
| 442 | 202715_at | HG-U133A | NM_004341 | 411 | carbamoyl-phosphate synthetase 2, aspartate transcarbamylase, and dihydroorotase | CAD | 790 | — | | TTP | 152 |
| 443 | 202171_at | HG-U133A | AU146275 | 412 | zinc finger protein 161 | ZNF161 | 7716 | — | | TTP | 155 |
| 444 | 203999_at | HG-U133A | AV731490 | 413 | synaptotagmin I | SYT1 | 6857 | — | | TTP | 159 |
| 445 | 214526_x_at | HG-U133A | NM_005394 | 414 | | | | — | | TTP | 160 |
| 446 | 212282_at | HG-U133A | BF038366 | 415 | hypothetical protein MAC30 | MAC30 | 27346 | — | | TTP | 164 |
| 447 | 202779_s_at | HG-U133A | NM_014501 | 416 | ubiquitin-conjugating enzyme E2S | UBE2S | 27338 | — | | TTP | 166 |
| 448 | 201115_at | HG-U133A | NM_006230 | 417 | polymerase (DNA directed), delta 2, regulatory subunit 50 kDa | POLD2 | 5425 | — | | TTP | 174 |
| 449 | 214756_x_at | HG-U133A | AB017004 | 418 | H2A histone family, member Z | H2AFZ | 3015 | — | | TTP | 180 |
| 450 | 200853_at | HG-U133A | NM_002106 | 419 | anaphase promoting complex subunit 5 | ANAPC5 | 51433 | — | | TTP | 182 |
| 451 | 200098_s_at | HG-U133A | T33068 | 404 | SVAP1 protein | IMAGE3451454 | 116841 | — | | TTP | 184 |
| 452 | 225244_at | HG-U133B | AA019893 | 420 | TSPY-like 5 | TSPYL5 | 85453 | — | | TTP | 187 |
| 453 | 213122_at | HG-U133A | AI096375 | 421 | tubulin, beta polypeptide | TUBB | 203068 | — | | TTP | 193 |
| 454 | 211714_x_at | HG-U133A | BC005838 | 422 | TBC1 (tre-2/USP6, BUB2, cdc16) domain family, member 1 | TBC1D1 | 23216 | — | | TTP | 197 |
| 455 | 212350_at | HG-U133A | AB029031 | 423 | | | | — | | TTP | 199 |
| 456 | 215714_s_at | HG-U133A | AF254822 | 424 | SWI/SNF related, matrix associated, actin dependent regulator of chromatin, subfamily a, member 4 | SMARCA4 | 6597 | — | | TTP | 203 |
| 457 | 204053_x_at | HG-U133A | U96180 | 425 | phosphatase and tensin homolog (mutated in multiple advanced cancers 1) | PTEN | 5728 | — | | TTP | 206 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 458 | 212058_at | HG-U133A | AI184562 | 426 | U2-associated SR140 protein | SR140 | 23350 | — | — | TTP | 208 |
| 459 | 225265_at | HG-U133B | AI580100 | 427 | RNA binding motif, single stranded interacting protein 1 | RBMS1 | 5937 | — | — | TTP | 212 |
| 460 | 212281_s_at | HG-U133A | BF038366 | 415 | hypothetical protein MAC30 | MAC30 | 27346 | — | — | TTP | 213 |
| 461 | 228361_at | HG-U133B | AL561296 | 428 | E2F transcription factor 2 | E2F2 | 1870 | — | — | TTP | 215 |
| 462 | 208974_x_at | HG-U133A | BC003572 | 429 | karyopherin (importin) beta 1 | KPNB1 | 3837 | — | — | TTP | 221 |
| 463 | 201652_at | HG-U133A | NM_006837 | 430 | COP9 constitutive photomorphogenic homolog subunit 5 (Arabidopsis) | COPS5 | 10987 | — | — | TTP | 224 |
| 464 | 222398_s_at | HG-U133B | BC002360 | 431 | U5 snRNP-specific protein, 116 kD | U5-116KD | 9343 | — | — | TTP | 228 |
| 465 | 212610_at | HG-U133A | U79291 | 432 | protein tyrosine phosphatase, non-receptor type 11 (Noonan syndrome 1) | PTPN11 | 5781 | — | — | TTP | 230 |
| 466 | 222987_s_at | HG-U133B | NM_016456 | 433 | transmembrane protein 9 | TMEM9 | 252839 | — | — | TTP | 231 |
| 467 | 241224_x_at | HG-U133B | AA770014 | 434 | Down syndrome critical region gene 8 | DSCR8 | 84677 | — | — | TTP | 232 |
| 468 | 207057_at | HG-U133A | NM_004731 | 435 |  | STARD3NL | 203068 | — | — | TTP | 233 |
| 469 | 209026_x_at | HG-U133A | AF141349 | 436 | tubulin, beta polypeptide | TUBB |  | — | — | TTP | 237 |
| 470 | 200773_x_at | HG-U133A | NM_002823 | 437 | prothymosin, alpha (gene sequence 28) | PTMA | 5757 | — | — | TTP | 241 |
| 471 | 204033_at | HG-U133A | NM_004237 | 438 | thyroid hormone receptor interactor 13 | TRIP13 | 9319 | — | — | TTP | 242 |
| 472 | 225068_at | HG-U133B | AK024412 | 439 | kelch-like 12 (Drosophila) | KLHL12 | 59349 | — | — | TTP | 245 |
| 473 | 203022_at | HG-U133A | NM_006397 | 440 | ribonuclease H2, large subunit | RNASEH2A | 10535 | — | — | TTP | 249 |
| 474 | 213720_at | HG-U133A | AI831675 | 441 | SWI/SNF related, matrix associated, actin dependent regulator of chromatin, subfamily a, member 4 | SMARCA4 | 6597 | — | — | TTP | 251 |
| 475 | 225081_s_at | HG-U133B | AK022955 | 442 | transcription factor RAM2 | RAM2 | 55536 | — | — | TTP | 255 |
| 476 | 201680_x_at | HG-U133A | NM_015908 | 443 | arsenate resistance protein ARS2 | ARS2 | 51593 | — | — | TTP | 256 |
| 477 | 223065_at | HG-U133B | BC003074 | 444 | STARD3 N-terminal like | STARD3NL | 83930 | — | — | TTP | 257 |
| 478 | 205436_s_at | HG-U133A | NM_002105 | 445 | H2A histone family, member X | H2AFX | 3014 | — | — | TTP | 263 |
| 479 | 213069_at | HG-U133A | AI148659 | 446 | HEG homolog | HEG | 57493 | — | — | TTP | 267 |
| 480 | 200073_s_at | HG-U133A | M94630 | 447 | heterogeneous nuclear ribonucleoprotein D (AU-rich element RNA binding protein 1, 37 kDa) | HNRPD | 3184 | — | — | TTP | 269 |
| 481 | 200060_s_at | HG-U133A | BC001659 | 448 | RNA binding protein S1, serine-rich domain | RNPS1 | 10921 | — | — | TTP | 270 |
| 482 | 205124_at | HG-U133A | NM_005919 | 449 | MADS box transcription enhancer factor 2, polypeptide B (myocyte enhancer factor 2B) | MEF2B | 4207 | — | — | TTP | 275 |
| 483 | 206052_s_at | HG-U133A | NM_006527 | 450 | stem-loop (histone) binding protein | SLBP | 7884 | — | — | TTP | 276 |
| 484 | 222619_at | HG-U133B | AU150752 | 451 | Zinc finger protein 281 | ZNF281 | 23528 | — | — | TTP | 277 |
| 485 | 225684_at | HG-U133B | BG496998 | 452 |  |  |  | — | — | TTP | 284 |
| 486 | 202362_at | HG-U133A | NM_002884 | 453 | RAP1A, member of RAS oncogene family | RAP1A | 5906 | — | — | TTP | 286 |
| 487 | 221505_at | HG-U133A | AW612574 | 454 | acidic (leucine-rich) nuclear phosphoprotein 32 family, member E | ANP32E | 81611 | — | — | TTP | 291 |
| 488 | 213947_s_at | HG-U133A | AI867102 | 455 | nucleoporin 210 kDa | NUP210 | 23225 | — | — | TTP | 18 |
| 489 | 209188_x_at | HG-U133A | BC002809 | 456 | down-regulator of transcription 1, TBP-binding (negative cofactor 2) | DR1 | 1810 | — | — | TTP | 98 |
| 490 | 210243_s_at | HG-U133A | AF038661 | 457 | UDP-Gal:betaGlcNAc beta 1,4-galactosyltransferase, polypeptide 3 | B4GALT3 | 8703 | — | — | TTP | 162 |
| 491 | 205449_at | HG-U133A | NM_013299 | 458 | Sac3 homology domain 1 (S. cerevisiae) | SHD1 | 29901 | — | — | TTP | 170 |
| 492 | 217988_at | HG-U133A | NM_021178 | 459 | cyclin B1 interacting protein 1 | CCNB1IP1 | 57820 | — | — | TTP/resp | 4 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 493 | 205361_s_at | HG-U133A | AI718295 | 460 | prefoldin 4 | PFDN4 | 5203 | — | — | TTP/resp | 7 |
| 494 | 202605_at | HG-U133A | NM_000181 | 461 | glucuronidase, beta | GUSB | 2990 | — | — | TTP/resp | 9 |
| 495 | 225315_at | HG-U133B | BF344406 | 462 | mitochondrial ribosomal protein L21 | MRPL21 | 219927 | — | — | TTP/resp | 9 |
| 496 | 225261_x_at | HG-U133B | AJ238376 | 463 | TH1-like (*Drosophila*) | TH1L | 51497 | — | — | TTP/resp | 10 |
| 497 | 223474_at | HG-U133B | AI932310 | 464 | chromosome 14 open reading frame 4 | C14orf4 | 64207 | — | — | TTP/resp | 12 |
| 498 | 216306_x_at | HG-U133B | X62006 | 465 | polypyrimidine tract binding protein 1 | PTBP1 | 5725 | — | — | TTP/resp | 14 |
| 499 | 201066_at | HG-U133A | NM_001916 | 466 | cytochrome c-1 | CYC1 | 1537 | — | — | TTP/resp | 16 |
| 500 | 202189_x_at | HG-U133A | NM_002819 | 467 | polypyrimidine tract binding protein 1 | PTBP1 | 5725 | — | — | TTP/resp | 20 |
| 501 | 211270_x_at | HG-U133A | BC002397 | 468 | polypyrimidine tract binding protein 1 | PTBP1 | 5725 | — | — | TTP/resp | 22 |
| 502 | 225006_x_at | HG-U133B | AJ238379 | 469 | TH1-like (*Drosophila*) | TH1L | 51497 | — | — | TTP/resp | 24 |
| 503 | 201754_at | HG-U133A | NM_004374 | 470 | cytochrome c oxidase subunit VIc | COX6C | 1345 | — | — | TTP/resp | 27 |
| 504 | 212015_x_at | HG-U133A | BF690062 | 471 | polypyrimidine tract binding protein 1 | PTBP1 | 5725 | — | — | TTP/resp | 29 |
| 505 | 41577_at | HG-U133A | AB020630 | 472 | protein phosphatase 1, regulatory (inhibitor) subunit 16B | PPP1R16B | 26051 | — | — | TTP/resp | 31 |
| 506 | 225865_x_at | HG-U133B | AJ238374 | 473 | TH1-like (*Drosophila*) | TH1L | 51497 | — | — | TTP/resp | 40 |
| 507 | 211271_x_at | HG-U133A | BC004383 | 474 | polypyrimidine tract binding protein 1 | PTBP1 | 5725 | — | — | TTP/resp | 42 |
| 508 | 200040_at | HG-U133A | NM_006559 | 475 | KH domain containing, RNA binding, signal transduction associated 1 | KHDRBS1 | 10657 | — | — | TTP/resp | 43 |
| 509 | 211755_s_at | HG-U133B | BC005960 | 476 | ATP synthase, H+ transporting, mitochondrial F0 complex, subunit b, isoform 1 | ATP5F1 | 515 | — | — | TTP/resp | 48 |
| 510 | 222445_at | HG-U133B | AK025831 | 477 | solute carrier family 39 (zinc transporter), member 9 | SLC39A9 | 55334 | — | — | TTP/resp | 48 |
| 511 | 226434_at | HG-U133B | BF000655 | 478 | hypothetical protein MGC22793 | MGC22793 | 221908 | — | — | TTP/resp | 50 |
| 512 | 202596_at | HG-U133A | BC000436 | 479 | endosulfine alpha | ENSA | 2029 | — | — | TTP/resp | 52 |
| 513 | 203739_at | HG-U133A | NM_006526 | 480 | zinc finger protein 217 | ZNF217 | 7764 | — | — | TTP/resp | 53 |
| 514 | 201987_at | HG-U133A | NM_001068 | 481 | topoisomerase (DNA) II beta 180 kDa | TOP2B | 7155 | — | — | TTP/resp | 59 |
| 515 | 217492_s_at | HG-U133A | AF023139 | 482 | phosphatase and tensin homolog (mutated in multiple advanced cancers 1) | PTEN | 5728 | — | — | TTP/resp | 65 |
| 516 | 223354_x_at | HG-U133B | BC003191 | 483 | chromosome 2 open reading frame 33 | C2orf33 | 56947 | — | — | TTP/resp | 67 |
| 517 | 210792_x_at | HG-U133A | AF033111 | 484 | CD27-binding (Siva) protein | SIVA | 10572 | — | — | TTP/resp | 71 |
| 518 | 209187_at | HG-U133A | AW516932 | 485 | down-regulator of transcription 1, TBP-binding (negative cofactor 2) | DR1 | 1810 | — | — | TTP/resp | 73 |
| 519 | 226032_at | HG-U133B | AU153405 | 486 | caspase 2, apoptosis-related cysteine protease (neural precursor cell expressed, developmentally down-regulated 2) | CASP2 | 835 | — | — | TTP/resp | 74 |
| 520 | 201493_s_at | HG-U133A | BE778078 | 487 | pumilio homolog 2 (*Drosophila*) | PUM2 | 23369 | — | — | TTP/resp | 78 |
| 521 | 204031_s_at | HG-U133A | NM_005016 | 488 | poly(rC) binding protein 2 | PCBP2 | 5094 | — | — | TTP/resp | 86 |
| 522 | 202720_at | HG-U133A | NM_015641 | 489 | testis derived transcript (3 LIM domains) | TES | 26136 | — | — | TTP/resp | 94 |
| 523 | 212279_at | HG-U133A | BE779865 | 490 | hypothetical protein MAC30 | MAC30 | 27346 | — | — | TTP/resp | 103 |
| 524 | 211858_x_at | HG-U133A | AF088184 | 491 | GNAS complex locus | GNAS | 2778 | — | — | TTP/resp | 115 |
| 525 | 226574_at | HG-U133B | AI872384 | 492 | paraspeckle component 1 /// TPTE and PTEN homologous inositol lipid phosphatase pseudogene | PSPC1 /// LOC374491 | 374491 /// 55269 | — | — | TTP/resp | 119 |
| 526 | 201390_s_at | HG-U133A | NM_001320 | 493 | casein kinase 2, beta polypeptide | CSNK2B | 1460 | — | — | TTP/resp | 123 |
| 527 | 211940_x_at | HG-U133A | BE869922 | 494 | H3 histone, family 3A | H3F3A | 3020 | — | — | TTP/resp | 134 |
| 528 | 223231_at | HG-U133B | AF212250 | 495 | TatD DNase domain containing 1 | TATDN1 | 83940 | — | — | TTP/resp | 134 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 529 | 225222_at | HG-U133B | AI243268 | 496 | hippocampus abundant transcript 1 | HIAT1 | 64645 | — | — | TTP/resp | 139 |
| 530 | 212315_s_at | HG-U133B | AA502912 | 388 | nucleoporin 210 kDa | NUP210 | 23225 | — | — | TTP/resp | 149 |
| 531 | 216515_x_at | HG-U133B | AL121585 | 497 | prothymosin, alpha (gene sequence 28) | PTMA | 5757 | — | — | TTP/resp | 153 |
| 532 | 201019_s_at | HG-U133A | NM_001412 | 498 | eukaryotic translation initiation factor 1A, X-linked | EIF1AX | 1964 | — | — | TTP/resp | 168 |
| 533 | 222230_s_at | HG-U133A | AK022248 | 499 | actin-related protein 10 homolog (S. cerevisiae) | ACTR10 | 55860 | — | — | TTP/resp | 173 |
| 534 | 222992_s_at | HG-U133B | AF261090 | 500 | NADH dehydrogenase (ubiquinone) 1 beta subcomplex, 9, 22 kDa | NDUFB9 | 4715 | — | — | TTP/resp | 176 |
| 535 | 201901_s_at | HG-U133A | Z14077 | 501 | YY1 transcription factor | YY1 | 7528 | — | — | TTP/resp | 196 |
| 536 | 202487_s_at | HG-U133A | NM_012412 | 502 | H2A histone family, member V | H2AFV | 94239 | — | — | TTP/resp | 209 |
| 537 | 207614_s_at | HG-U133A | NM_003592 | 503 | cullin 1 | CUL1 | 8454 | — | — | TTP/resp | 210 |
| 538 | 202495_at | HG-U133A | NM_003192 | 504 | tubulin-specific chaperone c | TBCC | 6903 | — | — | TTP/resp | 219 |
| 539 | 210949_s_at | HG-U133A | BC000533 | 505 | eukaryotic translation initiation factor 3, subunit 8, 110 kDa | EIF3S8 | 8663 | — | — | TTP/resp | 234 |
| 540 | 218247_s_at | HG-U133A | NM_016626 | 506 | ring finger and KH domain containing 2 | RKHD2 | 51320 | — | — | TTP/resp | 236 |
| 541 | 211931_s_at | HG-U133A | BG505670 | 507 | heterogeneous nuclear ribonucleoprotein A3 | HNRPA3 | 220988 | — | — | TTP/resp | 238 |
| 542 | 200647_x_at | HG-U133A | NM_003752 | 508 | eukaryotic translation initiation factor 3, subunit 8, 110 kDa | EIF3S8 | 8663 | — | — | TTP/resp | 244 |
| 543 | 223091_x_at | HG-U133B | AF258660 | 509 | chromosome 2 open reading frame 33 | C2orf33 | 56947 | — | — | TTP/resp | 244 |
| 544 | 215230_x_at | HG-U133A | AA679705 | 510 | eukaryotic translation initiation factor 3, subunit 8, 110 kDa | EIF3S8 | 8663 | — | — | TTP/resp | 272 |
| 545 | 200893_at | HG-U133A | NM_004593 | 511 | splicing factor, arginine/serine-rich 10 (transformer 2 homolog, Drosophila) | SFRS10 | 6434 | — | — | TTP/resp | 285 |
| 546 | 218738_s_at | HG-U133A | NM_016271 | 512 | ring finger protein 138 | RNF138 | 51444 | — | — | TTP/resp | 289 |
| 547 | 200844_s_at | HG-U133A | BE869583 | 513 | peroxiredoxin 6 | PRDX6 | 9588 | — | — | TTP/resp | 292 |
| 548 | 200082_s_at | HG-U133A | AI805587 | 514 | ribosomal protein S7 | RPS7 | 6201 | — | — | resp | 1 |
| 549 | 224841_x_at | HG-U133B | BF316352 | 515 | growth arrest-specific 5 | GAS5 | 60674 | — | — | resp | 1 |
| 550 | 200082_s_at | HG-U133A | AI805587 | 514 | ribosomal protein S7 | RPS7 | 6201 | — | — | resp | 2 |
| 551 | 206790_s_at | HG-U133A | NM_004545 | 516 | NADH dehydrogenase (ubiquinone) 1 beta subcomplex, 1, 7 kDa | NDUFB1 | 4707 | — | — | resp | 2 |
| 552 | 224741_x_at | HG-U133B | BG329175 | 517 | growth arrest-specific 5 | GAS5 | 60674 | — | — | resp | 2 |
| 553 | 226835_s_at | HG-U133B | BG330520 | 518 | Similar to RPE-spondin | | 441951 | — | — | resp | 3 |
| 554 | 224915_s_at | HG-U133B | AV756131 | 519 | Similar to RPE-spondin | | 441951 | — | — | resp | 4 |
| 555 | 200937_s_at | HG-U133A | NM_000969 | 520 | ribosomal protein L5 | RPL5 | 6125 | — | — | resp | 5 |
| 556 | 220755_s_at | HG-U133B | NM_016947 | 521 | chromosome 6 open reading frame 48 | C6orf48 | 50854 | — | — | resp | 11 |
| 557 | 201520_s_at | HG-U133A | BF034561 | 522 | G-rich RNA sequence binding factor 1 | GRSF1 | 2926 | — | — | resp | 14 |
| 558 | 217719_at | HG-U133A | NM_016091 | 523 | eukaryotic translation initiation factor 3, subunit 6 interacting protein | EIF3S6IP | 51386 | — | — | resp | 15 |
| 559 | 226227_x_at | HG-U133B | BF185165 | 524 | Similar to RPE-spondin | | 441951 | — | — | resp | 16 |
| 560 | 202232_s_at | HG-U133A | NM_006360 | 52 | dendritic cell protein | GA17 | 10480 | — | — | resp | 17 |
| 561 | 208796_s_at | HG-U133A | BC000196 | 525 | cyclin G1 | CCNG1 | 900 | — | — | resp | 23 |
| 562 | 200023_s_at | HG-U133A | NM_003754 | 526 | eukaryotic translation initiation factor 3, subunit 5 epsilon, 47 kDa | EIF3S5 | 8665 | — | — | resp | 26 |
| 563 | 200834_s_at | HG-U133A | NM_001024 | 527 | ribosomal protein S21 | RPS21 | 6227 | — | — | resp | 27 |
| 564 | 201258_at | HG-U133A | NM_001020 | 528 | ribosomal protein S16 | RPS16 | 6217 | — | — | resp | 36 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 565 | 200023_s_at | HG-U133A | NM_003754 | 526 | eukaryotic translation initiation factor 3, subunit 5 epsilon, 47 kDa | EIF3S5 | 8665 | — | — | resp | 40 |
| 566 | 225698_at | HG-U133B | BF314746 | 529 | TIGA1 | TIGA1 | 114915 | — | — | resp | 41 |
| 567 | 200024_at | HG-U133B | NM_001009 | 530 | | | | — | — | resp | 58 |
| 568 | 221434_s_at | HG-U133A | NM_031210 | 531 | chromosome 14 open reading frame 156 | C14orf156 | 81892 | — | — | resp | 63 |
| 569 | 225190_x_at | HG-U133B | AW402660 | 532 | ribosomal protein L35a | RPL35A | 6165 | — | — | resp | 70 |
| 570 | 200024_at | HG-U133A | NM_001009 | 530 | | | | — | — | resp | 71 |
| 571 | 200903_s_at | HG-U133A | NM_000687 | 533 | S-adenosylhomocysteine hydrolase | AHCY | 191 | — | — | resp | 76 |
| 572 | 234875_at | HG-U133B | AJ224082 | 534 | | | | — | — | resp | 84 |
| 573 | 225065_x_at | HG-U133B | AI826279 | 535 | hypothetical protein MGC40157 | MGC40157 | 125144 | — | — | resp | 98 |
| 574 | 217969_at | HG-U133A | NM_013265 | 536 | chromosome 11 open reading frame2 | C11orf2 | 738 | — | — | resp | 104 |
| 575 | 201653_at | HG-U133A | NM_005776 | 537 | cornichon homolog (Drosophila) | CNIH | 10175 | — | — | resp | 105 |
| 576 | 200019_s_at | HG-U133B | NM_001997 | 538 | Finkel-Biskis-Reilly murine sarcoma virus (FBR-MuSV) ubiquitously expressed (fox derived); ribosomal protein S30 | FAU | 2197 | — | — | resp | 107 |
| 577 | 200030_s_at | HG-U133A | NM_002635 | 539 | solute carrier family 25 (mitochondrial carrier; phosphate carrier), member 3 | SLC25A3 | 5250 | — | — | resp | 112 |
| 578 | 216380_x_at | HG-U133A | AC005011 | 540 | | | | — | — | resp | 121 |
| 579 | 200826_at | HG-U133A | NM_004597 | 541 | small nuclear ribonucleoprotein D2 polypeptide 16.5 kDa | SNRPD2 | 6633 | — | — | resp | 122 |
| 580 | 200030_s_at | HG-U133B | NM_002635 | 539 | solute carrier family 25 (mitochondrial carrier; phosphate carrier), member 3 | SLC25A3 | 5250 | — | — | resp | 124 |
| 581 | 221691_x_at | HG-U133A | AB042278 | 542 | nucleophosmin (nucleolar phosphoprotein B23, numatrin) | NPM1 | 4869 | — | — | resp | 127 |
| 582 | 211937_at | HG-U133A | NM_001417 | 543 | eukaryotic translation initiation factor 4B | EIF4B | 1975 | — | — | resp | 132 |
| 583 | 208742_s_at | HG-U133A | U78303 | 544 | sin3-associated polypeptide, 18 kDa | SAP18 | 10284 | — | — | resp | 146 |
| 584 | 200869_at | HG-U133A | NM_000980 | 545 | ribosomal protein L18a | RPL18A | 6142 | — | — | resp | 158 |
| 585 | 212644_s_at | HG-U133A | AI671747 | 546 | chromosome 14 open reading frame 32 | C14orf32 | 93487 | — | — | resp | 160 |
| 586 | 222975_at | HG-U133B | AI423180 | 547 | upstream of NRAS | UNR | 7812 | — | — | resp | 176 |
| 587 | 219030_at | HG-U133A | NM_016058 | 548 | CGI-121 protein | CGI-121 | 51002 | — | — | resp | 189 |
| 588 | 201682_at | HG-U133A | NM_004279 | 549 | peptidase (mitochondrial processing) beta | PMPCB | 9512 | — | — | resp | 195 |
| 589 | 207573_x_at | HG-U133A | NM_006476 | 550 | ATP synthase, H+ transporting, mitochondrial F0 complex, subunit g | ATP5L | 10632 | — | — | resp | 206 |
| 590 | 209786_at | HG-U133A | BC001282 | 193 | high mobility group nucleosomal binding domain 4 | HMGN4 | 10473 | — | — | resp | 219 |
| 591 | 200019_s_at | HG-U133A | NM_001997 | 538 | Finkel-Biskis-Reilly murine sarcoma virus (FBR-MuSV) ubiquitously expressed (fox derived); ribosomal protein S30 | FAU | 2197 | — | — | resp | 236 |
| 592 | 210453_x_at | HG-U133A | AL050277 | 551 | ATP synthase, H+ transporting, mitochondrial F0 complex, subunit g | ATP5L | 10632 | — | — | resp | 248 |
| 593 | 226243_at | HG-U133B | BF590958 | 552 | Similar to CG14903-PA | | 391356 | — | — | resp | 253 |
| 594 | 222465_at | HG-U133B | AF165521 | 553 | chromosome 15 open reading frame 15 | C15orf15 | 51187 | — | — | resp | 255 |
| 595 | 229050_s_at | HG-U133B | AL533103 | 554 | hypothetical protein MGC16037 | MGC16037 | 84973 | — | — | resp | 294 |
| 596 | 217915_s_at | HG-U133A | NM_016304 | 555 | chromosome 15 open reading frame 15 | C15orf15 | 51187 | — | — | resp | 296 |
| 597 | 201532_at | HG-U133A | NM_002788 | 556 | proteasome (prosome, macropain) subunit, alpha type, 3 | PSMA3 | 5684 | — | — | resp | 309 |

TABLE 1-continued

PROTEASOME INHIBITOR PREDICTIVE MARKER IDENTIFICATION
1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 598 | 239237_at | HG-U133B | AI798822 | 557 | LOC442534 | — | 442534 | — | — | resp | 322 |
| 599 | 202026_at | HG-U133A | NM_003002 | 558 | succinate dehydrogenase complex, subunit D, integral membrane protein | SDHD | 6392 | — | — | resp | 325 |
| 600 | 221726_at | HG-U133A | BE250348 | 559 | ribosomal protein L22 | RPL22 | 6146 | — | — | resp | 326 |
| 601 | 201177_s_at | HG-U133A | NM_005499 | 560 | SUMO-1 activating enzyme subunit 2 | UBA2 | 10054 | — | — | resp | 357 |
| 602 | 201892_s_at | HG-U133A | NM_000884 | 561 | IMP (inosine monophosphate) dehydrogenase 2 | IMPDH2 | 3615 | — | — | resp | 360 |
| 603 | 200037_s_at | HG-U133B | NM_016587 | 562 | chromobox homolog 3 (HP1 gamma homolog, Drosophila) | CBX3 | 11335 | — | — | resp | 368 |
| 604 | 216274_s_at | HG-U133A | N99438 | 563 | SEC11-like 1 (S. cerevisiae) | SEC11L1 | 23478 | — | — | resp | 376 |
| 605 | 214167_s_at | HG-U133A | AA555113 | 564 | ribosomal protein, large, P0 | RPLP0 | 6175 | — | — | resp | 389 |
| 606 | 213738_s_at | HG-U133A | AI587323 | 565 | ATP synthase, H+ transporting, mitochondrial F1 complex, alpha subunit, isoform 1, cardiac muscle | ATP5A1 | 498 | — | — | resp | 424 |
| 607 | 222410_s_at | HG-U133B | AF121856 | 566 | sorting nexin 6 | SNX6 | 58533 | — | — | resp | 495 |
| 608 | 222784_at | HG-U133B | AJ249900 | 567 | | | | — | — | resp | 496 |
| 609 | 200003_s_at | HG-U133B | NM_000991 | 568 | ribosomal protein L28 | RPL28 | 6158 | — | — | resp | 503 |
| 610 | 222427_s_at | HG-U133A | AK021413 | 569 | leucyl-tRNA synthetase | LARS | 51520 | — | — | resp | 516 |
| 611 | 200715_x_at | HG-U133B | BC000514 | 570 | ribosomal protein L13a | RPL13A | 23521 | — | — | resp | 524 |
| 612 | 201554_x_at | HG-U133A | NM_004130 | 571 | glycogenin | GYG | 2992 | — | — | resp | 526 |
| 613 | 200047_s_at | HG-U133B | NM_003403 | 572 | YY1 transcription factor | YY1 | 7528 | — | — | resp | 529 |
| 614 | 215733_x_at | HG-U133B | AJ012833 | 573 | cancer/testis antigen 2 | CTAG2 | 30848 | — | — | resp | 3 |
| 615 | 201491_at | HG-U133A | NM_012111 | 574 | AHA1, activator of heat shock 90 kDa protein ATPase homolog 1 (yeast) | AHSA1 | 10598 | — | — | TTP | 266 |
| 616 | 210467_x_at | HG-U133B | BC003408 | 575 | melanoma antigen family A, 12 | MAGEA12 | 4111 | — | — | TTP | 283 |
| 617 | 210546_x_at | HG-U133A | U87459 | 576 | cancer/testis antigen 1B /// cancer/testis antigen 1A | CTAG1B /// CTAG1A | 1485 /// 246100 | — | — | TTP/resp | 1 |
| 618 | 211674_x_at | HG-U133A | AF038567 | 577 | cancer/testis antigen 1B /// cancer/testis antigen 1A | CTAG1B /// CTAG1A | 1485 /// 246100 | — | — | TTP/resp | 1 |
| 619 | 224985_at | HG-U133B | BE964484 | 578 | Neuroblastoma RAS viral (v-ras) oncogene homolog | NRAS | 4893 | — | — | TTP/resp | 2 |
| 620 | 200043_at | HG-U133A | NM_004450 | 579 | enhancer of rudimentary homolog (Drosophila) | ERH | 2079 | — | — | TTP/resp | 3 |
| 621 | 200043_at | HG-U133B | NM_004450 | 579 | enhancer of rudimentary homolog (Drosophila) | ERH | 2079 | — | — | TTP/resp | 13 |
| 622 | 222783_s_at | HG-U133B | BF516292 | 580 | SPARC related modular calcium binding 1 | SMOC1 | 64093 | — | — | TTP/resp | 21 |
| 623 | 211747_s_at | HG-U133B | BC005938 | 581 | LSM5 homolog, U6 small nuclear RNA associated (S. cerevisiae) | LSM5 | 23658 | — | — | TTP/resp | 25 |
| 624 | 223358_s_at | HG-U133B | AW269834 | 582 | Phosphodiesterase 7A | PDE7A | 5150 | — | — | TTP/resp | 37 |
| 625 | 200921_s_at | HG-U133A | NM_001731 | 583 | B-cell translocation gene 1, anti-proliferative | BTG1 | 694 | — | — | TTP/resp | 67 |
| 626 | 200037_s_at | HG-U133A | NM_016587 | 562 | chromobox homolog 3 (HP1 gamma homolog, Drosophila) | CBX3 | 11335 | — | — | TTP/resp | 99 |
| 627 | 208743_s_at | HG-U133A | BC001359 | 584 | tyrosine 3-monooxygenase/tryptophan 5-monooxygenase activation protein, beta polypeptide | YWHAB | 7529 | — | — | TTP/resp | 118 |

TABLE 1-continued

PROTEASOME INHIBITOR PREDICTIVE MARKER IDENTIFICATION

1A Predictive Markers Upregulated Indicators of Non-Response and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 628 | 201825_s_at | HG-U133A | AL572542 | 585 | CGI-49 protein | CGI-49 | 51097 | — | — | TTP/resp | 143 |
| 629 | 200047_s_at | HG-U133A | NM_003403 | 572 | YY1 transcription factor | YY1 | 7528 | — | — | TTP/resp | 240 |
| 630 | 202591_s_at | HG-U133A | NM_003143 | 586 | single-stranded DNA binding protein 1 | SSBP1 | 6742 | — | — | TTP/resp | 248 |
| 631 | 209036_s_at | HG-U133A | BC001917 | 587 | malate dehydrogenase 2, NAD (mitochondrial) | MDH2 | 4191 | — | — | TTP/resp | 271 |
| 632 | 200949_x_at | HG-U133A | NM_001023 | 588 | ribosomal protein S20 | RPS20 | 6224 | | — | resp | 30 |
| 633 | 219939_s_at | HG-U133A | NM_007158 | 589 | upstream of NRAS | UNR | 7812 | | — | resp | 82 |
| 634 | 214003_x_at | HG-U133A | BF184532 | 590 | ribosomal protein S20 | RPS20 | 6224 | | — | resp | 118 |
| 635 | 208764_s_at | HG-U133A | D13119 | 591 | ATP synthase, H+ transporting, mitochondrial F0 complex, subunit c (subunit 9), isoform 2 | ATP5G2 | 517 | | — | resp | 170 |
| 636 | 201011_at | HG-U133A | NM_002950 | 592 | ribophorin I | RPN1 | 6184 | | — | resp | 179 |
| 637 | 222035_s_at | HG-U133A | AI984479 | 593 | poly(A) polymerase alpha | PAPOLA | 10914 | | — | resp | 187 |
| 638 | 209066_x_at | HG-U133A | M26700 | 594 | ubiquinol-cytochrome c reductase binding protein | UQCRB | 7381 | | — | resp | 298 |
| 639 | 212807_s_at | HG-U133A | BF447105 | 595 | sortilin 1 | SORT1 | 6272 | | — | resp | 349 |
| 640 | 212266_s_at | HG-U133A | AW084582 | 596 | splicing factor, arginine/serine-rich 5 | SFRS5 | 6430 | | — | resp | 362 |
| 641 | 217846_at | HG-U133A | NM_005051 | 597 | glutaminyl-tRNA synthetase | QARS | 5859 | | — | resp | 379 |
| 642 | 202579_x_at | HG-U133A | NM_006353 | 598 | high mobility group nucleosomal binding domain 4 | HMGN4 | 10473 | | — | resp | 451 |
| 643 | 202105_at | HG-U133A | NM_001551 | 599 | immunoglobulin (CD79A) binding protein 1 | IGBP1 | 3476 | | — | resp | 599 |
| 644 | 203380_x_at | HG-U133A | NM_006925 | 600 | splicing factor, arginine/serine-rich 5 | SFRS5 | 6430 | | — | resp | 683 |
| 645 | 208668_x_at | HG-U133A | BC003689 | 601 | high-mobility group nucleosomal binding domain 2 | HMGN2 | 3151 | — | | TTP | 67 |
| 646 | 212718_at | HG-U133A | BF797555 | 602 | poly(A) polymerase alpha | PAPOLA | 10914 | — | | TTP | 85 |
| 647 | 218233_s_at | HG-U133A | NM_017601 | 603 | chromosome 6 open reading frame 49 | C6orf49 | 29964 | — | | TTP | 127 |
| 648 | 218482_at | HG-U133A | NM_020189 | 604 | e(y)2 protein | e(y)2 | 56943 | — | | TTP | 226 |
| 649 | 218850_at | HG-U133A | NM_014240 | 605 | LIM domains containing 1 | LIMD1 | 8994 | — | | TTP | 264 |
| 650 | 230769_at | HG-U133B | AI916261 | 606 | FLJ37099 protein | FLJ37099 | 163259 | — | | TTP | 1 |
| 651 | 207654_x_at | HG-U133A | NM_001938 | 607 | down-regulator of transcription 1, TBP-binding (negative cofactor 2) | DR1 | 1810 | — | | TTP | 227 |
| 652 | 210532_s_at | HG-U133A | AF116639 | 608 | chromosome 14 open reading frame 2 | C14orf2 | 9556 | — | — | TTP/resp | 1 |
| 653 | 209899_s_at | HG-U133A | AF217197 | 609 | fuse-binding protein-interacting repressor | SIAHBP1 | 22827 | — | — | TTP/resp | 4 |
| 654 | 211783_s_at | HG-U133A | BC006177 | 610 | metastasis associated 1 | MTA1 | 9112 | — | — | TTP/resp | 55 |
| 655 | 201840_at | HG-U133A | NM_006156 | 611 | neural precursor cell expressed, developmentally down-regulated 8 | NEDD8 | 4738 | — | — | TTP/resp | 71 |
| 656 | 200920_s_at | HG-U133A | AL535380 | 612 | B-cell translocation gene 1, anti-proliferative | BTG1 | 694 | — | — | TTP/resp | 87 |
| 657 | 222789_at | HG-U133B | R45958 | 613 | round spermatid basic protein 1 | RSBN1 | 54665 | — | — | TTP/resp | 222 |

1B Predictive Markers Unregulated Indicators of Response and/or Long Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 658 | 219073_s_at | HG-U133A | NM_017784 | 614 | oxysterol binding protein-like 10 | OSBPL10 | 114884 | + | + | resp | 116 |
| 659 | 227168_at | HG-U133B | BF475488 | 615 | hypothetical gene supported by AK098833 | LOC440823 | 440823 | | + | resp | 3 |
| 660 | 204122_at | HG-U133A | NM_003332 | 616 | TYRO protein tyrosine kinase binding protein | TYROBP | 7305 | | + | resp | 6 |
| 661 | 209101_at | HG-U133A | M92934 | 617 | connective tissue growth factor | CTGF | 1490 | | + | resp | 6 |
| 662 | 204208_at | HG-U133A | NM_003800 | 618 | RNA guanylyltransferase and 5′-phosphatase | RNGTT | 8732 | | + | resp | 8 |
| 663 | 223044_at | HG-U133B | AL136944 | 619 | solute carrier family 40 (iron-regulated transporter), member 1 | SLC40A1 | 30061 | | + | resp | 9 |
| 664 | 213915_at | HG-U133A | NM_005601 | 620 | natural killer cell group 7 sequence | NKG7 | 4818 | | + | resp | 10 |
| 665 | 224616_at | HG-U133B | BG110975 | 621 | dynein, cytoplasmic, light intermediate polypeptide 2 | DNCLI2 | 1783 | | + | resp | 11 |
| 666 | 214574_x_at | HG-U133A | NM_007161 | 622 | leukocyte specific transcript 1 | LST1 | 7940 | | + | resp | 12 |
| 667 | 204834_at | HG-U133A | NM_006682 | 623 | fibrinogen-like 2 | FGL2 | 10875 | | + | resp | 13 |
| 668 | 212646_at | HG-U133A | D42043 | 624 | raft-linking protein | RAFTLIN | 23180 | | + | resp | 18 |
| 669 | 231078_at | HG-U133B | H69701 | 625 | Mitochondrial solute carrier protein | MSCP | 51312 | | + | resp | 20 |
| 670 | 230499_at | HG-U133B | AA805622 | 626 | Baculoviral IAP repeat-containing 3 | BIRC3 | 330 | | + | resp | 21 |
| 671 | 208540_x_at | HG-U133A | NM_021039 | 627 | | | | | + | resp | 24 |
| 672 | 203568_s_at | HG-U133A | NM_006355 | 628 | tripartite motif-containing 38 | TRIM38 | 10475 | | + | resp | 29 |
| 673 | 200941_at | HG-U133A | AK026575 | 629 | heat shock factor binding protein 1 | HSBP1 | 3281 | | + | resp | 31 |
| 674 | 222368_at | HG-U133A | AW972351 | 630 | | | | | + | resp | 33 |
| 675 | 1729_at | HG-U133A | L41690 | 631 | TNFRSF1A-associated via death domain | TRADD | 8717 | | + | resp | 34 |
| 676 | 212136_at | HG-U133A | AW517686 | 632 | ATPase, Ca++ transporting, plasma membrane 4 | ATP2B4 | 493 | | + | resp | 36 |
| 677 | 213193_x_at | HG-U133A | AL559122 | 633 | T cell receptor beta constant 1 | TRBC1 | 28639 | | + | resp | 38 |
| 678 | 203290_at | HG-U133A | NM_002122 | 634 | major histocompatibility complex, class II, DQ alpha 1 /// major histocompatibility complex, class II, DQ alpha 2 | HLA-DQA1 /// HLA-DQA2 | 3117 /// 3118 | | + | resp | 40 |
| 679 | 229147_at | HG-U133B | AW070877 | 635 | | | | | + | resp | 42 |
| 680 | 221495_at | HG-U133A | AF322111 | 636 | KIAA1049 protein | KIAA1049 | 22980 | | + | resp | 46 |
| 681 | 203221_at | HG-U133A | AI758763 | 637 | transducin-like enhancer of split 1 (E(sp1) homolog, Drosophila) | TLE1 | 7088 | | + | resp | 56 |
| 682 | 203542_s_at | HG-U133A | AI690205 | 638 | Kruppel-like factor 9 | KLF9 | 687 | | + | resp | 57 |
| 683 | 213275_x_at | HG-U133A | W47179 | 639 | Cathepsin B | CTSB | 1508 | | + | resp | 64 |
| 684 | 216063_at | HG-U133A | N55205 | 640 | | | | | + | resp | 65 |
| 685 | 213311_s_at | HG-U133A | BF000251 | 641 | KIAA1049 protein | KIAA1049 | 22980 | | + | resp | 66 |
| 686 | 202436_s_at | HG-U133A | AU144855 | 642 | cytochrome P450, family 1, subfamily B, polypeptide 1 | CYP1B1 | 1545 | | + | resp | 70 |
| 687 | 215051_x_at | HG-U133A | BF213829 | 643 | allograft inflammatory factor 1 | AIF1 | 199 | | + | resp | 73 |
| 688 | 238025_at | HG-U133B | AA706818 | 644 | mixed lineage kinase domain-like | MLKL | 197259 | | + | resp | 73 |

1B Predictive Markers Unregulated Indicators of Response and/or Long Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 689 | 200860_s_at | HG-U133A | BC000779 | 645 | CCR4-NOT transcription complex, subunit 1 | CNOT1 | 23019 | | + | resp | 74 |
| 690 | 200696_s_at | HG-U133A | NM_000177 | 646 | gelsolin (amyloidosis, Finnish type) | GSN | 2934 | | + | resp | 79 |
| 691 | 201705_at | HG-U133A | NM_002811 | 647 | proteasome (prosome, macropain) 26S subunit, non-ATPase, 7 (Mov34 homolog) | PSMD7 | 5713 | | + | resp | 79 |
| 692 | 220792_at | HG-U133A | NM_018699 | 648 | PR domain containing 5 | PRDM5 | 11107 | | + | resp | 80 |
| 693 | 219910_at | HG-U133A | NM_007076 | 649 | Huntingtin interacting protein E | HYPE | 11153 | | + | resp | 83 |
| 694 | 211981_at | HG-U133A | NM_001845 | 650 | collagen, type IV, alpha 1 | COL4A1 | 1282 | | + | resp | 85 |
| 695 | 210950_s_at | HG-U133A | BC003573 | 651 | farnesyl-diphosphate farnesyltransferase 1 | FDFT1 | 2222 | | + | resp | 86 |
| 696 | 212135_s_at | HG-U133A | AW517686 | 632 | ATPase, Ca++ transporting, plasma membrane 4 | ATP2B4 | 493 | | + | resp | 86 |
| 697 | 217889_s_at | HG-U133A | NM_024843 | 652 | Cytochrome b reductase 1 | CYBRD1 | 79901 | | + | resp | 90 |
| 698 | 204207_s_at | HG-U133A | AB012142 | 653 | RNA guanylyltransferase and 5'-phosphatase | RNGTT | 8732 | | + | resp | 91 |
| 699 | 213274_s_at | HG-U133A | AA020826 | 654 | cathepsin B | CTSB | 1508 | | + | resp | 93 |
| 700 | 243780_at | HG-U133B | AW575863 | 655 | CDNA FLJ46553 fis, clone THYMU3038879 | | | | + | resp | 96 |
| 701 | 209118_s_at | HG-U133A | AF141347 | 656 | tubulin, alpha 3 | TUBA3 | 7846 | | + | resp | 98 |
| 702 | 205051_s_at | HG-U133A | NM_000222 | 657 | v-kit Hardy-Zuckerman 4 feline sarcoma viral oncogene homolog | KIT | 3815 | | + | resp | 101 |
| 703 | 202497_x_at | HG-U133A | AI631159 | 658 | solute carrier family 2 (facilitated glucose transporter), member 3 | SLC2A3 | 6515 | | + | resp | 102 |
| 704 | 208791_at | HG-U133A | M25915 | 659 | clusterin (complement lysis inhibitor, SP-40,40, sulfated glycoprotein 2, testosterone-repressed prostate message 2, apolipoprotein J) | CLU | 1191 | | + | resp | 105 |
| 705 | 209607_x_at | HG-U133A | U08032 | 660 | sulfotransferase family, cytosolic, 1A, phenol-preferring, member 3 | SULT1A3 | 6818 | | + | resp | 108 |
| 706 | 203973_s_at | HG-U133A | NM_005195 | 661 | CCAAT/enhancer binding protein (C/EBP), delta | CEBPD | 1052 | | + | resp | 111 |
| 707 | 209047_at | HG-U133A | AL518391 | 662 | aquaporin 1 (channel-forming integral protein, 28 kDa) | AQP1 | 358 | | + | resp | 117 |
| 708 | 212007_at | HG-U133A | AI927512 | 663 | UBX domain containing 2 | UBXD2 | 23190 | | + | resp | 119 |
| 709 | 224917_at | HG-U133B | BF674052 | 664 | likely ortholog of rat vacuole membrane protein 1 | VMP1 | 81671 | | + | resp | 124 |
| 710 | 213574_s_at | HG-U133A | AA861608 | 665 | Karyopherin (importin) beta 1 | KPNB1 | 3837 | | + | resp | 129 |
| 711 | 206666_at | HG-U133A | NM_002104 | 666 | granzyme K (serine protease, granzyme 3; tryptase II) | GZMK | 3003 | | + | resp | 146 |
| 712 | 210666_at | HG-U133A | AF050145 | 667 | iduronate 2-sulfatase (Hunter syndrome) | IDS | 3423 | | + | resp | 148 |
| 713 | 209013_x_at | HG-U133A | AF091395 | 668 | triple functional domain (PTPRF interacting) | TRIO | 7204 | | + | resp | 153 |

1B Predictive Markers Unregulated Indicators of Response and/or Long Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 714 | 213164_at | HG-U133A | AI867198 | 669 | solute carrier family 5 (Inositol transporters), member 3 | SLC5A3 | 6526 | | + | resp | 153 |
| 715 | 205641_s_at | HG-U133A | NM_003789 | 670 | TNFRSF1A-associated via death domain | TRADD | 8717 | | + | resp | 155 |
| 716 | 226599_at | HG-U133B | AA527080 | 671 | KIAA1727 protein | KIAA1727 | 85462 | | + | resp | 155 |
| 717 | 210835_s_at | HG-U133A | AF222711 | 672 | C-terminal binding protein 2 | CTBP2 | 1488 | | + | resp | 159 |
| 718 | 226430_at | HG-U133B | AI394438 | 673 | hypothetical protein LOC253981 | LOC253981 | 253981 | | + | resp | 160 |
| 719 | 213396_s_at | HG-U133A | AA456929 | 674 | A kinase (PRKA) anchor protein 10 | AKAP10 | 11216 | | + | resp | 161 |
| 720 | 209018_s_at | HG-U133A | BF432478 | 675 | PTEN induced putative kinase 1 | PINK1 | 65018 | | + | resp | 164 |
| 721 | 239629_at | HG-U133B | AI634046 | 676 | | | | | + | resp | 168 |
| 722 | 212724_at | HG-U133A | BG054844 | 677 | Rho family GTPase 3 | RND3 | 390 | | + | resp | 172 |
| 723 | 219577_s_at | HG-U133A | NM_019112 | 678 | ATP-binding cassette, sub-family A (ABC1), member 7 | ABCA7 | 10347 | | + | resp | 175 |
| 724 | 206150_at | HG-U133A | NM_001242 | 679 | tumor necrosis factor receptor superfamily, member 7 | TNFRSF7 | 939 | | + | resp | 177 |
| 725 | 238063_at | HG-U133B | AA806283 | 680 | hypothetical protein FLJ32028 | FLJ32028 | 201799 | | + | resp | 188 |
| 726 | 202292_x_at | HG-U133A | NM_007260 | 681 | lysophospholipase II | LYPLA2 | 11313 | | + | resp | 191 |
| 727 | 212041_at | HG-U133A | AL566172 | 682 | ATPase, H+ transporting, lysosomal 38 kDa, V0 subunit d isoform 1 | ATP6V0D1 | 9114 | | + | resp | 199 |
| 728 | 205990_s_at | HG-U133A | NM_003392 | 683 | wingless-type MMTV integration site family, member 5A | WNT5A | 7474 | | + | resp | 200 |
| 729 | 212944_at | HG-U133A | AK024896 | 684 | Mitochondrial ribosomal protein S6 | MRPS6 | 64968 | | + | resp | 203 |
| 730 | 224159_x_at | HG-U133B | AF220023 | 685 | tripartite motif-containing 4 | TRIM4 | 89122 | | + | resp | 205 |
| 731 | 235638_at | HG-U133B | AI167789 | 686 | Ras association (RalGDS/AF-6) domain family 6 | RASSF6 | 166824 | | + | resp | 206 |
| 732 | 212588_at | HG-U133A | Y00062 | 687 | protein tyrosine phosphatase, receptor type, C | PTPRC | 5788 | | + | resp | 209 |
| 733 | 202283_at | HG-U133A | NM_002615 | 688 | serine (or cysteine) proteinase inhibitor, clade F (alpha-2 antiplasmin, pigment epithelium derived factor), member 1 | SERPINF1 | 5176 | | + | resp | 211 |
| 734 | 221804_s_at | HG-U133A | BE565675 | 689 | family with sequence similarity 45, member B /// family with sequence similarity 45, member A | FAM45B /// FAM45A | 404636 /// 55855 | | + | resp | 215 |
| 735 | 203909_at | HG-U133A | NM_006359 | 690 | solute carrier family 9 (sodium/hydrogen exchanger), isoform 6 | SLC9A6 | 10479 | | + | resp | 216 |
| 736 | 200675_at | HG-U133A | NM_004356 | 691 | CD81 antigen (target of antiproliferative antibody 1) | CD81 | 975 | | + | resp | 217 |
| 737 | 209939_x_at | HG-U133A | AF005775 | 692 | CASP8 and FADD-like apoptosis regulator | CFLAR | 8837 | | + | resp | 218 |
| 738 | 212884_x_at | HG-U133A | AI358867 | 693 | | | | | + | resp | 219 |
| 739 | 206337_at | HG-U133A | NM_001838 | 694 | chemokine (C-C motif) receptor 7 | CCR7 | 1236 | | + | resp | 220 |
| 740 | 208178_x_at | HG-U133A | NM_007118 | 695 | triple functional domain (PTPRF interacting) | TRIO | 7204 | | + | resp | 220 |
| 741 | 225626_at | HG-U133B | AK000680 | 696 | phosphoprotein associated with glycosphingolipid-enriched microdomains | PAG | 55824 | | + | resp | 221 |

1B Predictive Markers Unregulated Indicators of Response and/or Long Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 742 | 201024_x_at | HG-U133A | BG261322 | 697 | eukaryotic translation initiation factor 5B | EIF5B | 9669 | | + | resp | 223 |
| 743 | 204115_at | HG-U133A | NM_004126 | 698 | guanine nucleotide binding protein (G protein), gamma 11 | GNG11 | 2791 | | + | resp | 224 |
| 744 | 212240_s_at | HG-U133A | AI679268 | 699 | phosphoinositide-3-kinase, regulatory subunit 1 (p85 alpha) | PIK3R1 | 5295 | | + | resp | 224 |
| 745 | 202615_at | HG-U133A | BF222895 | 700 | guanine nucleotide binding protein (G protein), q polypeptide | GNAQ | 2776 | | + | resp | 225 |
| 746 | 210580_x_at | HG-U133A | L25275 | 701 | sulfotransferase family, cytosolic, 1A, phenol-preferring, member 3 | SULT1A3 | 6818 | | + | resp | 226 |
| 747 | 242121_at | HG-U133B | AW973232 | 702 | Ring finger protein 12 | RNF12 | 51132 | | + | resp | 226 |
| 748 | 213539_at | HG-U133A | NM_000732 | 703 | CD3D antigen, delta polypeptide (TiT3 complex) | CD3D | 915 | | + | resp | 233 |
| 749 | 218505_at | HG-U133A | NM_024673 | 704 | FLJ12270 protein | FLJ12270 | 79726 | | + | resp | 235 |
| 750 | 212982_at | HG-U133A | AI621223 | 705 | zinc finger, DHHC domain containing 17 | ZDHHC17 | 23390 | | + | resp | 249 |
| 751 | 202803_s_at | HG-U133A | NM_000211 | 706 | integrin, beta 2 (antigen CD18 (p95), lymphocyte function-associated antigen 1; macrophage antigen 1 (mac-1) beta subunit) | ITGB2 | 3689 | | + | resp | 251 |
| 752 | 236368_at | HG-U133B | BF059292 | 707 | KIAA0368 | KIAA0368 | 23392 | | + | resp | 261 |
| 753 | 218223_at | HG-U133A | NM_016274 | 708 | CK2 interacting protein 1; HQ0024c protein | CKIP-1 | 51177 | | + | resp | 262 |
| 754 | 203186_s_at | HG-U133A | NM_002961 | 709 | S100 calcium binding protein A4 (calcium protein, calvasculin, metastasin, murine placental homolog) | S100A4 | 6275 | | + | resp | 264 |
| 755 | 219563_at | HG-U133A | NM_024633 | 710 | chromosome 14 open reading frame 139 | C14orf139 | 79686 | | + | resp | 266 |
| 756 | 219290_x_at | HG-U133A | NM_014395 | 711 | dual adaptor of phosphotyrosine and 3-phosphoinositides | DAPP1 | 27071 | | + | resp | 268 |
| 757 | 214085_x_at | HG-U133A | AI912583 | 712 | valosin-containing protein | VCP | 7415 | | + | resp | 270 |
| 758 | 208648_at | HG-U133A | W60953 | 713 | IL2-inducible T-cell kinase | ITK | 3702 | | + | resp | 272 |
| 759 | 211339_s_at | HG-U133A | D13720 | 714 | allograft inflammatory factor 1 | AIF1 | 199 | | + | resp | 274 |
| 760 | 213095_x_at | HG-U133A | AF299327 | 715 | allograft inflammatory factor 1 | AIF1 | 199 | | + | resp | 291 |
| 761 | 221731_x_at | HG-U133A | BF218922 | 716 | chondroitin sulfate proteoglycan 2 (versican) | CSPG2 | 1462 | | + | resp | 302 |
| 762 | 201828_x_at | HG-U133A | NM_003928 | 717 | CAAX box 1 | CXX1 | 8933 | | + | resp | 305 |
| 763 | 203988_s_at | HG-U133A | NM_004480 | 718 | fucosyltransferase 8 (alpha (1,6) fucosyltransferase) | FUT8 | 2530 | | + | resp | 306 |
| 764 | 225918_at | HG-U133B | AI742940 | 719 | Hypothetical protein LOC146346 | LOC146346 | 146346 | | + | resp | 311 |
| 765 | 215949_x_at | HG-U133A | BF002659 | 720 | immunoglobulin heavy constant mu | IGHM | 3507 | | + | resp | 312 |
| 766 | 209164_s_at | HG-U133A | BC002976 | 721 | cytochrome b-561 | CYB561 | 1534 | | + | resp | 314 |
| 767 | 201998_at | HG-U133A | AI743792 | 722 | ST6 beta-galactosamide alpha-2,6-sialyltranferase 1 | ST6GAL1 | 6480 | | + | resp | 315 |
| 768 | 202484_s_at | HG-U133A | AF072242 | 723 | methyl-CpG binding domain protein 2 | MBD2 | 8932 | | + | resp | 316 |
| 769 | 215588_x_at | HG-U133A | AK024958 | 724 | RIO kinase 3 (yeast) | RIOK3 | 8780 | | + | resp | 316 |

1B Predictive Markers Unregulated Indicators of Response and/or Long Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 770 | 235028_at | HG-U133B | BG288330 | 725 | CDNA FLJ42313 fis, clone TRACH2019425 | | | | + | resp | 317 |
| 771 | 238701_x_at | HG-U133B | BE176566 | 726 | FLJ45803 protein | FLJ45803 | 399948 | | + | resp | 319 |
| 772 | 202771_at | HG-U133A | NM_014745 | 727 | family with sequence similarity 38, member A | FAM38A | 9780 | | + | resp | 320 |
| 773 | 235327_x_at | HG-U133B | BG111015 | 728 | UBX domain containing 4 | UBXD4 | 165324 | | + | resp | 326 |
| 774 | 210357_x_at | HG-U133A | BC000669 | 729 | spermine oxidase | SMOX | 54498 | | + | resp | 328 |
| 775 | 204588_s_at | HG-U133A | NM_003982 | 730 | solute carrier family 7 (cationic amino acid transporter, y+ system), member 7 | SLC7A7 | 9056 | | + | resp | 333 |
| 776 | 32069_at | HG-U133A | AB014515 | 731 | Nedd4 binding protein 1 | N4BP1 | 9683 | | + | resp | 334 |
| 777 | 203868_s_at | HG-U133A | NM_001078 | 732 | vascular cell adhesion molecule 1 | VCAM1 | 7412 | | + | resp | 336 |
| 778 | 201012_at | HG-U133A | NM_000700 | 733 | annexin A1 | ANXA1 | 301 | | + | resp | 337 |
| 779 | 231093_at | HG-U133B | BF514552 | 734 | Fc receptor-like protein 3 | FCRH3 | 115352 | | + | resp | 340 |
| 780 | 213425_at | HG-U133A | AI968085 | 735 | wingless-type MMTV integration site family, member 5A | WNT5A | 7474 | | + | resp | 342 |
| 781 | 214494_s_at | HG-U133A | NM_005200 | 736 | spastic paraplegia 7, paraplegin (pure and complicated autosomal recessive) | SPG7 | 6687 | | + | resp | 344 |
| 782 | 214902_x_at | HG-U133A | AL080232 | 737 | FLJ42393 protein | FLJ42393 | 401105 | | + | resp | 344 |
| 783 | 202908_at | HG-U133A | NM_006005 | 738 | Wolfram syndrome 1 (wolframin) | WFS1 | 7466 | | + | resp | 348 |
| 784 | 205968_at | HG-U133A | NM_002252 | 739 | potassium voltage-gated channel, delayed-rectifier, subfamily S, member 3 | KCNS3 | 3790 | | + | resp | 349 |
| 785 | 202449_s_at | HG-U133A | NM_002957 | 740 | retinoid X receptor, alpha | RXRA | 6256 | | + | resp | 355 |
| 786 | 209539_at | HG-U133A | D25304 | 741 | Rac/Cdc42 guanine nucleotide exchange factor (GEF) 6 | ARHGEF6 | 9459 | | + | resp | 355 |
| 787 | 241223_at | HG-U133B | AI821721 | 742 | CDNA: FLJ23566 fis, clone LNG10880 | | | | + | resp | 356 |
| 788 | 234675_x_at | HG-U133B | AK027219 | 743 | THO complex 2 | THOC2 | 57187 | | + | resp | 369 |
| 789 | 212994_at | HG-U133A | BE543527 | 744 | chromosome 17 open reading frame 27 | C17orf27 | 57674 | | + | resp | 375 |
| 790 | 225929_at | HG-U133B | AA233374 | 745 | transforming growth factor beta 1 induced transcript 4 | TGFB1I4 | 8848 | | + | resp | 377 |
| 791 | 215111_s_at | HG-U133A | AK027071 | 746 | | | | | + | resp | 381 |
| 792 | 204872_at | HG-U133A | NM_007005 | 747 | transducin-like enhancer of split 4 (E(sp1) homolog, Drosophila) | TLE4 | 7091 | | + | resp | 382 |
| 793 | 208082_x_at | HG-U133A | NM_030757 | 748 | Transcribed locus | | | | + | resp | 398 |
| 794 | 227749_at | HG-U133B | AI703496 | 749 | | | | | + | resp | 407 |
| 795 | 213572_s_at | HG-U133A | AI54300 | 750 | serine (or cysteine) proteinase inhibitor, clade B (ovalbumin), member 1 | SERPINB1 | 1992 | | + | resp | 408 |
| 796 | 212754_s_at | HG-U133A | AI760249 | 751 | KIAA1040 protein | KIAA1040 | 23041 | | + | resp | 410 |
| 797 | 203123_s_at | HG-U133A | AU154469 | 752 | solute carrier family 11 (proton-coupled divalent metal ion transporters), member 2 | SLC11A2 | 4891 | | + | resp | 412 |

1B Predictive Markers Unregulated Indicators of Response and/or Long Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 798 | 214726_x_at | HG-U133A | AL556041 | 753 | adducin 1 (alpha) | ADD1 | 118 | | + | resp | 415 |
| 799 | 212810_s_at | HG-U133A | W72527 | 754 | solute carrier family 1 (glutamate/neutral amino acid transporter), member 4 | SLC1A4 | 6509 | | + | resp | 434 |
| 800 | 207730_x_at | HG-U133A | NM_017932 | 755 | KIAA1881 | KIAA1881 | 114782 | | + | resp | 437 |
| 801 | 225361_s_at | HG-U133B | AI348001 | 756 | similar to hypothetical protein MGC17347 | LOC159090 | 159090 | | + | resp | 439 |
| 802 | 201778_s_at | HG-U133A | NM_014774 | 757 | KIAA0494 gene product | KIAA0494 | 9813 | | + | resp | 442 |
| 803 | 216858_x_at | HG-U133A | AL080112 | 758 | | | | | + | resp | 445 |
| 804 | 214696_at | HG-U133A | AF070569 | 759 | hypothetical protein MGC14376 | MGC14376 | 84981 | | + | resp | 456 |
| 805 | 218066_at | HG-U133A | NM_006598 | 760 | solute carrier family 12 (potassium/chloride transporters), member 7 | SLC12A7 | 10723 | | + | resp | 457 |
| 806 | 210563_x_at | HG-U133A | U97075 | 761 | CASP8 and FADD-like apoptosis regulator | CFLAR | 8837 | | + | resp | 461 |
| 807 | 201057_s_at | HG-U133A | NM_004487 | 762 | golgi autoantigen, golgin subfamily b, macrogolgin (with transmembrane signal), 1 | GOLGB1 | 2804 | | + | resp | 465 |
| 808 | 209183_s_at | HG-U133A | AL136653 | 763 | chromosome 10 open reading frame 10 | C10orf10 | 11067 | | + | resp | 469 |
| 809 | 226474_at | HG-U133B | AA005023 | 764 | nucleotide-binding oligomerization domains 27 | NOD27 | 84166 | | + | resp | 472 |
| 810 | 225507_at | HG-U133B | BF591408 | 765 | chromosome 6 open reading frame 111 | C6orf111 | 25957 | | + | resp | 474 |
| 811 | 212177_at | HG-U133A | AW081113 | 766 | chromosome 6 open reading frame 111 | C6orf111 | 25957 | | + | resp | 476 |
| 812 | 216510_x_at | HG-U133A | AB035175 | 767 | immunoglobulin heavy constant gamma 1 (G1m marker) /// similar to Ig heavy chain V-III region VH26 precursor | IGHG1 /// LOC390714 | 3500 /// 390714 | | + | resp | 478 |
| 813 | 215600_x_at | HG-U133A | AK022174 | 768 | F-box and WD-40 domain protein 12 | FBXW12 | 285231 | | + | resp | 483 |
| 814 | 215811_at | HG-U133A | AF238870 | 769 | | | | | + | resp | 484 |
| 815 | 220940_at | HG-U133A | NM_025190 | 770 | KIAA1641 | KIAA1641 | 57730 | | + | resp | 497 |
| 816 | 217728_at | HG-U133A | NM_014624 | 771 | S100 calcium binding protein A6 (calcyclin) | S100A6 | 6277 | | + | resp | 499 |
| 817 | 232266_at | HG-U133B | AK024379 | 772 | Cell division cycle 2-like 5 (cholinesterase-related cell division controller) | CDC2L5 | 8621 | | + | resp | 507 |
| 818 | 201674_s_at | HG-U133A | BC000729 | 773 | A kinase (PRKA) anchor protein 1 | AKAP1 | 8165 | | + | resp | 511 |
| 819 | 206846_s_at | HG-U133A | NM_006044 | 774 | histone deacetylase 6 | HDAC6 | 10013 | | + | resp | 515 |
| 820 | 202587_s_at | HG-U133A | BC001116 | 775 | adenylate kinase 1 | AK1 | 203 | | + | resp | 519 |
| 821 | 211034_s_at | HG-U133A | BC006270 | 776 | AF-1 specific protein phosphatase | FLJ30092 | 196515 | | + | resp | 523 |
| 822 | 209485_s_at | HG-U133A | W19983 | 777 | oxysterol binding protein-like 1A | OSBPL1A | 114876 | | + | resp | 524 |
| 823 | 232008_at | HG-U133B | AF283775 | 778 | bobby sox homolog (Drosophila) | BBX | 56987 | | + | resp | 528 |
| 824 | 218155_at | HG-U133A | AK026565 | 779 | hypothetical protein FLJ10534 | FLJ10534 | 55720 | | + | resp | 529 |
| 825 | 207986_x_at | HG-U133A | NM_001915 | 780 | | | | | + | resp | 534 |
| 826 | 234981_at | HG-U133B | BE537881 | 781 | similar to mouse 2310016A09Rik gene | LOC134147 | 134147 | | + | resp | 537 |
| 827 | 226659_at | HG-U133B | Z97832 | 782 | differentially expressed in FDCP 6 homolog (mouse) | DEF6 | 50619 | | + | resp | 540 |
| 828 | 201141_at | HG-U133A | NM_002510 | 783 | glycoprotein (transmembrane) nmb | GPNMB | 10457 | | + | resp | 549 |
| 829 | 221973_at | HG-U133A | AI983904 | 784 | Hypothetical protein LOC150759 | LOC150759 | 150759 | | + | resp | 551 |

1B Predictive Markers Unregulated Indicators of Response and/or Long Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 830 | 206380_s_at | HG-U133A | NM_002621 | 785 | properdin P factor, complement | PFC | 5199 | | + | resp | 552 |
| 831 | 215179_x_at | HG-U133A | AK023843 | 786 | Placental growth factor, vascular endothelial growth factor-related protein | PGF | 5228 | | + | resp | 554 |
| 832 | 211582_x_at | HG-U133A | AF000424 | 787 | leukocyte specific transcript 1 | LST1 | 7940 | | + | resp | 556 |
| 833 | 217761_at | HG-U133A | NM_018269 | 788 | membrane-type 1 matrix metalloproteinase cytoplasmic tail binding protein-1 | MTCBP-1 | 55256 | | + | resp | 557 |
| 834 | 210915_x_at | HG-U133A | M15564 | 789 | T cell receptor beta constant 1 | TRBC1 | 28639 | | + | resp | 561 |
| 835 | 233702_s_at | HG-U133B | AK024599 | 790 | CDNA: FLJ20946 fis, clone ADSE01819 | | | | + | resp | 562 |
| 836 | 204842_x_at | HG-U133A | BC002763 | 791 | protein kinase, cAMP-dependent, regulatory, type II, alpha | PRKAR2A | 5576 | | + | resp | 563 |
| 837 | 33323_r_at | HG-U133A | X57348 | 792 | stratifin | SFN | 2810 | | + | resp | 565 |
| 838 | 204232_at | HG-U133A | NM_004106 | 793 | Fc fragment of IgE, high affinity I, receptor for; gamma polypeptide | FCER1G | 2207 | | + | resp | 567 |
| 839 | 233056_at | HG-U133B | AK024674 | 794 | discs, large (Drosophila) homolog-associated protein 4 | DLGAP4 | 22839 | | + | resp | 569 |
| 840 | 215553_x_at | HG-U133A | AK024315 | 795 | WD repeat domain 45 | WDR45 | 11152 | | + | resp | 574 |
| 841 | 222380_s_at | HG-U133A | AI907083 | 796 | Similar to Micronemé antigen | | 391733 | | + | resp | 578 |
| 842 | 60471_at | HG-U133A | AA625133 | 797 | Ras and Rab interactor 3 | RIN3 | 79890 | | + | resp | 586 |
| 843 | 206929_s_at | HG-U133A | NM_005597 | 798 | nuclear factor I/C (CCAAT-binding transcription factor) | NFIC | 4782 | | + | resp | 591 |
| 844 | 211452_x_at | HG-U133A | AF130054 | 799 | Ras-GTPase-activating protein SH3-domain-binding protein | G3BP | 10146 | | + | resp | 592 |
| 845 | 239748_x_at | HG-U133B | H09533 | 800 | | | | | + | resp | 596 |
| 846 | 222187_at | HG-U133A | X78262 | 801 | | | | | + | resp | 603 |
| 847 | 208246_x_at | HG-U133A | NM_017618 | 802 | Thymidine kinase 2, mitochondrial | TK2 | 7084 | | + | resp | 605 |
| 848 | 243198_at | HG-U133B | AA020920 | 803 | testis expressed gene 9 | TEX9 | 374618 | | + | resp | 609 |
| 849 | 211992_at | HG-U133A | AI445745 | 804 | WNK lysine deficient protein kinase 1 | WNK1 | 65125 | | + | resp | 612 |
| 850 | 217198_x_at | HG-U133A | U80164 | 805 | immunoglobulin heavy locus /// immunoglobulin heavy constant gamma 1 (G1m marker) | IGH@ /// IGHG1 | 3492 /// 3500 | | + | resp | 614 |
| 851 | 34210_at | HG-U133A | N90866 | 806 | CD52 antigen (CAMPATH-1 antigen) | CD52 | 1043 | | + | resp | 616 |
| 852 | 231828_at | HG-U133B | AL117474 | 807 | Homo sapiens, clone IMAGE: 5218355, mRNA | | | | + | resp | 619 |
| 853 | 202040_s_at | HG-U133A | NM_005056 | 808 | Jumonji, AT rich interactive domain 1A (RBBP2-like) | JARID1A | 5927 | | + | resp | 622 |
| 854 | 223357_at | HG-U133A | AW974823 | 809 | zinc finger and BTB domain containing 20 | ZBTB20 | 26137 | | + | resp | 631 |
| 855 | 238668_at | HG-U133B | AI130690 | 810 | Transcribed locus | | | | + | resp | 633 |
| 856 | 236715_x_at | HG-U133B | BF056139 | 811 | | | | | + | resp | 640 |
| 857 | 241347_at | HG-U133B | AA936632 | 812 | KIAA1618 | KIAA1618 | 57714 | | + | resp | 645 |
| 858 | 208459_s_at | HG-U133A | NM_015024 | 813 | exportin 7 | XPO7 | 23039 | | + | resp | 648 |
| 859 | 208238_x_at | HG-U133A | NM_013344 | 814 | | | | | + | resp | 667 |
| 860 | 204661_at | HG-U133A | NM_001803 | 815 | CD52 antigen (CAMPATH-1 antigen) | CD52 | 1043 | | + | resp | 668 |
| 861 | 202450_s_at | HG-U133A | NM_000396 | 816 | cathepsin K (pycnodysostosis) | CTSK | 1513 | | + | resp | 675 |

1B Predictive Markers Unregulated Indicators of Response and/or Long Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 862 | 209377_s_at | HG-U133A | AF274949 | 817 | high mobility group nucleosomal binding domain 3 | HMGN3 | 9324 | | + | resp | 681 |
| 863 | 215577_at | HG-U133A | AU146791 | 818 | Ubiquitin-conjugating enzyme E2E 1 (UBC4/5 homolog, yeast) | UBE2E1 | 7324 | | + | resp | 688 |
| 864 | 221253_s_at | HG-U133A | NM_030810 | 819 | thioredoxin domain containing 5 | TXNDC5 | 81567 | + | | TTP | 92 |
| 865 | 216231_at | HG-U133A | AW188940 | 820 | beta-2-microglobulin | B2M | 567 | + | | TTP | 156 |
| 866 | 223577_x_at | HG-U133B | AA827878 | 821 | | | | + | | TTP | 194 |
| 867 | 228759_at | HG-U133B | BG236289 | 822 | cAMP responsive element binding protein3-like 2 | CREB3L2 | 64764 | + | | TTP | 204 |
| 868 | 221992_at | HG-U133A | AI925734 | 823 | Hypothetical protein LOC283970 | LOC283970 | 283970 | + | | TTP | 207 |
| 869 | 212739_s_at | HG-U133A | AL523860 | 824 | non-metastatic cells 4, protein expressed in | NME4 | 4833 | + | | TTP | 246 |
| 870 | 201063_at | HG-U133A | NM_002901 | 825 | reticulocalbin 1, EF-hand calcium binding domain | RCN1 | 5954 | + | | TTP | 247 |
| 871 | 227013_at | HG-U133B | AI535735 | 826 | LATS, large tumor suppressor, homolog 2 (Drosophila) | LATS2 | 26524 | + | | TTP | 250 |
| 872 | AFFX-BioC-3_at | HG-U133B | AFFX-BioC-3 | | | | | + | | TTP | 254 |
| 873 | 210889_s_at | HG-U133A | M31933 | 827 | Fc fragment of IgG, low affinity IIb, receptor (CD32) | FCGR2B | 2213 | + | | TTP | 274 |
| 874 | 213601_at | HG-U133A | AB011537 | 828 | slit homolog 1 (Drosophila) | SLIT1 | 6585 | + | + | TTP/resp | 111 |
| 875 | 210944_s_at | HG-U133A | BC003169 | 829 | calpain 3, (p94) | CAPN3 | 825 | + | + | TTP/resp | 122 |
| 876 | 32811_at | HG-U133A | X98507 | 830 | myosin IC | MYO1C | 4641 | + | + | resp | 150 |
| 877 | 213348_at | HG-U133A | N33167 | 831 | cyclin-dependent kinase inhibitor 1C (p57, Kip2) | CDKN1C | 1028 | | + | resp | 132 |
| 878 | 200710_at | HG-U133A | NM_000018 | 832 | acyl-Coenzyme A dehydrogenase, very long chain | ACADVL | 37 | | + | resp | 198 |
| 879 | 220232_at | HG-U133A | NM_024906 | 833 | stearoyl-CoA desaturase 4 | SCD4 | 79966 | | + | resp | 272 |
| 880 | 209345_s_at | HG-U133A | AL561930 | 834 | phosphatidylinositol 4-kinase type II | PI4KII | 55361 | | + | resp | 350 |
| 881 | 231825_x_at | HG-U133B | AK025060 | 835 | activating transcription factor 7 interacting protein | ATF7IP | 55729 | | + | resp | 374 |
| 882 | 215067_x_at | HG-U133A | AU147942 | 836 | peroxiredoxin 2 | PRDX2 | 7001 | | + | resp | 447 |
| 883 | 215499_at | HG-U133A | AA780381 | 837 | Mitogen-activated protein kinase kinase 3 | MAP2K3 | 5606 | | + | resp | 482 |
| 884 | 206323_x_at | HG-U133A | NM_002547 | 838 | oligophrenin 1 | OPHN1 | 4983 | | + | resp | 505 |
| 885 | 220725_at | HG-U133A | NM_025095 | 839 | Dynein, axonemal, heavy polypeptide 3 | DNAH3 | 55567 | | + | resp | 537 |
| 886 | 237475_x_at | HG-U133B | AI151104 | 840 | Homo sapiens, clone IMAGE: 4829003, mRNA | | | | + | resp | 581 |
| 887 | 228919_at | HG-U133B | AA601031 | 841 | | | | | + | resp | 589 |
| 888 | 215504_x_at | HG-U133A | AF131777 | 842 | Homo sapiens, clone IMAGE: 4822875, mRNA | | | | + | resp | 604 |
| 889 | 216524_x_at | HG-U133A | AL049260 | 843 | | | | | + | resp | 657 |
| 890 | 221569_at | HG-U133A | AL136797 | 844 | Abelson helper integration site | AHI1 | 54806 | + | + | TTP/resp | 253 |

1B Predictive Markers Unregulated Indicators of Response and/or Long Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 891 | 228658_at | HG-U133B | R54042 | 845 | hypothetical protein LOC150271 | LOC150271 | 150271 | | + | resp | 16 |
| 892 | 210538_s_at | HG-U133A | U37546 | 846 | baculoviral IAP repeat-containing 3 | BIRC3 | 330 | | + | resp | 37 |
| 893 | 202439_s_at | HG-U133A | NM_000202 | 847 | iduronate 2-sulfatase (Hunter syndrome) | IDS | 3423 | | + | resp | 107 |
| 894 | 212221_x_at | HG-U133A | AV703259 | 848 | iduronate 2-sulfatase (Hunter syndrome) | IDS | 3423 | | + | resp | 165 |
| 895 | 211316_x_at | HG-U133A | AF009616 | 849 | CASP8 and FADD-like apoptosis regulator | CFLAR | 8837 | | + | resp | 196 |
| 896 | 209136_s_at | HG-U133A | BG390445 | 850 | ubiquitin specific protease 10 | USP10 | 9100 | | + | resp | 318 |
| 897 | 201811_x_at | HG-U133A | NM_004844 | 851 | SH3-domain binding protein 5 (BTK-associated) | SH3BP5 | 9467 | | + | resp | 359 |
| 898 | 222391_at | HG-U133B | AL080250 | 852 | transmembrane protein 30A | TMEM30A | 55754 | | + | resp | 421 |
| 899 | 214179_s_at | HG-U133A | H93013 | 853 | nuclear factor (erythroid-derived 2)-like 1 | NFE2L1 | 4779 | | + | resp | 439 |
| 900 | 201810_s_at | HG-U133A | AL562152 | 854 | SH3-domain binding protein 5 (BTK-associated) | SH3BP5 | 9467 | | + | resp | 474 |
| 901 | 212616_at | HG-U133A | BF668950 | 855 | chromodomain helicase DNA binding protein 9 | CHD9 | 80205 | | + | resp | 475 |
| 902 | 205504_at | HG-U133A | NM_000061 | 856 | Bruton agammaglobulinemia tyrosine kinase | BTK | 695 | | + | resp | 487 |
| 903 | 200759_x_at | HG-U133A | NM_003204 | 857 | nuclear factor (erythroid-derived 2)-like 1 | NFE2L1 | 4779 | | + | resp | 611 |
| 904 | 209276_s_at | HG-U133A | AF162769 | 858 | glutaredoxin (thioltransferase) | GLRX | 2745 | + | | TTP | 151 |
| 905 | 202727_s_at | HG-U133A | NM_000416 | 859 | interferon gamma receptor 1 | IFNGR1 | 3459 | + | | TTP | 168 |
| 906 | 202011_at | HG-U133A | NM_003257 | 860 | tight junction protein 1 (zona occludens 1) | TJP1 | 7082 | + | + | TTP | 63 |
| 907 | 206662_at | HG-U133A | NM_002064 | 861 | glutaredoxin (thioltransferase) | GLRX | 2745 | + | + | TTP/resp | 30 |
| 908 | 209475_at | HG-U133A | AF106069 | 862 | ubiquitin specific protease 15 | USP15 | 9958 | + | + | TTP/resp | 46 |
| 909 | 235661_at | HG-U133B | T99553 | 863 | Transcribed locus | | | + | | TTP/resp | 201 |
| 910 | 235875_at | HG-U133B | BF510711 | 864 | Solute carrier family 1 (glutamate/neutral amino acid transporter), member 4 | SLC1A4 | 6509 | | + | resp | 329 |
| 911 | 225373_at | HG-U133B | BE271644 | 865 | PP2135 protein | PP2135 | 64115 | + | | TTP | 189 |

TABLE 2

GLUOCORTICOID PREDICTIVE MARKER IDENTIFICATION

2A Predictive Markers Up regulated Indicators of Non-Reponse and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 912 | 208918_s_at | HG-U133A | AI334128 | 866 | NAD kinase | FLJ13052 | 65220 | | – | resp | 2 |
| 913 | 208235_x_at | HG-U133A | NM_021123 | 867 | G antigen 5 /// G antigen 7 /// G antigen 7B | GAGE5 /// GAGE7 /// GAGE7B | 2577 /// 2579 /// 26748 | | – | resp | 3 |
| 914 | 221810_at | HG-U133A | AA631242 | 868 | RAB15, member RAS onocogene family | RAB15 | 376267 | | – | resp | 5 |
| 915 | 212725_s_at | HG-U133A | N37081 | 869 | hypothetical protein TI-227H | TI-227H | 29793 | | – | resp | 8 |
| 916 | 200964_at | HG-U133A | NM_003334 | 870 | ubiquitin-activating enzyme E1 (A1S9T and BN75 temperature sensitivity complementing) | UBE1 | 7317 | | – | resp | 9 |
| 917 | 226670_s_at | HG-U133B | AL109839 | 871 | Chromosome 20 open reading frame 119 | C20orf119 | 80336 | | – | resp | 12 |
| 918 | 222753_s_at | HG-U133B | AL136660 | 872 | signal peptidase complex subunit 3 homolog (S. cerevisiae) | SPCS3 | 60559 | | – | resp | 13 |
| 919 | 213373_s_at | HG-U133A | BF439983 | 873 | caspase 8, apoptosis-related cysteine protease | CASP8 | 841 | | – | resp | 19 |
| 920 | 202148_s_at | HG-U133A | NM_006907 | 874 | pyrroline-5-carboxylate reductase 1 | PYCR1 | 5831 | | – | resp | 26 |
| 921 | 212337_at | HG-U133A | AI687738 | 875 | hypothetical protein TI-227H | TI-227H | 29793 | | – | resp | 28 |
| 922 | 211761_s_at | HG-U133A | BC005975 | 876 | calcyclin binding protein | CACYBP | 27101 | | – | resp | 36 |
| 923 | 201381_x_at | HG-U133A | AF057356 | 877 | calcyclin binding protein | CACYBP | 27101 | | – | resp | 38 |
| 924 | 225364_at | HG-U133B | BE222274 | 878 | serine/threonine kinase 4 | STK4 | 6789 | | – | resp | 39 |
| 925 | 200665_s_at | HG-U133A | NM_003118 | 879 | secreted protein, acidic, cysteine-rich (osteonectin) | SPARC | 6678 | | – | resp | 48 |
| 926 | 201577_at | HG-U133A | NM_000269 | 880 | non-metastatic cells 1, protein (NM23A) expressed in | NME1 | 4830 | | – | resp | 50 |
| 927 | 226914_at | HG-U133B | AU158936 | 881 | Actin related protein 2/3 complex, subunit 5-like | ARPC5L | 81873 | | – | resp | 51 |
| 928 | 225401_at | HG-U133B | BF977145 | 882 | kidney predominant protein NCU-G1 | MGC31963 | 112770 | | – | resp | 52 |
| 929 | 222154_s_at | HG-U133A | AK002064 | 883 | DNA polymerase-transactivated protein 6 | DNAPTP6 | 26010 | | – | resp | 57 |
| 930 | 200791_s_at | HG-U133A | NM_003870 | 884 | IQ motif containing GTPase activating protein 1 | IQGAP1 | 8826 | | – | resp | 65 |
| 931 | 202555_s_at | HG-U133A | NM_005965 | 885 | myosin, light polypeptide kinase | MYLK | 4638 | | – | resp | 66 |
| 932 | 208801_at | HG-U133A | BE856385 | 886 | signal recognition particle 72 kDa | SRP72 | 6731 | | – | resp | 72 |
| 933 | 227556_at | HG-U133B | AI094580 | 887 | non-metastatic cells 7, protein expressed in (nucleoside-diphosphate kinase) | NME7 | 29922 | | – | resp | 84 |
| 934 | 213135_at | HG-U133A | U90902 | 888 | T-cell lymphoma invasion and metastasis 1 | TIAM1 | 7074 | | – | resp | 98 |
| 935 | 206656_s_at | HG-U133A | BC000353 | 889 | chromosome 20 open reading frame 3 | C20orf3 | 57136 | | – | resp | 104 |

TABLE 2-continued

GLUOCORTICOID PREDICTIVE MARKER IDENTIFICATION
2A Predictive Markers Up regulated Indicators of Non-Reponse and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 936 | 206640_x_at | HG-U133A | NM_001477 | 890 | G antigen 2 /// G antigen 4 /// G antigen 5 /// G antigen 6 /// G antigen 7B | GAGE2 /// GAGE4 /// GAGE5 /// GAGE6 /// GAGE7B | 2574 /// 2576 /// 2577 /// 2578 /// 2579 /// 26748 | | – | resp | 1 |
| 937 | 208155_x_at | HG-U133A | NM_001476 | 891 | G antigen 4 /// G antigen 5 /// G antigen 6 /// G antigen 7B | GAGE4 /// GAGE5 /// GAGE6 /// GAGE7B | 2576 /// 2577 /// 2578 /// 2579 /// 26748 | | – | resp | 2 |
| 938 | 207086_x_at | HG-U133A | NM_001474 | 892 | G antigen 2 /// G antigen 4 /// G antigen 5 /// G antigen 6 /// G antigen 7B /// G antigen 8 | GAGE2 /// GAGE4 /// GAGE5 /// GAGE6 /// GAGE7B /// GAGE8 | 2574 /// 2576 /// 2577 /// 2578 /// 2579 /// 26748 /// 26749 | | – | | 3 |
| 939 | 207739_s_at | HG-U133A | NM_001472 | 893 | G antigen 1 /// G antigen 2 /// G antigen 3 /// G antigen 4 /// G antigen 5 /// G antigen 6 /// G antigen 7B /// G antigen 8 | GAGE1 /// GAGE2 /// GAGE3 /// GAGE4 /// GAGE5 /// GAGE6 /// GAGE7B /// GAGE8 | 2543 /// 2574 /// 2575 /// 2576 /// 2577 /// 2578 /// 2579 /// 26748 /// 26749 | | – | resp | 5 |
| 940 | 207663_x_at | HG-U133A | NM_001473 | 894 | G antigen 3 | GAGE3 | 2575 | | – | resp | 8 |
| 941 | 205013_s_at | HG-U133A | NM_000675 | 895 | adenosine A2a receptor | ADORA2A | 135 | | – | resp | 13 |
| 942 | 201506_at | HG-U133A | NM_000358 | 896 | transforming growth factor, beta-induced, 68 kDa | TGFBI | 7045 | | – | resp | 17 |
| 943 | 241224_x_at | HG-U133B | AA770014 | 434 | Down syndrome critical region gene 8 | DSCR8 | 84677 | | – | resp | 21 |
| 944 | 204960_at | HG-U133A | NM_005608 | 897 | protein tyrosine phosphatase, receptor type, C-associated protein | PTPRCAP | 5790 | | – | resp | 24 |
| 945 | 235863_at | HG-U133B | AI805145 | 898 | homolog of mouse skeletal muscle sarcoplasmic reticulum protein JP-45 | FLJ32416 | 126306 | | – | resp | 28 |
| 946 | 228116_at | HG-U133B | AW167298 | 899 | Hypothetical LOC283029 | | 283029 | | – | resp | 29 |
| 947 | 208890_s_at | HG-U133A | BC004542 | 900 | plexin B2 | PLXNB2 | 23654 | | – | resp | 30 |
| 948 | 242881_s_at | HG-U133B | BG285837 | 901 | hypothetical LOC389048 | LOC389048 | 389048 | | – | resp | 33 |
| 949 | 212311_at | HG-U133A | AA522514 | 902 | KIAA0746 protein | KIAA0746 | 23231 | | – | resp | 35 |
| 950 | 224318_s_at | HG-U133B | AF311326 | 903 | hypothetical protein FLJ10081 | FLJ10081 | 55683 | | – | resp | 37 |
| 951 | 224806_at | HG-U133B | BE563152 | 904 | LOC440448 | LOC440448 | 440448 | | – | resp | 54 |
| 952 | 208072_s_at | HG-U133A | NM_003648 | 905 | diacylglycerol kinase, delta 130 kDa | DGKD | 8527 | | – | resp | 57 |
| 953 | 231887_s_at | HG-U133B | AB033100 | 906 | KIAA1274 | KIAA1274 | 27143 | | – | resp | 58 |
| 954 | 212443_at | HG-U133A | AB011112 | 907 | KIAA0540 protein | KIAA0540 | 23218 | | – | resp | 60 |

TABLE 2-continued

GLUOCORTICOID PREDICTIVE MARKER IDENTIFICATION
2A Predictive Markers Up regulated Indicators of Non-Reponse and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 955 | 200859_x_at | HG-U133A | NM_001456 | 908 | filamin A, alpha (actin binding protein 280) | FLNA | 2316 | | – | resp | 63 |
| 956 | 204912_at | HG-U133A | NM_001558 | 909 | interleukin 10 receptor, alpha | IL10RA | 3587 | | – | resp | 66 |
| 957 | 211373_s_at | HG-U133A | U34349 | 910 | presenilin 2 (Alzheimer disease 4) | PSEN2 | 5664 | | – | resp | 68 |
| 958 | 213008_at | HG-U133A | BG403615 | 911 | hypothetical protein FLJ10719 | FLJ10719 | 55215 | | – | resp | 77 |
| 959 | 218695_at | HG-U133A | NM_019037 | 912 | exosome component 4 | EXOSC4 | 54512 | | – | resp | 77 |
| 960 | 43427_at | HG-U133A | AI970898 | 913 | hypothetical protein LOC283445 | LOC283445 | 283445 | | – | resp | 84 |
| 961 | 203523_at | HG-U133A | NM_002339 | 914 | lymphocyte-specific protein 1 | LSP1 | 4046 | | – | resp | 87 |
| 962 | 212287_at | HG-U133A | BF382924 | 915 | suppressor of zeste 12 homolog (Drosophila) | SUZ12 | 23512 | | – | resp | 88 |
| 963 | 203020_at | HG-U133A | NM_014857 | 916 | RAB GTPase activating protein 1-like | RABGAP1L | 9910 | | – | resp | 99 |
| 964 | 201071_x_at | HG-U133A | NM_012433 | 917 | splicing factor 3b, subunit 1, 155 kDa | SF3B1 | 23451 | | – | resp | 105 |
| 965 | 47553_at | HG-U133A | AA813332 | 918 | deafness, autosomal recessive 31 | DFNB31 | 25861 | | – | resp | 106 |
| 966 | 222244_s_at | HG-U133A | AK000749 | 919 | hypothetical protein FLJ20618 | FLJ20618 | 55000 | | – | resp | 117 |
| 967 | 208794_s_at | HG-U133A | D26156 | 920 | SWI/SNF related, matrix associated, actin dependent regulator of chromatin, subfamily a, member 4 | SMARCA4 | 6597 | | – | resp | 119 |
| 968 | 239481_at | HG-U133B | AI864183 | 921 | hypothetical protein FLJ37659 | FLJ37659 | 286499 | | – | resp | 133 |
| 969 | 208858_s_at | HG-U133A | BC004998 | 922 | likely ortholog of mouse membrane bound C2 domain containing protein | MBC2 | 23344 | – | | TTP | 3 |
| 970 | 200011_s_at | HG-U133A | NM_001659 | 923 | ADP-ribosylation factor 3 | ARF3 | 377 | – | | TTP | 16 |
| 971 | 201003_x_at | HG-U133A | NM_003349 | 924 | | | | – | | TTP | 18 |
| 972 | 216194_s_at | HG-U133A | AD001527 | 925 | cytoskeleton associated protein 1 | CKAP1 | 1155 | – | | TTP | 19 |
| 973 | 202670_at | HG-U133A | AI571419 | 926 | mitogen-activated protein kinase kinase 1 | MAP2K1 | 5604 | – | | TTP | 25 |
| 974 | 205903_s_at | HG-U133A | NM_002249 | 927 | potassium intermediate/small conductance calcium-activated channel, subfamily N, member 3 | KCNN3 | 3782 | – | | TTP | 26 |
| 975 | 226760_at | HG-U133B | BF666325 | 928 | hypothetical protein LOC203411 | LOC203411 | 203411 | – | | TTP | 29 |
| 976 | 204839_at | HG-U133A | NM_015918 | 929 | processing of precursor 5, ribonuclease P/MRP subunit (S. cerevisiae) | POP5 | 51367 | – | | TTP | 30 |
| 977 | 224233_s_at | HG-U133B | BC002535 | 930 | misato | FLJ10504 | 55154 | – | | TTP | 36 |
| 978 | 204808_s_at | HG-U133A | NM_014254 | 931 | transmembrane protein 5 | TMEM5 | 10329 | – | | TTP | 42 |
| 979 | 212013_at | HG-U133A | D86983 | 932 | Melanoma associated gene | D2S448 | 7837 | – | | TTP | 43 |
| 980 | 201012_at | HG-U133A | NM_000700 | 733 | annexin A1 | ANXA1 | 301 | – | | TTP | 47 |
| 981 | 225685_at | HG-U133B | AI801777 | 933 | CDC42 effector protein (Rho GTPase binding) 3 | CDC42EP3 | 10602 | – | | TTP | 48 |
| 982 | 202001_at | HG-U133A | NM_002490 | 934 | NADH dehydrogenase (ubiquinone) 1 alpha subcomplex, 6, 14 kDa | NDUFA6 | 4700 | – | | TTP | 51 |
| 983 | 202911_at | HG-U133A | NM_000179 | 935 | mutS homolog 6 (E. coli) | MSH6 | 2956 | – | | TTP | 52 |
| 984 | 221807_s_at | HG-U133A | BG399562 | 936 | hypothetical protein PP2447 | PP2447 | 80305 | – | | TTP | 53 |
| 985 | 210978_s_at | HG-U133A | BC002616 | 937 | transgelin 2 | TAGLN2 | 8407 | – | | TTP | 54 |
| 986 | 201475_x_at | HG-U133A | NM_004990 | 938 | methionine-tRNA synthetase | MARS | 4141 | – | | TTP | 60 |

TABLE 2-continued

GLUOCORTICOID PREDICTIVE MARKER IDENTIFICATION
2A Predictive Markers Up regulated Indicators of Non-Reponse and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 987 | 207918_s_at | HG-U133A | NM_003308 | 939 | testis specific protein, Y-linked 1 /// testis specific protein, Y-linked 2 | TSPY1 /// TSPY2 | 64591 /// 7258 | — | | TTP | 65 |
| 988 | 208270_s_at | HG-U133A | NM_020216 | 940 | arginyl aminopeptidase (aminopeptidase B) | RNPEP | 6051 | — | | TTP | 66 |
| 989 | 201157_s_at | HG-U133A | AF020500 | 941 | N-myristoyltransferase 1 | NMT1 | 4836 | — | | TTP | 67 |
| 990 | 218135_at | HG-U133B | NM_016570 | 942 | PTX1 protein | PTX1 | 51290 | — | | TTP | 76 |
| 991 | 222606_at | HG-U133B | AA824298 | 943 | | | | — | | TTP | 83 |
| 992 | 208679_s_at | HG-U133A | AF279893 | 944 | actin related protein 2/3 complex, subunit 2, 34 kDa | ARPC2 | 10109 | — | | TTP | 84 |
| 993 | 215171_s_at | HG-U133A | AK023063 | 945 | translocase of inner mitochondrial membrane 17 homolog A (yeast) | TIMM17A | 10440 | — | | TTP | 86 |
| 994 | 208284_x_at | HG-U133A | NM_013421 | 946 | gamma-glutamyltransferase 1 | GGT1 | 2678 | — | | TTP | 92 |
| 995 | 230172_at | HG-U133B | AL039706 | 947 | family with sequence similarity 14, member B | FAM14B | 122509 | — | | TTP | 95 |
| 996 | 217900_at | HG-U133A | NM_018060 | 948 | mitochondrial isoleucine tRNA synthetase | FLJ10326 | 55699 | — | | TTP | 96 |
| 997 | 201804_x_at | HG-U133A | NM_001281 | 949 | cytoskeleton associated protein 1 | CKAP1 | 1155 | — | | TTP | 107 |
| 998 | 231736_x_at | HG-U133B | NM_020300 | 950 | microsomal glutathione S-transferase 1 | MGST1 | 4257 | — | | TTP | 110 |
| 999 | 201966_at | HG-U133A | NM_004550 | 951 | NADH dehydrogenase (ubiquinone) Fe—S protein 2, 49 kDa (NADH-coenzyme Q reductase) | NDUFS2 | 4720 | — | | TTP | 112 |
| 1000 | 212024_x_at | HG-U133A | U80184 | 952 | flightless I homolog (Drosophila) | FLII | 2314 | — | | TTP | 115 |
| 1001 | 200980_at | HG-U133A | NM_000284 | 953 | pyruvate dehydrogenase (lipoamide) alpha 1 | PDHA1 | 5160 | — | | TTP | 116 |
| 1002 | 218296_x_at | HG-U133A | NM_018116 | 954 | misato | FLJ10504 | 55154 | — | | TTP | 117 |
| 1003 | 232520_s_at | HG-U133B | AK023585 | 955 | NSFL1 (p97) cofactor (p47) | NSFL1C | 55968 | — | | TTP | 120 |
| 1004 | 218556_at | HG-U133A | NM_014182 | 956 | ORM1-like 2 (S. cerevisiae) | ORMDL2 | 29095 | — | | TTP | 124 |
| 1005 | 203371_s_at | HG-U133A | NM_002491 | 957 | NADH dehydrogenase (ubiquinone) 1 beta subcomplex, 3, 12 kDa | NDUFB3 | 4709 | — | | TTP | 126 |
| 1006 | 209919_x_at | HG-U133A | L20490 | 958 | gamma-glutamyltransferase 1 | GGT1 | 2678 | — | | TTP | 129 |
| 1007 | 217966_s_at | HG-U133A | NM_022083 | 959 | chromosome 1 open reading frame 24 | C1orf24 | 116496 | — | | TTP | 136 |
| 1008 | 218720_s_at | HG-U133A | NM_012410 | 960 | seizure related 6 homolog (mouse)-like 2 | SEZ6L2 | 26470 | — | | TTP | 141 |
| 1009 | 214853_s_at | HG-U133A | AI091079 | 961 | SHC (Src homology 2 domain containing) transforming protein 1 | SHC1 | 6464 | — | | TTP | 144 |
| 1010 | 212012_at | HG-U133A | BF342851 | 962 | Melanoma associated gene | D2S448 | 7837 | — | | TTP | 145 |
| 1011 | 214749_s_at | HG-U133A | AK000818 | 963 | armadillo repeat containing, X-linked 6 | ARMCX6 | 54470 | — | | TTP | 147 |
| 1012 | 202017_at | HG-U133A | NM_000120 | 964 | epoxide hydrolase 1, microsomal (xenobiotic) | EPHX1 | 2052 | — | | TTP | 148 |
| 1013 | 225313_at | HG-U133B | AI627538 | 965 | chromosome 20 open reading frame 177 | C20orf177 | 63939 | — | | TTP | 151 |
| 1014 | 217967_s_at | HG-U133A | AF288391 | 966 | chromosome 1 open reading frame 24 | C1orf24 | 116496 | — | | TTP | 154 |

TABLE 2-continued

GLUOCORTICOID PREDICTIVE MARKER IDENTIFICATION
2A Predictive Markers Up regulated Indicators of Non-Reponse and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 1015 | 205902_at | HG-U133A | AJ251016 | 967 | potassium intermediate/small conductance calcium-activated channel, subfamily N, member 3 | KCNN3 | 3782 | — | | TTP | 161 |
| 1016 | 200616_s_at | HG-U133A | BC000371 | 968 | KIAA0152 | KIAA0152 | 9761 | — | | TTP | 162 |
| 1017 | 201387_s_at | HG-U133A | NM_004181 | 969 | ubiquitin carboxyl-terminal esterase L1 (ubiquitin thiolesterase) | UCHL1 | 7345 | — | | TTP | 171 |
| 1018 | 200916_at | HG-U133A | NM_003564 | 970 | transgelin 2 | TAGLN2 | 8407 | — | | TTP | 180 |
| 1019 | 224955_at | HG-U133B | AI590088 | 971 | TEA domain family member 1 (SV40 transcriptional enhancer factor) | TEAD1 | 7003 | — | | TTP | 183 |
| 1020 | 244040_at | HG-U133B | N47474 | 972 | Potassium intermediate/small conductance calcium-activated channel, subfamily N, member 3 | KCNN3 | 3782 | — | | TTP | 185 |
| 1021 | 212371_at | HG-U133B | AL049397 | 973 | CGI-146 protein | PNAS-4 | 51029 | — | | TTP | 186 |
| 1022 | 238761_at | HG-U133B | BE645241 | 974 | Mediator of RNA polymerase II transcription, subunit 28 homolog (yeast) | MED28 | 80306 | — | | TTP | 187 |
| 1023 | 216705_s_at | HG-U133A | X02189 | 975 | adenosine deaminase | ADA | 100 | | — | resp | 6 |
| 1024 | 218058_at | HG-U133A | NM_014593 | 976 | CXXC finger 1 (PHD domain) | CXXC1 | 30827 | | — | resp | 7 |
| 1025 | 201377_at | HG-U133A | NM_014847 | 977 | ubiquitin associated protein 2-like | UBAP2L | 9898 | | — | resp | 17 |
| 1026 | 204639_at | HG-U133A | NM_000022 | 978 | adenosine deaminase | ADA | 100 | | — | resp | 21 |
| 1027 | 201307_at | HG-U133A | AL534972 | 979 | septin 11 | SEPT11 | 55752 | | — | resp | 22 |
| 1028 | 225105_at | HG-U133B | BF969397 | 980 | hypothetical protein | LOC387882 | 387882 | | — | resp | 41 |
| 1029 | 209836_x_at | HG-U133A | AF060511 | 981 | LAT1-3TM protein | LAT1-3TM | 81893 | | — | resp | 43 |
| 1030 | 201897_s_at | HG-U133A | NM_001826 | 982 | CDC28 protein kinase regulatory subunit 1B | CKS1B | 1163 | | — | resp | 53 |
| 1031 | 201349_at | HG-U133A | NM_004252 | 983 | solute carrier family 9 (sodium/hydrogen exchanger), isoform 3 regulator 1 | SLC9A3R1 | 9368 | | — | resp | 66 |
| 1032 | 217836_s_at | HG-U133A | NM_018253 | 984 | YY1 associated protein 1 | YY1AP1 | 55249 | | — | resp | 70 |
| 1033 | 208972_s_at | HG-U133A | AL080089 | 985 | ATP synthase, H+ transporting, mitochondrial F0 complex, subunit c (subunit 9), isoform 1 | ATP5G1 | 516 | | — | resp | 71 |
| 1034 | 226219_at | HG-U133B | AW575123 | 986 | hypothetical protein LOC257106 | LOC257106 | 257106 | | — | resp | 88 |
| 1035 | 202403_s_at | HG-U133A | AA788711 | 987 | collagen, type I, alpha 2 | COL1A2 | 1278 | — | | TTP | 1 |
| 1036 | 213513_x_at | HG-U133A | BG034239 | 988 | actin related protein 2/3 complex, subunit 2, 34 kDa | ARPC2 | 10109 | — | | TTP | 2 |
| 1037 | 207988_s_at | HG-U133A | NM_005731 | 989 | actin related protein 2/3 complex, subunit 2, 34 kDa | ARPC2 | 10109 | | — | TTP | 6 |
| 1038 | 207493_x_at | HG-U133A | NM_003147 | 990 | synovial sarcoma, X breakpoint 2 | SSX2 | 6757 | — | | TTP | 13 |
| 1039 | 218151_x_at | HG-U133A | NM_024531 | 991 | G protein-coupled receptor 172A | GPR172A | 79581 | — | | TTP | 15 |

TABLE 2-continued

GLUOCORTICOID PREDICTIVE MARKER IDENTIFICATION
2A Predictive Markers Up regulated Indicators of Non-Reponse and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 1040 | 222518_at | HG-U133B | BF525399 | 992 | ADP-ribosylation factor guanine nucleotide-exchange factor 2 (brefeldin A-inhibited) | ARFGEF2 | 10564 | — | — | TTP | 47 |
| 1041 | 218041_x_at | HG-U133A | NM_018573 | 993 | solute carrier family 38, member 2 | SLC38A2 | 54407 | — | — | TTP | 53 |
| 1042 | 217871_s_at | HG-U133A | NM_002415 | 994 | macrophage migration inhibitory factor (glycosylation-inhibiting factor) | MIF | 4282 | — | — | TTP | 108 |
| 1043 | 215603_x_at | HG-U133A | AI344075 | 995 | gamma-glutamyltransferase 1 /// gamma-glutamyltransferase-like 4 | GGT1 /// GGTL4 | 2678 /// 91227 | — | — | TTP/resp | 3 |
| 1044 | 202671_s_at | HG-U133A | NM_003681 | 996 | pyridoxal (pyridoxine, vitamin B6) kinase | PDXK | 8566 | — | — | TTP/resp | 7 |
| 1045 | 243606_at | HG-U133B | BE883167 | 997 | Transcribed locus, moderately similar to NP_055301.1 neuronal thread protein AD7c-NTP [Homo sapiens] | | | — | — | TTP/resp | 8 |
| 1046 | 216829_at | HG-U133A | X72475 | 998 | immunoglobulin kappa constant | IGKC | 3514 | — | — | TTP/resp | 12 |
| 1047 | 207131_x_at | HG-U133A | NM_013430 | 999 | gamma-glutamyltransferase 1 | GGT1 | 2678 | — | — | TTP/resp | 21 |
| 1048 | 212539_at | HG-U133A | AI42099 | 1000 | chromodomain helicase DNA binding protein 1-like | CHD1L | 9557 | — | — | TTP/resp | 26 |
| 1049 | 221676_at | HG-U133A | BC002342 | 1001 | coronin, actin binding protein, 1C | CORO1C | 23603 | — | — | TTP/resp | 31 |
| 1050 | 221970_at | HG-U133A | AU158148 | 1002 | DKFZP586L0724 protein | DKFZP586L0724 | 25926 | — | — | TTP/resp | 31 |
| 1051 | 200991_s_at | HG-U133A | NM_014748 | 1003 | sorting nexin 17 | SNX17 | 9784 | — | — | TTP/resp | 34 |
| 1052 | 218592_s_at | HG-U133A | NM_017829 | 1004 | cat eye syndrome chromosome region, candidate 5 | CECR5 | 27440 | — | — | TTP/resp | 42 |
| 1053 | 205213_at | HG-U133A | NM_014716 | 1005 | centaurin, beta 1 | CENTB1 | 9744 | — | — | TTP/resp | 43 |
| 1054 | 229711_s_at | HG-U133B | AA902480 | 1006 | Carboxypeptidase M | CPM | 1368 | — | — | TTP/resp | 45 |
| 1055 | 211759_x_at | HG-U133A | BC005969 | 1007 | cytoskeleton associated protein 1 | CKAP1 | 1155 | — | — | TTP/resp | 46 |
| 1056 | 205788_s_at | HG-U133A | NM_014827 | 1008 | | | | — | — | TTP/resp | 49 |
| 1057 | 200793_s_at | HG-U133A | NM_001098 | 1009 | aconitase 2, mitochondrial | ACO2 | 50 | — | — | TTP/resp | 56 |
| 1058 | 211417_x_at | HG-U133A | L20493 | 1010 | gamma-glutamyltransferase 1 | GGT1 | 2678 | — | — | TTP/resp | 61 |
| 1059 | 208095_s_at | HG-U133A | NM_001222 | 1011 | signal recognition particle 72 kDa | SRP72 | 6731 | — | — | TTP/resp | 66 |

TABLE 2-continued

GLUOCORTICOID PREDICTIVE MARKER IDENTIFICATION
2A Predictive Markers Up regulated Indicators of Non-Reponse and/or Short Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 1060 | 200782_at | HG-U133A | NM_001154 | 1012 | annexin A5 | ANXA5 | 308 | - | - | TTP/resp | 72 |
| 1061 | 218014_at | HG-U133A | NM_024844 | 1013 | pericentrin 1 | PCNT1 | 79902 | - | - | TTP/resp | 75 |
| 1062 | 223096_at | HG-U133B | AF161469 | 1014 | nucleolar protein NOP5/NOP58 | NOP5/NOP58 | 51602 | - | - | TTP/resp | 112 |
| 1063 | 232010_at | HG-U133B | AA129444 | 1015 | follistatin-like 5 | FSTL5 | 56884 | - | - | resp | 27 |
| 1064 | 227167_s_at | HG-U133B | AW511319 | 1016 | Mesenchymal stem cell protein DSC96 | KIAA0746 | | - | - | TTP | 14 |
| 1065 | 224918_x_at | HG-U133B | AI220117 | 1017 | microsomal glutathione S-transferase 1 | MGST1 | 4257 | - | - | TTP | 105 |
| 1066 | 225904_at | HG-U133B | N64686 | 1018 | LOC126731 | LOC126731 | 126731 | - | - | resp | 13 |
| 1067 | 235353_at | HG-U133B | AI887866 | 1019 | KIAA0746 protein | KIAA0746 | 23231 | - | - | resp | 46 |
| 1068 | 203606_at | HG-U133A | NM_004553 | 1020 | NADH dehydrogenase (ubiquinone) Fe—S protein 6, 13 kDa (NADH-coenzyme Q reductase) | NDUFS6 | 4726 | - | - | resp | 127 |
| 1069 | 208683_at | HG-U133A | M23254 | 1021 | calpain 2, (m/II) large subunit | CAPN2 | 824 | - | - | TTP | 177 |
| 1070 | 200734_s_at | HG-U133A | BG341906 | 1022 | ADP-ribosylation factor 3 | ARF3 | 377 | - | - | TTP/resp | 5 |

2B Predictive Markers Upregulated Indicators of Response and/or Long Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 1071 | 229233_at | HG-U133B | H05240 | 1023 | neuregulin 3 | NRG3 | 10718 | | + | resp | 1 |
| 1072 | 225524_at | HG-U133B | AU152178 | 1024 | anthrax toxin receptor 2 | ANTXR2 | 118429 | | + | resp | 4 |
| 1073 | 201465_s_at | HG-U133A | BC002646 | 1025 | v-jun sarcoma virus 17 oncogene homolog (avian) | JUN | 3725 | | + | resp | 6 |
| 1074 | 201464_x_at | HG-U133A | BG491844 | 1026 | v-jun sarcoma virus 17 oncogene homolog (avian) | JUN | 3725 | | + | resp | 11 |
| 1075 | 217731_s_at | HG-U133A | NM_021999 | 1027 | integral membrane protein 2B | ITM2B | 9445 | | + | resp | 12 |
| 1076 | 208961_s_at | HG-U133B | AB017493 | 1028 | Kruppel-like factor 6 | KLF6 | 1316 | | + | resp | 14 |
| 1077 | 230493_at | HG-U133B | AW664964 | 1029 | WGAR9166 | LOC387914 | 387914 | | + | resp | 15 |
| 1078 | 221220_s_at | HG-U133A | NM_017988 | 1030 | SCY1-like 2 (S. cerevisiae) | SCYL2 | 55681 | | + | resp | 16 |
| 1079 | 211560_s_at | HG-U133A | AF130113 | 1031 | aminolevulinate, delta-, synthase 2 (sideroblastic/hypochromic anemia) | ALAS2 | 212 | | + | resp | 19 |
| 1080 | AFFX-r2-Hs18SrRNA-5_at | HG-U133A | AFFX-Hs18SrRNA-5 | | | | | | + | resp | 22 |
| 1081 | 220751_s_at | HG-U133A | NM_016348 | 1032 | chromosome 5 open reading frame 4 | C5orf4 | 10826 | | + | resp | 23 |
| 1082 | 201432_at | HG-U133A | NM_001752 | 1033 | catalase | CAT | 847 | | + | resp | 24 |
| 1083 | 206871_at | HG-U133A | NM_001972 | 1034 | elastase 2, neutrophil | ELA2 | 1991 | | + | resp | 24 |
| 1084 | 208781_x_at | HG-U133A | AF062483 | 1035 | sorting nexin 3 | SNX3 | 8724 | | + | resp | 32 |
| 1085 | 202687_s_at | HG-U133A | U57059 | 1036 | tumor necrosis factor (ligand) superfamily, member 10 | TNFSF10 | 8743 | | + | resp | 33 |
| 1086 | 212603_at | HG-U133A | NM_005830 | 1037 | mitochondrial ribosomal protein S31 | MRPS31 | 10240 | | + | resp | 34 |
| 1087 | 217144_at | HG-U133A | X04801 | 1038 | ubiquitin B | UBB | 7314 | | + | resp | 34 |
| 1088 | AFFX-HUMRGE/M10098_5_at | HG-U133A | AFFX-HUMRGE/M10098_5 | | | | | | + | resp | 35 |
| 1089 | 208960_s_at | HG-U133A | BE675435 | 1039 | Kruppel-like factor 6 | KLF6 | 1316 | | + | resp | 38 |
| 1090 | 224688_at | HG-U133B | BE962299 | 1040 | Hypothetical protein FLJ10099 | FLJ10099 | 55069 | | + | resp | 40 |
| 1091 | 209930_s_at | HG-U133A | L13974 | 1041 | nuclear factor (erythroid-derived 2), 45 kDa | NFE2 | 4778 | | + | resp | 42 |
| 1092 | 224606_at | HG-U133B | BG250721 | 1042 | Homo sapiens, clone IMAGE: 4096273, mRNA | | | | + | resp | 42 |
| 1093 | 205225_at | HG-U133A | NM_000125 | 1043 | estrogen receptor 1 | ESR1 | 2099 | | + | resp | 46 |
| 1094 | AFFX-r2-Hs18SrRNA-5_at | HG-U133B | AFFX-Hs18SrRNA-5 | | | | | | + | resp | 46 |
| 1095 | 205383_s_at | HG-U133A | NM_015642 | 1044 | zinc finger and BTB domain containing 20 | ZBTB20 | 26137 | | + | resp | 47 |
| 1096 | 207459_x_at | HG-U133A | NM_002100 | 1045 | glycophorin B (includes Ss blood group) | GYPB | 2994 | | + | resp | 50 |
| 1097 | 221824_s_at | HG-U133A | AA770170 | 1046 | membrane-associated ring finger (C3HC4) 8 | MARCH8 | 220972 | | + | resp | 56 |
| 1098 | 210504_at | HG-U133A | U65404 | 1047 | Kruppel-like factor 1 (erythroid) | KLF1 | 10661 | | + | resp | 57 |

2B Predictive Markers Upregulated Indicators of Response and/or Long Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 1099 | 56256_at | HG-U133A | AA150165 | 1048 | SID1 transmembrane family, member 2 | SIDT2 | 51092 | | + | resp | 57 |
| 1100 | 214407_x_at | HG-U133A | AI240545 | 1049 | glycophorin B (includes Ss blood group) | GYPB | 2994 | | + | resp | 58 |
| 1101 | 213281_at | HG-U133A | BE327172 | 1050 | hypothetical protein LOC130576 | LOC130576 | 130576 | | + | resp | 61 |
| 1102 | 228360_at | HG-U133B | BF060747 | 1051 | ankyrin 1, erythrocytic | ANK1 | 286 | | + | resp | 69 |
| 1103 | 205389_s_at | HG-U133A | AI659683 | 1052 | major histocompatibility complex, class I, B | HLA-B | 3106 | | + | resp | 74 |
| 1104 | 209140_x_at | HG-U133A | L42024 | 1053 | | | | | + | resp | 76 |
| 1105 | 205838_at | HG-U133A | NM_002099 | 1054 | glycophorin A (includes MN blood group) | GYPA | 2993 | | + | resp | 79 |
| 1106 | 216389_s_at | HG-U133A | AF283773 | 1055 | WD repeat domain 23 | WDR23 | 80344 | | + | resp | 79 |
| 1107 | AFFX-HUMRGE/M10098_5_at | HG-U133B | AFFX-HUMRGE/M10098_5 | | | | | | + | resp | 80 |
| 1108 | 202364_at | HG-U133A | NM_005962 | 1056 | MAX interactor 1 | MXI1 | 4601 | | + | resp | 81 |
| 1109 | 223309_x_at | HG-U133B | BG025248 | 1057 | intracellular membrane-associated calcium-independent phospholipase A2 gamma | IPLA2 (GAMMA) | 50640 | | + | resp | 83 |
| 1110 | 219497_s_at | HG-U133A | NM_022893 | 1058 | B-cell CLL/lymphoma 11A (zinc finger protein) | BCL11A | 53335 | | + | resp | 88 |
| 1111 | 206834_at | HG-U133A | NM_000519 | 1059 | hemoglobin, delta | HBD | 3045 | | + | resp | 89 |
| 1112 | 210648_x_at | HG-U133A | AB047360 | 1060 | sorting nexin 3 | SNX3 | 8724 | | + | resp | 97 |
| 1113 | 211820_x_at | HG-U133A | U00179 | 1061 | glycophorin A (includes MN blood group) | GYPA | 2993 | | + | resp | 116 |
| 1114 | 208621_s_at | HG-U133A | BF663141 | 1062 | villin 2 (ezrin) | VIL2 | 7430 | | + | resp | 5 |
| 1115 | 213515_x_at | HG-U133A | AI133353 | 1063 | hemoglobin, gamma G | HBG2 | 3048 | | + | resp | 9 |
| 1116 | 217732_s_at | HG-U133A | AF092128 | 1064 | integral membrane protein 2B | ITM2B | 9445 | | + | resp | 9 |
| 1117 | 223952_x_at | HG-U133B | AF240698 | 1065 | dehydrogenase/reductase (SDR family) member 9 | DHRS9 | 10170 | | + | resp | 10 |
| 1118 | 204419_x_at | HG-U133A | NM_000184 | 1066 | hemoglobin, gamma G | HBG2 | 3048 | | + | resp | 11 |
| 1119 | 204848_x_at | HG-U133A | NM_000559 | 1067 | hemoglobin, gamma A /// hemoglobin, gamma G | HBG1 /// HBG2 | 3047 /// 3048 | | + | resp | 12 |
| 1120 | 218717_s_at | HG-U133A | NM_018192 | 1068 | leprecan-like 1 | LEPREL1 | 55214 | | + | resp | 13 |
| 1121 | 221911_at | HG-U133B | BE881590 | 1069 | hypothetical protein LOC221810 | LOC221810 | 221810 | | + | resp | 14 |
| 1122 | 224009_x_at | HG-U133B | AF240697 | 1070 | dehydrogenase/reductase (SDR family) member 9 | DHRS9 | 10170 | | + | resp | 16 |
| 1123 | 235278_at | HG-U133B | BF032500 | 1071 | Homo sapiens, clone IMAGE: 4513167, mRNA | | | | + | resp | 18 |
| 1124 | 234419_x_at | HG-U133B | AJ275401 | 1072 | IG rearranged H-chain mRNA V-region | | | | + | resp | 20 |
| 1125 | 234390_x_at | HG-U133B | Z27446 | 1073 | | | | | + | resp | 21 |
| 1126 | 216542_x_at | HG-U133A | AJ275355 | 1074 | hypothetical protein MGC27165 | MGC27165 | 283650 | | + | resp | 22 |
| 1127 | 219799_s_at | HG-U133A | NM_005771 | 1075 | dehydrogenase/reductase (SDR family) member 9 | DHRS9 | 10170 | | + | resp | 26 |

2B Predictive Markers Upregulated Indicators of Response and/or Long Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 1128 | 221841_s_at | HG-U133A | BF514079 | 1076 | Kruppel-like factor 4 (gut) | KLF4 | 9314 | | + | resp | 27 |
| 1129 | 206181_at | HG-U133A | NM_003037 | 1077 | signaling lymphocytic activation molecule family member 1 | SLAMF1 | 6504 | | + | resp | 29 |
| 1130 | 219377_at | HG-U133A | NM_022751 | 1078 | chromosome 18 open reading frame 11 | C18orf11 | 64762 | | + | resp | 30 |
| 1131 | 228415_at | HG-U133B | AA205444 | 1079 | Adaptor-related protein complex 1, sigma 2 subunit | AP1S2 | 8905 | | + | resp | 31 |
| 1132 | 204466_s_at | HG-U133A | BG260394 | 1080 | synuclein, alpha (non A4 component of amyloid precursor) | SNCA | 6622 | | + | resp | 38 |
| 1133 | 203751_x_at | HG-U133A | AI762296 | 1081 | jun D proto-oncogene | JUND | 3727 | | + | resp | 44 |
| 1134 | 220059_at | HG-U133A | NM_012108 | 1082 | BCR downstream signaling 1 | BRDG1 | 26228 | | + | resp | 49 |
| 1135 | 203502_at | HG-U133A | NM_001724 | 1083 | 2,3-bisphosphoglycerate mutase | BPGM | 669 | | + | resp | 51 |
| 1136 | 217865_at | HG-U133A | NM_018434 | 1084 | ring finger protein 130 | RNF130 | 55819 | | + | resp | 51 |
| 1137 | 202206_at | HG-U133A | AW450363 | 1085 | ADP-ribosylation factor-like 7 | ARL7 | 10123 | | + | resp | 52 |
| 1138 | 209968_s_at | HG-U133A | U63041 | 1086 | neural cell adhesion molecule 1 | NCAM1 | 4684 | | + | resp | 52 |
| 1139 | 208729_x_at | HG-U133A | D83043 | 1087 | major histocompatibility complex, class I, B | HLA-B | 3106 | | + | resp | 53 |
| 1140 | 208029_s_at | HG-U133A | NM_018407 | 1088 | lysosomal associated protein transmembrane 4 beta | LAPTM4B | 55353 | | + | resp | 54 |
| 1141 | 217478_s_at | HG-U133A | X76775 | 1089 | major histocompatibility complex, class II, DM alpha | HLA-DMA | 3108 | | + | resp | 55 |
| 1142 | 201849_at | HG-U133A | NM_004052 | 1090 | BCL2/adenovirus E1B 19 kDa interacting protein 3 | BNIP3 | 664 | | + | resp | 58 |
| 1143 | 216833_x_at | HG-U133A | U05255 | 1091 | glycophorin B (includes Ss blood group) /// glycophorin E | GYPB /// GYPE | 2994 /// 2996 | | + | resp | 61 |
| 1144 | 37028_at | HG-U133A | U83981 | 1092 | protein phosphatase 1, regulatory (inhibitor) subunit 15A | PPP1R15A | 23645 | | + | resp | 74 |
| 1145 | 209357_at | HG-U133A | AF109161 | 1093 | Cbp/p300-interacting transactivator, with Glu/Asp-rich carboxy-terminal domain, 2 | CITED2 | 10370 | | + | resp | 75 |
| 1146 | 209295_at | HG-U133A | AF016266 | 1094 | tumor necrosis factor receptor superfamily, member 10b | TNFRSF10B | 8795 | | + | resp | 82 |
| 1147 | 202511_s_at | HG-U133A | AK001899 | 1095 | APG5 autophagy 5-like (S. cerevisiae) | APG5L | 9474 | | + | resp | 86 |
| 1148 | 208812_x_at | HG-U133A | BC004489 | 1096 | major histocompatibility complex, class I, B /// major histocompatibility complex, class I, C | HLA-B /// HLA-C | 3106 /// 3107 | | + | resp | 91 |
| 1149 | 204992_s_at | HG-U133A | NM_002628 | 1097 | profilin 2 | PFN2 | 5217 | | + | resp | 92 |
| 1150 | 203685_at | HG-U133A | NM_000633 | 1098 | B-cell CLL/lymphoma 2 | BCL2 | 596 | | + | resp | 93 |
| 1151 | 224693_at | HG-U133B | AI133137 | 1099 | chromosome 20 open reading frame 108 | C20orf108 | 116151 | | + | resp | 94 |

2B Predictive Markers Upregulated Indicators of Response and/or Long Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 1152 | 211530_x_at | HG-U133A | M90686 | 1100 | HLA-G histocompatibility antigen, class I, G | HLA-G | 3135 | | + | resp | 98 |
| 1153 | 204621_s_at | HG-U133A | AI935096 | 1101 | nuclear receptor subfamily 4, group A, member 2 | NR4A2 | 4929 | | + | resp | 102 |
| 1154 | 200633_at | HG-U133A | NM_018955 | 1102 | ubiquitin B | UBB | 7314 | | + | resp | 104 |
| 1155 | 221004_s_at | HG-U133A | NM_030926 | 1103 | integral membrane protein 2C | ITM2C | 81618 | | + | resp | 105 |
| 1156 | 229713_at | HG-U133B | AW665227 | 1104 | | | | | + | resp | 108 |
| 1157 | 203428_s_at | HG-U133A | AB028628 | 1105 | ASF1 anti-silencing function 1 homolog A (S. cerevisiae) | ASF1A | 25842 | | + | resp | 110 |
| 1158 | 218858_at | HG-U133A | NM_022783 | 1106 | DEP domain containing 6 | DEPDC6 | 64798 | | + | resp | 116 |
| 1159 | 204622_x_at | HG-U133A | NM_006186 | 1107 | nuclear receptor subfamily 4, group A, member 2 | NR4A2 | 4929 | | + | resp | 117 |
| 1160 | 200628_s_at | HG-U133A | M61715 | 1108 | tryptophanyl-tRNA synthetase | WARS | 7453 | | + | resp | 124 |
| 1161 | 216248_s_at | HG-U133A | S77154 | 1109 | nuclear receptor subfamily 4, group A, member 2 | NR4A2 | 4929 | | + | resp | 130 |
| 1162 | 235341_at | HG-U133B | AL119957 | 1110 | DnaJ (Hsp40) homolog, subfamily C, member 3 | DNAJC3 | 5611 | | + | resp | 135 |
| 1163 | 200905_x_at | HG-U133A | NM_005516 | 1111 | major histocompatibility complex, class I, E | HLA-E | 3133 | + | | TTP | 64 |
| 1164 | 218539_at | HG-U133A | NM_017943 | 1112 | F-box protein 34 | FBXO34 | 55030 | + | | TTP | 68 |
| 1165 | 200912_s_at | HG-U133A | NM_001967 | 1113 | eukaryotic translation initiation factor 4A, isoform 2 | EIF4A2 | 1974 | + | | TTP | 69 |
| 1166 | 217456_x_at | HG-U133A | M31183 | 1114 | major histocompatibility complex, class I, E | HLA-E | 3133 | + | | TTP | 85 |
| 1167 | 212510_at | HG-U133A | AA135522 | 1115 | glycerol-3-phosphate dehydrogenase 1-like | GPD1L | 23171 | + | | TTP | 98 |
| 1168 | 201334_s_at | HG-U133A | AB002380 | 1116 | Rho guanine nucleotide exchange factor (GEF) 12 | ARHGEF12 | 23365 | + | | TTP | 130 |
| 1169 | 202333_s_at | HG-U133A | AA877765 | 1117 | ubiquitin-conjugating enzyme E2B (RAD6 homolog) | UBE2B | 7320 | + | | TTP | 131 |
| 1170 | 214080_x_at | HG-U133A | AI815793 | 1118 | protein kinase C substrate 80K-H | PRKCSH | 5589 | + | | TTP | 138 |
| 1171 | 223356_s_at | HG-U133B | BG529919 | 1119 | mitochondrial translational initiation factor 3 | MTIF3 | 219402 | + | | TTP | 139 |
| 1172 | 201886_at | HG-U133A | NM_025230 | 1120 | WD repeat domain 23 | WDR23 | 80344 | + | | TTP | 146 |
| 1173 | 228831_s_at | HG-U133B | AL039870 | 1121 | guanine nucleotide binding protein (G protein), gamma 7 | GNG7 | 2788 | + | | TTP | 167 |
| 1174 | 201637_s_at | HG-U133A | NM_005087 | 1122 | fragile X mental retardation, autosomal homolog 1 | FXR1 | 8087 | + | | TTP | 170 |
| 1175 | 202812_at | HG-U133A | NM_000152 | 1123 | glucosidase, alpha; acid (Pompe disease, glycogen storage disease type II) | GAA | 2548 | + | | TTP | 174 |
| 1176 | 201871_s_at | HG-U133A | NM_015853 | 1124 | ORF | LOC51035 | 51035 | + | | TTP | 182 |
| 1177 | 225582_at | HG-U133B | AA425726 | 1125 | KIAA1754 | KIAA1754 | 85450 | + | + | resp | 1 |
| 1178 | 208855_s_at | HG-U133A | AF083420 | 1126 | serine/threonine kinase 24 (STE20 homolog, yeast) | STK24 | 8428 | + | + | TTP | 27 |
| 1179 | 212760_at | HG-U133A | AB002347 | 1127 | ubiquitin protein ligase E3 component n-recognin 2 | UBR2 | 23304 | + | + | TTP | 30 |

2B Predictive Markers Upregulated Indicators of Response and/or Long Time to Progression

| No. | ProbeSet ID | chip | Rep Public ID | SEQ ID NO: | Title | Gene Symbol | Entrez Gene ID | TTP marker | Response marker | Type of specificity | Rank |
|---|---|---|---|---|---|---|---|---|---|---|---|
| 1180 | 203836_s_at | HG-U133A | D84476 | 1128 | mitogen-activated protein kinase kinase kinase 5 | MAP3K5 | 4217 | + | + | TTP | 40 |
| 1181 | 221555_x_at | HG-U133A | AU145941 | 1129 | CDC14 cell division cycle 14 homolog B (S. cerevisiae) | CDC14B | 8555 | + | + | TTP | 44 |
| 1182 | 209966_x_at | HG-U133A | AF094518 | 1130 | estrogen-related receptor gamma | ESRRG | 2104 | + | + | TTP/resp | 14 |
| 1183 | 210347_s_at | HG-U133A | AF080216 | 1131 | B-cell CLL/lymphoma 11A (zinc finger protein) | BCL11A | 53335 | + | + | TTP/resp | 23 |
| 1184 | 201466_s_at | HG-U133A | NM_002228 | 1132 | v-jun sarcoma virus 17 oncogene homolog (avian) | JUN | 3725 | + | + | TTP/resp | 34 |
| 1185 | 204710_s_at | HG-U133A | NM_016003 | 1133 | WIPI49-like protein 2 | WIPI-2 | 26100 | + | + | TTP/resp | 80 |
| 1186 | 209054_s_at | HG-U133A | AF083389 | 1134 | Wolf-Hirschhorn syndrome candidate 1 | WHSC1 | 7468 |  | + | resp | 33 |
| 1187 | 222891_s_at | HG-U133B | AI912275 | 1135 | B-cell CLL/lymphoma 11A (zinc finger protein) | BCL11A | 53335 |  | + | resp | 35 |
| 1188 | 219759_at | HG-U133A | NM_022350 | 1136 | leukocyte-derived arginine aminopeptidase | LRAP | 64167 |  | + | resp | 40 |
| 1189 | 202442_at | HG-U133A | NM_001284 | 1137 | adaptor-related protein complex 3, sigma 1 subunit | AP3S1 | 1176 |  | + | resp | 83 |
| 1190 | 218191_s_at | HG-U133A | NM_018368 | 1138 | chromosome 6 open reading frame 209 | C6orf209 | 55788 |  | + | resp | 15 |
| 1191 | 202643_s_at | HG-U133A | AI738896 | 1139 | tumor necrosis factor, alpha-induced protein 3 | TNFAIP3 | 7128 |  | + | resp | 36 |
| 1192 | 221297_at | HG-U133A | NM_018654 | 1140 | G protein-coupled receptor, family C, group 5, member D | GPRC5D | 55507 |  | + | resp | 43 |
| 1193 | 211529_x_at | HG-U133A | M90684 | 1141 | HLA-G histocompatibility antigen, class I, G | HLA-G | 3135 |  | + | resp | 50 |
| 1194 | 217436_x_at | HG-U133A | M80469 | 1142 | HLA-G histocompatibility antigen, class I, G | HLA-G | 3135 |  | + | resp | 59 |
| 1195 | 211528_x_at | HG-U133A | M90685 | 1143 |  |  |  |  | + | resp | 83 |
| 1196 | 211911_x_at | HG-U133A | L07950 | 1144 | major histocompatibility complex, class I, B /// major histocompatibility complex, class I, C | HLA-B /// HLA-C | 3106 /// 3107 |  | + | resp | 93 |
| 1197 | 222146_s_at | HG-U133A | AK026674 | 1145 | transcription factor 4 | TCF4 | 6925 |  | + | resp | 107 |
| 1198 | 224566_at | HG-U133B | AI042152 | 1146 | trophoblast-derived noncoding RNA | TncRNA | 283131 |  | + | resp | 113 |
| 1199 | 225282_at | HG-U133B | AL137764 | 1147 | hypothetical protein AL133206 | LOC64744 | 64744 | + | + | resp | 118 |
| 1200 | 201951_at | HG-U133A | BF242905 | 1148 | Activated leukocyte cell adhesion molecule | ALCAM | 214 | + | + | resp | 28 |
| 1201 | 203845_at | HG-U133A | AV727449 | 1149 | p300/CBP-associated factor | PCAF | 8850 | + | + | TTP | 14 |
| 1202 | 221778_at | HG-U133A | BE217882 | 1150 | KIAA1718 protein | KIAA1718 | 80853 | + | + | TTP/resp | 59 |

TABLE 3

AGRESSIVENESS PREDICTIVE MARKER IDENTIFICATION

| No. | ProbeSet ID | chip | Rep Public ID | SEQ ID NO: | Title | Gene Symbol | Entrez Gene ID | proteasome inhibitor TTP marker | proteasome inhibitor Response marker | gluco-corticoid TTP marker | gluco-corticoid Response marker | Rank |
|---|---|---|---|---|---|---|---|---|---|---|---|---|
| 1203 | 210386_s_at | HG-U133A | BC001906 | 1151 | metaxin 1 | MTX1 | 4580 | | | | − | 1 |
| 1204 | 211639_x_at | HG-U133A | L23518 | 1152 | Immunoglobulin heavy constant mu | IGHM | 3507 | | | | − | 2 |
| 1205 | 211637_x_at | HG-U133A | L23516 | 1153 | similar to Ig heavy chain V-I region HG3 precursor | LOC388078 | 388078 | | | | − | 3 |
| 1206 | 211644_x_at | HG-U133A | L14458 | 1154 | HRV Fab 027-VL /// HRV Fab 026-VL /// Ig light chain gene variable domain (CLL-L3B) /// HRV Fab N27-VL /// Immunoglobulin kappa constant | IGKC | 3514 | | | | + | 4 |
| 1207 | 219593_at | HG-U133A | NM_016582 | 1155 | solute carrier family 15, member 3 | SLC15A3 | 51296 | | | | + | 7 |
| 1208 | 208671_at | HG-U133A | AF164794 | 1156 | tumor differentially expressed 2 | TDE2 | 57515 | | | | + | 8 |
| 1209 | 201438_at | HG-U133A | NM_004369 | 1157 | collagen, type VI, alpha 3 | COL6A3 | 1293 | | | | − | 11 |
| 1210 | 201937_s_at | HG-U133A | NM_012100 | 1158 | aspartyl aminopeptidase | DNPEP | 23549 | | | | − | 12 |
| 1211 | 216576_x_at | HG-U133A | AF103529 | 1159 | | | | | | | − | 12 |
| 1212 | 217281_x_at | HG-U133A | AJ239383 | 1160 | immunoglobulin heavy constant gamma 1 (G1m marker) /// immunoglobulin heavy constant mu /// hypothetical protein MGC27165 | IGHG1 /// IGHM /// MGC27165 | 283650 /// 3500 /// 3507 | | | | + | 13 |
| 1213 | 224634_at | HG-U133B | AI911518 | 1161 | G patch domain containing 4 | GPATC4 | 54865 | | | | | 15 |
| 1214 | 235802_at | HG-U133B | BE676703 | 1162 | chromosome 14 open reading frame 175 | C14orf175 | 122618 | | | − | | 16 |
| 1215 | 203182_s_at | HG-U133A | NM_003138 | 1163 | SFRS protein kinase 2 | SRPK2 | 6733 | | | | − | 17 |
| 1216 | 211643_x_at | HG-U133A | L14457 | 1164 | | | | | | | + | 18 |
| 1217 | 226646_at | HG-U133B | AI831932 | 1165 | Kruppel-like factor 2 (lung) | KLF2 | 10365 | | | | + | 18 |
| 1218 | 203641_s_at | HG-U133A | BF002844 | 1166 | COBL-like 1 | COBLL1 | 22837 | | | | + | 19 |
| 1219 | 207238_s_at | HG-U133A | NM_002838 | 1167 | protein tyrosine phosphatase, receptor type, C | PTPRC | 5788 | | | | − | 19 |
| 1220 | 220807_at | HG-U133A | NM_005331 | 1168 | hemoglobin, theta 1 | HBQ1 | 3049 | | | | + | 22 |
| 1221 | 205890_s_at | HG-U133A | NM_006398 | 1169 | ubiquitin D | UBD | 10537 | | | | + | 23 |
| 1222 | 208850_s_at | HG-U133A | AL558479 | 1170 | Thy-1 cell surface antigen /// Thy-1 co-transcribed | THY1 /// LOC94105 | 7070 /// 94105 | | | − | | 23 |
| 1223 | 226350_at | HG-U133B | AU155565 | 1171 | choroideremia-like (Rab escort protein 2) | CHML | 1122 | | | − | | 24 |
| 1224 | 225636_at | HG-U133B | H98105 | 1172 | signal transducer and activator of transcription 2, 113 kDa | STAT2 | 6773 | | | − | | 36 |
| 1225 | 208677_s_at | HG-U133A | AL550657 | 1173 | basigin (OK blood group) | BSG | 682 | | | | + | 37 |
| 1226 | 212473_s_at | HG-U133A | BE965029 | 1174 | flavoprotein oxidoreductase MICAL2 | MICAL2 | 9645 | | | | + | 39 |
| 1227 | 212987_at | HG-U133A | AL031178 | 1175 | F-box protein 9 | FBXO9 | 26268 | | | | + | 39 |
| 1228 | 211919_s_at | HG-U133A | AF348491 | 1176 | Chemokine (C-X-C motif) receptor 4 | CXCR4 | 7852 | | | | + | 40 |
| 1229 | 212139_at | HG-U133A | D86973 | 1177 | GCN1 general control of amino-acid synthesis 1-like 1 (yeast) | GCN1L1 | 10985 | | | − | | 41 |

TABLE 3-continued

AGRESSIVENESS PREDICTIVE MARKER IDENTIFICATION

| No. | ProbeSet ID | chip | Rep Public ID | SEQ ID NO: | Title | Gene Symbol | Entrez Gene ID | proteasome inhibitor TTP marker | proteasome inhibitor Response marker | gluco- corticoid TTP marker | gluco- corticoid Response marker | Rank |
|---|---|---|---|---|---|---|---|---|---|---|---|---|
| 1230 | 213730_x_at | HG-U133A | BE962186 | 1178 | transcription factor 3 (E2A immunoglobulin enhancer binding factors E12/E47) | TCF3 | 6929 | | | | − | 42 |
| 1231 | 216398_at | HG-U133A | U05255 | 1091 | | | | | | | + | 43 |
| 1232 | 211254_x_at | HG-U133A | AF031549 | 1179 | Rhesus blood group-associated glycoprotein | RHAG | 6005 | | | | + | 45 |
| 1233 | 217028_at | HG-U133A | AJ224869 | 1180 | Chemokine (C-X-C motif) receptor 4 | CXCR4 | 7852 | | | | + | 46 |
| 1234 | 212226_s_at | HG-U133A | AA628586 | 1181 | phosphatidic acid phosphatase type 2B | PPAP2B | 8613 | | | | + | 47 |
| 1235 | 213457_at | HG-U133A | BF739959 | 1182 | malignant fibrous histiocytoma amplified sequence 1 | MFHAS1 | 9258 | | | | + | 47 |
| 1236 | 202124_s_at | HG-U133A | AV705253 | 1183 | amyotrophic lateral sclerosis 2 (juvenile) chromosome region, candidate 3 | ALS2CR3 | 66008 | | | | + | 48 |
| 1237 | 205859_at | HG-U133A | NM_004271 | 1184 | lymphocyte antigen 86 | LY86 | 9450 | | | | + | 49 |
| 1238 | 214157_at | HG-U133A | AA401492 | 1185 | GNAS complex locus | GNAS | 2778 | | | | − | 51 |
| 1239 | 212956_at | HG-U133A | AI348094 | 1186 | KIAA0882 protein | KIAA0882 | 23158 | | | | + | 52 |
| 1240 | 219371_s_at | HG-U133A | NM_016270 | 1187 | Kruppel-like factor 2 (lung) | KLF2 | 10365 | | | | + | 52 |
| 1241 | 218847_at | HG-U133A | NM_006548 | 1188 | IGF-II mRNA-binding protein 2 | IMP-2 | 10644 | | | | + | 54 |
| 1242 | 222976_s_at | HG-U133B | BC000771 | 1189 | tropomyosin 3 | TPM3 | 7170 | | | − | | 58 |
| 1243 | 203837_at | HG-U133A | NM_005923 | 1190 | mitogen-activated protein kinase kinase kinase 5 | MAP3K5 | 4217 | | | | + | 63 |
| 1244 | 201178_at | HG-U133A | NM_012179 | 1191 | F-box protein 7 | FBXO7 | 25793 | | | | + | 64 |
| 1245 | 210776_x_at | HG-U133A | M31222 | 1192 | transcription factor 3 (E2A immunoglobulin enhancer binding factors E12/E47) | TCF3 | 6929 | | | | + | 64 |
| 1246 | 203697_at | HG-U133A | U91903 | 1193 | frizzled-related protein | FRZB | 2487 | | | − | | 67 |
| 1247 | 229721_x_at | HG-U133B | AI655697 | 1194 | Der1-like domain family, member 3 | DERL3 | 91319 | | | | − | 72 |
| 1248 | 200984_s_at | HG-U133A | X16447 | 1195 | CD59 antigen p18-20 (antigen identified by monoclonal antibodies 16.3A5, EJ16, EJ30, EL32 and G344) | CD59 | 966 | | | | + | 74 |
| 1249 | 223322_at | HG-U133B | BC004270 | 1196 | Ras association (RalGDS/AF-6) domain family 5 | RASSF5 | 83593 | | | − | | 77 |
| 1250 | 201061_s_at | HG-U133A | M81635 | 1197 | stomatin | STOM | 2040 | | | | + | 78 |
| 1251 | 203132_at | HG-U133A | NM_000321 | 1198 | retinoblastoma 1 (including osteosarcoma) | RB1 | 5925 | | | | + | 79 |
| 1252 | 205308_at | HG-U133A | NM_016010 | 1199 | CGI-62 protein | CGI-62 | 51101 | | | | + | 81 |
| 1253 | 221478_at | HG-U133A | AL132665 | 1200 | BCL2/adenovirus E1B 19 kDa interacting protein 3-like | BNIP3L | 665 | | | | + | 82 |
| 1254 | 214170_x_at | HG-U133A | AA669797 | 1201 | fumarate hydratase | FH | 2271 | | | − | | 87 |
| 1255 | 202345_s_at | HG-U133A | NM_001444 | 1202 | fatty acid binding protein 5 (psoriasis-associated) | FABP5 | 2171 | | | − | | 91 |

TABLE 3-continued

AGRESSIVENESS PREDICTIVE MARKER IDENTIFICATION

| No. | ProbeSet ID | chip | Rep Public ID | SEQ ID NO: | Title | Gene Symbol | Entrez Gene ID | proteasome inhibitor TTP marker | proteasome inhibitor Response marker | gluco-corticoid TTP marker | gluco-corticoid Response marker | Rank |
|---|---|---|---|---|---|---|---|---|---|---|---|---|
| 1256 | 210088_x_at | HG-U133A | M36172 | 1203 | myosin, light polypeptide 4, alkali; atrial, embryonic | MYL4 | 4635 | | | | + | 92 |
| 1257 | 200044_at | HG-U133A | NM_003769 | 1204 | splicing factor, arginine/serine-rich 9 | SFRS9 | 8683 | | | | | 93 |
| 1258 | 205390_s_at | HG-U133A | NM_000037 | 1205 | ankyrin 1, erythrocytic | ANK1 | 286 | | | | + | 95 |
| 1259 | 209160_at | HG-U133A | AB018580 | 1206 | aldo-keto reductase family 1, member C3 (3-alpha hydroxysteroid dehydrogenase, type II) | AKR1C3 | 8644 | | | | + | 97 |
| 1260 | 201561_s_at | HG-U133A | NM_014944 | 1207 | calsyntenin 1 | CLSTN1 | 22883 | | | | | 101 |
| 1261 | 201803_at | HG-U133A | NM_000938 | 1208 | polymerase (RNA) II (DNA directed) polypeptide B, 140 kDa | POLR2B | 5431 | | | − | − | 101 |
| 1262 | 214948_s_at | HG-U133A | AL050136 | 1209 | TATA element modulatory factor 1 /// Similar to family with sequence similarity 9, member C | TMF1 | 441347 /// 7110 | | | − | | 102 |
| 1263 | 204158_s_at | HG-U133A | NM_006019 | 1210 | T-cell, immune regulator 1, ATPase, H+ transporting, lysosomal V0 protein a isoform 3 | TCIRG1 | 10312 | | | − | | 103 |
| 1264 | 200792_at | HG-U133A | NM_001469 | 1211 | thyroid autoantigen 70 kDa (Ku antigen) | G22P1 | 2547 | | | − | | 106 |
| 1265 | 200593_s_at | HG-U133A | BC003621 | 1212 | heterogeneous nuclear ribonucleoprotein U (scaffold attachment factor A) | HNRPU | 3192 | | | − | | 114 |
| 1266 | 200872_at | HG-U133A | NM_002966 | 1213 | S100 calcium binding protein A10 (annexin II ligand, calpactin I, light polypeptide (p11)) | S100A10 | 6281 | | | | + | 114 |
| 1267 | 225532_at | HG-U133B | AI889160 | 1214 | Cdk5 and Abl enzyme substrate 1 | CABLES1 | 91768 | | | − | | 121 |
| 1268 | 210105_s_at | HG-U133A | M14333 | 1215 | FYN oncogene related to SRC, FGR, YES | FYN | 2534 | | | − | | 122 |
| 1269 | 217274_x_at | HG-U133A | X52005 | 1216 | myosin, light polypeptide 4, alkali; atrial, embryonic | MYL4 | 4635 | | | | + | 122 |
| 1270 | 200654_at | HG-U133A | J02783 | 1217 | procollagen-proline, 2-oxoglutarate 4-dioxygenase (proline 4-hydroxylase), beta polypeptide (protein disulfide isomerase; thyroid hormone binding protein p55) | P4HB | 5034 | | | − | − | 123 |
| 1271 | 208851_s_at | HG-U133A | AL161958 | 1218 | Thy-1 cell surface antigen /// Thy-1 co-transcribed | THY1 /// LOC94105 | 7070 /// 94105 | | | − | | 137 |
| 1272 | 225716_at | HG-U133B | AI357639 | 1219 | Full-length cDNA clone CS0DK008YI09 of HeLa cells Cot 25-normalized of *Homo sapiens* (human) | | | | | − | | 140 |
| 1273 | 200619_at | HG-U133A | NM_006842 | 1220 | | | | | | | | 142 |
| 1274 | 200634_at | HG-U133A | NM_005022 | 1221 | profilin 1 | PFN1 | 5216 | | | − | | 149 |
| 1275 | 222584_at | HG-U133B | AL573591 | 1222 | misato | FLJ10504 | 55154 | | | − | | 156 |
| 1276 | 212591_at | HG-U133A | AA887480 | 1223 | KIAA0117 protein | KIAA0117 | 23029 | | | − | | 158 |

TABLE 3-continued

AGRESSIVENESS PREDICTIVE MARKER IDENTIFICATION

| No. | ProbeSet ID | chip | Rep Public ID | SEQ ID NO: | Title | Gene Symbol | Entrez Gene ID | proteasome inhibitor TTP marker | proteasome inhibitor Response marker | gluco- corticoid TTP marker | gluco- corticoid Response marker | Rank |
|---|---|---|---|---|---|---|---|---|---|---|---|---|
| 1277 | 224855_at | HG-U133B | AL561868 | 1224 | pyrroline-5-carboxylate reductase family, member 2 | PYCR2 | 29920 | | | | | 159 |
| 1278 | 202004_x_at | HG-U133A | NM_003001 | 1225 | succinate dehydrogenase complex, subunit C, integral membrane protein, 15 kDa | SDHC | 6391 | | | | | 168 |
| 1279 | 218885_s_at | HG-U133A | NM_016448 | 1226 | RA-regulated nuclear matrix-associatedprotein | RAMP | 51514 | | | | | 175 |
| 1280 | 210131_x_at | HG-U133A | D49737 | 1227 | farnesyl diphosphate synthase (farnesyl pyrophosphate synthetase, dimethylallyltranstransferase, geranyltranstransferase) | FDPS | 2224 | | | | | 178 |
| 1281 | 201275_at | HG-U133A | NM_002004 | 1228 | | | | | | | – | 4 |
| 1282 | 223531_x_at | HG-U133B | AF151035 | 1229 | G protein-coupled receptor 89 | GPR89 | 51463 | | | | – | 5 |
| 1283 | 208694_at | HG-U133A | U47077 | 1230 | protein kinase, DNA-activated, catalytic polypeptide | PRKDC | 5591 | | | | – | 6 |
| 1284 | 225463_x_at | HG-U133B | BF941168 | 1231 | G protein-coupled receptor 89 | GPR89 | 51463 | | | – | – | 10 |
| 1285 | 200090_at | HG-U133A | BG168896 | 398 | farnesyltransferase, CAAX box, alpha | FNTA | 2339 | | | – | – | 11 |
| 1286 | 212165_at | HG-U133A | AF070537 | 1232 | chromosome 1 open reading frame 37 | C1orf37 | 92703 | | | – | – | 11 |
| 1287 | 217978_s_at | HG-U133A | NM_017582 | 1233 | ubiquitin-conjugating enzyme E2Q (putative) | UBE2Q | 55585 | | | – | – | 11 |
| 1288 | 220642_x_at | HG-U133A | NM_016334 | 1234 | G protein-coupled receptor 89 | GPR89 | 51463 | | | – | – | 22 |
| 1289 | 201209_at | HG-U133A | NM_004964 | 1235 | histone deacetylase 1 | HDAC1 | 3065 | | | – | – | 24 |
| 1290 | 222140_s_at | HG-U133A | AK021758 | 1236 | G protein-coupled receptor 89 | GPR89 | 51463 | | | – | – | 27 |
| 1291 | 201764_at | HG-U133A | NM_024056 | 1237 | hypothetical protein MGC5576 | MGC5576 | 79022 | | | – | – | 33 |
| 1292 | 201698_s_at | HG-U133A | NM_003769 | 1204 | splicing factor, arginine/ serine-rich 9 | SFRS9 | 8683 | | | – | – | 40 |
| 1293 | 203362_s_at | HG-U133A | NM_002358 | 1238 | MAD2 mitotic arrest deficient-like 1 (yeast) | MAD2L1 | 4085 | | | – | | 41 |
| 1294 | 225793_at | HG-U133B | AW500180 | 1239 | Lix1 homolog (mouse) like | LIX1L | 128077 | | | – | | 41 |
| 1295 | 201664_at | HG-U133A | AL136877 | 1240 | SMC4 structural maintenance of chromosomes 4-like 1 (yeast) | SMC4L1 | 10051 | | | – | | 44 |
| 1296 | 220607_x_at | HG-U133A | NM_016397 | 1241 | TH1-like (Drosophila) | TH1L | 51497 | | | | – | 62 |
| 1297 | 226525_at | HG-U133B | N51102 | 1242 | Serine/threonine kinase 17b (apoptosis-inducing) | STK17B | 9262 | | | | | 63 |
| 1298 | 222654_at | HG-U133A | AI302253 | 1243 | myo-inositol monophosphatase A3 | IMPA3 | 54928 | | | | – | 68 |
| 1299 | 205367_at | HG-U133A | NM_020979 | 1244 | adaptor protein with Pleckstrin homology and src homology 2 domains | APS | 10603 | | | | – | 74 |
| 1300 | 200080_s_at | HG-U133B | AI955655 | 1245 | H3 histone, family 3A | H3F3A | 3020 | | | | | 81 |
| 1301 | 208775_at | HG-U133A | D89729 | 1246 | exportin 1 (CRM1 homolog, yeast) | XPO1 | 7514 | | | | | 93 |
| 1302 | 206102_at | HG-U133A | NM_021067 | 1247 | KIAA0186 gene product | KIAA0186 | 9837 | | | | | 103 |
| 1303 | 222998_at | HG-U133B | AL136937 | 1248 | homolog of yeast MAF1 | MAF1 | 84232 | | | | | 114 |
| 1304 | 225644_at | HG-U133B | BF060776 | 1249 | hypothetical protein FLJ33814 | FLJ33814 | 150275 | | | | | 125 |
| 1305 | 224815_at | HG-U133B | AA148301 | 1250 | COMM domain containing 7 | COMMD7 | 149951 | | | | | 128 |
| 1306 | 210460_s_at | HG-U133A | AB033605 | 1251 | proteasome (prosome, macropain) 26S subunit, non-ATPase, 4 | PSMD4 | 5710 | | | | | 137 |

TABLE 3-continued

AGRESSIVENESS PREDICTIVE MARKER IDENTIFICATION

| No. | ProbeSet ID | chip | Rep Public ID | SEQ ID NO: | Title | Gene Symbol | Entrez Gene ID | proteasome inhibitor TTP marker | proteasome inhibitor Response marker | gluco-corticoid TTP marker | gluco-corticoid Response marker | Rank |
|---|---|---|---|---|---|---|---|---|---|---|---|---|
| 1307 | 203316_s_at | HG-U133A | NM_003094 | 1252 | small nuclear ribonucleoprotein polypeptide E | SNRPE | 6635 | | | | | 141 |
| 1308 | 219010_at | HG-U133A | NM_018265 | 1253 | hypothetical protein FLJ10901 | FLJ10901 | 55765 | − | | | | 144 |
| 1309 | 211946_s_at | HG-U133A | AL096857 | 1254 | BAT2 domain containing 1 | BAT2D1 | 23215 | | | − | | 154 |
| 1310 | 200080_s_at | HG-U133A | AI955655 | 1245 | H3 histone, family 3A | H3F3A | 3020 | | | | | 157 |
| 1311 | 222443_s_at | HG-U133B | AF182415 | 1255 | RNA binding motif protein 8 A | RBM8A | 9939 | | | | | 157 |
| 1312 | 202282_at | HG-U133A | NM_004493 | 1256 | hydroxyacyl-Coenzyme A dehydrogenase, type II | HADH2 | 3028 | − | | | | 158 |
| 1313 | 203344_s_at | HG-U133A | NM_002894 | 1257 | retinoblastoma binding protein 8 | RBBP8 | 5932 | | | | | 163 |
| 1314 | 231715_s_at | HG-U133B | NM_013328 | 1258 | pyrroline-5-carboxylate reductase family, member 2 | PYCR2 | 29920 | | | | | 169 |
| 1315 | 211036_x_at | HG-U133A | BC006301 | 1259 | anaphase promoting complex subunit 5 | ANAPC5 | 51433 | | | | | 186 |
| 1316 | 200044_at | HG-U133B | NM_003769 | 1204 | splicing factor, arginine/serine-rich 9 | SFRS9 | 8683 | | | | | 195 |
| 1317 | 208755_x_at | HG-U133A | BF312331 | 1260 | H3 histone, family 3A | H3F3A | 3020 | − | | | | 205 |
| 1318 | 211609_x_at | HG-U133A | U51007 | 1261 | proteasome (prosome, macropain) 26S subunit, non-ATPase, 4 | PSMD4 | 5710 | − | | | | 214 |
| 1319 | 201663_s_at | HG-U133A | NM_005496 | 1262 | SMC4 structural maintenance of chromosomes 4-like 1 (yeast) | SMC4L1 | 10051 | | | | | 216 |
| 1320 | 212766_s_at | HG-U133A | AW294587 | 1263 | hypothetical protein FLJ12671 | FLJ12671 | 81875 | − | | | | 225 |
| 1321 | 219816_s_at | HG-U133A | NM_018107 | 1264 | RNA binding motif protein 23 | RBM23 | 55147 | − | | | | 236 |
| 1322 | 200614_at | HG-U133A | NM_004859 | 1265 | clathrin, heavy polypeptide (Hc) | CLTC | 1213 | − | | | | 243 |
| 1323 | 200843_s_at | HG-U133A | NM_004446 | 1266 | glutamyl-prolyl-tRNA synthetase | EPRS | 2058 | − | | | | 281 |
| 1324 | 200709_at | HG-U133A | NM_000801 | 1267 | FK506 binding protein 1A, 12 kDa | FKBP1A | 2280 | − | | | | 288 |
| 1325 | 208758_at | HG-U133A | D89976 | 1268 | 5-aminoimidazole-4-carboxamide ribonucleotide formyltransferase/IMP cyclohydrolase | ATIC | 471 | − | | | | 293 |
| 1326 | 212345_s_at | HG-U133A | BE675139 | 1269 | cAMP responsive element binding protein3-like 2 | CREB3L2 | 64764 | + | | | | 119 |
| 1327 | 212699_at | HG-U133A | BE222801 | 1270 | secretory carrier membrane protein 5 | SCAMP5 | 192683 | + | | | | 171 |
| 1328 | 206626_x_at | HG-U133A | BC001003 | 1271 | synovial sarcoma, X breakpoint 1 | SSX1 | 6756 | | | | | 10 |
| 1329 | 211678_s_at | HG-U133A | AF090934 | 1272 | zinc finger protein 313 | ZNF313 | 55905 | | − | | | 12 |
| 1330 | 208854_s_at | HG-U133A | AA586774 | 1273 | serine/threonine kinase 24 (STE20 homolog, yeast) | STK24 | 8428 | | | | | 14 |
| 1331 | 218051_s_at | HG-U133A | NM_022908 | 1274 | hypothetical protein FLJ12442 | FLJ12442 | 64943 | | − | | | 18 |
| 1332 | 206621_s_at | HG-U133A | NM_022170 | 1275 | Williams-Beuren syndrome chromosome region 1 | WBSCR1 | 7458 | | − | | | 23 |
| 1333 | 216471_x_at | HG-U133A | X79200 | 1276 | synovial sarcoma, X breakpoint 2 | SSX2 | 6757 | | | | | 24 |
| 1334 | 212433_x_at | HG-U133A | AA630314 | 1277 | ribosomal protein S2 | RPS2 | 6187 | | − | | | 26 |
| 1335 | 202929_s_at | HG-U133A | NM_001355 | 1278 | D-dopachrome tautomerase | DDT | 1652 | | − | | | 33 |
| 1336 | 217972_at | HG-U133A | NM_017812 | 1279 | coiled-coil-helix-coiled-coil-helix domain containing 3 | CHCHD3 | 54927 | | − | | | 41 |
| 1337 | 39835_at | HG-U133A | U93181 | 1280 | SET binding factor 1 | SBF1 | 6305 | | − | | | 42 |
| 1338 | 213166_x_at | HG-U133A | BG332462 | 1281 | | | | | − | | | 63 |

TABLE 3-continued

AGGRESSIVENESS PREDICTIVE MARKER IDENTIFICATION

| No. | ProbeSet ID | chip | Rep Public ID | SEQ ID NO: | Title | Gene Symbol | Entrez Gene ID | proteasome inhibitor TTP marker | proteasome inhibitor Response marker | gluco-corticoid TTP marker | gluco-corticoid Response marker | Rank |
|---|---|---|---|---|---|---|---|---|---|---|---|---|
| 1339 | 210006_at | HG-U133A | BC002571 | 1282 | DKFZP564O243 protein | DKFZP564O243 | 25864 | | | | | 75 |
| 1340 | 232652_x_at | HG-U133B | AF207829 | 1283 | SCAN domain containing 1 | SCAND1 | 51282 | − | − | | − | 108 |
| 1341 | 201630_s_at | HG-U133A | NM_004300 | 1284 | acid phosphatase 1, soluble | ACP1 | 52 | | | | | 144 |
| 1342 | 200966_x_at | HG-U133A | NM_000034 | 1285 | aldolase A, fructose-bisphosphate | ALDOA | 226 | | | | | 165 |
| 1343 | 218561_s_at | HG-U133A | NM_020408 | 1286 | chromosome 6 open reading frame 149 | C6orf149 | 57128 | | | | | 202 |
| 1344 | 200652_at | HG-U133A | NM_003145 | 1287 | signal sequence receptor, beta (translocon-associated protein beta) | SSR2 | 6746 | | | | | 212 |
| 1345 | 225359_at | HG-U133B | BF666961 | 1288 | homolog of yeast TIM14 | TIM14 | 131118 | | | | | 225 |
| 1346 | 201486_at | HG-U133A | NM_002902 | 1289 | reticulocalbin 2, EF-hand calcium binding domain | RCN2 | 5955 | | | | | 242 |
| 1347 | 55093_at | HG-U133A | AA534198 | 1290 | Chondroitin sulfate glucuronyltransferase | CSGlcA-T | 54480 | | | | | 253 |
| 1348 | 224890_s_at | HG-U133B | BE727643 | 1291 | similar to CG14977-PA | LOC389541 | 389541 | | | | | 257 |
| 1349 | 203258_at | HG-U133A | NM_006442 | 1292 | DR1-associated protein 1 (negative cofactor 2 alpha) | DRAP1 | 10589 | | | | | 285 |
| 1350 | 202012_s_at | HG-U133A | AA196245 | 1293 | exostoses (multiple) 2 | EXT2 | 2132 | | | | | 351 |
| 1351 | 209669_s_at | HG-U133A | BC003049 | 1294 | PAI-1 mRNA-binding protein | PAI-RBP1 | 26135 | | | | | 361 |
| 1352 | 215096_s_at | HG-U133A | AU145746 | 1295 | esterase D/formylglutathione hydrolase | ESD | 2098 | | | | | 386 |
| 1353 | 224576_at | HG-U133B | AK000752 | 1296 | endoplasmic reticulum-golgi intermediate compartment 32 kDa protein | KIAA1181 | 57222 | | | | | 415 |
| 1354 | 224217_s_at | HG-U133B | AF094700 | 1297 | Fas (TNFRSF6) associated factor 1 | FAF1 | 11124 | | | | | 448 |
| 1355 | 225502_at | HG-U133B | AL161725 | 1298 | dedicator of cytokinesis 8 | DOCK8 | 81704 | | | | | 467 |
| 1356 | 218802_at | HG-U133A | NM_017918 | 1299 | hypothetical protein FLJ20647 | FLJ20647 | 55013 | | | | | 487 |
| 1357 | 209609_s_at | HG-U133A | BC004517 | 1300 | mitochondrial ribosomal protein L9 | MRPL9 | 65005 | − | | | | 19 |
| 1358 | 211060_x_at | HG-U133A | BC006383 | 1301 | GPAA1P anchor attachment protein 1 homolog (yeast) | GPAA1 | 8733 | − | | | | 28 |
| 1359 | 222997_s_at | HG-U133B | BC004566 | 1302 | mitochondrial ribosomal protein S21 | MRPS21 | 54460 | | | | | 57 |
| 1360 | 201144_s_at | HG-U133A | NM_004094 | 1303 | eukaryotic translation initiation factor 2, subunit 1 alpha, 35 kDa | EIF2S1 | 1965 | | | − | | 59 |
| 1361 | 200910_at | HG-U133A | NM_005998 | 1304 | chaperonin containing TCP1, subunit 3 (gamma) | CCT3 | 7203 | | | | | 61 |
| 1362 | 218336_at | HG-U133A | NM_012394 | 1305 | prefoldin 2 | PFDN2 | 5202 | | | − | | 61 |
| 1363 | 203832_at | HG-U133A | NM_003095 | 1306 | enolase 1, (alpha) /// small nuclear ribonucleoprotein polypeptide F | ENO1 /// SNRPF | 2023 /// 6636 | | | | | 90 |
| 1364 | 208822_s_at | HG-U133A | U18321 | 1307 | death associated protein 3 | DAP3 | 7818 | | | | | 99 |
| 1365 | 200057_s_at | HG-U133A | NM_007363 | 201 | non-POU domain containing, octamer-binding | NONO | 4841 | | | | | 113 |
| 1366 | 202244_at | HG-U133A | NM_002796 | 1308 | proteasome (prosome, macropain) subunit, beta type, 4 | PSMB4 | 5692 | | | | | 129 |
| 1367 | 203594_at | HG-U133A | NM_003729 | 1309 | RNA terminal phosphate cyclase domain 1 | RTCD1 | 8634 | | | | | 171 |
| 1368 | 215450_at | HG-U133B | W87901 | 1310 | | | | | | | | 178 |
| 1369 | 223377_x_at | HG-U133B | AF035947 | 1311 | cytokine inducible SH2-containing protein | CISH | 1154 | + | + | + | + | 2 |

TABLE 3-continued

AGGRESSIVENESS PREDICTIVE MARKER IDENTIFICATION

| No. | ProbeSet ID | chip | Rep Public ID | SEQ ID NO: | Title | Gene Symbol | Entrez Gene ID | proteasome inhibitor TTP marker | proteasome inhibitor Response marker | gluco-corticoid TTP marker | gluco-corticoid Response marker | Rank |
|---|---|---|---|---|---|---|---|---|---|---|---|---|
| 1370 | 209813_x_at | HG-U133A | M16768 | 1312 | T cell receptor gamma variable 9 /// TCR gamma alternate reading frame protein | TRGV9 /// TARP | 445347 /// 6983 | | + | | | 5 |
| 1371 | 216491_x_at | HG-U133A | U80139 | 1313 | Immunoglobulin heavy constant mu /// Immunoglobulin heavy constant gamma 1 (G1m marker) | IGHM /// IGHG1 | 3500 /// 3507 | | + | | − | 9 |
| 1372 | 204891_s_at | HG-U133A | NM_005356 | 1314 | lymphocyte-specific protein tyrosine kinase | LCK | 3932 | | + | | | 13 |
| 1373 | 204141_at | HG-U133A | NM_001069 | 1315 | tubulin, beta 2 | TUBB2 | 7280 | | + | | + | 26 |
| 1374 | 203661_s_at | HG-U133A | BC002660 | 1316 | tropomodulin 1 | TMOD1 | 7111 | | + | | + | 31 |
| 1375 | 221558_s_at | HG-U133A | AF288571 | 1317 | lymphoid enhancer-binding factor 1 | LEF1 | 51176 | | + | | − | 39 |
| 1376 | 200660_at | HG-U133A | NM_005620 | 1318 | S100 calcium binding protein A11 (calgizzarin) | S100A11 | 6282 | | + | | + | 41 |
| 1377 | 206206_at | HG-U133A | NM_005582 | 1319 | lymphocyte antigen 64 homolog, radioprotective 105 kDa (mouse) | LY64 | 4064 | | + | | | 59 |
| 1378 | 211719_x_at | HG-U133A | BC005858 | 1320 | fibronectin 1 | FN1 | 2335 | | + | | | 69 |
| 1379 | 212332_at | HG-U133A | BF110947 | 1321 | retinoblastoma-like 2 (p130) | RBL2 | 5934 | | + | | | 70 |
| 1380 | 214486_x_at | HG-U133A | AF041459 | 1322 | CASP8 and FADD-like apoptosis regulator | CFLAR | 8837 | | + | | | 93 |
| 1381 | 217202_s_at | HG-U133A | U08626 | 1323 | glutamate-ammonia ligase (glutamine synthase) | GLUL | 2752 | | + | | | 115 |
| 1382 | 203567_s_at | HG-U133A | AU157590 | 1324 | tripartite motif-containing 38 | TRIM38 | 10475 | | + | | | 121 |
| 1383 | 205590_at | HG-U133A | NM_005739 | 1325 | RAS guanyl releasing protein 1 (calcium and DAG-regulated) | RASGRP1 | 10125 | | + | | | 142 |
| 1384 | 226505_x_at | HG-U133B | AI148567 | 1326 | ubiquitin specific protease 32 | USP32 | 84669 | | + | | | 143 |
| 1385 | 210972_x_at | HG-U133A | M15565 | 1327 | T cell receptor alpha locus | TRA@ | 6955 | | + | | | 144 |
| 1386 | 209473_at | HG-U133A | AV717590 | 1328 | ectonucleoside triphosphate diphosphohydrolase 1 | ENTPD1 | 953 | | + | | | 158 |
| 1387 | 226085_at | HG-U133B | AA181060 | 1329 | Chromobox homolog 5 (HP1 alpha homolog, Drosophila) | CBX5 | 23468 | | + | | | 167 |
| 1388 | 37831_at | HG-U133A | AB011117 | 1330 | signal-induced proliferation-associated 1 like 3 | SIPA1L3 | 23094 | | + | | | 170 |
| 1389 | 210426_x_at | HG-U133A | U04897 | 1331 | RAR-related orphan receptor A | RORA | 6095 | | + | | | 176 |
| 1390 | 210987_x_at | HG-U133A | M19267 | 1332 | Tropomyosin 1 (alpha) | TPM1 | 7168 | | + | | | 182 |
| 1391 | 217878_s_at | HG-U133A | AI203880 | 1333 | cell division cycle 27 | CDC27 | 996 | | + | | | 192 |
| 1392 | 220169_at | HG-U133A | NM_024943 | 1334 | hypothetical protein FLJ23235 | FLJ23235 | 80008 | | + | | | 197 |
| 1393 | 220681_at | HG-U133A | AF153604 | 1335 | ubiquitin specific protease 15 | USP15 | 9958 | | + | | | 199 |
| 1394 | 213327_s_at | HG-U133A | AI820101 | 1336 | | | | | + | | | 199 |
| 1395 | 211994_at | HG-U133A | AI742553 | 1337 | Clone A9A2BRB5 (CAC)n/(GTG)n repeat-containing mRNA. | | | | + | | | 205 |
| 1396 | 216557_x_at | HG-U133A | U92706 | 1338 | Immunoglobulin heavy constant gamma 1 (G1m marker) | IGHG1 | 3500 | | + | | | 222 |
| 1397 | 202096_s_at | HG-U133A | NM_000714 | 1339 | benzodiazepine receptor (peripheral) | BZRP | 706 | | + | | | 233 |
| 1398 | 212660_at | HG-U133A | AI735639 | 1340 | PHD finger protein 15 | PHF15 | 23338 | | + | | | 246 |

TABLE 3-continued

AGGRESSIVENESS PREDICTIVE MARKER IDENTIFICATION

| No. | ProbeSet ID | chip | Rep Public ID | SEQ ID NO: | Title | Gene Symbol | Entrez Gene ID | proteasome inhibitor TTP marker | proteasome inhibitor Response marker | gluco-corticoid TTP marker | gluco-corticoid Response marker | Rank |
|---|---|---|---|---|---|---|---|---|---|---|---|---|
| 1399 | 243699_at | HG-U133B | BG432887 | 1341 | Full-length cDNA clone CS0DI020YI19 of Placenta Cot 25-normalized of *Homo sapiens* (human) | | | | | | | 249 |
| 1400 | 45749_at | HG-U133A | AA400206 | 1342 | hypothetical protein FLJ13725 | FLJ13725 | 79567 | | + | | | 273 |
| 1401 | 207571_x_at | HG-U133B | NM_004848 | 1343 | chromosome 1 open reading frame 38 | C1orf38 | 9473 | | + | | | 281 |
| 1402 | 211993_at | HG-U133A | AI768512 | 1344 | WNK lysine deficient protein kinase 1 | WNK1 | 65125 | | + | | | 286 |
| 1403 | 226682_at | HG-U133B | AW006185 | 1345 | hypothetical protein LOC283666 | LOC283666 | 283666 | | + | | | 299 |
| 1404 | 205464_at | HG-U133A | NM_000336 | 1346 | sodium channel, nonvoltage-gated 1, beta (Liddle syndrome) | SCNN1B | 6338 | | + | | | 306 |
| 1405 | 202748_at | HG-U133A | NM_004120 | 1347 | guanylate binding protein 2, interferon-inducible | GBP2 | 2634 | | + | | | 309 |
| 1406 | 204151_x_at | HG-U133A | NM_001353 | 1348 | aldo-keto reductase family 1, member C1 (dihydrodiol dehydrogenase 1; 20-alpha (3-alpha)-hydroxysteroid dehydrogenase) | AKR1C1 | 1645 | | + | | | 315 |
| 1407 | 205442_at | HG-U133A | NM_021647 | 1349 | Microfibrillar-associated protein 3-like | MFAP3L | 9848 | | | | | 329 |
| 1408 | 218559_s_at | HG-U133A | NM_005461 | 1350 | v-maf musculoaponeurotic fibrosarcoma oncogene homolog B (avian) | MAFB | 9935 | | + | | | 329 |
| 1409 | 210479_s_at | HG-U133A | L14611 | 1351 | RAR-related orphan receptor A | RORA | 6095 | | + | | | 333 |
| 1410 | 228157_at | HG-U133B | AI125646 | 1352 | Zinc finger protein 207 | ZNF207 | 7756 | | + | | | 340 |
| 1411 | 216449_x_at | HG-U133B | AK025862 | 1353 | tumor rejection antigen (gp96) 1 | TRA1 | 7184 | | + | | | 357 |
| 1412 | 204416_x_at | HG-U133A | NM_001645 | 1354 | apolipoprotein C-I | APOC1 | 341 | | + | | | 368 |
| 1413 | 219229_at | HG-U133A | NM_013272 | 1355 | solute carrier organic anion transporter family, member 3A1 | SLCO3A1 | 28232 | | + | | | 377 |
| 1414 | 201853_s_at | HG-U133A | NM_021873 | 1356 | cell division cycle 25B | CDC25B | 994 | | + | | | 382 |
| 1415 | 201039_s_at | HG-U133A | BF572938 | 1357 | RAD23 homolog A (*S. cerevisiae*) | RAD23A | 5886 | | + | | | 406 |
| 1416 | 212607_at | HG-U133A | N32526 | 1358 | v-akt murine thymoma viral oncogene homolog 3 (protein kinase B, gamma) | AKT3 | 10000 | | + | | | 433 |
| 1417 | 209901_x_at | HG-U133A | U19713 | 1359 | allograft inflammatory factor 1 | AIF1 | 199 | | + | | | 522 |
| 1418 | 205896_at | HG-U133A | NM_003059 | 1360 | solute carrier family 22 (organic cation transporter), member 4 | SLC22A4 | 6583 | | + | | | 525 |
| 1419 | 213566_at | HG-U133A | NM_005615 | 1361 | ribonuclease, RNase A family, k6 | RNASE6 | 6039 | | + | | | 535 |
| 1420 | 211986_at | HG-U133A | BG287862 | 1362 | AHNAK nucleoprotein (desmoyokin) | AHNAK | 195 | | + | | | 547 |
| 1421 | 201220_x_at | HG-U133A | NM_001329 | 1363 | C-terminal binding protein 2 | CTBP2 | 1488 | | + | | | 627 |
| 1422 | 202201_at | HG-U133A | NM_000713 | 1364 | biliverdin reductase B (flavin reductase (NADPH)) | BLVRB | 645 | | + | | | 664 |
| 1423 | 224920_x_at | HG-U133B | AA909044 | 1365 | myeloid-associated differentiation marker | MYADM | 91663 | | + | | | 686 |
| 1424 | 209340_at | HG-U133A | S73498 | 1366 | UDP-N-acetylglucosamine pyrophosphorylase 1 | UAP1 | 6675 | | | − | − | 1 |

TABLE 3-continued

AGRESSIVENESS PREDICTIVE MARKER IDENTIFICATION

| No. | ProbeSet ID | chip | Rep Public ID | SEQ ID NO: | Title | Gene Symbol | Entrez Gene ID | proteasome inhibitor TTP marker | proteasome inhibitor Response marker | gluco-corticoid TTP marker | gluco-corticoid Response marker | Rank |
|---|---|---|---|---|---|---|---|---|---|---|---|---|
| 1425 | 208642_s_at | HG-U133A | AA205834 | 1367 | X-ray repair complementing defective repair in Chinese hamster cells 5 (double-strand-break rejoining; Ku autoantigen, 80 kDa) | XRCC5 | 7520 | | | − | | 38 |
| 1426 | 206632_s_at | HG-U133A | NM_004900 | 1368 | apolipoprotein B mRNA editing enzyme, catalytic polypeptide-like 3B | APOBEC3B | 9582 | | | | | 59 |
| 1427 | 206218_at | HG-U133A | NM_002364 | 1369 | melanoma antigen family B, 2 | MAGEB2 | 4113 | | | | | 63 |
| 1428 | 214612_x_at | HG-U133A | U10691 | 1370 | melanoma antigen family A, 6 | MAGEA6 | 4105 | | | | − | 65 |
| 1429 | 232231_at | HG-U133B | AL353944 | 1371 | Runt-related transcription factor 2 | RUNX2 | 860 | | | | − | 87 |
| 1430 | 220057_at | HG-U133A | NM_020411 | 1372 | X antigen family, member 1 | XAGE1 | 9503 | | | | − | 15 |
| 1431 | 220565_at | HG-U133A | NM_016602 | 1373 | Chemokine (C-C motif) receptor 10 | CCR10 | 2826 | − | | | | 177 |
| 1432 | 224518_s_at | HG-U133B | BC006436 | 1374 | zinc finger protein 559 | ZNF559 | 84527 | − | | | | 200 |
| 1433 | 200713_s_at | HG-U133A | NM_012325 | 1375 | microtubule-associated protein, RP/EB family, member 1 | MAPRE1 | 22919 | − | | | | 289 |
| 1434 | 210497_x_at | HG-U133A | BC002818 | 1376 | synovial sarcoma, X breakpoint 2 | SSX2 | 6757 | | | | − | 2 |
| 1435 | 209486_at | HG-U133A | BC004546 | 1377 | disrupter of silencing 10 | SAS10 | 57050 | | − | | | 104 |
| 1436 | 217466_x_at | HG-U133A | L48784 | 1378 | ribosomal protein S2 | RPS2 | 6187 | | − | | | 135 |
| 1437 | 204836_at | HG-U133A | NM_000170 | 1379 | glycine dehydrogenase (decarboxylating; glycine decarboxylase, glycine cleavage system protein P) | GLDC | 2731 | | − | | | 14 |
| 1438 | 212750_at | HG-U133A | AB020630 | 472 | protein phosphatase 1, regulatory (inhibitor) subunit 16B | PPP1R16B | 26051 | − | + | | | 32 |
| 1439 | 225239_at | HG-U133B | AI355441 | 1380 | CDNA FLJ26120 fis, clone SYN00419 | | | | + | | + | 45 |
| 1440 | 211474_s_at | HG-U133A | BC004948 | 1381 | serine (or cysteine) proteinase inhibitor, clade B (ovalbumin), member 6 | SERPINB6 | 5269 | | + | | | 343 |
| 1441 | 53987_at | HG-U133A | AL041852 | 1382 | RAN binding protein 10 | RANBP10 | 57610 | | | | | 364 |
| 1442 | 203642_s_at | HG-U133A | NM_014900 | 1383 | COBL-like 1 | COBLL1 | 22837 | | | | + | 6 |
| 1443 | 208908_s_at | HG-U133A | AF327443 | 1384 | calpastatin | CAST | 831 | | | + | + | 21 |
| 1444 | 207467_x_at | HG-U133A | NM_001750 | 1385 | calpastatin | CAST | 831 | | | + | + | 32 |
| 1445 | 213011_s_at | HG-U133A | BF116254 | 1386 | triosephosphate isomerase 1 | TPI1 | 7167 | | | − | | 35 |
| 1446 | 200953_s_at | HG-U133A | NM_001759 | 1387 | Cyclin D2 | CCND2 | 894 | | | | + | 36 |
| 1447 | 216526_x_at | HG-U133A | AK024836 | 1388 | major histocompatibility complex, class I, C | HLA-C | 3107 | | | | + | 89 |
| 1448 | 201952_at | HG-U133A | AA156721 | 1389 | | | | | | + | | 184 |
| 1449 | 222680_s_at | HG-U133B | AK001261 | 1390 | RA-regulated nuclear matrix-associated protein | RAMP | 51514 | | | − | | 5 |
| 1450 | 201697_s_at | HG-U133A | NM_001379 | 1391 | DNA (cytosine-5-)-methyl-transferase 1 | DNMT1 | 1786 | − | | | | 7 |
| 1451 | 209644_x_at | HG-U133A | U38945 | 1392 | cyclin-dependent kinase inhibitor 2A (melanoma, p16, inhibits CDK4) | CDKN2A | 1029 | | | | − | 25 |
| 1452 | 215690_x_at | HG-U133A | AL157437 | 1393 | GPAA1P anchor attachment protein 1 homolog (yeast) | GPAA1 | 8733 | | | | | 35 |

TABLE 3-continued

AGRESSIVENESS PREDICTIVE MARKER IDENTIFICATION

| No. | ProbeSet ID | chip | Rep Public ID | SEQ ID NO: | Title | Gene Symbol | Entrez Gene ID | proteasome inhibitor TTP marker | proteasome inhibitor Response marker | gluco-corticoid TTP marker | gluco-corticoid Response marker | Rank |
|---|---|---|---|---|---|---|---|---|---|---|---|---|
| 1453 | 200822_x_at | HG-U133A | NM_000365 | 1394 | triosephosphate isomerase 1 | TPI1 | 7167 | – | | | | 100 |
| 1454 | 213828_x_at | HG-U133A | AA477655 | 1395 | H3 histone, family 3A | H3F3A | 3020 | – | | – | | 287 |
| 1455 | 218603_at | HG-U133A | NM_016217 | 1396 | headcase homolog (Drosophila) | HECA | 51696 | + | | + | + | 43 |
| 1456 | 218795_at | HG-U133A | NM_016361 | 1397 | acid phosphatase 6, lysophosphatidic | ACP6 | 51205 | | – | | | 158 |
| 1457 | 215823_x_at | HG-U133A | U64661 | 1398 | poly(A) binding protein, cytoplasmic 3 /// poly(A) binding protein, cytoplasmic 1 | PABPC3 /// PABPC1 | 26986 /// 5042 | | – | | | 339 |
| 1458 | 213160_at | HG-U133A | D86964 | 1399 | dedicator of cytokinesis 2 | DOCK2 | 1794 | – | – | | | 460 |
| 1459 | 213811_x_at | HG-U133A | AW062341 | 1400 | transcription factor 3 (E2A immunoglobulin enhancer binding factors E12/E47) | TCF3 | 6929 | | – | – | – | 12 |
| 1460 | 201618_x_at | HG-U133A | NM_003801 | 1401 | GPAA1P anchor attachment protein 1 homolog (yeast) | GPAA1 | 8733 | – | – | – | – | 39 |
| 1461 | 203560_at | HG-U133A | NM_003878 | 1402 | gamma-glutamyl hydrolase (conjugase, folylpolygammaglutamyl hydrolase) | GGH | 8836 | | | | | 76 |
| 1462 | 225317_at | HG-U133B | AL574669 | 1403 | acyl-Coenzyme A binding domain containing 6 | ACBD6 | 84320 | – | | | | 95 |
| 1463 | 215001_s_at | HG-U133A | AL161952 | 1404 | glutamate-ammonia ligase (glutamine synthase) | GLUL | 2752 | | + | | + | 52 |
| 1464 | 220547_s_at | HG-U133A | NM_019054 | 1405 | family with sequence similarity 35, member A | FAM35A | 54537 | | + | | | 77 |
| 1465 | 213415_at | HG-U133A | AI768628 | 1406 | chloride intracellular channel 2 | CLIC2 | 1193 | | + | | + | 78 |
| 1466 | 203038_at | HG-U133A | NM_002844 | 1407 | protein tyrosine phosphatase, receptor type, K | PTPRK | 5796 | | + | | + | 111 |
| 1467 | 210564_x_at | HG-U133A | AF009619 | 1408 | CASP8 and FADD-like apoptosis regulator | CFLAR | 8837 | | + | | | 149 |
| 1468 | 209508_x_at | HG-U133A | AF005774 | 1409 | CASP8 and FADD-like apoptosis regulator | CFLAR | 8837 | | + | | | 234 |
| 1469 | 208485_x_at | HG-U133A | NM_003879 | 1410 | CASP8 and FADD-like apoptosis regulator | CFLAR | 8837 | | + | | | 254 |
| 1470 | 37986_at | HG-U133A | M60459 | 1411 | erythropoietin receptor | EPOR | 2057 | | + | | | 354 |
| 1471 | 232213_at | HG-U133B | AU147506 | 1412 | Pellino homolog 1 (Drosophila) | PELI1 | 57162 | | | | + | 32 |
| 1472 | 232304_at | HG-U133B | AK026714 | 1413 | Pellino homolog 1 (Drosophila) | PELI1 | 57162 | | | | + | 37 |
| 1473 | 218319_at | HG-U133A | NM_020651 | 1414 | pellino homolog 1 (Drosophila) | PELI1 | 57162 | | | | + | 85 |
| 1474 | 204173_at | HG-U133A | NM_002475 | 1415 | myosin light chain 1 slow a | MLC1SA | 140465 | – | – | | – | 25 |

Classification Methods

Various algorithms are currently available that can be used to classify patient samples using a given set of features. Therefore, the combination of markers selected through the feature selection process may be used in any of the available algorithms in order to derive a prediction equation as to whether the patient sample is sensitive or resistant. The classification methods used to illustrate the use of multiple markers for patient sample clasdification in the present invention were: 1) Linear Predictive Score ("LPS"); and 2) k-nearest neighbors.

The Linear Predictive Score was implemented as described by Wright et al., "A gene-expression based method to diagnose clinically distinct groups of diffuse large B cell lymphoma." PNAS 100(17):9991-9996 (2003), the contents of which are incorporated herein by reference. As described by Wright et al., the LPS score for a vector X is computed as:

$$LPS(X) = \sum_j a_j X_j$$

where $X_j$ represents the log expression value for the $j^{th}$ feature in the set, and $a_j$ is a scaling factor representing the degree to which the $j^{th}$ feature is associated with the outcome to be predicted. As in Wright et al., we used the t-statistics of the features for the scaling factors. Given the LPS score, the likelihood that a sample is in the first of the two classes is determined using this formula:

$$P(X \in S_1) = \frac{\phi(LPS(X); \hat{\mu}_1, \hat{\sigma}_1^2)}{\phi(LPS(X); \hat{\mu}_1, \hat{\sigma}_1^2) + \phi(LPS(X); \hat{\mu}_2, \hat{\sigma}_2^2)},$$

where $\phi(x; \mu, \sigma^2)$ represents the normal density function with mean $\mu$ and variance $\sigma^2$, and $\hat{\mu}_1$, $\hat{\sigma}_1^2$, $\hat{\mu}_2$ and $\hat{\sigma}_2^2$ are the observed means and variances of the LPS scores for category 1 and category 2. In our case, for example, category 1 would be responders, and category 2 would be non-responders. Then the prediction for a new sample would be that it would be in the first class with probability $P(X \in S_1)$ and in the second class with probability $P(X \in S_2)=1-P(X \in S_1)$.

The k-nearest neighbor classification method computes the similarity between a query profile and each of the profiles in the training set [Introduction to Machine Learning by Ethem ALPAYDIN, The MIT Press, October 2004, ISBN 0-262-01211-1]. The k most similar profiles are selected, and a vote is taken amongst their class labels to determine the prediction for the query profile. Here, we used k=1.

Feature Selection

Feature selection is the process of determining a subset of the thousands of available features in the dataset, resulting in a combination of features that form a marker set or model, to classify patients by treatment outcome. There are many approaches to selecting features. Here we report two approaches to generate example marker sets: (1) top N most significant features, and (2) a standard feature selection method, sequential forward feature selection (See, Dash and Liu, "Feature Selection for Classification," Intelligent Data Analysis 1:131-156, 1997). We now describe how feature selection is applied to our dataset.

As a first step, only features associated with the outcome variable are considered as candidates for a feature set. For the LPS models, all features with multiple-test-adjusted p-values less than 0.05 were determined. For the k-nearest-neighbor models, the top 100 PFC markers were determined. In either case, sequential forward selection starts with no markers in the set. At each iteration, a new feature set is formed by adding a feature selected by an evaluation function. Iteration terminates when no feature can be added that improves the evaluation function. The evaluation function is the number of samples correctly predicted either (1) by the model built on all of the samples, or (2) in leave-one-out cross-validation (Dash and Liu, 1997). Ties are broken by using the feature that has a higher univariate association with the outcome variable. Multiple marker sets can be generated by repeated rounds of feature selection, each time removing the features already selected.

Specific Application of Class Prediction

Linear Predictor Score (LPS)

Using the 162 bortezomib-treated patients classified into Responsive or Nonresponsive groups, the table below shows the markers in the first LPS predictive set we built from our data set. Also indicated is whether the marker is more highly expressed in Responsive (R) or in Non-responsive (N) patients. The probe set annotations are those provided by Affymetrix.

TABLE 4

LPS Predictive Marker Set

| Subset | Order | Probe Set | Chip | Gene Symbol | Description | SEQ ID NO: | Direction |
|---|---|---|---|---|---|---|---|
| 1 | 1 | 210532_s_at | A | C14orf2 | chromosome 14 open reading frame 2 | 608 | N |
| 1 | 2 | 206790_s_at | A | NDUFB1 | NADH dehydrogenase (ubiquinone) 1 beta subcomplex, 1, 7 kDa | 516 | N |
| 1 | 3 | 200082_s_at | A | RPS7 | ribosomal protein S7 | 514 | N |
| 2 | 4 | 217988_at | A | CCNB1IP1 | cyclin B1 interacting protein 1 | 459 | N |
| 2 | 5 | 200937_s_at | A | RPL5 | ribosomal protein L5 | 520 | N |
| 2 | 6 | 213941_x_at | A | RPS7 | ribosomal protein S7 | 2 | N |
| 2 | 7 | 224616_at | A | DNCLI2 | dynein, cytoplasmic, light intermediate polypeptide 2 | 621 | R |
| 2 | 8 | 224985_at | A | SS18 | synovial sarcoma translocation, chromosome 18 | 578 | N |
| 2 | 9 | 233252_s_at | A | STRBP | spermatid perinuclear RNA binding protein | 9 | N |

TABLE 4-continued

LPS Predictive Marker Set

| Sub set | Order | Probe Set | Chip | Gene Symbol | Description | SEQ ID NO: | Direction |
|---|---|---|---|---|---|---|---|
| 3 | 10 | 206621_s_at | A | WBSCR1 | Williams-Beuren syndrome chromosome region 1 | 1275 | N |
| 3 | 11 | 208540_x_at | B | S100A11P | S100 calcium binding protein A11 pseudogene | 627 | R |
| 3 | 12 | 202605_at | A | GUSB | glucuronidase, beta | 461 | N |
| 4 | 13 | 201637_s_at | A | FXR1 | fragile X mental retardation, autosomal homolog 1 | 1122 | N |
| 4 | 14 | 209475_at | B | USP15 | ubiquitin specific protease 15 | 862 | R |
| 4 | 15 | 200626_s_at | B | MATR3 | matrin 3 | 54 | N |
| 4 | 16 | 219939_s_at | A | UNR | upstream of NRAS | 589 | N |
| 4 | 17 | 219910_at | A | HYPE | Huntingtin interacting protein E | 649 | R |
| 5 | 18 | 200034_s_at | A | RPL6 | ribosomal protein L6 | 29 | N |
| 5 | 19 | 201784_s_at | A | SMAP | small acidic protein | 134 | N |
| 5 | 20 | 211316_x_at | A | CFLAR | CASP8 and FADD-like apoptosis regulator | 849 | R |
| 5 | 21 | 213080_x_at | A | RPL5 | ribosomal protein L5 | 145 | N |

It will be appreciated that additional marker sets may be obtained by employing the methods described herein, and methods standard in the field, for identifying models. There are many highly correlated features that could be substituted for each other in the models; these are not all listed. Similar methods may be employed utilizing one or more markers from the identified marker sets of the present invention in order to generate Predictive Marker Sets.

The present invention is not to be limited in scope by the specific embodiments described that are intended as illustrations of aspects of the invention. Functionally equivalent methods and components are within the scope of the invention, in addition to those shown and described herein and will become apparent to those skilled in the art from the foregoing description, using no more than routine experimentation. Such equivalents are intended to be encompassed by the following claims.

All references cited herein, including journal articles, patents, and databases are expressly incorporated by reference.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08889354B2). An electronic copy of the "Sequence Listing" will also be available from the USPTO upon request and payment of the fee set forth in 37 CFR 1.19(b)(3).

What is claimed is:

1. A method for determining whether to continue a cancer therapy regimen for treating a hematological cancer in a patient comprising:
   a) measuring the level of expression of at least one nucleic acid sequence selected from the group consisting of sequences recognized by probesets of predictive marker or markers numbered 1-547 in Table 1A, 658-871 in Table 1B, 873-876 in Table 1B, 912-1062 in Table 2A, 1071-1079, 1081-1087, 1089-1093, 1095-1106, 1108-1185 in Table 2B, and/or 1203-1423 in Table 3 in a first patient sample comprising hematological tumor cells, wherein the sequences recognized by probesets of the predictive marker or markers:
      i) numbered 1-547 consist of SEQ ID NOs: 1-513,
      ii) numbered 658-871 and 873-876 consist of SEQ ID NOs:614-830,
      iii) numbered 912-1062 consist of SEQ ID NOs:866-1014, 434 and 733,
      iv) numbered 1071-1079, 1081-1087, 1089-1093, 1095-1106 and 1108-1185 consist of SEQ ID NOs:1023-1133, and
      v) numbered 1203-1423 consist of SEQ ID NOs:201, 398, 1091 and 1151-1365, thereby determining a baseline expression level of the predictive marker or markers;
   b) treating the patient with the cancer therapy regimen;
   c) measuring the level of expression of the at least one nucleic acid measured in step a) in a successive patient sample comprising hematological tumor cells;
   d) comparing the expression level in step c) to the baseline level in step a), thereby identifying whether expression in the successive sample includes a profile of expression of the predictive marker or markers; and
   e) continuing treatment of the hematological cancer if the expression profile of the predictive marker or markers in the successive sample demonstrates responsiveness, wherein the hematological cancer is multiple myeloma, wherein the hematological tumor cells are multiple myeloma tumor cells, and wherein the cancer therapy regimen is selected from the group consisting of proteasome inhibition therapy and glucocorticoid therapy.

2. The method of claim 1 wherein the level of expression of the at least one nucleic acid is determined by detection of mRNA.

3. The method of claim 1 wherein the cancer therapy regimen comprises a proteasome inhibition-based therapy.

4. The method of claim 1 wherein the expression profile is determined by a predictive marker set comprising two or more predictive markers.

5. The method of claim 1, wherein the proteasome inhibition-based therapy comprises treatment with a proteasome inhibitor selected from the group consisting of a peptidyl aldehyde, a peptidyl boronic acid, a peptidyl boronic ester, a vinyl sulfone, an epoxyketone, and a lactacystin analog.

6. The method of claim 1, wherein the first patient sample comprising hematological tumor cells is obtained from the subject prior to the cancer therapy.

7. The method of claim 3, wherein the proteasome inhibition-based therapy comprises treatment with bortezomib.

8. The method of claim 4, wherein the predictive marker set comprises at least 20 markers.

9. The method of claim 4, wherein the predictive marker set comprises a subset of markers identified in Table 4.

10. The method of claim 1, wherein the glucocorticoid inhibition therapy comprises dexamethasone therapy.

11. The method of claim 7, wherein the level of expression is measured on at least one nucleic acid sequence selected from the group consisting of sequences recognized by probesets of predictive marker or markers numbered 1-547 in Table 1A, 658-871 in Table 1B, 873-876 in Table 1B, and 1203-1423 in Table 3.

* * * * *